(12) United States Patent
Shimma et al.

(10) Patent No.: US 8,362,236 B2
(45) Date of Patent: Jan. 29, 2013

(54) MACROCYCLIC COMPOUND

(75) Inventors: Nobuo Shimma, Kanagawa (JP); Takuo Tsukuda, Kanagawa (JP); Hiroshi Koyano, Kanagawa (JP); Atsushi Suda, Kanagawa (JP); Tadakatsu Hayase, Kanagawa (JP); Kihito Hada, Kanagawa (JP); Ken-Ichi Kawasaki, Kanagawa (JP); Susumu Komiyama, Kanagawa (JP); Naomi Ono, Kanagawa (JP); Toshikazu Yamazaki, Kanagawa (JP); Ryoichi Saitoh, Kanagawa (JP); Masami Kohchi, Kanagawa (JP); Kiyoshi Hasegawa, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 367 days.

(21) Appl. No.: 12/529,222

(22) PCT Filed: Feb. 29, 2008

(86) PCT No.: PCT/JP2008/053599
§ 371 (c)(1),
(2), (4) Date: Oct. 2, 2009

(87) PCT Pub. No.: WO2008/105526
PCT Pub. Date: Sep. 4, 2008

(65) Prior Publication Data
US 2010/0056510 A1 Mar. 4, 2010

(30) Foreign Application Priority Data
Mar. 1, 2007 (JP) .................. 2007-052072

(51) Int. Cl.
C07D 497/08 (2006.01)
C07D 513/08 (2006.01)
C07D 513/20 (2006.01)
A61K 31/529 (2006.01)
A61K 31/53 (2006.01)
A61K 31/5377 (2006.01)
A61P 35/00 (2006.01)

(52) U.S. Cl. ........ 540/450; 514/183; 514/245; 514/272; 544/194; 544/219; 544/321

(58) Field of Classification Search ............. 544/194, 544/219, 321; 514/245, 272, 183; 540/450
See application file for complete search history.

(56) References Cited

U.S. PATENT DOCUMENTS

| 6,210,974 B1 | 4/2001 | Gold |
| 2004/0204386 A1 | 10/2004 | Bhatt et al. |
| 2008/0214586 A1 | 9/2008 | Eggenweiler et al. |
| 2009/0247524 A1 * | 10/2009 | Tsukuda et al. ........... 514/236.2 |

FOREIGN PATENT DOCUMENTS

| EP | 0 165 653 | 12/1985 |
| EP | 1321169 A1 | 6/2003 |
| JP | 51070780 A | 6/1976 |
| JP | 60-208968 | 10/1985 |
| JP | 2001505554 A | 4/2001 |
| JP | 2005225787 A | 8/2005 |
| JP | 2005530689 A1 | 10/2005 |
| JP | 2009067729 A1 | 4/2009 |
| WO | WO9744326 A1 | 11/1997 |
| WO | WO 98/19648 | 5/1998 |
| WO | WO9951223 A1 | 10/1999 |
| WO | WO 01/27088 | 4/2001 |
| WO | WO0162233 A1 | 8/2001 |
| WO | WO0202123 A1 | 1/2002 |
| WO | WO0209696 A1 | 2/2002 |
| WO | WO0236075 A2 | 5/2002 |
| WO | WO0236171 A1 | 5/2002 |
| WO | WO03037346 A1 | 5/2003 |
| WO | WO03037860 A2 | 5/2003 |
| WO | WO03055860 A1 | 7/2003 |
| WO | WO2004050087 A1 | 6/2004 |
| WO | WO2005021552 A1 | 3/2005 |
| WO | WO2006008503 A1 | 1/2006 |

(Continued)

OTHER PUBLICATIONS

Japanese Patent Office, International Search Report for App. Ser. No. PCT/JP2007/060666 mailed Jun. 19, 2007, 7 pages.

(Continued)

*Primary Examiner* — Venkataraman Balasubramanian
(74) *Attorney, Agent, or Firm* — Fish & Richardson P.C.

(57) ABSTRACT

The present invention provides a novel class of compounds that have the activity of inhibiting HSP90 enzyme and are useful as anti-cancer agents or such, and compounds that are useful as synthetic intermediates thereof. Specifically, the present invention provides compounds represented by the following formula (1), and pharmaceutically acceptable salts thereof:

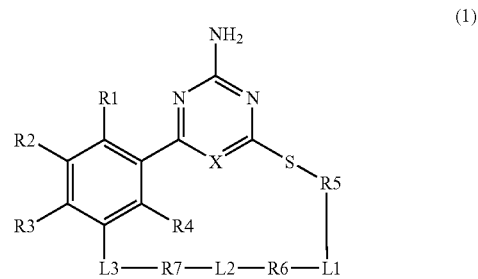

(1)

wherein X, $R^1$, $R^2$, $R^3$, $R^4$, $R^5$, $R^6$, $R^7$, $L^1$, $L^2$, and $L^3$ are as defined in the specification.

20 Claims, No Drawings

FOREIGN PATENT DOCUMENTS

| | | |
|---|---|---|
| WO | WO2006122631 A1 | 11/2006 |
| WO | WO2006123165 A2 | 11/2006 |
| WO | WO2007058627 A1 | 5/2007 |
| WO | WO2007138994 A1 | 12/2007 |
| WO | WO2008105526 A1 | 9/2008 |
| WO | WO2009097578 A1 | 8/2009 |

OTHER PUBLICATIONS

Augustin et al., "Reaktionen mit N-Acyliminodithiokohlensaurediestern," Journal fur praktische Chemie (Leipzig), 322(1):55-68 (1980) (English abstract).

Banerji et al., "The Clinical Applications of Heat Shock Protein Inhibitors in Cancer—Present and Future," Curr. Cancer Drug Targets, 3:385-390 (2003).

Chiosis et al., "A small molecule designed to bind the adenine nucleotide pocket of Hsp90 causes Her2 degradation and the growth arrest and differentiation of breast cancer cells," Chem. Biol., 8:289-299 (2001).

Dai et al., "HSP90: a rising star on the horizon of anticancer targets," Future Oncol., 1(4):529-540 (2005).

Database Caplus on STN, AN 1932:57919, DN 26:57919, Dziewonski et al, "Derivatives of naphthalic acid. Synthesis of 3,4-dihydroxynaphthalic acid," Roczniki Chemii, 11:870-883 (1931).

Gong et al., "Synthesis, SAR, and antitumor properties of diamino-C,N-diarylpyrimidine positional isomers: inhibitors of lysophosphatidic acid acyltransferase-beta," Bioorg. Med. Chem. Letters, 14:2303-2308 (2004).

Neckers et al., "Heat-shock protein 90 inhibitors as novel cancer chemotherapeutics—an update," Expert Opin. Emerg. Drugs, 137-149 (2005).

International Preliminary Report on Patentability for App. Ser. No. PCT/JP2008/053599, dated Sep. 1, 2009, 5 pages.

Japanese Patent Office, International Search Report for App. Ser. No. PCT/JP2008/053599, mailed May 13, 2008, 3 pages.

Fish & Richardson P.C., Amendment in Reply to Action dated Aug. 8, 2011, U.S. Appl. No. 12/302,149, filed Jan. 12, 2012, 31 pages.

USPTO Notice of Allowance in U.S. Appl. No. 12,302,149, dated Jan. 27, 2012, 5 pages.

Fish & Richardson P.C., Amendment in Reply to Action dated Feb. 23, 2011, in U.S. Appl. No. 12/302,149, filed May 10, 2011, 37 pages.

USPTO Final Office Action in U.S. Appl. No. 12,302,149, dated Aug. 8, 2011, 21 pages.

Cecil Textbook of Medicine, edited by J.C. Bennett and F. Plum, $20^{th}$ edition, vol. 1, 1004-1010 (1996).

Cohen et al., "The development and therapeutic potential of protein kinase inhibitors," Curr. Opin. Chem. Biol., 3:459-465 (1999).

Dermer et al., "Another anniversary for the war on cancer," Bio/Technology, 12:320 (1994).

Fabbro et al., "Protein kinases as targets for anticancer agents: from inhibitors to useful drugs," Pharmacol. Ther., 93:79-98 (2002).

Freshney et al., "Culture of Animal Cells," A Manual of Basic Technique, Alan R. Liss, Inc., New York, p. 4 (1983).

Golub et al., "Molecular classification of cancer: class discovery and class prediction by gene expression monitoring," Science, 286:531-537 (1999).

Mass, "The HER receptor family: a rich target for therapeutic development," Int. J. Radiat. Oncol. Biol. Phys., 58(3):932-940 (2004).

Paull et al., "Display and analysis of patterns of differential activity of drugs against human tumor cell lines: development of mean graph and COMPARE algorithm," J. Natl. Cancer Inst., 81:1088-92 (1989).

Powell et al., "Growth inhibition of psoriatic keratinocytes by quinazoline tyrosine kinase inhibitors," Br. J. Dermatol., 141:802-810 (1999).

Yamazaki et al., "Nucleotide sequence of a full-length cDNA for 90 kDa heat-shock protein from human peripheral blood lymphocytes," Nucleic Acids Res., 17 (17):7108 (1989).

USPTO Restriction Requirement in U.S. Appl. No. 12/302,149, dated Nov. 11, 2010, 8 pages.

Fish & Richardson P.C., Preliminary Amendment and Response to Restriction Requirement dated Nov. 11, 2010 in U.S. Appl. No. 12/302,149, filed Feb. 8, 2011, 40 pages.

Supplementary European Search Report for App. Ser. No. EP 07 74 4100, dated Nov. 5, 2010, 3 pages.

USPTO Non-Final Office Action in U.S. Appl. No. 12/302,149, dated Feb. 23, 2011, 18 pages.

* cited by examiner

MACROCYCLIC COMPOUND

CROSS-REFERENCE TO RELATED APPLICATIONS

This application is the National Stage of International Application Serial No. PCT/JP2008/053599, filed on Feb. 29, 2008, which claims the benefit of Japanese Application Serial No. 2007-052072, filed on Mar. 1, 2007.

TECHNICAL FIELD

The present invention relates to macrocyclic 6-aryl-4-mercapto-[1,3,5]triazin/[13]pyrimidin-2-amine derivatives and pharmaceutically acceptable salts thereof, pharmaceuticals comprising them, synthetic intermediates of said derivatives and salts, and such.

BACKGROUND ART

Molecular chaperones are a group of proteins that are catalytically involved in the folding or association of other proteins. Heat-shock protein 90 (HSP90) is a constitutively expressed molecular chaperone that governs the maturation of many regulatory factors that are key to cell growth and survival, as well as the maintenance of their stability. HSP90 is a molecular chaperone with a molecular weight of approximately 90,000, and is abundant in cells (approximately 1% to 2% of total soluble proteins) and uniformly distributed in the cytoplasm. HSP90 is known to interact with many molecules involved in the intracellular signal transduction system.

More specifically, it is known to be involved in the functional expression of not only signal transduction system proteins (for example, RAF-1, AKT/PKB, c-SRC, and ERBB2) and cell-cycle regulatory proteins (for example, CDK-1, CDK-4, mouse double minute 2, and TP53), but also apoptosis pathway proteins (for example, survivin and apoptosis protease activating factor 1) and such, and is suggested to be deeply involved in cell cycle regulation and malignant transformation, growth, and survival signals. It is considered that inhibiting the function of HSP90 can at the same time inhibit the function of the above-mentioned proteins; therefore, HSP90 is recently receiving attention as a target of anticancer agents. Furthermore, there are reports that a number of genetic defects accumulate in the process of malignant transformation, and that in tumor cells, such modified proteins require chaperone activity more so than normal proteins. It is also reported that the expression level of HSP90 is increased in various cancers (Non-Patent Documents 1 and 2).

Accordingly, research and development of HSP90 inhibitors as anticancer agents is progressing. For example, clinical trials of single agent 17-allylamino-17-demethoxygeldanamycin (17-AAG) are being carried out on advanced epithelial ovarian carcinoma, primary peritoneal carcinoma, metastatic renal cell carcinoma, von Hippel-Lindau disease, renal tumors, chemotherapy refractory breast cancer, advanced medullary carcinoma, differentiated thyroid carcinoma, metastatic melanoma, relapsed/refractory pediatric malignancies, and relapsed/refractory pediatric patients with solid tumors or leukemia.

Clinical trials are also being performed to evaluate the concomitant use of 17-AAG with various anticancer agents. The diseases targeted by this concomitant use are solid tumors (concomitant agent: bortezomib), advanced solid tumors (concomitant agent: gemcitabine and cisplatin, docetaxel, paclitaxel), relapsed, refractory, and high-risk acute leukemia (concomitant agent: cytarabine), chronic myelogenous leukemia (concomitant agent: cytarabine, imatinib), fludarabine-refractory B-cell chronic lymphocytic leukemia (concomitant agent: fludarabine and rituximab), and hematologic malignancies (concomitant agent: bortezomib). Single-agent clinical trials for 17-dimethylaminoethylamino-17-demethoxygeldanamycin (17-DMAG) are being carried out on solid tumors and advanced solid tumors (Non-Patent Documents 1 and 2).

According to a press release by Infinity Pharmaceutical Inc., clinical trials on IPI-504, which is a 17-AAG analog, are being performed on gastrointestinal tumors and multiple myeloma.

Additionally, research and development of Radicicol (KF-58333) (Non-Patent Document 3), purine derivatives such as PU24FCI (Patent Documents 1 and 2, and Non-Patent Document 4), pyrazole derivatives such as CCT-018159 (Patent Documents 3 to 5), pyrimidothiophene derivatives (Patent Document 6), 2-amino-4-phenylquinazoline derivatives (Patent Document 7), 2-amino-4-phenylpyrimidine derivatives (Patent Document 8) and such as low-molecular weight HSP90 inhibitors is under progress. Moreover, 6-aryl-4-mercapto-[1,3,5]triazin/[13]pyrimidin-2-amine derivatives, which exhibit HSP90 inhibitory activity, are disclosed in a patent application copending with the present application (published after the priority date of the present application; Patent Document 14)

Cancer cells which are under stressful conditions such as abnormal protein expression, hypoxia, and nutritional starvation, are highly dependent on HSP90. Therefore, cancer cells are considered to show higher sensitivity towards HSP90 inhibitors. This is also supported by the pharmacokinetic analysis of 17-AAG in animal models, which shows higher accumulation potential of 17-AAG in cancerous regions than in normal tissues. Accordingly, HSP90 inhibitors are expected to act specifically on cancer cells but not on normal cells, and may become a new type of anticancer agent not found in conventional anticancer agents. In addition, HSP90 inhibitors have been reported to enhance the efficacy of cytotoxic agents (Patent Document 9), which also makes them interesting anticancer agents.

However, it has been pointed out that the use of geldanamycin derivatives and radicicol derivatives as pharmaceuticals is problematic in terms of their physical properties such as toxicity, stability, and water solubility. So far, there are no HSP90 inhibitors that have actually reached the market. Therefore, there has been a demand for a new compound class of HSP90 inhibitors that are different from these compounds.

In addition to anticancer and antitumor activity, HSP90 inhibitors have been reported to be useful as anti-inflammatory agents, anti-infectious-disease agents, agents for treating autoimmunity, agents for treating ischemia, and agents for enhancing nerve regeneration (Patent Documents 10-12). They are also reported to be useful as therapeutic agents for disorders, in which fibrogenesis is induced, including pulmonary fibrosis, scleroderma, polymyositis, systemic lupus erythematosus, rheumatoid arthritis, hepatic cirrhosis, keloid formation, interstitial nephritis, and such (Patent Document 13). Single-agent clinical trials of the aforementioned 17-AAG are also underway for systemic mastocytosis.

[Patent Document 1] WO2002/036075
[Patent Document 2] WO2003/037860
[Patent Document 3] WO2003/055860
[Patent Document 4] WO2004/050087
[Patent Document 5] Japanese Patent Application Kokai Publication No. (JP-A) 2005-225787 (unexamined, published Japanese patent application)
[Patent Document 6] WO2005/021552

[Patent Document 7] WO2006/122631
[Patent Document 8] WO2006/123165
[Patent Document 9] WO2002/036171
[Patent Document 10] WO2002/009696
[Patent Document 11] WO99/51223
[Patent Document 12] U.S. Pat. No. 6,210,974
[Patent Document 13] WO2002/002123
[Patent Document 14] WO2007/138994
[Non-patent Document 1] Future Oncol. (2005), 1(4), 529-540
[Non-patent Document 2] Expert Opin. on Emerging Drugs (2005), 10(1), 137-149
[Non-patent Document 3] Curr. Cancer Drug Targets. 2003 Oct., 3(5), 385-390
[Non-patent Document 4] Chem. Biol. 2001 Mar., 8(3), 289-299

DISCLOSURE OF THE INVENTION

Problems to be Solved by the Invention

The present invention was made based on the above circumstances. An objective of the present invention is to provide a new class of compounds having HSP90 inhibitory activity, which are useful as anticancer agents or such, and to provide compounds that are useful as synthetic intermediates thereof.

Means for Solving the Problems

In view of the above circumstances, the present inventors completed the present invention by searching for compounds having HSP90 inhibitory activity, and discovering that certain types of macrocyclic 6-aryl-4-mercapto-[1,3,5]triazin/[13]pyrimidin-2-amine derivatives surprisingly have HSP90 inhibitory activity.

Specifically, the present invention provides the compounds described below and pharmaceutical compositions comprising the compounds.

[1] a compound represented by formula (I) or a pharmaceutically acceptable salt thereof:

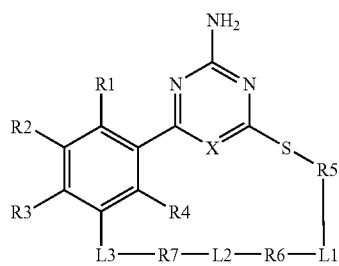

(1)

wherein X represents CH or N;
$R^1$ represents a hydrogen atom, a halogen atom, a cyano group, a $C_{1-6}$ alkyl group, a $C_{1-4}$ haloalkyl group, a $C_{2-6}$ alkenyl group, a $C_{2-6}$ alkynyl group, a $C_{1-6}$ alkoxy group, or a $C_{1-6}$ alkylthio group;
$R^2$ represents a hydrogen atom, a halogen atom, a $C_{1-6}$ alkyl group, a $C_{2-6}$ alkenyl group, or a $C_{2-6}$ alkynyl group, or $R_2$ and $R_3$ together form a ring;
$R^3$ represents a hydrogen atom, a halogen atom, a cyano group, a $C_{1-6}$ alkyl group, a $C_{2-6}$ alkenyl group, a $C_{2-6}$ alkynyl group, or a $C_{1-6}$ alkoxy group, or $R^2$ and $R^3$ together form a ring;
$R^4$ represents a hydrogen atom, a halogen atom, a $C_{1-6}$ alkyl group, a $C_{2-6}$ alkenyl group, or a $C_{2-6}$ alkynyl group;
$R^5$, $R^6$, and $R^7$ each independently represent a $C_{1-6}$ alkylene group, a $C_{2-6}$ alkenylene group, a $C_{2-6}$ alkynylene group, a $C_{3-10}$ cycloalkylene group, a $C_{3-10}$ cycloalkenylene group, a $C_{6-12}$ arylene group, or -3 to 12-membered monocyclic heterocyclic ring-, each of which may have a substituent;
$L^1$, $L^2$, and $L^3$ each independently represent a single bond, —CONR$^8$—, —NR$^8$CO—, —NR$^3$—, —O—, —SO$_2$NR$^8$—, —NR$^8$SO$_2$—, —COO—, —NR$^8$CONR$^{8'}$—, —NR$^8$COO—, or —OCONR$^8$—;
$R^8$ and $R^{8'}$ each independently represent a hydrogen atom or a $C_{1-6}$ alkyl group which may have a substituent;
[2] the compound of [1], or a pharmaceutically acceptable salt thereof, wherein $R^1$ represents a halogen atom, a cyano group, a $C_{1-6}$ alkyl group, a $C_{1-4}$ haloalkyl group, or a $C_{2-6}$ alkynyl group;
[3] the compound of [1] or [2], or a pharmaceutically acceptable salt thereof, wherein $R^1$ represents a chlorine atom, a cyano group, a methyl group, or an ethinyl group;
[4] the compound of any one of [1] to [3], or a pharmaceutically acceptable salt thereof, wherein $R^1$ represents a chlorine atom or a methyl group;
[5] the compound of any one of [1] to [4], or a pharmaceutically acceptable salt thereof, wherein $R^2$ represents a hydrogen atom;
[6] the compound of any one of [1] to [5], or a pharmaceutically acceptable salt thereof, wherein $R^3$ represents a hydrogen atom, a halogen atom, a $C_{1-4}$ alkyl group, or a $C_{1-4}$ alkoxy group;
[7] the compound of any one of [1] to [6], or a pharmaceutically acceptable salt thereof, wherein $R^3$ represents a methyl group;
[8] the compound of any one of [1] to [6], or a pharmaceutically acceptable salt thereof, wherein $R^3$ represents a chlorine atom;
[9] the compound of any one of [1] to [6], or a pharmaceutically acceptable salt thereof, wherein $R^3$ represents a methoxy group or an ethoxy group;
[10] the compound of any one of [1] to [9], or a pharmaceutically acceptable salt thereof, wherein $R^4$ represents a hydrogen atom;
[11] the compound of any one of [1] to [10], or a pharmaceutically acceptable salt thereof, wherein $R^5$, $R^6$, and $R^7$ each independently represents a $C_{1-6}$ alkylene group, phenylene group, or -3- to 12-membered monocyclic heterocyclic ring-, which may have a substituent selected from Group A:
  Group A: a $C_{1-6}$ alkyl group which may have a substituent (wherein the substituent is a hydroxyl group or a dimethylamino group), a halogen atom, a hydroxyl group, a cyano group, a group represented by —NR$^9$R$^{10}$ (wherein R$^9$ and R$^{10}$ each independently represents a hydrogen atom, a $C_{1-3}$ alkyl group, or a group represented by —C(=O)CH$_3$, —C(=O)CF$_3$, —C(=O)CH(NH$_2$)CH(CH$_3$)$_2$, or —C(=O)CH(NH$_2$)(4-OH)Ph), and a group represented by —C(=O)NR$^{11}$R$^{12}$ (wherein R$^{11}$ and R$^{12}$ each independently represents a hydrogen atom or a $C_{1-6}$ alkyl group which may have a substituent (wherein the substituent is at least one selected from the group consisting of a hydroxyl group, $C_{1-6}$ alkoxy group, a $C_{1-3}$ alkoxy $C_{1-3}$ alkoxy group, a morpholinyl group, a piperidinyl group, and a 4-methylpiperidinyl group), or R$^{11}$ and R$^{12}$ together form a 3- to 12-membered monocyclic heterocyclic ring), or a group represented by —C(=O)OR$^{13}$ (R$^{13}$ represents a hydrogen atom or a $C_{1-3}$ alkyl group);
[12] the compound of any one of [1] to [10], or a pharmaceutically acceptable salt thereof, wherein any one of R$^5$, R$^6$, and R$^7$ is a $C_{1-6}$ alkylene group substituted with a 3- to 12-membered monocyclic alicyclic monospiro ring which may have a substituent, or a $C_{1-6}$ alkylene group substituted with a 3- to 12-membered monocyclic heterocyclic monospiro ring which may have a substituent;

[13] the compound of any one of [1] to [12], or a pharmaceutically acceptable salt thereof, wherein $L^1$ and $L^2$ each independently represents a single bond, —CONR$^8$—, —NR$^8$CO—, —NR$^8$CONR$^{8'}$—, —NR$^8$COO—, —NR$^8$—, or —O—;

[14] the compound of any one of [1] to [13], or a pharmaceutically acceptable salt thereof, wherein $L^1$ represents —CONR$^8$—, —NR$^8$CO—, —NR$^8$CONR$^{8'}$—, —NR$^8$COO—, or —O—;

[15] the compound of any one of [1] to [14], or a pharmaceutically acceptable salt thereof, wherein $L^2$ represent a single bond, —O—, or —NR$^3$—;

[16] the compound of any one of [1] to [15], or a pharmaceutically acceptable salt thereof, wherein $L^3$ represents —CONR$^8$— or —O— (wherein R$^8$ is as defined in [1]);

[17] the compound of any one of [1] to [16], or a pharmaceutically acceptable salt thereof, wherein X represents CH;

[18] the compound of [1], or a pharmaceutically acceptable salt thereof, wherein the compound is selected from the group consisting of:

(1) 4-amino-20,22-dimethyl-7-thia-3,5,11,17-tetraazatricyclo[17.3.1.1$^{2,6}$]tetracosa-1(22),2(24),3,5,19(23),20-hexaene-10,18-dione;
(2) 4-amino-18,20-dimethyl-7-thia-3,5,11,15-tetraazatricyclo[15.3.1.1$^{2,6}$]docosa-1(20),2(22),3,5,17(21),18-hexane-10,16-dione;
(3) 4-amino-15,18,20-trimethyl-7-thia-3,5,11,15-tetraazatricyclo[15.3.1.1$^{2,6}$]docosa-1(20),2(22),3,5,17(21),18-hexane-10,16-dione;
(4) 4-amino-18,20-dimethyl-7-thia-3,5,12,15-tetraazatricyclo[15.3.1.1$^{2,6}$]docosa-1(20),2(22),3,5,17(21),18-hexaene-11,16-dione;
(5) 4-amino-20,22-dimethyl-7-thia-3,5,12,17-tetraazatricyclo[17.3.1.1$^{2,6}$]tetracosa-1(22),2(24),3,5,19(23),20-hexane-11,18-dione;
(6) 4-amino-19,21-dimethyl-7-thia-3,5,11,16-tetraazatricyclo[16.3.1.1$^{2,6}$]tricosa-1(21),2(23),3,5,18(22),19-hexaene-10,17-dione;
(7) 4-amino-9,20,22-trimethyl-7-thia-3,5,11,17-tetraazatricyclo[17.3.1.1$^{2,6}$]tetracosa-1(22),2(24),3,5,19(23),20-hexaene-10,18-dione;
(8) 4-amino-18,20-dichloro-7-thia-3,5,11,15-tetraazatricyclo[15.3.1.1$^{2,6}$]docosa-1(20),2(22),3,5,17(21),18-hexaene-10,16-dione;
(9) 4-amino-18-methoxy-20-methyl-7-thia-3,5,10,15-tetraazatricyclo[15.3.1.1$^{2,6}$]docosa-1(20),2(22),3,5,17(21),18-hexaene-11,16-dione;
(10) 4-amino-18-methoxy-15,20-dimethyl-7-thia-3,5,10,15-tetraazatricyclo[15.3.1.1$^{2,6}$]docosa-1(20),2(22),3,5,17(21),18-hexaene-11,16-dione;
(11) 4-amino-18,20-dimethyl-7-thia-3,5,10,15-tetraazatricyclo[15.3.1.1$^{2,6}$]docosa-1(20),2(22),3,5,17(21),18-hexaene-11,16-dione;
(12) 4-amino-17,19-dimethyl-7-thia-3,5,10,14-tetraazatricyclo[14.3.1.1$^{2,6}$]henicosa-1(19),2(21),3,5,16(20),17-hexaene-11,15-dione;
(13) 4-amino-15,18,20-trimethyl-7-thia-3,5,10,15-tetraazatricyclo[15.3.1.1$^{2,6}$]docosa-1(20),2(22),3,5,17(21),18-hexaene-11,16-dione;
(14) 4-amino-20,22-dimethyl-7-thia-3,5,10,17-tetraazatricyclo[17.3.1.1$^{2,6}$]tetracosa-1(22),2(24),3,5,19(23),20-hexaene-11,18-dione;
(15) 4-amino-18,20-dichloro-7-thia-3,5,10,15-tetraazatricyclo[15.3.1.1$^{2,6}$]docosa-1(20),2(22),3,5,17(21),18-hexaene-11,16-dione;
(16) 4-amino-20-methoxy-22-methyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one;
(17) 4-amino-20-ethoxy-22-methyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one;
(18) 4-amino-20,22-dimethyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one;
(19) 4-amino-21,23-dimethyl-13-oxa-7-thia-3,5,18-triazatricyclo[18.3.1.1$^{2,6}$.1$^{8,12}$]hexacosa-1(23),2(25),3,5,8(26),9,11,20(24),21-nonaen-19-one;
(20) 4-amino-22,24-dimethyl-13-oxa-7-thia-3,5,19-triazatricyclo[19.3.1.1$^{2,6}$.1$^{8,12}$]heptacosa-1(24),2(26),3,5,8(27),9,11,21(25),22-nonaen-20-one;
(21) 4-amino-20,22-dichloro-13,18-dioxa-7-thia-3,5-diazatricyclo[17.3.1.1$^{2,6}$.1$^{8,12}$]pentacosa-1(23),2,4,6(24),8,10,12(25),19,21-nonaene;
(22) 4-amino-21,23-dichloro-13,19-dioxa-7-thia-3,5-diazatricyclo[18.3.1.1$^{2,6}$.1$^{8,12}$]hexacosa-1(24),2,4,6(24),8,10,12(26),20,22-nonaene;
(23) 21,23-dichloro-13,16,19-trioxa-7-thia-3,5-diazatricyclo[18.3.1.1$^{2,6}$.1$^{8,12}$]hexacosa-1(23),2(25),3,5,8(26),9,11,20(24),21-nonaen-4-ylamine;
(24) 4-amino-22-methyl-13,18-dioxa-7-thia-3,5-diazatricyclo[17.3.1.1$^{2,6}$.1$^{8,12}$]pentacosa-1(23),2(24),3,5,8(25),9,11,19,21-nonaene;
(25) 4-amino-23-methyl-13,19-dioxa-7-thia-3,5-diazatricyclo[18.3.1.1$^{2,6}$.1$^{8,12}$]hexacosa-1(24),2(25),3,5,8(26),9,11,20,22-nonaene;
(26) 20,22-dichloro-13,18-dioxa-7-thia-3,5,24-triazatricyclo[17.3.1.1$^{2,6}$.1$^{8,12}$]pentacosa-1(22),2(24),3,5,8(25),9,11,19(23),20-nonaen-4-ylamine;
(27) 21,23-dichloro-13,16,19-trioxa-7-thia-3,5,25-triazatricyclo[18.3.1.1$^{2,6}$.1$^{8,12}$]hexacosa-1(23),2(25),3,5,8(25),9,11,20(24),21-nonaen-4-ylamine;
(28) 4-amino-20,22-dichloro-7-thia-3,5,10,17-tetraazatricyclo[17.3.1.1$^{2,6}$]tetracosa-1(22),2(24),3,5,19(23),20-hexaene-11,18-dione;
(29) 4-amino-20,22-dimethyl-14-oxa-7-thia-3,5,11,17-tetraazatricyclo[17.3.1.1$^{2,6}$]tetracosa-1(22),2(24),3,5,19(23),20-hexaene-10,18-dione;
(30) 4-amino-14,20,22-trimethyl-7-thia-3,5,11,14,17-pentaazatricyclo[17.3.1.1$^{2,6}$]tetracosa-1(22),2(24),3,5,19(23),20-hexaene-10,18-dione;
(31) 4-amino-13-hydroxy-18,20-dimethyl-7-thia-3,5,11,15-tetraazatricyclo[15.3.1.1$^{2,6}$]docosa-1(20),2(22),3,5,17(21),18-hexaene-10,16-dione;
(32) 4-amino-11,18,20-trimethyl-7-thia-3,5,11,15-tetraazatricyclo[15.3.1.1$^{2,6}$]docosa-1(20),2,4,6(22),17(21),18-hexaene-10,16-dione;
(33) 4-amino-11,19,21-trimethyl-7-thia-3,5,11,16-tetraazatricyclo[16.3.1.1$^{2,6}$]tricosa-1(21),2(23),3,5,18(22),19-hexaene-10,17-dione;
(34) 4-amino-11-(2-hydroxyethyl)-18,20-dimethyl-7-thia-3,5,11,15-tetraazatricyclo[15.3.1.1$^{2,6}$]docosa-1(20),2,4,6(22),17(21),18-hexaene-10,16-dione;
(35) 4-amino-1'-(2-hydroxyethyl)-19,21-dimethyl-7-thia-3,5,11,16-tetraazatricyclo[16.3.1.1$^{2,6}$]tricosa-1(21),2(23),3,5,18(22),19-hexaene-10,17-dione;
(36) 4-amino-18,20-dimethyl-1'-(2-morpholin-4-ylethyl)-7-thia-3,5,11,15-tetraazatricyclo[15.3.1.1$^{2,6}$]docosa-1(20),2,4,6(22),17(21),18-hexaene-10,16-dione;

(37) 4-amino-19,21-dimethyl-1'-(2-morpholin-4-ylethyl)-7-thia-3,5,11,16-tetraazatricyclo[16.3.1.1$^{2,6}$]tricosa-1(21),2(23),3,5,18(22),19-hexaene-10,17-dione;

(38) 4-amino-18,20-dimethyl-1'-[2-(4-methylpiperazin-1-yl)ethyl]-7-thia-3,5,11,15-tetraazatricyclo[15.3.1.1$^{2,6}$]docosa-1(20),2(22),3,5,17(21),18-hexaene-10,16-dione;

(39) 4-amino-19,21-dimethyl-1'-[2-(4-methylpiperazin-1-yl)ethyl]-7-thia-3,5,11,16-tetraazatricyclo[16.3.1.1$^{2,6}$]tricosa-1(21),2(23),3,5,18(22),19-hexaene-10,17-dione;

(40) 4,9-diamino-18,20-dimethyl-7-thia-3,5,11,15-tetraazatricyclo[15.3.1.1$^{2,6}$]docosa-1(20),2(22),3,5,17(21),18-hexaene-10,16-dione;

(41) 4,9-diamino-19,21-dimethyl-7-thia-3,5,11,16-tetraazatricyclo[16.3.1.1$^{2,6}$]tricosa-1(21),2(23),3,5,18(22),19-hexaene-10,17-dione;

(42) N-(4-amino-18,20-dimethyl-10,16-dioxo-7-thia-3,5,11,15-tetraazatricyclo[15.3.1.1$^{2,6}$]docosa-1(20),2(22),3,5,17(21),18-hexaen-9-yl)acetamide;

(43) N-(4-amino-19,21-dimethyl-10,17-dioxo-7-thia-3,5,11,16-tetraazatricyclo[16.3.1.1$^{2,6}$]tricosa-1(21),2(23),3,5,18(22),19-hexaen-9-yl)acetamide;

(44) 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid amide;

(45) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid amide;

(46) 4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid (2-hydroxyethyl)amide;

(47) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid (2-hydroxyethyl)amide;

(48) 4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid (2,3-dihydroxypropyl)amide;

(49) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid (2,3-dihydroxypropyl)amide;

(50) 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid [2-(2-methoxyethoxy)ethyl]amide;

(51) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid [2-(2-methoxyethoxy)ethyl]amide;

(52) 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid (2-morpholin-4-ylethyl)amide;

(53) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid (2-morpholin-4-ylethyl)amide;

(54) 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid [2-(4-methylpiperazin-1-yl)ethyl]amide;

(55) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid [2-(4-methylpiperazin-1-yl)ethyl]amide;

(56) 4-amino-18,20-dimethyl-7-thia-3,5,10,12,15-pentaazatricyclo[15.3.1.1$^{2,6}$]docosa-1(20),2(22),3,5,17(21),18-hexaene-11,16-dione;

(57) 4-amino-19,21-dimethyl-7-thia-3,5,10,12,16-pentaazatricyclo[16.3.1.1$^{2,6}$]tricosa-1(21),2(23),3,5,18(22),19-hexaene-11,17-dione;

(58) 4-amino-18,20-dimethyl-10-oxa-7-thia-3,5,12,15-tetraazatricyclo[15.3.1.1$^{2,6}$]docosa-1(20),2(22),3,5,17(21),18-hexaene-11,16-dione;

(59) 4-amino-19,21-dimethyl-11-oxa-7-thia-3,5,13,16-tetraazatricyclo[16.3.1.1$^{2,6}$]tricosa-1(21),2(23),3,5,18(22),19-hexaene-12,17-dione;

(60) 4-amino-12-hydroxymethyl-18,20-dimethyl-7-thia-3,5,11,15-tetraazatricyclo[15.3.1.1$^{2,6}$]docosa-1(20),2(22),3,5,17(21),18-hexaene-10,16-dione;

(61) 4-amino-12-dimethylaminomethyl-18,20-dimethyl-7-thia-3,5,11,15-tetraazatricyclo[15.3.1.1$^{2,6}$]docosa-1(20),2(22),3,5,17(21),18-hexaene-10,16-dione;

(62) (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid methyl ester;

(63) (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid methyl ester;

(64) (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid;

(65) (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid methylamide;

(66) (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid (2-methoxyethyl)amide;

(67) (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid dimethylamide;

(68) (S)-4-amino-14-hydroxymethyl-18,20-dimethyl-7-thia-3,5,11,15-tetraazatricyclo[15.3.1.1$^{2,6}$]docosa-1(20),2(22),3,5,17(21),18-hexaene-10,16-dione;

(69) (R)-4-amino-18,20-dimethyl-10,16-dioxo-7-thia-3,5,11,15-tetraazatricyclo[15.3.1.1$^{2,6}$]docosa-1(20),2,4,6(22),17(21),18-hexaene-12-carboxylic acid methyl ester;

(70) (S)-4-amino-18,20-dimethyl-12-(morpholine-4-carbonyl)-7-thia-3,5,11,15-tetraazatricyclo[15.3.1.1$^{2,6}$]docosa-1(20),2,4,6(22),17(21),18-hexaene-10,16-dione;

(71) (S)-4-amino-18,20-dimethyl-12-morpholin-4-ylmethyl-7-thia-3,5,11,15-tetraazatricyclo[15.3.1.1$^{2,6}$]docosa-1(20),2(22),3,5,17(21),18-hexaene-10,16-dione;

(72) 4-amino-18,20-dimethyl-13-oxetan-3-yl-7-thia-3,5,11,15-tetraazatricyclo[15.3.1.1$^{2,6}$]docosa-1(20),2(22),3,5,17(21),18-hexaene-10,16-dione;

(73) 4,12-diamino-18,20-dimethyl-7-thia-3,5,10,15-tetraazatricyclo[15.3.1.1$^{2,6}$]docosa-1(20),2(22),3,5,17(21),18-hexaene-11,16-dione;

(74) N-(4-amino-18,20-dimethyl-10,16-dioxo-7-thia-3,5,10,15-tetraazatricyclo[15.3.1.1$^{2,6}$]docosa-1(20),2(22),3,5,17(21),18-hexaen-12-yl)acetamide;

(75) N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-2,2,2-trifluoroacetamide;

(76) (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-methylbutylamide;

(77) (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-(4-hydroxyphenyl)propionamide;

(78) 4-amino-12-dimethylamino-18,20-dimethyl-7-thia-3,5,10,15-tetraazatricyclo[15.3.1.1$^{2,6}$]docosa-1(20),2(22),3,5,17(21),18-hexaene-11,16-dione;

(79) 4-amino-10-(2-hydroxyethyl)-18,20-dimethyl-7-thia-3,5,10,15-tetraazatricyclo[15.3.1.1$^{2,6}$]docosa-1(20),2(22),3,5,17(21),18-hexaene-11,16-dione;

(80) 4-amino-10-(2-methoxyethyl)-18,20-dimethyl-7-thia-3,5,10,15-tetraazatricyclo[15.3.1.1$^{2,6}$]docosa-1(20),2(22),3,5,17(21),18-hexaene-11,16-dione;

(81) 4-amino-10-(2-morpholin-4-ylethyl)-18,20-dimethyl-7-thia-3,5,10,15-tetraazatricyclo[15.3.1.1$^{2,6}$]docosa-1(20),2(22),3,5,17(21),18-hexaene-11,16-dione;

(82) 4-amino-10,18,20-trimethyl-7-thia-3,5,10,15-tetraazatricyclo[15.3.1.1$^{2,6}$]docosa-1(20),2(22),3,5,17(21),18-hexaene-11,16-dione; and

(83) (S)-4-amino-19,21-dimethyl-10-oxo-7-thia-16-oxa-3,5,11,24-tetraazatetracyclo[16.3.1.1$^{2,6}$.1$^{7,10}$]tetracosa-1(22),2(23),3,5,17(24),19,21-heptaen-10-one;

[19] a pharmaceutical comprising as an active ingredient the compound of any one of [1] to [18], or a pharmaceutically acceptable salt thereof,

[20] an anti-cancer agent comprising as an active ingredient the compound of any one of [1] to [18], or a pharmaceutically acceptable salt thereof,

[21] an HSP90 inhibitor comprising as an active ingredient the compound of any one of [1] to [18], or a pharmaceutically acceptable salt thereof, and

[22] a pharmaceutical composition comprising as an active ingredient the compound of any one of [1] to [18], or a pharmaceutically acceptable salt thereof.

[23] Furthermore, the present invention also relates to methods for treating or preventing cancer, which comprise the step of administering an effective amount of the compound of any one of [1] to [18], or a pharmaceutically acceptable salt thereof, to patients in need of treatment or prevention of cancer.

[24] Furthermore, the present invention also relates to the use of the compound of any one of [1] to [18], or a pharmaceutically acceptable salt thereof, in producing agents for preventing or treating cancer.

Effects of the Invention

The compounds of the present invention represented by formula (1) have the activity of inhibiting HSP90, and are metabolically stable because of their macrocyclic structure. Thus, the compounds of the present invention are useful as anti-tumor or anti-cancer agents when used alone or in combination with various other anti-cancer agents. Furthermore, some of the compounds represented by formula (1) are also useful as synthetic intermediates of other compounds. The compounds represented by formulas (7) and (8) are useful as synthetic intermediates of the compounds represented by formula (1).

BEST MODE FOR CARRYING OUT THE INVENTION

The compounds of the present invention, methods for producing the compounds, and pharmaceuticals comprising the compounds are described below.

Terms used herein are defined below.

Herein, the "$C_{1-6}$ alkyl group" refers to a linear or branched saturated monovalent $C_{1-6}$ hydrocarbon group such as a methyl group, an ethyl group, a propyl group, a butyl group, a pentyl group, a hexyl group, an isopropyl group, a sec-butyl group, a tert-butyl group, 1-methylpropyl group, a 1,1-dimethylpropyl group, a 2,2-dimethylpropyl group, a 1,2-dimethylpropyl group, a 1,1,2-trimethylpropyl group, a 1,2,2-trimethylpropy group, a 1,1,2,2-tetramethylpropyl group, a 1-methylbutyl group, a 2-methylbutyl group, a 3-methylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1-ethylbutyl group, a 2-ethylbutyl group, an isopentyl group, or a neopentyl group.

The "$C_{1-3}$ alkyl group" refers to a linear or branched saturated monovalent $C_{1-3}$ hydrocarbon group such as a methyl group, an ethyl group, a propyl group, or an isopropyl group.

The "$C_{1-4}$ alkyl group" refers to a linear or branched saturated monovalent $C_{1-4}$ hydrocarbon group such as a methyl group, an ethyl group, a propyl group, a butyl group, an isopropyl group, a sec-butyl group, or a tert-butyl group.

The "$C_{1-4}$ haloalkyl group" refers to a "$C_{1-4}$ alkyl group" substituted by one or more halogen atoms. Preferred $C_{1-4}$ haloalkyl groups are $C_{1-2}$ alkyl groups substituted by one or more fluorine or chlorine atoms. Such groups include, for example, a trifluoromethyl group, a difluoromethyl group, a fluoromethyl group, a pentafluoroethyl group, a tetrafluoroethyl group, a trifluoroethyl group, a difluoroethyl group, a fluoroethyl group, a trichloromethyl group, a dichloromethyl group, a chloromethyl group, a pentachloroethyl group, a tetrachloroethyl group, a trichloroethyl group, a dichloroethyl group, and a chloroethyl group.

The "$C_{2-6}$ alkenyl group" refers to a $C_{2-6}$ hydrocarbon group having at least one double bond. The $C_{2-6}$ alkenyl group includes, for example, an ethenyl (vinyl) group, a 1-propenyl group, a 2-propenyl (allyl) group, an isopropenyl group, a 1-butenyl group, a 2-butenyl group, a 3-butenyl (homoallyl) group, a pentenyl group, and a hexenyl group.

The "$C_{2-6}$ alkynyl group" refers to a $C_{2-6}$ hydrocarbon group having at least one triple bond. The $C_{2-6}$ alkynyl group includes, for example, an ethynyl group a 1-propynyl group, a 2-propynyl group, a 1-butynyl group, a 2-butynyl group, a 3-butynyl group, a pentynyl group, and a hexynyl group.

The "$C_{1-6}$ alkoxy group" refers to —O—$C_{1-6}$ alkyl group such as a methoxy group, an ethoxy group, a propoxy group, an isopropoxy group, a butoxy group, a sec-butoxy group, an isobutoxy group, a tert-butoxy group, a pentoxy group, a 3-methylbutoxy group, a 2-methylbutoxy group, a 1-methylbutoxy group, a 1-ethylpropoxy group, a hexyloxy group, a 4-methylpentoxy group, a 3-methylpentoxy group, a 2-methylpentoxy group, a 1-methylpentoxy group, a 3-ethylbutoxy group, or a 2-ethylbutoxy group.

The "$C_{1-4}$ alkoxy group" refers to —O—$C_{1-4}$ alkyl group such as a methoxy group, an ethoxy group, a propoxy group, an isopropoxy group, a butoxy group, a sec-butoxy group, an isobutoxy group, or a tert-butoxy group.

The "$C_{1-3}$ alkoxy $C_{1-3}$ alkoxy group" refers to —O—$C_{1-3}$ alkyl-O—$C_{1-3}$ alkyl group such as a methoxymethoxy group, a methoxyethoxy group, or an ethoxyethoxy group.

The "$C_{1-6}$ alkylthio group" refers to —S—$C_{1-6}$ alkyl group such as a methylthio group, an ethylthio group, a propylthio group, an isopropylthio group, a butylthio group, a sec-butylthio group, an isobutylthio group, a tert-butylthio group, a pentylthio group, a 3-methylbutylthio group, a 2-methylbutylthio group, a 1-methylbutylthio group, a 1-ethylpropylthio group, a hexylthio group, a 4-methylpentylthio group, a 3-methylpentylthio group, a 2-methylpentylthio group, a 1-methylpentylthio group, a 3-ethylbutylthio group, or a 2-ethylbutylthio group.

The "halogen" refers to fluorine (F), chlorine (Cl), bromine, (Br), or iodine (I). It is preferably fluorine or chlorine.

The "$C_{3\text{-}10}$ cycloalkyl group" refers to a saturated $C_{3\text{-}10}$ carbocyclic group such as a cyclopropyl group, a cyclobutyl group, a cyclopentyl group, a cyclohexyl group, a cycloheptyl group, a cyclooctyl group, a cyclononyl group, or a cyclodecyl group.

The "$C_{3\text{-}10}$ cycloalkenyl group" refers to a $C_{3\text{-}10}$ carbocyclic group having at least one double bond. The $C_{3\text{-}10}$ cycloalkenyl group includes, for example, a cyclopentenyl group, a cyclohexenyl group, and a cycloheptenyl group.

The "$C_{6\text{-}12}$ aryl group" refers to a monocyclic or bicyclic aromatic carbon ring having 6 to 12 carbon atoms. The $C_{6\text{-}12}$ aryl group includes, for example, a phenyl group, a naphthyl group, an indanyl group, an indenyl group, and an isoindenyl group. A preferred $C_{6\text{-}12}$ aryl group is a phenyl group.

The "3- to 12-membered monocyclic heterocyclic ring" refers to an aromatic or non-aromatic monocyclic heterocyclic ring having 3 to 12 ring-constituting atoms that include one or more (for example, 1 to 4) heteroatoms selected from N, O, and S. The binding position of heteroatoms is not particularly limited, and they may be linked at a desired position. Specifically, the 3- to 12-membered monocyclic heterocyclic ring includes, for example, pyrrolidine, oxazolidine, isooxazolidine, oxazoline, isooxazoline, thiazolidine, isothiazolidine, thiazoline, isothiazoline, imidazolidine, imidazoline, furan, thiophene, pyrrole, oxazole, isoxazole, thiazole, isothiazole, furazan, imidazole, pyrazole, piperidine, piperazine, morpholine, thiomorpholine, tetrahydropyran, dioxane, tetrahydrothiopyran, pyran, thiopyran, pyridine, pyrazine, pyrimidine, and pyridazine.

The "3- to 12-membered monocyclic alicyclic monospiro ring" refers to a group in which a monocyclic alicyclic hydrocarbon having 3 to 12 ring-constituting atoms forms a ring together with one carbon atom in a $C_{1\text{-}6}$ alkylene group. The position of a spiro atom in a $C_{1\text{-}6}$ alkylene group is not particularly limited, and it may be shared by a $C_{1\text{-}6}$ alkylene group at a desired position. Specifically, the 3- to 12-membered monocyclic alicyclic monospiro ring includes, for example, cyclopropanone, cyclobutanone, cyclopentanone, cyclohexanone, cyclopropane, cyclobutane, cyclopentane, cyclohexane, cyclopropene, cyclobutene, cyclopentene, and cyclohexene.

The "3- to 12-membered monocyclic heterocyclic monospiro ring" refers to a group in which a monocyclic non-aromatic heterocyclic ring having 3 to 12 ring-constituting atoms that include one or more (for example, 1 to 4) heteroatoms selected from N, O, and S forms a ring together with one carbon atom in a $C_{1\text{-}6}$ alkylene group. The binding position of heteroatoms is not particularly limited, and they may be linked at a desired position. Moreover, the position of a spiro atom in a $C_{1\text{-}6}$ alkylene group is not particularly limited, and it may be shared by a $C_{1\text{-}6}$ alkylene group at a desired position. Specifically, the 3- to 12-membered monocyclic heterocyclic monospiro ring includes, for example, oxetane, tetrahydrofuran, tetrahydropyran, thietane, tetrahydrothiophene, tetrahydrothiopyran, azetidine, pyrrolidine, piperidine, oxetanone, tetrahydrofuranone, tetrahydropyranone, azetidinone, pyrrolidinone, piperidinone, dioxolane, dioxane, dithiolane, and dithiane.

The "$C_{1\text{-}6}$ alkylene group" refers to a divalent group derived by removing an arbitrary hydrogen atom from the above-defined "$C_{1\text{-}6}$ alkyl group".

The "$C_{2\text{-}6}$ alkenylene group" refers to a divalent group derived by removing an arbitrary hydrogen atom from the above-defined "$C_{2\text{-}6}$ alkenyl group".

The "$C_{2\text{-}6}$ alkynylene group" refers to a divalent group derived by removing an arbitrary hydrogen atom from the above-defined "$C_{2\text{-}6}$ alkynyl group".

The "$C_{3\text{-}10}$ cycloalkylene group" refers to a divalent group derived by removing an arbitrary hydrogen atom from the above-defined "$C_{3\text{-}10}$ cycloalkyl group".

The "$C_{3\text{-}10}$ cycloalkenylene group" refers to a divalent group derived by removing an arbitrary hydrogen atom from the above-defined "$C_{3\text{-}10}$ cycloalkenyl group".

The "$C_{6\text{-}12}$ arylene group" refers to a divalent group derived by removing an arbitrary hydrogen atom from the above-defined "$C_{6\text{-}12}$ aryl group".

The "-3- to 12-membered monocyclic heterocyclic ring-" refers to a divalent group derived by removing arbitrary two hydrogen atoms from the above-defined "3- to 12-membered monocyclic heterocyclic ring".

The term "ring" singly used herein means groups including all of the above-defined "$C_{3\text{-}10}$ cycloalkyl group", "$C_{3\text{-}10}$ cycloalkenyl group", "$C_{6\text{-}12}$ aryl group, and "5- to 12-membered monocyclic heterocyclic ring".

When $R^5$, $R^6$, and $R^7$ represent a "$C_{1\text{-}6}$ alkylene group which may have a substituent" in the formula, the substituent preferably includes groups selected from Group A shown below. Group A: a $C_{1\text{-}6}$ alkyl group which may have a substituent (a hydroxyl group or a dimethylamino group), a halogen atom, a hydroxyl group, a cyano group, a group represented by —NR$^9$R$^{10}$ (R$^9$ and R$^{10}$ each independently represents a hydrogen atom, a $C_{1\text{-}3}$ alkyl group, or a group represented by —C(=O)CH$_3$, —C(=O)CF$_3$, —C(=O)CH(NH$_2$)CH(CH$_3$)$_2$, or —C(=O)CH(NH$_2$)(4-OH)Ph), a group represented by —C(=O)NR$^{11}$R$^{12}$ (R$^{11}$ and R$^{12}$ each independently represents a hydrogen atom or a $C_{1\text{-}6}$ alkyl group which may have a substituent (at least one substituent selected from the group consisting of: a hydroxyl group, a $C_{1\text{-}6}$ alkoxy group, a $C_{1\text{-}3}$ alkoxy $C_{1\text{-}3}$ alkoxy group, a morpholinyl group, a piperidinyl group, and a 4-methylpiperidinyl group), or R$^{11}$ and R$^{12}$ together form a 3- to 12-membered monocyclic heterocyclic ring), a group represented by —C(=O)OR$^{13}$ (R$^{13}$ represents a hydrogen atom or a $C_{1\text{-}3}$ alkyl group, 3- to 12-membered monocyclic alicyclic monospiro ring which may have a substituent (at least one substituent selected from the group consisting of: a hydrogen atom, a halogen atom, a cyano group, a hydroxyl group, a $C_{1\text{-}6}$ alkyl group, a $C_{2\text{-}6}$ alkenyl group, a $C_{1\text{-}6}$ alkoxy group, a $C_{1\text{-}6}$ alkylthio group, a $C_{1\text{-}6}$ acyl group, a carboxyl group, a carbamoyl group, a $C_{1\text{-}6}$ alkoxycarbonyl group, a $C_{1\text{-}6}$ alkoxycarbonyloxy group, a mono $C_{1\text{-}6}$ alkylaminocarbonyl group, a mono $C_{1\text{-}6}$ alkylaminocarbonyloxy group, a di $C_{1\text{-}6}$ alkylaminocarbonyl group, a di $C_{1\text{-}6}$ alkylaminocarbonyloxy group, an amino group, a mono $C_{1\text{-}6}$ alkylamino group, a di $C_{1\text{-}6}$ alkylamino group, a mono $C_{1\text{-}6}$ acylamino group, a $C_{1\text{-}6}$ alkylsulfonylamino group, a $C_{1\text{-}6}$ alkoxycarbonylamino group, an N'-mono $C_{1\text{-}6}$ alkylureido group, an N',N'-di $C_{1\text{-}6}$ alkylureido group, and such), or 3- to 12-membered monocyclic heterocyclic monospiro ring which may have a substituent (at least one substituent selected from the group consisting of: a hydrogen atom, a halogen atom, a cyano group, a hydroxyl group, an oxo group, a $C_{1\text{-}6}$ alkyl group, a $C_{2\text{-}6}$ alkenyl group, a $C_{1\text{-}6}$ alkoxy group, a $C_{1\text{-}6}$ alkylthio group, a $C_{1\text{-}6}$ acyl group, a carboxyl group, a carbamoyl group, a $C_{1\text{-}6}$ alkoxycarbonyl group, a $C_{1\text{-}6}$ alkoxycarbonyloxy group, a mono $C_{1\text{-}6}$ alkylaminocarbonyl group, a mono $C_{1\text{-}6}$ alkylaminocarbonyloxy group, a di $C_{1\text{-}6}$ alkylaminocarbonyl group, a di $C_{1\text{-}6}$ alkylaminocarbonyloxy group, an amino group, a mono $C_{1\text{-}6}$ alkylamino group, a di $C_{1-6}$ alkylamino group, a mono $C_{1-6}$ acylamino group, a $C_{1-6}$ alkylsulfonylamino group, a $C_{1-6}$ alkoxycarbonylamino group, an N'-mono $C_{1-6}$ alkylureido group, an N',N'-di $C_{1-6}$ alkylureido group, and such).

The number of such substituents may be more than one. When multiple substituents are present, they may be the same or different. The preferred number of such substituents is one or two.

When $R^8$ and $R^{8'}$ represent a "$C_{1-6}$ alkyl group which may have a substituent" in the formula, the substituent preferably includes groups selected from Group B shown below. Group B: a hydroxyl group, a morpholinyl group, a piperidinyl group, a 4-methylpiperidinyl group, a halogen atom, a hydroxyl group, an amino group, a cyano group, a $C_{6-12}$ aryl group, or a $C_{1-6}$ alkoxy group.

The number of such substituents may be more than one. When multiple substituents are present, they may be the same or different. The preferred number of such substituents is one or two.

(Salts)

The present invention includes pharmaceutically acceptable salts of the compounds represented by formula (1). These salts are produced by contacting the compounds with acids or bases that may be used in the production of pharmaceuticals. Examples of such salts include hydrochloride, hydrobromide, hydroiodide, sulfate, sulfonate, phosphate, phosphonate, carboxylate such as acetate, citrate, malate, and salicylate; alkali metal salts such as sodium salts and potassium salts; alkaline earth metal salts such as magnesium salts and calcium salts; and ammonium salts such as ammonium salts, alkylammonium salts, dialkylammonium salts, trialkylammonium salts, and tetraalkylammonium salts.

In addition, the salts of the present invention include hydrates and solvates that can be formed by the above compound.

When the compounds of the present invention are obtained in their free form, they can be converted into salts that may be formed by the compounds, or into their hydrates or solvates, by standard methods.

(Isomers)

The compounds of the present invention include all stereoisomers (for example, enantiomers and diastereomers, including cis and trans geometric isomers), racemates of these isomers, and other mixtures.

The compounds of the present invention may exist in several tautomeric forms such as the enol and imine form, the keto and enamine form, or mixtures thereof. Tautomers exist as mixtures of a tautomeric set in solution. In solid form, usually one tautomer predominates. Even though one tautomer may be described, the present invention includes all tautomers of the compounds of the present invention.

(Diseases to be Treated)

The compounds of the present invention represented by formula (I) have HSP90 inhibitory effects. Therefore, the compounds of the present invention used alone or in combination with various types of anticancer agents are useful as antitumor agents or anticancer agents. Specific diseases to be treated include advanced epithelial ovarian carcinoma, primary peritoneal carcinoma, metastatic renal cell carcinoma, von Hippel-Lindau disease, renal tumors, chemotherapy-refractory breast cancer, advanced medullary carcinoma, differentiated thyroid carcinoma, metastatic melanoma, relapsed/refractory pediatric malignancies, and relapsed/refractory pediatric solid tumors or leukemia, solid tumors, advanced solid tumors, relapsed, refractory, and high-risk acute leukemia, chronic myelogenous leukemia, fludarabine-refractory B-cell chronic lymphocytic leukemia, hematologic malignancies, gastrointestinal tumor, multiple myeloma, and such, for which clinical studies have already been carried out with HSP90 inhibitors.

In addition to the above, the compounds are useful as anti-inflammatory agents, anti-infectious disease agents, agents for treating autoimmune diseases, agents for treating ischemia, and pharmaceutical agents for promoting nerve regeneration. Besides cancers and tumors, specific examples of diseases to be treated include fibrogenic disorders such as scleroderma, polymyositis, systemic lupus erythematosus, rheumatoid arthritis, hepatic cirrhosis, keloid formation, interstitial nephritis, and pulmonary fibrosis; systemic mastocytosis; and Alzheimer's disease.

(Methods of Administration and Formulation)

When using the pharmaceutical compositions of the present invention, the methods for administering the compositions include, for example, oral, rectal, parenteral (intravenous, intramuscular, or subcutaneous), intracisternal, intravaginal, intraperitoneal, intravesical, and local (drip infusion, powder, ointment, gel, or cream) administration, and inhalation (intraoral or nasal spray). The forms of administration include, for example, tablets, capsules, granules, powders, pills, aqueous and non-aqueous oral solutions and suspensions, and parenteral solutions loaded into a container that is suitable for individual administration in small amounts. Furthermore, the form of administration can be adjusted according to various administration methods involving controlled-release formulations, such as subcutaneous transplantation.

The above-mentioned formulations are produced by known methods using additives such as excipients, lubricants (coating agents), binders, disintegrators, stabilizers, flavors, diluents, solvents, surfactants, and emulsifiers.

Examples of excipients include starches such as potato starch, corn starch, and starch; lactose; crystalline cellulose; and calcium hydrogen phosphate.

Examples of coating agents include ethyl cellulose, hydroxypropyl cellulose, hydroxypropyl methylcellulose, shellac, talc, carnauba wax, and paraffin.

Examples of binders include polyvinylpyrrolidone, macrogol, and the same compounds described as the excipients above.

Examples of disintegrators include the same compounds described as excipients above, and chemically modified starches and celluloses such as croscarmellose sodium, sodium carboxymethylstarch, and crosslinked polyvinylpyrrolidone.

Examples of stabilizers include paraoxybenzoic acid esters such as methylparaben and propylparaben; alcohols such as chlorobutanol, benzylalcohol, and phenylethyl alcohol; benzalkonium chloride; phenols such as phenol and cresol; thimerosal; dehydroacetic acid; and sorbic acid.

Examples of flavors include commonly used sweeteners, acidifiers, and flavoring agents.

Furthermore, solvents used for producing liquid agents include ethanol, phenol, chlorocresol, purified water, distilled water, and such.

Examples of surfactants or emulsifiers include polysorbate 80, polyoxyl 40 stearate, and lauromacrogol.

When using the pharmaceutical compositions of the present invention, the doses of the compounds represented by formula (1) vary depending on the symptoms, age, weight, and relative health condition, presence of other medication, method of administration, and such. For example, when the compounds/pharmaceutical compositions of the present invention are used as anticancer agents, whether as oral agents or parenteral agents, the generally effective dose of an active ingredient (the compounds represented by formula (1))

for a patient (a warm-blooded animal, especially human) is preferably 1 mg/m$^2$-400 mg/m$^2$ per day, and more preferably 10 mg/m$^2$-200 mg/m$^2$ per day. The daily dose for an average adult patient is preferably in the range of 10 mg to 300 mg. This is desirably administered every day or once every two days, or administered in several portions depending on the symptoms.

Preferred Embodiments of the Compounds of the Present Invention

X preferably represents CH.

$R^1$ preferably represents a halogen atom, a cyano group, a $C_{1-6}$ alkyl group, a $C_{1-4}$ haloalkyl group, or a $C_{2-6}$ alkynyl group, more preferably a chlorine atom, a methyl group, or an ethynyl group, and even more preferably a chlorine atom or a methyl group.

$R^2$ preferably represents a hydrogen atom.

$R^3$ preferably represents a hydrogen atom, a halogen atom, a $C_{1-4}$ alkyl group, or a $C_{1-4}$ alkoxy group, more preferably a halogen atom, a $C_{1-4}$ alkyl group, or a $C_{1-4}$ alkoxy group.

A preferred halogen atom is a chlorine atom. A preferred $C_{1-4}$ alkyl group is a methyl group. Preferred $C_{1-4}$ alkoxy groups are methoxy group and ethoxy group.

$R^4$ preferably represents a hydrogen atom.

$R^5$, $R^6$, and $R^7$ preferably each independently represents a $C_{1-6}$ alkylene group, phenylene group, or -3- to 12-membered monocyclic heterocyclic ring-, which may have a substituent.

When the $C_{1-6}$ alkylene group has a substituent, the substituent preferably includes groups selected from Group A:
Group A: a $C_{1-6}$ alkyl group which may have a substituent (the substituent is a hydroxyl group or a dimethylamino group), a halogen atom, a hydroxyl group, a cyano group, a group represented by —NR$^9$R$^{10}$ (R$^9$ and R$^{10}$ each independently represents a hydrogen atom, a $C_{1-3}$ alkyl group, or a group represented by —C(=O)CH$_3$, —C(=O)CF$_3$, —C(=O)CH (NH$_2$)CH(CH$_3$)$_2$, or —C(=O)CH(NH$_2$)(4-OH)Ph), a group represented by —C(=O)NR$^{11}$R$^{12}$ (R$^{11}$ and R$^{12}$ each independently represents a hydrogen atom, a $C_{1-6}$ alkyl group which may have a substituent (the substituent is at least one selected from the group consisting of: a hydroxyl group, $C_{1-6}$ alkoxy group, a $C_{1-3}$ alkoxy $C_{1-3}$ alkoxy group, a morpholinyl group, a piperidinyl group, and a 4-methylpiperidinyl group), or R$^{11}$ and R$^{12}$ together form a 3- to 12-membered monocyclic heterocyclic ring), a group represented by —C(=O) OR$^{13}$ (R$^{13}$ represents a hydrogen atom or a $C_{1-3}$ alkyl group), 3- to 12-membered monocyclic alicyclic monospiro ring, or 3- to 12-membered monocyclic heterocyclic monospiro ring.

More preferably, $R^5$ represents a $C_{1-6}$ alkylene group or phenylene group, which may have as a substituent a $C_{1-6}$ alkyl group or —NR$^9$R$^{10}$ (R$^9$ and R$^{10}$ each independently represents a hydrogen atom or a group represented by —C(=O) CH$_3$). When $R^5$ has a substituent, the substituent is more preferably a methyl group (7), —NH$_2$, or —NHC(=O)CH$_3$.

More preferably, $R^6$ represents a $C_{1-6}$ alkylene group which may have a substituent. When $R^6$ has a substituent, the substituent is more preferably a $C_{1-6}$ alkyl group which may have a substituent (the substituent is a hydroxyl group or a dimethylamino group), a hydroxyl group, a group represented by —NR$^9$R$^{10}$ (R$^9$ and R$^{10}$ each independently represents a hydrogen atom, a $C_{1-3}$ alkyl group, or a group represented by —C(=O)CH$_3$, —C(=O)CF$_3$, —C(=O)CH(NH$_2$)CH (CH$_3$)$_2$, or —C(=O)CH(NH$_2$)(4-OH)Ph), a group represented by —C(=O)NR$^{11}$R$^{12}$ (R$^{11}$ and R$^{12}$ each independently represents a hydrogen atom or a $C_{1-6}$ alkyl group which may have a substituent (at least one substituent selected from the group consisting of a hydroxyl group, a $C_{1-3}$ alkoxy $C_{1-3}$ alkoxy group, a morpholinyl group, a piperidinyl group, and a 4-methylpiperidinyl group), or R$^{11}$ and R$^{12}$ together form a 3- to 12-membered monocyclic heterocyclic ring), 3- to 12-membered monocyclic alicyclic monospiro ring, or 3- to 12-membered monocyclic heterocyclic monospiro ring.

$R^7$ preferably represents a $C_{1-6}$ alkylene group which may have a substituent. When $R^7$ has a substituent, the substituent is more preferably a $C_{1-6}$ alkyl group which may have a substituent (the substituent is a hydroxyl group or a dimethylamino group), a hydroxyl group, a group represented by —NR$^9$R$^{10}$ (R$^9$ and R$^{10}$ each independently represents a hydrogen atom, a $C_{1-3}$ alkyl group, or a group represented by —C(=O)CH$_3$, —C(=O)CF$_3$, —C(=O)CH(NH$_2$)CH (CH$_3$)$_2$, or —C(=O)CH(NH$_2$)(4-OH)Ph), or a group represented by —C(=O)NR$^{11}$R$^{12}$ (R$^{11}$ and R$^{12}$ each independently represents a hydrogen atom or a $C_{1-6}$ alkyl group which may have a substituent (at least one substituent selected from the group consisting of a hydroxyl group, a $C_{1-3}$ alkoxy $C_{1-3}$ alkoxy group, a morpholinyl group, a piperidinyl group, and a 4-methylpiperidinyl group), or R$^{11}$ and R$^{12}$ together form a 3- to 12-membered monocyclic heterocyclic ring.

$L^1$ and $L^2$ preferably represent each independently a single bond, —CONR$^8$—, —NR$^8$CO—, —NR$^8$CONR$^{8'}$—, —NR$^8$COO—, —NR$^3$—, or —O—. $L^3$ preferably represents —CONR$^8$— or —O—. The right-side bonds of $L^1$, $L^2$, and $L^3$ are directed toward the position of a sulfur atom.

$R^8$ and $R^{8'}$ represent a hydrogen atom or a $C_{1-6}$ alkyl group which may have a substituent. In the case of a $C_{1-6}$ alkyl group which may have a substituent, the substituent is preferably selected from Group B shown below.
Group B: a hydroxyl group, a morpholinyl group, a piperidinyl group, a 4-methylpiperidinyl group, a halogen atom, an amino group, a cyano group, a $C_{6-12}$ aryl group, or a $C_{1-6}$ alkoxy group.

More preferably, $R^8$ and $R^{8'}$ include a hydrogen atom, a methyl group, a 2-hydroxyethyl group, a 2-morpholin-4-ylethyl group, a 2-(4-methylpiperazin-1-yl)ethyl group, and a methoxyethyl group.

More preferably, $L^1$ represents —CONR$^8$—, —NR$^8$CO—, —NR$^8$CONR$^{8'}$—, —NR$^8$COO—, or —O—, even more preferably —NR$^8$CO—. $R^8$ preferably include a hydrogen atom, a methyl group, a 2-hydroxyethyl group, a 2-morpholin-4-ylethyl group, and a 2-(4-methylpiperazin-1-yl)ethyl group.

More preferably, $L^2$ represents a single bond, —O—, or —NR$^8$—, and even more preferably —O—.

More preferably, $L^3$ represents —CONR$^8$—, even more preferably —CONH— or —CONCH$_3$—.

Furthermore, $R^5$, $R^6$, and $R^7$ preferably represent each independently a $C_{1-6}$ alkylene group or phenylene group, which may have a substituent; $L^1$ and $L^2$ each independently represents a single bond, —CONR$^8$—, —NR$^8$CO—, —NR$^8$—, or —O—; and $L^3$ represents a single bond, —CONR$^8$—, or —O—. When the groups have a substituent, the substituent is as described above.

Furthermore, $R^5$, $R^6$, and $R^7$ preferably represent each independently a $C_{1-6}$ alkylene group which may have a substituent; and $L^1$, $L^2$, and $L^3$ represent —NR$^8$CO—, a single bond, and —CONR$^8$—, respectively. When the groups have a substituent, the substituent is as described above.

Specifically, the compounds represented by formula (1) includes, for example:
(1) 4-amino-20,22-dimethyl-7-thia-3,5,11,17-tetraazatricyclo[17.3.1.1$^{2,6}$]tetracosa-1(22),2(24),3,5,19(23),20-hexaene-10,18-dione;

(2) 4-amino-18,20-dimethyl-7-thia-3,5,11,15-tetraazatricyclo[15.3.1.1$^{2,6}$]docosa-1(20),2(22),3,5,17(21),18-hexane-10,16-dione;

(3) 4-amino-15,18,20-trimethyl-7-thia-3,5,11,15-tetraazatricyclo[15.3.1.1$^{2,6}$]docosa-1(20),2(22),3,5,17(21),18-hexane-10,16-dione;

(4) 4-amino-18,20-dimethyl-7-thia-3,5,12,15-tetraazatricyclo[15.3.1.1$^{2,6}$]docosa-1(20),2(22),3,5,17(21),18-hexaene-11,16-dione;

(5) 4-amino-20,22-dimethyl-7-thia-3,5,12,17-tetraazatricyclo[17.3.1.1$^{2,6}$]tetracosa-1(22),2(24),3,5,19(23),20-hexane-11,18-dione;

(6) 4-amino-19,21-dimethyl-7-thia-3,5,11,16-tetraazatricyclo[16.3.1.1$^{2,6}$]tricosa-1(21),2(23),3,5,18(22),19-hexaene-10,17-dione;

(7) 4-amino-9,20,22-trimethyl-7-thia-3,5,11,17-tetraazatricyclo[17.3.1.1$^{2,6}$]tetracosa-1(22),2(24),3,5,19(23),20-hexaene-10,18-dione;

(8) 4-amino-18,20-dichloro-7-thia-3,5,11,15-tetraazatricyclo[15.3.1.1$^{2,6}$]docosa-1(20),2(22),3,5,17(21),18-hexaene-10,16-dione;

(9) 4-amino-18-methoxy-20-methyl-7-thia-3,5,10,15-tetraazatricyclo[15.3.1.1$^{2,6}$]docosa-1(20),2(22),3,5,17(21),18-hexaene-11,16-dione;

(10) 4-amino-18-methoxy-15,20-dimethyl-7-thia-3,5,10,15-tetraazatricyclo[15.3.1.1$^{2,6}$]docosa-1(20),2(22),3,5,17(21),18-hexaene-11,16-dione;

(11) 4-amino-18,20-dimethyl-7-thia-3,5,10,15-tetraazatricyclo[15.3.1.1$^{2,6}$]docosa-1(20),2(22),3,5,17(21),18-hexaene-11,16-dione;

(12) 4-amino-17,19-dimethyl-7-thia-3,5,10,14-tetraazatricyclo[14.3.1.1$^{2,6}$]henicosa-1(19),2(21),3,5,16(20),17-hexaene-11,15-dione;

(13) 4-amino-15,18,20-trimethyl-7-thia-3,5,10,15-tetraazatricyclo[15.3.1.1$^{2,6}$]docosa-1(20),2(22),3,5,17(21),18-hexaene-11,16-dione;

(14) 4-amino-20,22-dimethyl-7-thia-3,5,10,17-tetraazatricyclo[17.3.1.1$^{2,6}$]tetracosa-1(22),2(24),3,5,19(23),20-hexaene-11,18-dione;

(15) 4-amino-18,20-dichloro-7-thia-3,5,10,15-tetraazatricyclo[15.3.1.1$^{2,6}$]docosa-1(20),2(22),3,5,17(21),18-hexaene-11,16-dione;

(16) 4-amino-20-methoxy-22-methyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one;

(17) 4-amino-20-ethoxy-22-methyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one;

(18) 4-amino-20,22-dimethyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one;

(19) 4-amino-21,23-dimethyl-13-oxa-7-thia-3,5,18-triazatricyclo[18.3.1.1$^{2,6}$.1$^{8,12}$]hexacosa-1(23),2(25),3,5,8(26),9,11,20(24),21-nonaen-19-one;

(20) 4-amino-22,24-dimethyl-13-oxa-7-thia-3,5,19-triazatricyclo[19.3.1.1$^{2,6}$.1$^{8,12}$]heptacosa-1(24),2(26),3,5,8(27),9,11,21(25),22-nonaen-20-one;

(21) 4-amino-20,22-dichloro-13,18-dioxa-7-thia-3,5-diazatricyclo[17.3.1.1$^{2,6}$.1$^{8,12}$]pentacosa-1(23),2,4,6(24),8,10,12(25),19,21-nonaene;

(22) 4-amino-21,23-dichloro-13,19-dioxa-7-thia-3,5-diazatricyclo[18.3.1.1$^{2,6}$.1$^{8,12}$]hexacosa-1(24),2,4,6(24),8,10,12(26),20,22-nonaene;

(23) 21,23-dichloro-13,16,19-trioxa-7-thia-3,5-diazatricyclo[18.3.1.1$^{2,6}$.1$^{8,12}$]hexacosa-1(23),2(25),3,5,8(26),9,11,20(24),21-nonaen-4-ylamine;

(24) 4-amino-22-methyl-13,18-dioxa-7-thia-3,5-diazatricyclo[17.3.1.1$^{2,6}$.1$^{8,12}$]pentacosa-1(23),2(24),3,5,8(25),9,11,19,21-nonaene;

(25) 4-amino-23-methyl-13,19-dioxa-7-thia-3,5-diazatricyclo[18.3.1.1$^{2,6}$.1$^{8,12}$]hexacosa-1(24),2(25),3,5,8(26),9,11,20,22-nonaene;

(26) 20,22-dichloro-13,18-dioxa-7-thia-3,5,24-triazatricyclo[17.3.1.1$^{2,6}$.1$^{8,12}$]pentacosa-1(22),2(24),3,5,8(25),9,11,19(23),20-nonaen-4-ylamine;

(27) 21,23-dichloro-13,16,19-trioxa-7-thia-3,5,25-triazatricyclo[18.3.1.1$^{2,6}$.1$^{8,12}$]hexacosa-1(23),2(25),3,5,8(25),9,11,20(24),21-nonaen-4-ylamine;

(28) 4-amino-20,22-dichloro-7-thia-3,5,10,17-tetraazatricyclo[17.3.1.1$^{2,6}$]tetracosa-1(22),2(24),3,5,19(23),20-hexaene-11,18-dione;

(29) 4-amino-20,22-dimethyl-14-oxa-7-thia-3,5,11,17-tetraazatricyclo[17.3.1.1$^{2,6}$]tetracosa-1(22),2(24),3,5,19(23),20-hexaene-10,18-dione;

(30) 4-amino-14,20,22-trimethyl-7-thia-3,5,11,14,17-pentaazatricyclo[17.3.1.1$^{2,6}$]tetracosa-1(22),2(24),3,5,19(23),20-hexaene-10,18-dione;

(31) 4-amino-13-hydroxy-18,20-dimethyl-7-thia-3,5,11,15-tetraazatricyclo[15.3.1.1$^{2,6}$]docosa-1(20),2(22),3,5,17(21),18-hexaene-10,16-dione;

(32) 4-amino-11,18,20-trimethyl-7-thia-3,5,11,15-tetraazatricyclo[15.3.1.1$^{2,6}$]docosa-1(20),2,4,6(22),17(21),18-hexaene-10,16-dione;

(33) 4-amino-11,19,21-trimethyl-7-thia-3,5,11,16-tetraazatricyclo[16.3.1.1$^{2,6}$]tricosa-1(21),2(23),3,5,18(22),19-hexaene-10,17-dione;

(34) 4-amino-11-(2-hydroxyethyl)-18,20-dimethyl-7-thia-3,5,11,15-tetraazatricyclo[15.3.1.1$^{2,6}$]docosa-1(20),2,4,6(22),17(21),18-hexaene-10,16-dione;

(35) 4-amino-11-(2-hydroxyethyl)-19,21-dimethyl-7-thia-3,5,11,16-tetraazatricyclo[16.3.1.1$^{2,6}$]tricosa-1(21),2(23),3,5,18(22),19-hexaene-10,17-dione;

(36) 4-amino-18,20-dimethyl-1'-(2-morpholin-4-ylethyl)-7-thia-3,5,11,15-tetraazatricyclo[15.3.1.1$^{2,6}$]docosa-1(20),2,4,6(22),17(21),18-hexaene-10,16-dione;

(37) 4-amino-19,21-dimethyl-1'-(2-morpholin-4-ylethyl)-7-thia-3,5,11,16-tetraazatricyclo[16.3.1.1$^{2,6}$]tricosa-1(21),2(23),3,5,18(22),19-hexaene-10,17-dione;

(38) 4-amino-18,20-dimethyl-1'-[2-(4-methylpiperazin-1-yl)ethyl]-7-thia-3,5,11,15-tetraazatricyclo[15.3.1.1$^{2,6}$]docosa-1(20),2(22),3,5,17(21),18-hexaene-10,16-dione;

(39) 4-amino-19,21-dimethyl-1'-[2-(4-methylpiperazin-1-yl)ethyl]-7-thia-3,5,11,16-tetraazatricyclo[16.3.1.1$^{2,6}$]tricosa-1(21),2(23),3,5,18(22),19-hexaene-10,17-dione;

(40) 4,9-diamino-18,20-dimethyl-7-thia-3,5,11,15-tetraazatricyclo[15.3.1.1$^{2,6}$]docosa-1(20),2(22),3,5,17(21),18-hexaene-10,16-dione;

(41) 4,9-diamino-19,21-dimethyl-7-thia-3,5,11,16-tetraazatricyclo[16.3.1.1$^{2,6}$]tricosa-1(21),2(23),3,5,18(22),19-hexaene-10,17-dione;

(42) N-(4-amino-18,20-dimethyl-10,16-dioxo-7-thia-3,5,11,15-tetraazatricyclo[15.3.1.1$^{2,6}$]docosa-1(20),2(22),3,5,17(21),18-hexaen-9-yl)acetamide;

(43) N-(4-amino-19,21-dimethyl-10,17-dioxo-7-thia-3,5,11,16-tetraazatricyclo[16.3.1.1$^{2,6}$]tricosa-1(21),2(23),3,5,18(22),19-hexaen-9-yl)acetamide;

(44) 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid amide;

(45) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid amide;

(46) 4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid (2-hydroxyethyl)amide;
(47) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid (2-hydroxyethyl)amide;
(48) 4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid (2,3-dihydroxypropyl)amide;
(49) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid (2,3-dihydroxypropyl)amide;
(50) 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid [2-(2-methoxyethoxy)ethyl]amide;
(51) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid [2-(2-methoxyethoxy)ethyl]amide;
(52) 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid (2-morpholin-4-ylethyl)amide;
(53) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid (2-morpholin-4-ylethyl)amide;
(54) 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid [2-(4-methylpiperazin-1-yl)ethyl]amide;
(55) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid [2-(4-methylpiperazin-1-yl)ethyl]amide;
(56) 4-amino-18,20-dimethyl-7-thia-3,5,10,12,15-pentaazatricyclo[15.3.1.1$^{2,6}$]docosa-1(20),2(22),3,5,17(21),18-hexaene-11,16-dione;
(57) 4-amino-19,21-dimethyl-7-thia-3,5,10,12,16-pentaazatricyclo[16.3.1.1$^{2,6}$]tricosa-1(21),2(23),3,5,18(22),19-hexaene-11,17-dione;
(58) 4-amino-18,20-dimethyl-10-oxa-7-thia-3,5,12,15-tetraazatricyclo[15.3.1.1$^{2,6}$]docosa-1(20),2(22),3,5,17(21),18-hexaene-11,16-dione;
(59) 4-amino-19,21-dimethyl-11-oxa-7-thia-3,5,13,16-tetraazatricyclo[16.3.1.1$^{2,6}$]tricosa-1(21),2(23),3,5,18(22),19-hexaene-12,17-dione;
(60) 4-amino-12-hydroxymethyl-18,20-dimethyl-7-thia-3,5,11,15-tetraazatricyclo[15.3.1.1$^{2,6}$]docosa-1(20),2(22),3,5,17(21),18-hexaene-10,16-dione;
(61) 4-amino-12-dimethylaminomethyl-18,20-dimethyl-7-thia-3,5,11,15-tetraazatricyclo[15.3.1.1$^{2,6}$]docosa-1(20),2(22),3,5,17(21),18-hexaene-10,16-dione;
(62) (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid methyl ester;
(63) (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid methyl ester;
(64) (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid;
(65) (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid methylamide;
(66) (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid (2-methoxyethyl)amide;
(67) (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid dimethylamide;
(68) (S)-4-amino-14-hydroxymethyl-18,20-dimethyl-7-thia-3,5,11,15-tetraazatricyclo[15.3.1.1$^{2,6}$]docosa-1(20),2(22),3,5,17(21),18-hexaene-10,16-dione;
(69) (R)-4-amino-18,20-dimethyl-10,16-dioxo-7-thia-3,5,11,15-tetraazatricyclo[15.3.1.1$^{2,6}$]docosa-1(20),2,4,6(22),17(21),18-hexaene-12-carboxylic acid methyl ester;
(70) (S)-4-amino-18,20-dimethyl-12-(morpholine-4-carbonyl)-7-thia-3,5,11,15-tetraazatricyclo[15.3.1.1$^{2,6}$]docosa-1(20),2,4,6(22),17(21),18-hexaene-10,16-dione;
(71) (S)-4-amino-18,20-dimethyl-12-morpholin-4-ylmethyl-7-thia-3,5,11,15-tetraazatricyclo[15.3.1.1$^{2,6}$]docosa-1(20),2(22),3,5,17(21),18-hexaene-10,16-dione;
(72) 4-amino-18,20-dimethyl-13-oxetan-3-yl-7-thia-3,5,11,15-tetraazatricyclo[15.3.1.1$^{2,6}$]docosa-1(20),2(22),3,5,17(21),18-hexaene-10,16-dione;
(73) 4,12-diamino-18,20-dimethyl-7-thia-3,5,10,15-tetraazatricyclo[15.3.1.1$^{2,6}$]docosa-1(20),2(22),3,5,17(21),18-hexaene-11,16-dione;
(74) N-(4-amino-18,20-dimethyl-10,16-dioxo-7-thia-3,5,10,15-tetraazatricyclo[15.3.1.1$^{2,6}$]docosa-1(20),2(22),3,5,17(21),18-hexaen-12-yl)acetamide;
(75) N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-2,2,2-trifluoroacetamide;
(76) (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-methylbutylamide;
(77) (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-(4-hydroxyphenyl)propionamide;
(78) 4-amino-12-dimethylamino-18,20-dimethyl-7-thia-3,5,10,15-tetraazatricyclo[15.3.1.1$^{2,6}$]docosa-1(20),2(22),3,5,17(21),18-hexaene-11,16-dione;
(79) 4-amino-10-(2-hydroxyethyl)-18,20-dimethyl-7-thia-3,5,10,15-tetraazatricyclo[15.3.1.1$^{2,6}$]docosa-1(20),2(22),3,5,17(21),18-hexaene-11,16-dione;
(80) 4-amino-10-(2-methoxyethyl)-18,20-dimethyl-7-thia-3,5,10,15-tetraazatricyclo[15.3.1.1$^{2,6}$]docosa-1(20),2(22),3,5,17(21),18-hexaene-11,16-dione;
(81) 4-amino-10-(2-morpholin-4-ylethyl)-18,20-dimethyl-7-thia-3,5,10,15-tetraazatricyclo[15.3.1.1$^{2,6}$]docosa-1(20),2(22),3,5,17(21),18-hexaene-11,16-dione;
(82) 4-amino-10,18,20-trimethyl-7-thia-3,5,10,15-tetraazatricyclo[15.3.1.1$^{2,6}$]docosa-1(20),2(22),3,5,17(21),18-hexaene-11,16-dione; and
(83) (S)-4-amino-19,21-dimethyl-10-oxo-7-thia-16-oxa-3,5,11,24-tetraazatetracyclo[16.3.1.1$^{2,6}$.1$^{7,10}$]tetracosa-1(22),2(23),3,5,17(24),19,21-heptaen-10-one.

Representative Method for Producing Compounds Represented by Formula (1)

The compounds of the present invention represented by formula (1) can be produced by conventional organic synthesis methods, for example, the methods described below. However, the methods for producing the compounds of the present invention represented by formula (1) are not limited to these methods. In the production methods described below, if the defined groups undergo an undesired chemical conversion under the production method conditions, the production can be achieved, for example, by using a means such as protection/deprotection of functional groups, unless otherwise specified herein. Methods for selecting, attaching and removing protective groups are described in, for example, Greene and Wuts, "Protective Groups in Organic Synthesis" (3rd ed., John Wiley & Sons, Inc. 1999); these methods may be appropriately used depending on the reaction conditions. The order of reaction steps such as substituent introduction may be changed as necessary. Moreover, in the production methods described below, desired products can also be obtained by conducting a functional group modification reaction at a suitable stage during a series of reaction steps after raw materials having precursor functional groups are reacted. Such functional group modification reactions can be achieved, for example, by methods described in "Smith and March, 'March's Advanced Organic Chemistry' (5th ed., John Wiley & Sons, Inc. 2001)" or "Richard C. Larock, 'Comprehensive Organic Transformations: A Guide to Functional Group Preparations' (2nd ed., John Wiley & Sons, Inc. 1999)". Raw compounds to be used in the production may be those commercially available, or may be produced by conventional methods as necessary.

In the production methods and descriptions thereof mentioned below, $L^1$, $L^2$, and $L^3$ represent groups which are converted into $L^1$, $L^2$, and $L^3$ defined in formula (1), respectively, through an appropriate chemical conversion. Specifically, $L^{1'}$, $L^{2'}$, and $L^{3'}$ represent —COOH, —$SO_3H$, —OH, or —$NHR^8$, or alternatively represent these groups protected with a protective group in some cases.

Meanwhile, $LG_1$ represents a leaving group, for example, a halogen atom (preferably, a chlorine atom, a bromine atom, or an iodine atom); a sulfonyloxy leaving group such as a methanesulfonyloxy group, a trifluoromethanesulfonyloxy group, and a p-toluenesulfonyloxy group; a $C_{1-4}$ alkoxy group such as a methoxy group, an ethoxy group, and a tert-butoxy group; a $C_{1-4}$ alkylcarbonyloxy group such as an acetyloxy group, a propionyloxy group, or a tert-butylcarbonyloxy group; or a $C_{1-4}$ alkoxycarbonyloxy group such as a methoxycarbonyloxy group, an ethoxycarbonyloxy group, and a tert-butoxycarbonyloxy group. $LG_2$ represents, in addition to the groups represented by $LG_1$, a functional group that can serve as a leaving group after an appropriate chemical conversion; for example, substituents such as a hydroxy group and alkylthio group.

Furthermore, $PG_1$ represents a carboxyl group-protecting group, for example, a $C_{1-6}$ alkyl group such as a methyl group, an ethyl group, a tert-butyl group, or an aryl group; a functionalized alkyl group such as a methoxymethyl group, a methoxythiomethyl group, or a tetrahydropyranyl group; a phenyl group such as a 2,6-di-tert-butyl-4-methoxyphenyl group or a 4-(methylthio)phenyl group; a benzyl group such as a triphenylmethyl group or a 4-dimethoxybenzyl group; or a tri-$C_1$-$C_6$ alkylsilyl group such as a triethylsilyl group or a tert-butyldimethylsilyl group. $PG_2$ represents an amino group-protecting group, for example, a $C_1$-$C_6$ alkoxycarbonyl group such as a tert-butoxycarbonyl group; a functionalized alkoxycarbonyl group such as a trichloroethoxy-2-trimethylsilylethoxycarbonyl group; a benzyloxycarbonyl group such as a 9-fluorenylmethoxycarbonyl group or a 4-methoxybenzyloxycarbonyl group; an acyl group such as a formyl group, an acetyl group, or a trifluoroacetyl group; or a methylene group such as a 1,1-dimethylthiomethylene group or a phenylmethylene group.

Furthermore, the compounds represented by formula (1) described in the reaction steps below are the compounds of the present invention represented by formula (1) or such compounds whose substituents have been protected with an appropriate protecting group. Among the compounds represented by formula (1), compounds protected with a protecting group can be subjected to an appropriate deprotection step by a conventional method to obtain the compounds of the present invention represented by formula (1). The reaction steps described below include protection and deprotection steps based on conventional methods as necessary.

[General Method for Synthesizing Compounds Represented by Formula (1)]

The synthetic intermediate (1-C) of the compounds represented by formula (1) can be produced, for example, by the method described in Production method 1.

Production Method 1

This production method is used to obtain the synthetic intermediate (1-C) of the compound (1) of the present invention through the Suzuki coupling reaction from the halogenated aromatic compound (1-A) via the boronic acid ester derivative (1-B):

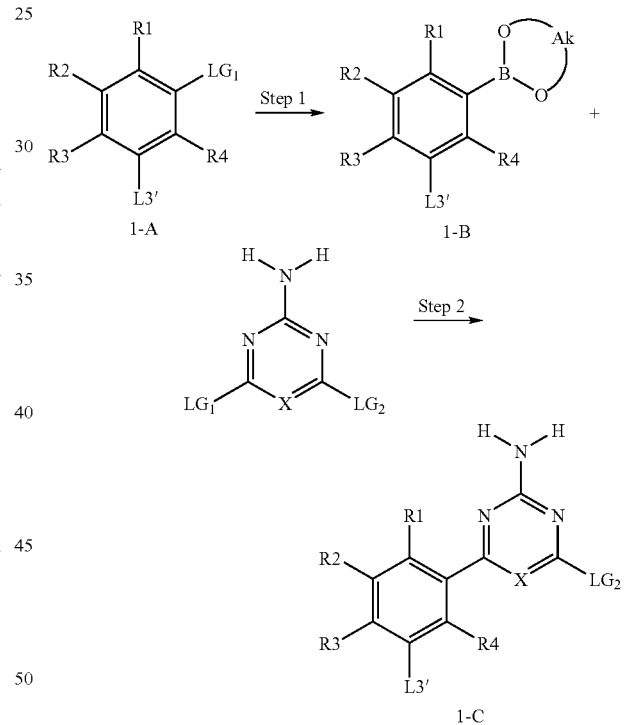

wherein $R^1$, $R^2$, $R^3$, $R^4$, and X are as defined in formula (1); $LG_1$, $LG_2$, and $L^{3'}$ are as defined above; -Ak- represents a linear or branched alkylene chain having 1 to 6 carbon atoms, preferably 1,1,2,2-tetramethylethylene or 2,2-dimethyltrimethylene.

Step 1 (The Miyaura Reaction)

This coupling reaction serves, for example, as a method for synthesizing an aromatic boronic acid ester based on a known coupling reaction of a halogenated aromatic compound with diborane or borane (J. Org. Chem., vol. 60, p. 7508 (1995); J. Organomet. Chem., vol. 611, p. 392 (2000)). Specifically, the aromatic boronic acid ester can be produced through the coupling reaction of the halogenated aromatic compound (1-A) using a palladium catalyst, in which compound 1-A is reacted with one equivalent to an excess amount of, preferably one to three equivalents of an alkoxydiborane or alkoxyborane in an appropriate solvent in the presence of a catalytic amount to an excess amount of, preferably a catalytic amount to one equivalent of an appropriate palladium catalyst, and in the presence or absence of a catalytic amount to an excess amount of, preferably a catalytic amount to two equivalents of an appropriate ligand, and in the presence of one equivalent to an excess amount of, preferably one to ten equivalents of an appropriate base, at an appropriate temperature.

The solvent used in the reaction is not particularly limited, as long as it is inactive for the reaction. The solvent includes, for example, toluene, 1,4-dioxane, 1,2-dimethoxyethane, tetrahydrofuran, dimethylsulfoxide, N,N-dimethylformamide, N,N-dimethylacetamide, and N-methylpyrrolidone, used either alone or in combination.

Suitable palladium catalysts include, for example, palladium dichloride-diphenylphosphinoferrocene dichloromethane complex, $PdCl_2$, $Pd(OAc)_2$, $Pd_2dba_3$, $PdCl_2[P(o-tol)_3]_2$, and $Pd(O_2CCF_3)_2$. When a ligand-free palladium catalyst is used, a suitable ligand needs to be added. Suitable ligands include, for example, triphenylphosphine, $P(o-tol)_3$, BINAP, DPPF, $P(tert-Bu)_3$, 2-dicyclohexylphosphino-2'-(N,N-dimethylamino)biphenyl, 2-(di-tert-butylphosphino)biphenyl, 2-(dicyclohexylphosphino)biphenyl, 2',6'-dimethoxy-2-(dicyclohexylphosphino)biphenyl, 2',4',6'-triisopropyl-2-(dicyclohexylphosphino)biphenyl, and 1,3-diallyldihydroimidazolium salt.

Suitable bases include, for example, sodium acetate, potassium acetate, sodium carbonate, potassium carbonate, cesium carbonate, potassium phosphate, triethylamine, and diisopropylethylamine.

The reaction temperature varies depending on the type of solvent, base, and such. For example, the temperature is from 0° C. up to the boiling point of the solvent. Preferably, the compound can be produced through the reaction at room temperature to the boiling point of the solvent. The reaction time varies depending on the reaction temperature and such. In general, the reaction time is about 10 minutes to about 100 hours, preferably about 30 minutes to about 24 hours. Alkoxydiboranes include, for example, bis(pinacolato)diborane and bis(neopentylglycolato)diborane. Alkoxyboranes include pinacolatoborane.

Step 2 (The Suzuki Reaction)

In this coupling reaction, for example, an aromatic ring group is introduced through a known coupling reaction with a halogenated aromatic ring group (Org. Lett., vol. 2, p. 1101 (2000); Tetrahedron Lett., vol. 42, p. 7155 (2001)). Specifically, the synthetic intermediate (1-C) can be produced by reacting one equivalent to an excess amount of, preferably one to three equivalents of boronic acid ester derivative (1-B) with one equivalent to an excess amount of, preferably one to three equivalents of 2-aminopyrimidine or 2-aminotriazine having leaving groups at positions 4 and 6, in an appropriate solvent in the presence of a catalytic amount to an excess amount of, preferably a catalytic amount to one equivalent of an appropriate palladium catalyst, in the presence or absence of a catalytic amount to an excess amount of, preferably a catalytic amount to two equivalents of an appropriate ligand, and in the presence of one equivalent to an excess amount of, preferably one to ten equivalents of an appropriate base, at an appropriate temperature.

The solvent used in the reaction is not particularly limited, as long as it is inactive for the reaction. The solvent includes, for example, tetrahydrofuran, 1,4-dioxane, diethyl ether, 1,2-dimethoxyethane, N,N-dimethylformamide, N,N-dimethylacetamide, N-methylpyrrolidone, dimethylsulfoxide, acetone, acetonitrile, toluene, benzene, and water, used either alone or in combination; preferably N,N-dimethylformamide, N,N-dimethylacetamide, N-methylpyrrolidone, toluene, 1,4-dioxane, 1,2-dimethoxyethane, tetrahydrofuran, and acetonitrile, used alone or in combination. When the base to be used is an inorganic substance, the solvent is preferably N,N-dimethylformamide, N,N-dimethylacetamide, N-methylpyrrolidone, toluene, 1,4-dioxane, 1,2-dimethoxyethane, tetrahydrofuran, and acetonitrile, used either alone or in combination with water.

Suitable palladium catalysts include, for example, palladium dichloride-diphenylphosphinoferrocene dichloromethane complex, $PdCl_2$, $Pd(OAc)_2$, $Pd_2dba_3$, $PdCl_2[P(o-tol)_3]_2$, dichloroditriphenylphosphine palladium, $Pd(O_2CCF_3)_2$, palladium carbon, palladium black, and $Pd(OH)_2$, preferably palladium dichloride-diphenylphosphinoferrocene dichloromethane complex, dichloroditriphenylphosphine palladium, $PdCl_2$, $Pd(OAc)_2$, $Pd_2dba_3$, $PdCl_2[P(o-tol)_3]_2$, and $Pd(O_2CCF_3)_2$.

When a ligand-free palladium catalyst is used, a suitable ligand needs to be added. Suitable ligands include, for example, triphenylphosphine, $P(o-tol)_3$, BINAP, DPPF, $P(tert-Bu)_3$, 2-dicyclohexylphosphino-2'-(N,N-dimethylamino)biphenyl, 2-(di-tert-butylphosphino)biphenyl, 2-(dicyclohexylphosphino)biphenyl, 2',6'-dimethoxy-2-(dicyclohexylphosphino)biphenyl, 2',4',6'-triisopropyl-2-(dicyclohexylphosphino)biphenyl, 4,5-bis(diphenylphosphanyl)-9,9-dimethyl-9H-xanthene, 4,5-bis[bis(3,5-bistrifluoromethylphenyl)phosphanyl]-9,9-dimethyl-9H-xanthene, and 1,3-diallyldihydroimidazolium salt, preferably triphenylphosphine, BINAP, and 2',6'-dimethoxy-2-(dicyclohexylphosphino)biphenyl.

Suitable bases include, for example, sodium hydroxide, potassium hydroxide, sodium methoxide, sodium ethoxide, potassium bis(trimethylsilyl)amide, sodium bis(trimethylsilyl)amide, lithium bis(trimethylsilyl)amide ($LiN(TMS)_2$), lithium diisopropylamide, sodium carbonate, potassium carbonate, cesium carbonate, sodium bicarbonate, potassium tert-butoxide, and potassium phosphate; preferably potassium carbonate, cesium carbonate, sodium bicarbonate, sodium hydroxide, potassium tert-butoxide, potassium phosphate, and lithium bis(trimethylsilyl) amide.

The reaction temperature varies depending on the type of solvent, base, and such. For example, the temperature is from 0° C. up to the boiling point of the solvent. Preferably, the compound can be produced through the reaction at room temperature to the boiling point of the solvent. The reaction time varies depending on the reaction temperature and such. In general, the reaction time is about 10 minutes to about 100 hours, preferably about 30 minutes to 24 hours. Microwaves may be applied to accelerate the reaction. Furthermore, preferred 2-aminopyrimidine and 2-aminotriazine that have leaving groups at positions 4 and 6 include 2-amino-4,6-dichloropyrimidine and 2-amino-4,6-dichlorotriazine.

The compounds represented by formula (1) can be produced, for example, by the methods described in Production methods 2, 3, 4, and 5.

The compounds represented by formula (1) in which $L^1$ and $L^3$ represent —CONH— and —CONH—, respectively, can be produced, for example, by the method described in Production method 2.

Production Method 2

In this production method, compound (1) of the present invention is obtained by thioalkylating the synthetic intermediate 1-C of compound (1) of the present invention, converting the resulting compound 2-A into compound 2-B through condensation with a diamine derivative, and deprotection followed by macrolactamization reaction.

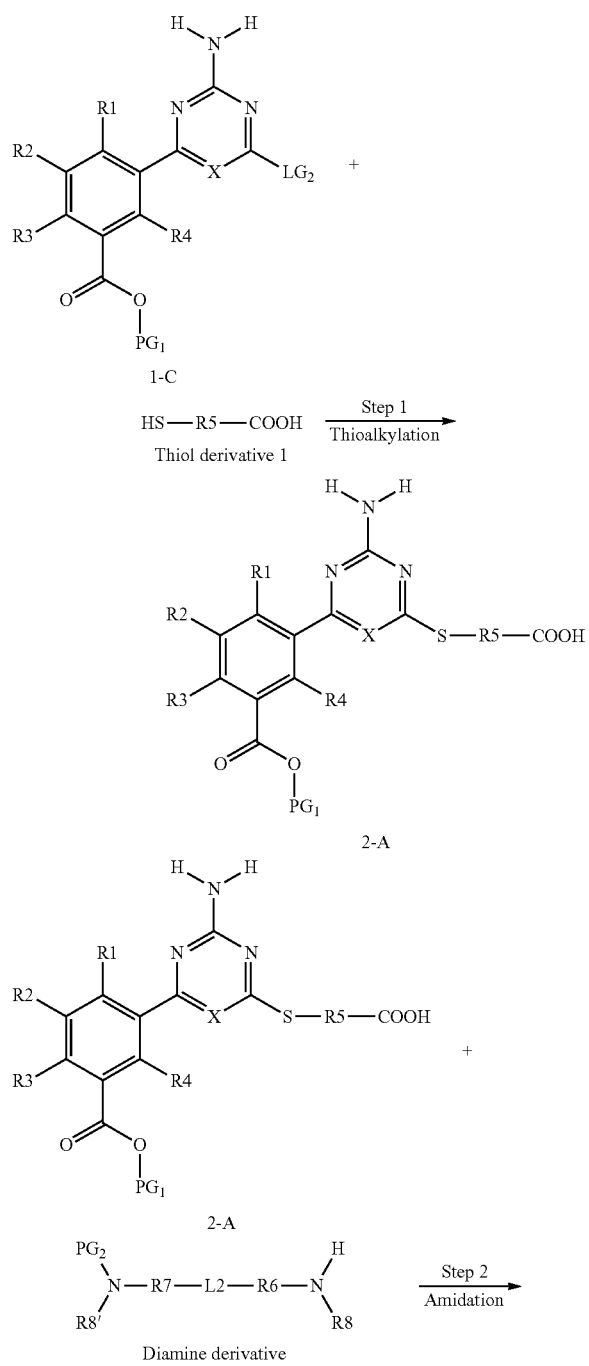
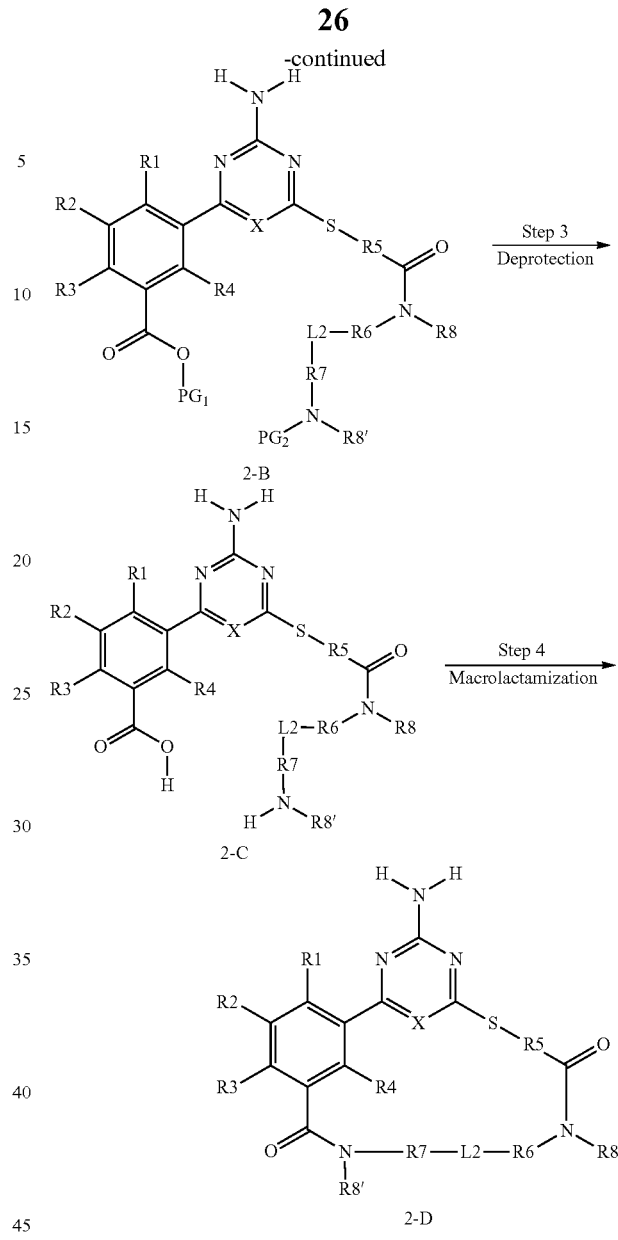

wherein $R^1$, $R^2$, $R^3$, $R^4$, $R^5$, $R^6$, $R^7$, $R^8$, $R^{8'}$, X, and $L^2$ are as defined in formula (1); $LG_2$, $PG_1$, and $PG_2$ are as defined above. $PG_1$ which serves as a protecting group of a carboxyl group preferably represents $C_{1-6}$ alkyl groups, and among them, a methyl group and a tert-butyl group are more preferred. $PG_2$ which serves as a protecting group of an amino group preferably represents a tert-butoxycarbonyl group.

Step 1 (Thioalkylation)

Compound 2-A can be produced by reacting the synthetic intermediate 1-C, which is obtained by the method described in Production method 1, with one equivalent to an excess amount of, preferably one to ten equivalents of a thiol derivative represented by the formula HS—$R^5$—COOH in an appropriate solvent in the presence of one equivalent to an excess amount of, preferably one to ten equivalents of an appropriate base at an appropriate temperature.

The solvent used in the reaction is not particularly limited, as long as it is inactive for the reaction. The solvent includes, for example, tetrahydrofuran, 1,4-dioxane, diethyl ether, 1,2-dimethoxyethane, N,N-dimethylformamide, N,N-dimethylacetamide, dimethylsulfoxide, acetone, acetonitrile, toluene, and benzene, and mixtures thereof, however, N,N-dimethylformamide, N,N-dimethylacetamide, and such are preferred. Appropriate bases include, for example, N,N-diisopropylethylamine, 1,8-diazabicyclo[5.4.0]-7-undecene (DBU), sodium hydroxide, potassium hydroxide, sodium carbonate, potassium carbonate, and cesium carbonate; however, 1,8-diazabicyclo[5.4.0]-7-undecene (DBU), cesium carbonate, potassium carbonate, and such are preferred.

The reaction temperature varies depending on the type of solvent, base, and such. For example, the temperature is 0° C. up to the boiling point of the solvent, and the compound can be preferably produced through a reaction at room temperature up to the boiling point of the solvent. The reaction time varies depending on the reaction temperature and such. In general, the reaction time is about 10 minutes to about 100 hours, preferably about 30 minutes to about 24 hours.

Step 2 (Amidation)

Compound 2-B can be produced by dehydrative condensation between the benzoic acid derivative (2-A) obtained as described in Step 1 of Production method 2 and one equivalent to an excess amount of, preferably one to three equivalents of a diamine derivative represented by the formula $PG_2(R^8)$—N—$R^7$-$L^2$-$R^6$—N($R^8$)H in an appropriate solvent in the presence of one equivalent to an excess amount of, preferably one to five equivalents of an appropriate base, in the presence of one equivalent to an excess amount of, preferably one to three equivalents of an appropriate acid-halogenation agent or one equivalent to an excess amount of, preferably one to three equivalents of an appropriate dehydration-condensation agent, and in the presence or absence of one equivalent to an excess amount of, preferably one to three equivalents of an appropriate active-esterification agent, at an appropriate temperature.

Acid-halogenation agents include, for example, oxalyl chloride and thionyl chloride. Dehydrative-condensation agents include, for example, polymer-supported carbodiimide compounds (for example, N-cyclohexylcarbodiimide-N'-propyloxymethylpolystyrene (PS-carbodiimide), 1,3-dicyclohexylcarbodiimide (DCC), 2-ethoxy-1-ethoxycarbonyl-1, 2-dihydroquinoline (EEDQ), bromo-tris-pyrrolidinophosphonium hexafluorophosphate (PyBrOP), 1-ethyl-3-(3'-dimethylaminopropyl)carbodiimide (EDC), and benzotriazol-1-yloxy-tris-pyrrolidinophosphonium hexafluorophosphate (PyBOP).

Activators derived from phosphate ester include diphenylphosphorodithioate (DPPA), diethyl phosphorocyanidate (DEPC), diphenylphosphinyl chloride, and bis(2-oxo-3-oxazolidinyl)phosphonic chloride (BOP-Cl).

Active-esterification agents include, for example, N-hydroxybenzotriazole (HOBt), di(N-succinimidyl)carbonate, carbonyldiimidazole, pentafluorophenol, and 2-chloro-1-methylpyridinium iodide.

Bases include, for example, triethylamine, N,N-diisopropyl ethylamine, and 1,8-diazabicyclo[5.4.0]-7-undecene (DBU).

The solvent used in the reaction is not particularly limited as long as it is inactive for the reaction. For example, the solvent includes carboxylic acid amides such as N,N-dimethylformamide and N,N-dimethylacetamide; halogenated hydrocarbons such as dichloromethane, chloroform, carbon tetrachloride, and chlorobenzene; ketones such as acetone; cyclic ethers such as tetrahydrofuran and 1,4-dioxane; esters such as ethyl acetate; and nitriles such as acetonitrile; and mixtures thereof.

The reaction temperature varies depending on the type of solvent, base, and such. For example, the temperature is 0° C. up to the boiling point of the solvent, and the compound can be preferably produced through a reaction at room temperature up to the boiling point of the solvent. The reaction time varies depending on the reaction temperature and such. In general, the reaction time is about 30 minutes to about 100 hours, preferably about 10 minutes to about 24 hours.

Step 3 (Deprotection Reaction)

Compound 2-C can be produced by removing the carboxyl-protecting group $PG_1$ and the amino-protecting group $PG_2$ from the benzoic acid derivative (2-B) obtained in Step 2 of Production method 2 in an appropriate solvent at an appropriate temperature. The deprotection treatment can be carried out, for example, by the methods described in Greene and Wuts, "Protective Groups in Organic Synthesis" (3rd ed., John Wiley & Sons, Inc. 1999) mentioned above. Such methods may be appropriately used depending on the reaction conditions.

$PG_1$ used as a carboxyl-protecting group can be deprotected under an alkaline, acidic, or neutral condition depending on the properties of the protecting group.

When $PG_1$ used as a carboxyl-protecting group is, for example, an alkyl group other than tert-butyl group, such as a methyl group or an ethyl group, deprotection methods preferably include hydrolysis using an excess volume of aqueous solution of an inorganic base, such as potassium hydroxide or sodium hydroxide, in an alcohol solvent such as ethanol. In this case, the reaction time is about 10 minutes to about 30 hours, preferably about 30 minutes to about 5 hours. The reaction temperature is in the range of 0° C. to the boiling point of the solvent, preferably about 80 to 100° C.

Furthermore, when $PG_1$ used as a carboxyl-protecting group is, for example, a substituent such as a tert-butyl group, deprotection methods preferably include methods using hydrolysis in the presence of acid. Suitable acids include, for example, trifluoroacetic acid, methanesulfonic acid, p-toluenesulfonic acid, hydrochloric acid, hydrobromic acid, sulfuric acid; preferably trifluoroacetic acid and methanesulfonic acid. The solvent used in the reaction is not particularly limited as long as it is inactive for the reaction; however, aprotic solvents such as dichloromethane, chloroform, ethyl acetate, 1,4-dioxane, dimethylsulfoxide, and sulfolane, and protic solvents such as trifluoroethanol, methanol, ethanol, and water, can be used alone or in appropriate combinations depending on the acid used. Alternatively, it may also possible to perform the reaction without solvent.

In addition, a cation-capturing agent such as anisole, thioanisole, or triethylsilane may be added to the reaction system. The reaction temperature varies depending on the type of solvent and acid. For example, the temperature is from 0° C. to the boiling point of the solvent. Preferably, Compound 2-C can be produced by carrying out the reaction at a temperature in the range of 0° C. to room temperature.

The reaction time varies depending on the reaction temperature and such. In general, the reaction time is about 10 minutes to about 30 hours, preferably about 30 minutes to about 5 hours.

$PG_2$ used as an amino-protecting group can be deprotected under an alkaline, acidic, or neutral condition depending on the properties of the protecting group.

When $PG_2$ used as an amino-protecting group is, for example, a tert-butoxycarbonyl group, deprotection methods preferably includes methods using hydrolysis in the presence of acid. Suitable acids include, for example, organic acids such as trifluoroacetic acid, methanesulfonic acid, and p-toluenesulfonic acid; inorganic acids such as hydrochloric acid and sulfuric acid; and Lewis acids such as aluminum chloride, chlorotrimethylsilane, iodotrimethylsilane, boron trifluoridediethyl ether complex, and tin tetrachloride. Preferred acids include trifluoroacetic acid and methanesulfonic acid.

The solvent used in the reaction is not particularly limited as long as it is inactive for the reaction. Aprotic solvents such as dichloromethane, chloroform, ethyl acetate, 1,4-dioxane, dimethylsulfoxide, and sulfolane, and protic solvents such as trifluoroethanol, methanol, ethanol, and water can be used alone or in appropriate combinations depending on the type of acid to be used. Alternatively, it may also possible to perform the reaction without solvent.

In addition, a cation-capturing agent such as anisole, thioanisole, thiophenol, or triethylsilane can be added to the reaction system. The reaction temperature varies depending on the type of solvent and acid. For example, the temperature is from 0° C. to the boiling point of the solvent. Preferably, the production can be achieved by carrying out the reaction at a temperature in the range of 0° C. to room temperature.

The reaction time varies depending on the reaction temperature and such. In general, the reaction time is about 10 minutes to about 30 hours, preferably about 30 minutes to about 5 hours.

Step 4 (Macrolactamization Reaction)

Compound 2-D can be produced by intramolecular dehydrative condensation of the amino acid derivative (2-C) obtained in Step 3 of Production method 2, in the appropriate solvent, reagents, and temperature conditions used in Step 2 of Production method 2. If required, the substrate may be highly diluted (about 0.1 to 10 mM), or the substrate may be added to the reaction system over a long time (for example, over 2 to 10 hours). (T. Shioiri et al., Tetrahedron Lett., vol. 25, p. 5303 (1984); U. Schmidt et al., Tetrahedron Lett., vol. 27, p. 163 (1986); T. K. Jones et al., J. Am. Chem. Soc., vol. 111, p. 1157 (1989))

When any one of $R^1$, $R^2$, $R^3$, and $R^4$ of formula (1) contains a halogen atom in this production method, synthetic intermediate 2-A may be more efficiently produced by the method described below.

Alternative Method for Producing Synthetic Intermediate 2-B

In this production method, synthetic intermediate 2-B is obtained by condensation between a diamine derivative and compound 2-E produced through thioalkylation of 2-aminopyrimidine or triazine having leaving groups at positions 4 and 6, followed by Suzuki reaction between the product and the boronic acid ester derivative (1-B) obtained in Step 1 of Production method 1.

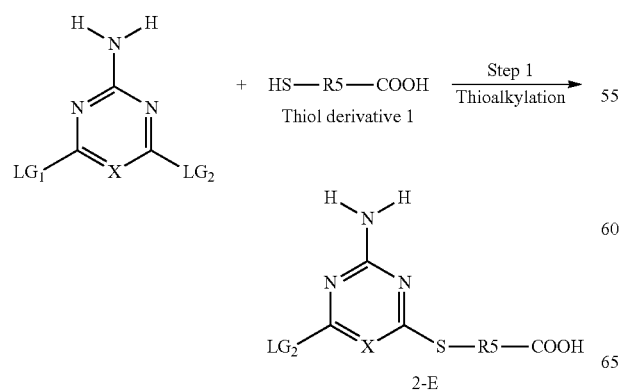

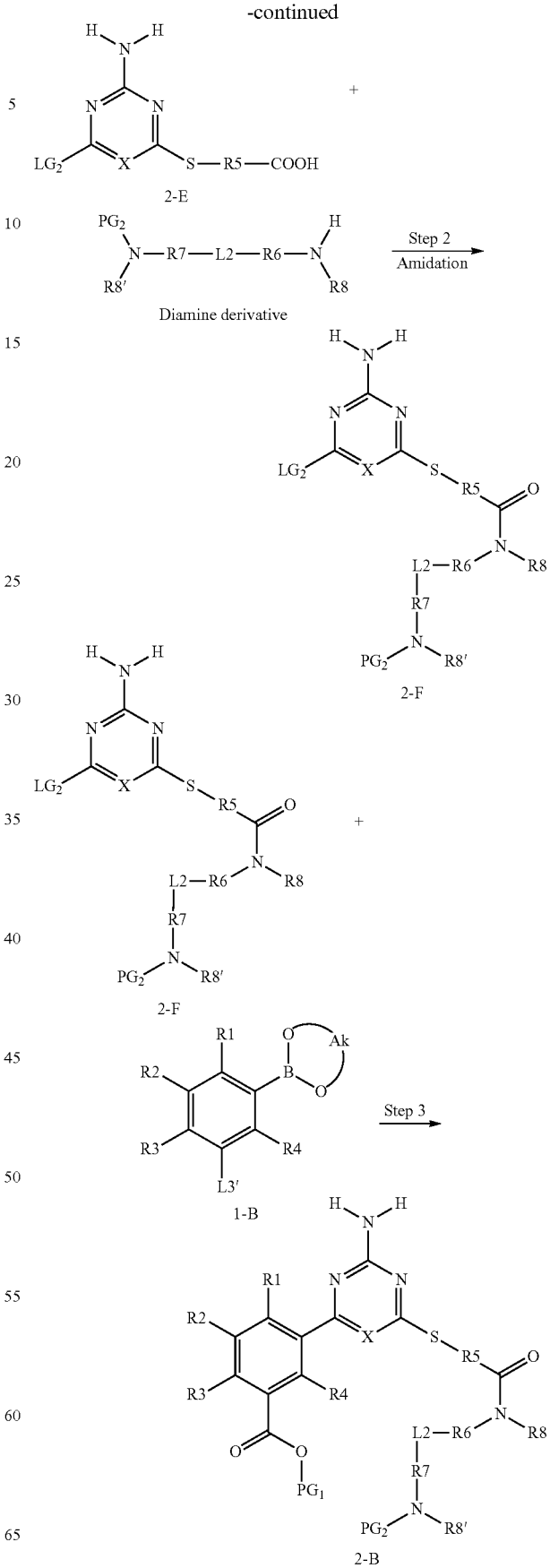

wherein $R^1$, $R^2$, $R^3$, $R^4$, $R^5$, $R^6$, $R^7$, $R^8$, $R^{8'}$, X, and $L^2$ are as defined in formula (1); and $L^{3'}$, $LG_2$, $PG_1$, and $PG_2$ are as defined above. -Ak- represents a linear or branched alkylene group composed of one to six carbon atoms, and preferably represents 1,1,2,2-tetramethylethylene or 2,2-dimethyltrimethylene. The carboxyl protecting group $PG_1$ is preferably a $C_{1-6}$ alkyl group, and more preferably a methyl group or a tert-butyl group. The amino protecting group $PG_2$ is preferably a tert-butoxycarbonyl group.

Step 1 (Thioalkylation)

The compound 2-E can be produced by reacting 2-aminopyrimidine or triazine having leaving groups at positions 4 and 6 with preferably 0.5 to one equivalent of a thiol derivative represented by the formula HS—$R^5$—COOH in an appropriate solvent in the presence of one equivalent to an excess amount of, preferably one to ten equivalents of an appropriate base, at an appropriate temperature. The reaction conditions and such are the same as in Step 1 of Production method 2 described above.

Step 2 (Amidation)

The compound 2-F can be produced by dehydrative condensation between the 2-aminopyrimidine or triazine derivative (2-E) obtained in Step 1 and one equivalent to an excess amount of, preferably one to three equivalents of a diamine derivative represented by the formula $PG_2(R^8)$—N—$R^7$-$L^2$-$R^6$—N($R^8$)H in an appropriate solvent in the presence of one equivalent to an excess amount of, preferably one to five equivalents of an appropriate base, in the presence of one equivalent to an excess amount of, preferably one to three equivalents of an appropriate acid-halogenation agent or one equivalent to an excess amount of, preferably one to three equivalents of an appropriate dehydrative-condensation agent, and in the presence or absence of one equivalent to an excess amount of, preferably one to three equivalents of an appropriate active-esterification agent, at an appropriate temperature.

The reaction conditions and such are the same as in Step 2 of Production method 2 described above.

Step 3 (Suzuki Reaction)

The synthetic intermediate 2-A can be produced by reacting compound 2-F with one equivalent to an excess amount of, preferably one to three equivalents of the boronic acid ester derivative (1-B) in an appropriate solvent in the presence of a catalytic amount to an excess amount of, preferably a catalytic amount to two equivalents of an appropriate palladium catalyst, in the presence or absence of a catalytic amount to an excess amount of, preferably a catalytic amount to one equivalent of an appropriate ligand, and in the presence of one equivalent to an excess amount of, preferably one to ten equivalents of an appropriate base, at an appropriate temperature. The reaction conditions and such are the same as in Step 2 of Production method 1 described above.

The compounds represented by formula (1) in which $L^1$ and $L^3$ represent —NHCO— and —CONH—, respectively, can be produced, for example, by the method described in Production method 3.

Production Method 3

In this production method, the compound (1) of the present invention is obtained by thioalkylating the synthetic intermediate 1-C of compound (1) of the present invention, converting the resulting compound 3-A into compound 3-B through deprotection, converting compound 3-B into compound 3-C through condensation with an amino acid derivative, and deprotection followed by the macrolactamization reaction.

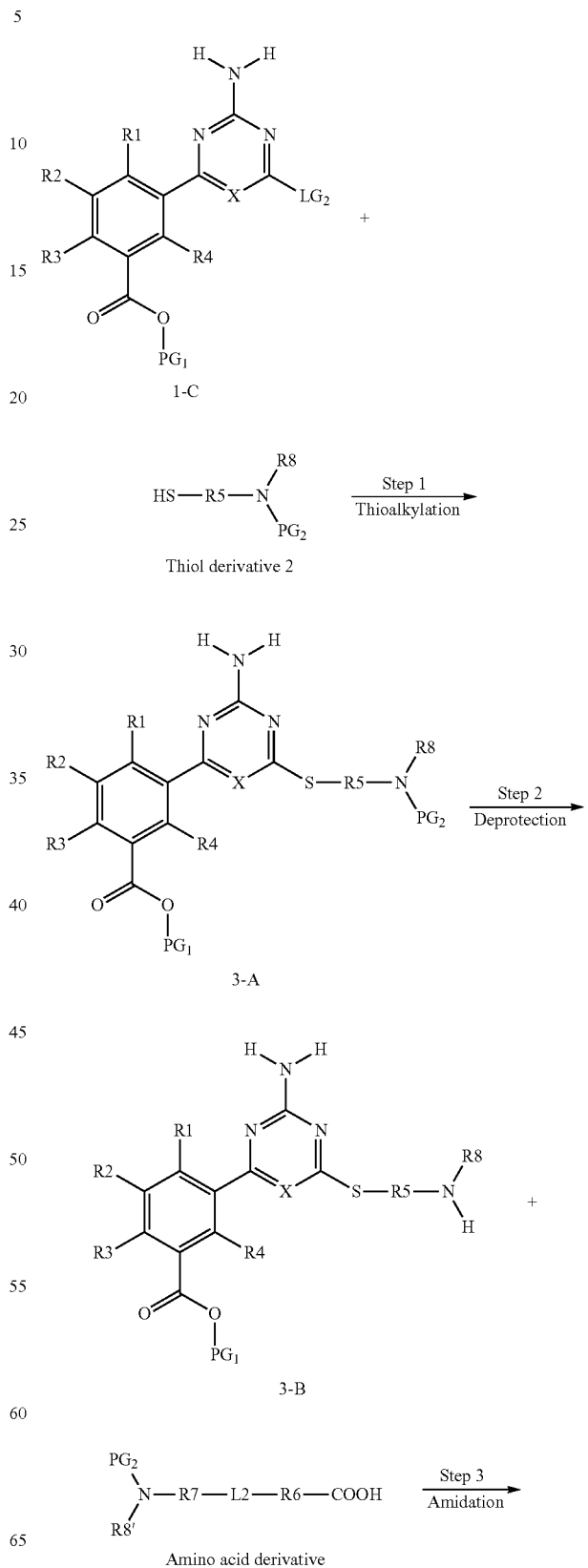

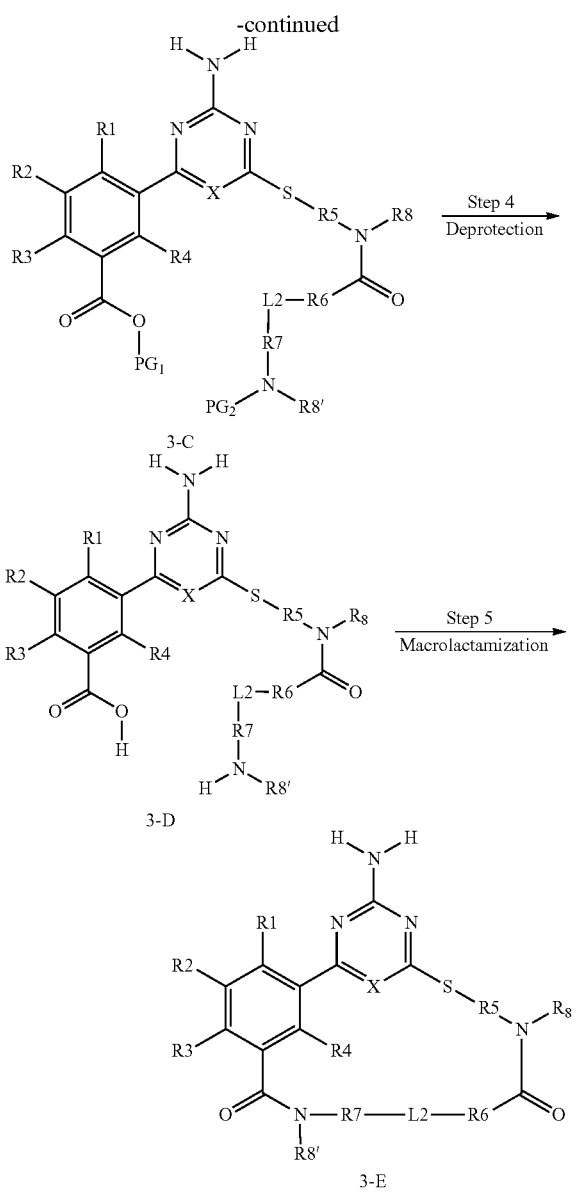

wherein $R^1$, $R^2$, $R^3$, $R^4$, $R^5$, $R^6$, $R^7$, $R^8$, $R^{8'}$, X, and $L^2$ are as defined in formula (1); and $LG_2$, $PG_1$, and $PG_2$ are as defined above.

Step 1 (Thioalkylation)

Compound 3-A can be produced by reacting the synthetic intermediate 1-C obtained by the method described in Production method 1 with one equivalent to an excess amount of, preferably one to ten equivalents of a thiol derivative represented by the formula HS—$R^5$—N($R^8$)$PG_2$ in an appropriate solvent in the presence of one equivalent to an excess amount of, preferably one to ten equivalents of an appropriate base, at an appropriate temperature. The amine-protecting group $PG_2$ is not necessarily required under some reaction conditions, in which case, Step 2 described below may be omitted. The reaction condition and such are the same as in Step 1 of Production method 2 described above.

Step 2 (Deprotection Reaction)

Compound 2-C can be produced by deprotecting the amino-protecting group $PG_2$ in the benzoic acid derivative (3-A) obtained in Step 1 of Production method 3 in an appropriate solvent at an appropriate temperature. The deprotection treatment can be carried out, for example, by the methods described in Greene and Wuts, "Protective Groups in Organic Synthesis" (3rd ed., John Wiley & Sons, Inc. 1999) mentioned above. Such methods may be appropriately used depending on the reaction conditions.

When $PG_2$ used as an amino-protecting group is, for example, a tert-butoxycarbonyl group or such, the deprotection of the amino group preferably includes methods of hydrolyzing in the presence of acid. The reaction conditions and such are the same as in Step 3 of Production method 2 described above.

Step 3 (Amidation)

Compound 3-C can be produced by dehydrative condensation between the benzoic acid derivative (3-B) obtained in Step 2 of Production method 3 and one equivalent to an excess amount of, preferably one to three equivalents of a diamine derivative represented by the formula $PG_2(R^{8'})$—N—$R^7$-$L^2$-$R^6$—N($R^8$)H in an appropriate solvent in the presence of one equivalent to an excess amount of, preferably one to five equivalents of an appropriate base, in the presence of one equivalent to an excess amount of, preferably one to three equivalents of an appropriate acid-halogenation agent or one equivalent to an excess amount of, preferably one to three equivalents of dehydrative-condensation agent, and in the presence or absence of one equivalent to an excess amount of, preferably one to three equivalents of an appropriate active-esterification agent, at an appropriate temperature. The reaction condition and such are the same as in Step 2 of Production method 2.

Step 4 (Deprotection Reaction)

The compound 3-D can be produced by deprotecting the carboxyl-protecting group $PG_1$ and the amino-protecting group $PG_2$ from the benzoic acid derivative (3-C) obtained in Step 3 of Production method 3 in an appropriate solvent at an appropriate temperature. The reaction conditions and such are the same as in Step 3 of Production method 2 described above.

Step 5 (Macrolactamization Reaction)

Using appropriate solvent, reagent, and temperature conditions, compound 2-D can be produced by intramolecular dehydrative condensation of the amino acid derivative (3-D) obtained as described above in Step 4 of Production method 3. The reaction conditions and such are the same as those described above in Step 4 of Production method 2.

When any one of $R^1$, $R^2$, $R^3$, and $R^4$ of formula (1) contains a halogen atom in this production method, synthetic intermediate 3-A may be more efficiently produced by the method described below.

Alternative Method for Producing Synthetic Intermediate 3-A

In this production method, compound 3-A is obtained by thioalkylating 2-aminopyrimidine or triazine having leaving groups at positions 4 and 6, and conducting the Suzuki reaction between the resulting compound 3-E and the boronic acid ester derivative (1-B) obtained in Step 1 of Production method 1.

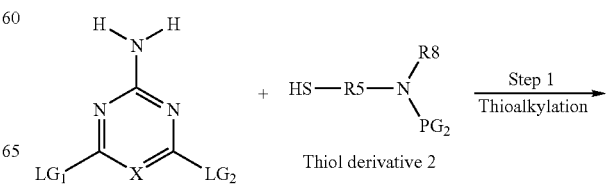

Thiol derivative 2

-continued

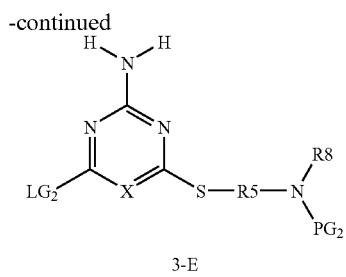

3-E

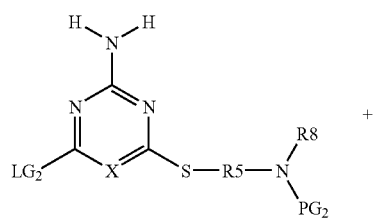

3-E

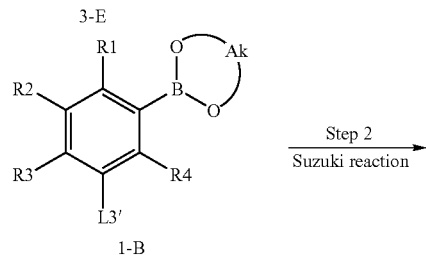

1-B

Step 2
Suzuki reaction

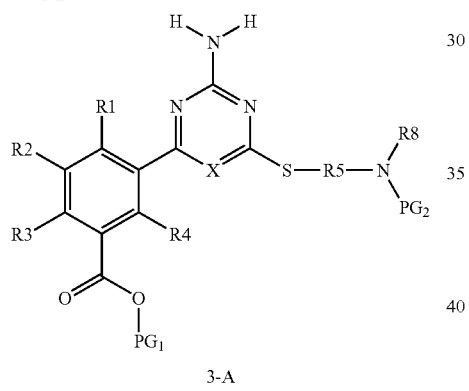

3-A wherein $R^1$, $R^2$, $R^3$, $R^4$, $R^5$, $R^8$, and X are as defined in formula (1); and $L^{3'}$, $LG_1$, $LG_2$, $PG_1$, and $PG_2$ are defined above. -Ak- represents a linear or branched alkylene group composed of one to six carbon atoms, and preferably represents a 1,1,2,2-tetramethylethylene or 2,2-dimethyltrimethylene.

Step 1 (Thioalkylation)

Compound 3-E can be produced by reacting the boronic acid ester derivative (1-B) obtained in Step 1 of Production method 1 with 0.5 to one equivalent of a thiol derivative represented by the formula HS—$R^5$—N($R^8$)$PG_2$ in an appropriate solvent in the presence of one equivalent to an excess amount of, preferably one to ten equivalents of an appropriate base, at an appropriate temperature. The reaction conditions and such are the same as in Step 1 of Production method 2 described above.

Step 2 (The Suzuki Reaction)

Synthetic intermediate 3-A can be produced by reacting compound 3-E with one equivalent to an excess amount of, preferably one to three equivalents of the boronic acid ester derivative (1-B) in an appropriate solvent in the presence of a catalytic amount to an excess amount of, preferably a catalytic amount to one equivalent of an appropriate palladium catalyst, in the presence or absence of a catalytic amount to an excess amount of, preferably a catalytic amount to two equivalents of an appropriate ligand, and in the presence of one equivalent to an excess amount of, preferably one to ten equivalents of an appropriate base, at an appropriate temperature. The reaction conditions and such are the same as in Step 2 of Production method 1.

The compounds represented by formula (1) in which $L^1$ and $L^3$ represent —O— and —CONH— respectively, can be produced, for example, by the method described in Production method 4.

Production Method 4

In this production method, compound (1) of the present invention is obtained by thioalkylating the synthetic intermediate 1-C of compound (1) of the present invention, converting the resulting compound 4-A into compound 4-B through ether-linkage formation reaction with an amine derivative having a leaving group, and deprotection followed by the macrolactamization reaction.

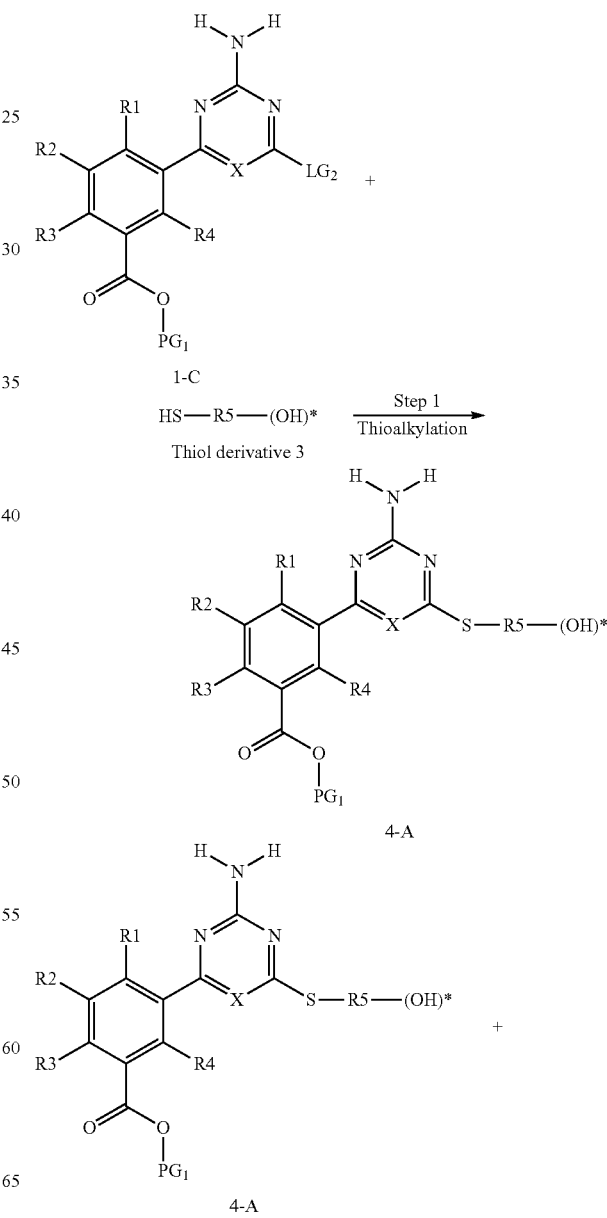

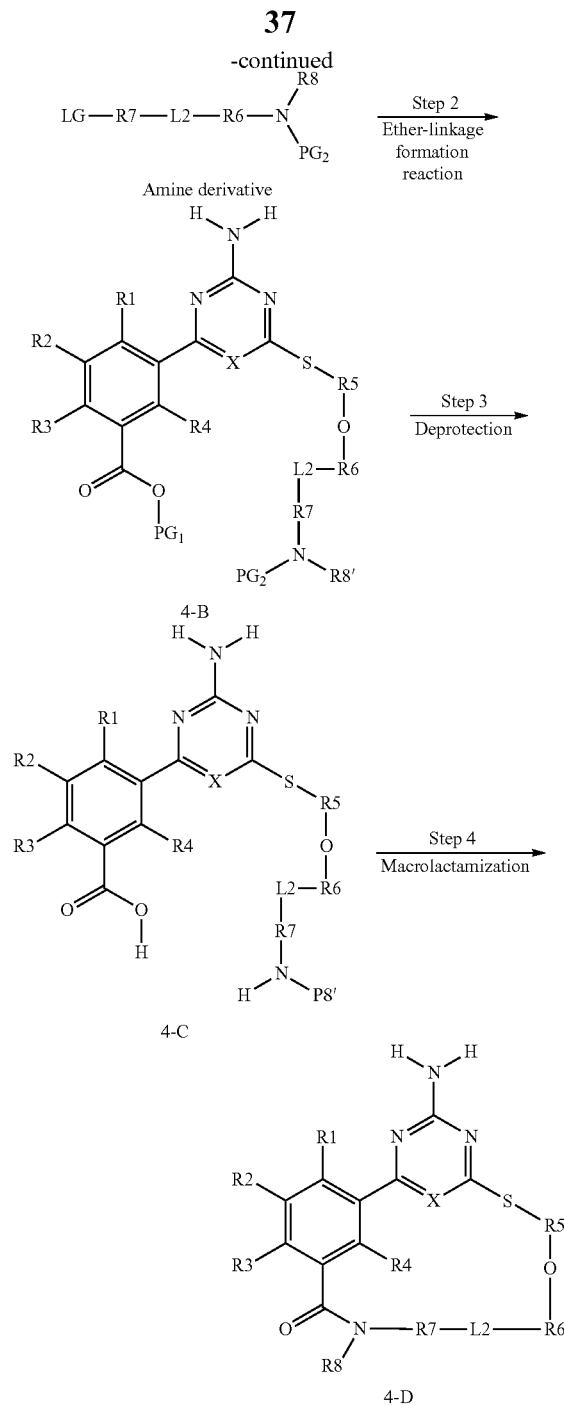

wherein $R^1$, $R^2$, $R^3$, $R^4$, $R^5$, $R^6$, $R^7$, $R^8$, X, and $L^2$ are as defined in formula (1); and $LG_2$, $PG_1$, and $PG_2$ are as defined above. (OH)* represents a phenolic hydroxyl group.

Step 1 (Thioalkylation)

Compound 4-A can be produced by reacting the synthetic intermediate 1-C obtained by the method described in Production method 1 with one equivalent to an excess amount of, preferably one to ten equivalents of a thiol derivative having a phenolic hydroxyl group represented by the formula HS—$R^5$—(OH)* in an appropriate solvent in the presence of one equivalent to an excess amount of, preferably one to ten equivalents of an appropriate base, at an appropriate temperature. The reaction conditions and such are the same as in Step 1 of Production method 2 described above.

Step 2 (Ether-Linkage Formation Reaction)

Compound 4-B can be produced by reacting the benzoic acid derivative (4-A) obtained in Step 1 of Production method 4 with one equivalent to an excess amount of, preferably one to three equivalents of an amine derivative having a leaving group represented by the formula LG-$R^7$-$L^2$-$R^6$—N($R^8$)$PG_2$ in an appropriate solvent in the presence of one equivalent to an excess amount of, preferably one to five equivalents of an appropriate base, at an appropriate temperature.

The solvent used in the reaction is not particularly limited as long as it is inactive for the reaction. For example, the solvent includes tetrahydrofuran, 1,4-dioxane, diethyl ether, 1,2-dimethoxyethane, N,N-dimethylformamide, N,N-dimethylacetamide, dimethylsulfoxide, toluene, and benzene, used either alone or in combination.

Suitable bases include, for example, sodium hydroxide, potassium hydroxide, sodium hydride, potassium hydride, sodium methoxide, sodium ethoxide, potassium tert-butoxide, potassium bistrimethylsilylamide, sodium bistrimethylsilylamide, lithium bistrimethylsilylamide (LiN(TMS)$_2$), lithium diisopropylamide, sodium carbonate, potassium carbonate, cesium carbonate, sodium bicarbonate, and potassium phosphate; preferably sodium carbonate, potassium carbonate, cesium carbonate, sodium hydride, and potassium hydride.

The reaction temperature varies depending on the type of solvent, base, and such. For example, the temperature is 0° C. up to the boiling point of the solvent, and the compound can be preferably produced through reaction at room temperature up to the boiling point of the solvent. The reaction time varies depending on the reaction temperature and such. In general, the reaction time is about 10 minutes to about 100 hours, preferably about 30 minutes to 24 hours.

Step 3 (Deprotection Reaction)

Compound 4-C can be produced by deprotecting the carboxyl-protecting group $E_1$ and the amino-protecting group $PG_2$ from the benzoic acid derivative (4-B) obtained in Step 2 of Production method 4 in an appropriate solvent at an appropriate temperature. The deprotection treatment can be carried out, for example, by the methods described in Greene and Wuts, "Protective Groups in Organic Synthesis" (3rd ed., John Wiley & Sons, Inc. 1999)" mentioned above. Such methods may be appropriately used depending on the reaction condition. The reaction conditions and such are the same as in Step 3 of Production method 2 described above.

Step 4 (Macrolactamization Reaction)

Compound 2-D can be produced by intramolecular dehydrative condensation of the amino acid derivative (4-C) obtained in Step 3 of Production method 4 in an appropriate solvent, reagents, and temperature condition. The reaction conditions and such are the same as in Step 4 of Production method 2 described above.

The compounds represented by formula (1) in which both $L^1$ and $L^3$ represent —O— can be produced, for example, by the method described in Production method 5.

Production Method 5 (Macrocyclic Ether Formation Reaction)

In this production method, the compound (1) of the present invention is obtained through macrocyclic ether formation reaction between a compound having two leaving groups and compound 5-A, which is prepared by thioalkylating the synthetic intermediate 1-C of compound (1) of the present invention.

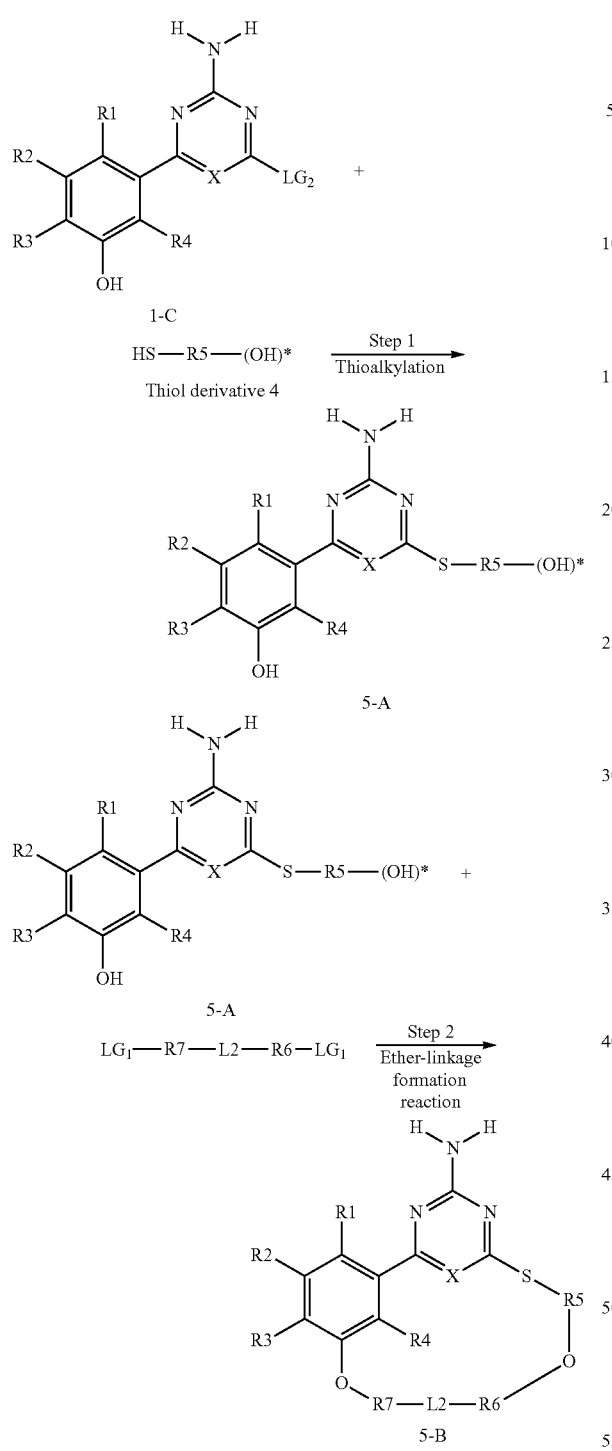

wherein $R^1$, $R^2$, $R^3$, $R^4$, $R^5$, $R^6$, $R^7$, X, and $L^2$ are as defined in formula (1); $LG_1$ and $(OH)^*$ are as defined above.

Step 1 (Thioalkylation)

Compound 4-A can be produced by reacting the synthetic intermediate 1-C obtained by the method described in Production method 1 with one equivalent to an excess amount of, preferably one to ten equivalents of a thiol derivative having a phenolic hydroxyl group represented by the formula HS—$R^5$—$(OH)^*$ in an appropriate solvent in the presence of one equivalent to an excess amount of, preferably one to ten equivalents of an appropriate base at an appropriate temperature. The reaction conditions and such are the same as in Step 1 of Production method 2.

Step 2 (Macrocyclic Etherification Reaction)

Compound 5-B can be produced by reacting the phenol derivative (5-A) obtained in Step 1 of Production method 5 with one equivalent to an excess amount of, preferably one to ten equivalents of a compound represented by the formula LG-$R^7$-$L^2$-$R^6$-LG in the appropriate solvent, base, and temperature conditions as used in Step 2 of Production method 4.

In this production method, compounds represented by formula (1) may be more efficiently produced by the method described below.

Production Method 6 (Alternative Method for Production Method 2)

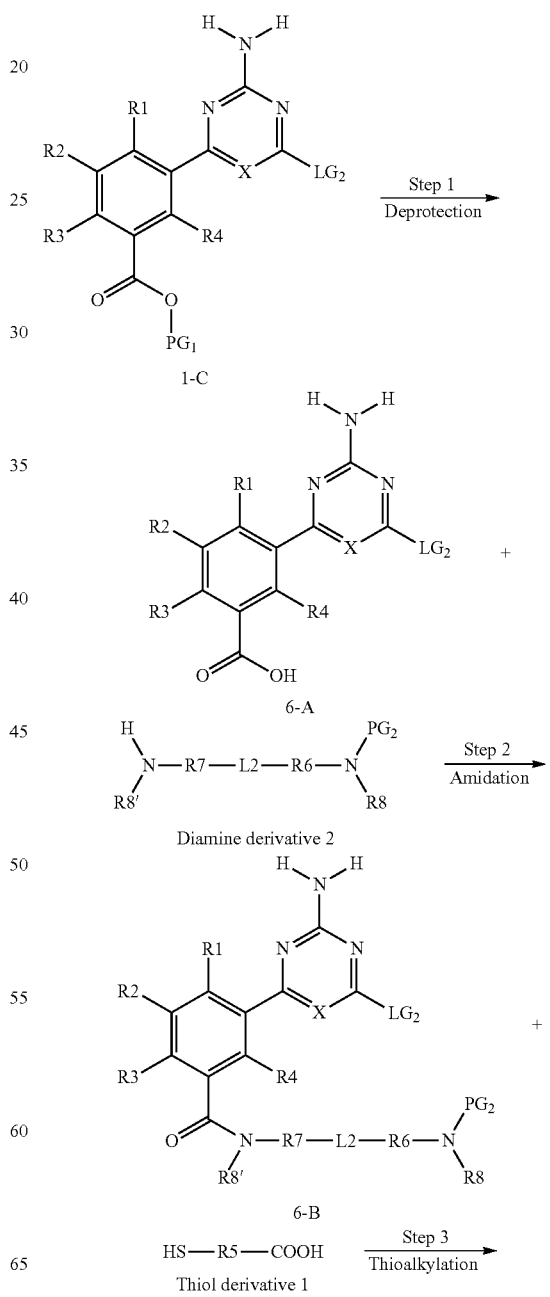

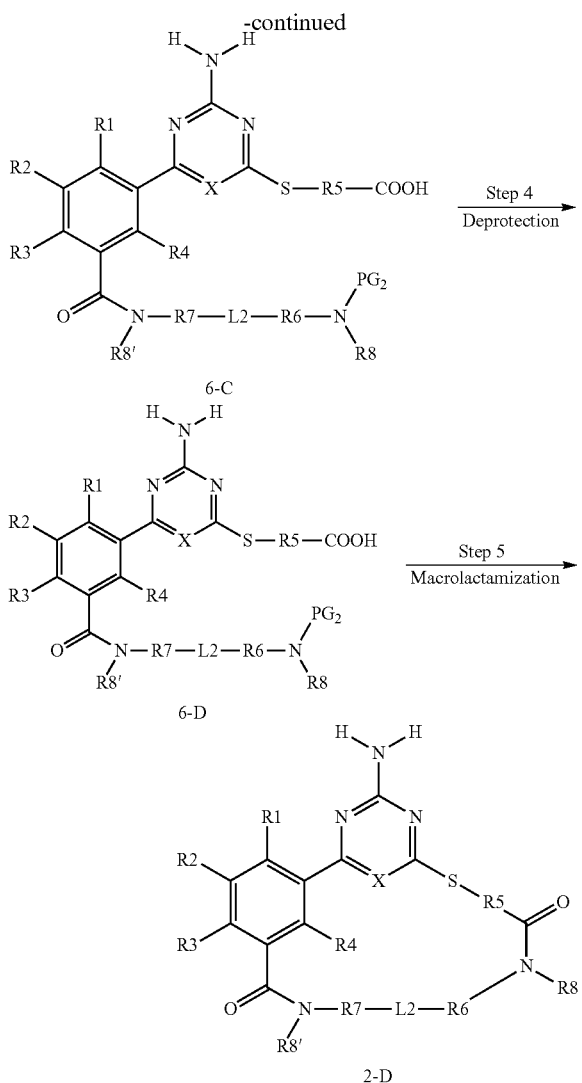

wherein, $R^1$, $R^2$, $R^3$, $R^4$, $R^5$, $R^6$, $R^7$, $R^8$, $R^{8'}$, X, and $L^2$ are as defined in formula (1); and $LG_2$, $PG_1$, and $PG_2$ are as defined above. The carboxyl protecting group $PG_1$ is preferably a $C_{1-6}$ alkyl group, and more preferably a tert-butyl group. The amino protecting group $PG_2$ is preferably a trityl group or a tert-butoxycarbonyl group.

Step 1 (Deprotection Reaction)

Compound 6-A can be produced by deprotecting the carboxyl-protecting group $PG_1$ from synthetic intermediate 1-C obtained in Production method 1 in an appropriate solvent at an appropriate temperature. The deprotection treatment can be carried out, for example, by the methods described in Greene and Wuts, "Protective Groups in Organic Synthesis" (3rd ed., John Wiley & Sons, Inc. 1999)" mentioned above. Such methods may be appropriately used depending on the reaction condition. The reaction conditions and such are the same as in Step 3 of Production method 2 described above.

Step 2 (Amidation)

Compound 6-B can be produced by dehydrative condensation between the benzoic acid derivative (6-A) obtained in Step 1 above and one equivalent to an excess amount of, preferably one to three equivalents of a diamine derivative represented by the formula $H(R^{8'})$—N—$R^7$-$L^2$-$R^6$—$N(R^5)$ $PG_2$ in an appropriate solvent in the presence of one equivalent to an excess amount of, preferably one to five equivalents of an appropriate base, in the presence of one equivalent to an excess amount of, preferably one to three equivalents of an appropriate acid-halogenation agent or one equivalent to an excess amount of, preferably one to three equivalents of an appropriate dehydration-condensation agent, and in the presence or absence of one equivalent to an excess amount of, preferably one to three equivalents of an appropriate active-esterification agent, at an appropriate temperature. The reaction conditions and such are the same as in Step 2 of Production method 2 described above.

Step 3 (Thioalkylation)

Compound 6-C can be produced by reacting the 2-aminopyrimidine or triazine derivative having a leaving group at position 4 (6-B), which is obtained in Step 2 above, with one equivalent to an excess amount of, preferably one to ten equivalents of a thiol derivative represented by the formula HS—$R^5$—COOH in an appropriate solvent in the presence of one equivalent to an excess amount of, preferably one to ten equivalents of an appropriate base at an appropriate temperature. The reaction conditions and such are the same as in Step 1 of Production method 2 described above.

Step 4 (Deprotection Reaction)

Compound 6-D can be produced by deprotecting the amino-protecting group $PG_2$ from synthetic intermediate 6-C obtained in Step 3 above in an appropriate solvent at an appropriate temperature. The deprotection treatment can be carried out, for example, by the methods described in Greene and Wuts, "Protective Groups in Organic Synthesis" (3rd ed., John Wiley & Sons, Inc. 1999)" mentioned above. Such methods may be appropriately used depending on the reaction condition. The reaction conditions and such are the same as in Step 2 of Production method 3 described above.

Step 5 (Macrolactamization Reaction)

Compound 2-D can be produced by intramolecular dehydrative condensation of the amino acid derivative (6-D) obtained in Step 4 above, in the appropriate solvent, reagents, and temperature conditions. The reaction conditions and such are the same as in Step 4 of Production method 2.

All prior art documents cited herein are incorporated herein by reference.

EXAMPLES

Hereinbelow, the present invention is specifically described using Examples, but it is not to be construed as being limited thereto.

NMR analyses were carried out using JNM-EX270 (270 MHz), JNM-GSX400 (400 MHz), or JNM-A500 (500 MHz), each manufactured by JEOL, or ARX300 (300 MHz) manufactured by Bruker. NMR data are shown in ppm (parts per million) (δ). The deuterium lock signal of the sample solvent was used as a reference. Mass spectrometry data were obtained using JMS-DX303 or JMS-SX/SX102A of JEOL. High performance liquid chromatography-mass spectrometric data were obtained using Micromass ZMD coupled with Waters 996-600E gradient high performance liquid chromatography system or Micromass ZQ coupled with Waters 2525 high performance liquid chromatography system.

Organic synthesis reactions were conducted using commercially available reagents without further purification. The room temperature refers to the range of 20 to 25° C. All moisture-sensitive reactions were performed under a nitrogen or argon atmosphere. Concentration or solvent removal under reduced pressure was carried out using a rotary evaporator, unless otherwise stated.

In the preparation of compounds, functional groups were protected as necessary with protecting groups, and the protecting groups were removed after protected forms of target compounds were prepared. The selection and attachment/detachment of such protecting groups were carried out, for example, by the methods described in Greene and Wuts, "Protective Groups in Organic Synthesis" (3rd ed., John Wiley & Sons, Inc. 1999).

Example 1-1

Production of 5-(2-amino-6-chloropyrimidin-4-yl)-2,4-dimethylbenzoic acid tert-butyl ester (Compound 1-1)

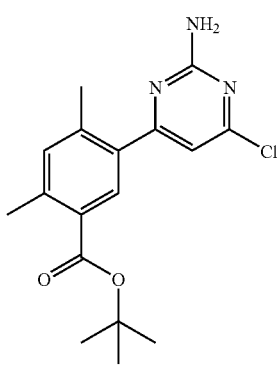 [SMILES: Cc1cc(C)c(-c2cc(Cl)nc(N)n2)cc1C(=O)OC(C)(C)C]

Step 1: Preparation of 5-iodo-2,4-dimethylbenzoic acid

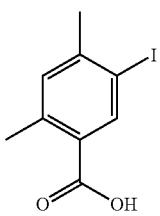

Commercially available 2,4-dimethylbenzoic acid (6.6 g, 44.0 mmol), iodine (12.1 g, 47.8 mmol), and sodium periodate (4.38 g, 22.1 mmol) were placed in a reaction vessel, and acetic acid (60 ml), anhydrous acetic acid (3 ml), and sulfuric acid (0.75 g) were added thereto. The resulting mixture was stirred at 105° C. for 6 hours. The reaction solution was poured into water (300 ml). The resulting insoluble material was isolated by filtration, washed with water (500 ml), and then dissolved in ethyl acetate (400 ml). The obtained solution was washed sequentially with 5% aqueous sodium thiosulfate solution (100 ml) and saturated sodium chloride solution (200 ml). Then, the solution was dried over anhydrous magnesium sulfate, and concentrated under reduced pressure. The resulting solid material was recrystallized with a 2:1 mixture of ethanol and water (450 ml) to yield 5-iodo-2,4-dimethylbenzoic acid (9.1 g, 75%) as needle crystals.

Physicochemical properties of 5-iodo-2,4-dimethylbenzoic acid

Molecular weight: 276.
Chemical shift value δ in $^1$H-NMR (400 MHz, in dimethylsulfoxide d-6): 2.37 (3H, s), 2.44 (3H, s), 7.27 (1H, s), 8.19 (1H, s), 12.9 (1H, brs).

Step 2: Preparation of 5-iodo-2,4-dimethylbenzoic acid tert-butyl ester

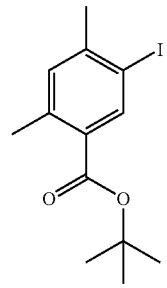 [SMILES: Cc1cc(C)c(C(=O)OC(C)(C)C)cc1I]

5-Iodo-2,4-dimethylbenzoic acid (4.5 g, 16.3 mmol) obtained in Step 1 above was placed in a reaction vessel, and then anhydrous toluene (10 ml) and N,N-dimethylformamide/di-tert-butyl acetal (25 ml) were added thereto. The resulting mixture was stirred at 80° C. for 2 hours. The reaction solution was diluted with ethyl acetate (300 ml), and washed three times with a saturated aqueous sodium bicarbonate solution (100 ml), twice with water (100 ml), and once with a saturated aqueous sodium chloride solution (100 ml). The washed ethyl acetate solution was dried over anhydrous sodium sulfate (50 g). After filtration, the filtrate was concentrated under reduced pressure. The resulting crude product was purified by silica gel column chromatography (developing solvent: n-hexane:ethyl acetate=10:1) to yield 5-iodo-2,4-dimethylbenzoic acid tert-butyl ester (3.8 g) as a white solid material.

Physicochemical properties of 5-iodo-2,4-dimethylbenzoic acid tert-butyl ester

Molecular weight: 332.
ESI (LC/MS positive mode): m/z=333 (M+H$^+$).
Chemical shift value δ in $^1$H-NMR (400 MHz, in dimethylsulfoxide d-6): 1.53 (9H, s), 2.36 (3H, s), 2.40 (3H, s), 7.27 (1H, s), 8.09 (1H, s).

Step 3: Preparation of 2,4-dimethyl-5-(4,4,5,5-tetramethyl-[1,3,2]dioxaborolan-2-yl)benzoic acid tert-butyl ester

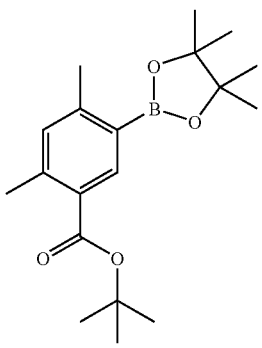

5-Iodo-2,4-dimethylbenzoic acid tert-butyl ester (664 mg, 2.0 mmol) obtained in Step 2 above, potassium acetate (589 mg, 6.0 mmol), bis(pinacolato)diborane (610 mg, 2.4 mmol), and palladium dichloride-diphenylphosphinoferrocene dichloromethane complex (82 mg, 0.1 mmol) were placed in a reaction vessel, and then anhydrous dimethylsulfoxide (10 ml) was added thereto. The resulting mixture was stirred at 80° C. for 18 hours. The reaction solution was diluted with ethyl acetate (150 ml), and sequentially washed with water (80 ml) twice, and with 1N hydrochloric acid (80 ml), water (80 ml), a saturated aqueous sodium bicarbonate solution (80 ml), water (80 ml), and a saturated aqueous sodium chloride solution (80 ml). The ethyl acetate solution was dried over anhydrous sodium sulfate (30 g). After filtration, the filtrate was concentrated under reduced pressure. The resulting crude product was purified by silica gel column chromatography (developing solvent: n-hexane:ethyl acetate=10:1) to yield 2,4-dimethyl-5-(4,4,5,5-tetramethyl[1,3,2]dioxaborolan-2-yl)benzoic acid tert-butyl ester (620 mg) as a white solid material.

Physicochemical properties of 2,4-dimethyl-5-(4,4,5,5-tetramethyl[1,3,2]dioxaborolan-2-yl)benzoic acid tert-butyl ester Molecular weight: 332.
ESI (LC/MS positive mode): m/z=333 (M+H$^+$).
Chemical shift value δ in $^1$H-NMR (400 MHz, in dimethylsulfoxide d-6): 1.30 (12H, s), 1.54 (9H, s), 2.45 (6H, s), 7.10 (1H, s), 8.00 (1H, s).

Step 4: Preparation of 5-(2-amino-6-chloropyrimidin-4-yl)-2,4-dimethylbenzoic acid tert-butyl ester (Compound 1-1)

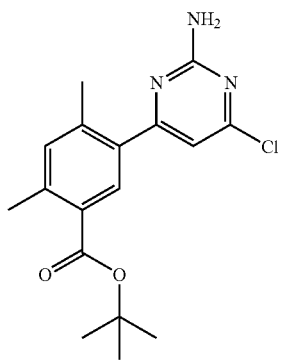 [SMILES: Cc1cc(C)c(-c2cc(Cl)nc(N)n2)cc1C(=O)OC(C)(C)C]

Commercially available 2-amino-4,6-dichloropyrimidine (460 mg, 2.8 mmol), palladium dichloride-diphenylphosphinoferrocene dichloromethane complex (98 mg, 0.12 mmol), sodium bicarbonate (471 mg, 5.61 mmol), 1,4-dioxane (4.5 ml), and water (2.5 ml) were placed in a reaction vessel. The resulting mixture was stirred at 80° C. for 10 minutes. 2,4-Dimethyl-5-(4,4,5,5-tetramethyl[1,3,2]dioxaborolan-2-yl) benzoic acid tert-butyl ester (620 mg, 1.8 mmol) obtained in Step 3 above that was dissolved in 1,4-dioxane (4.5 ml) was added dropwise to the mixture. The resulting mixture was stirred at 80° C. for 19 hours. The reaction solution was diluted with ethyl acetate (150 ml), and washed with water (80 ml) three times and then with a saturated aqueous sodium chloride solution (80 ml). The washed ethyl acetate solution was dried over anhydrous sodium sulfate (30 g). After filtration, the filtrate was concentrated under reduced pressure. The resulting residue was purified by silica gel column chromatography (developing solvent: n-hexane:ethyl acetate=10:1 to 5:1) to yield 5-(2-amino-6-chloropyrimidin-4-yl)-2,4-dimethylbenzoic acid tert-butyl ester (Compound 1-1) (422 mg) as a white solid material.

Physicochemical properties of 5-(2-amino-6-chloropyrimidin-4-yl)-2,4-dimethylbenzoic acid tert-butyl ester Molecular weight: 333.
ESI (LC/MS positive mode): m/z=334 (M+H$^+$).
Chemical shift value δ in $^1$H-NMR (400 MHz, in dimethylsulfoxide d-6): 1.54 (9H, s), 2.33 (3H, s), 2.46 (3H, s), 6.80 (1H, s) 7.21 (2H, brs), 7.24 (1H, s), 7.76 (1H, s).

Example 1-2

Production of 5-(2-amino-6-chloropyrimidin-4-yl)-2-methoxy-4-methylbenzoic acid methyl ester (Compound 1-2)

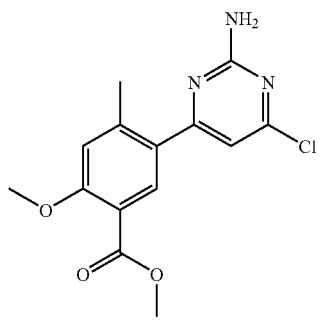 [SMILES: COC(=O)c1cc(-c2cc(Cl)nc(N)n2)c(C)cc1OC]

Step 1: Preparation of 2-methoxy-4-methylbenzoic acid methyl ester

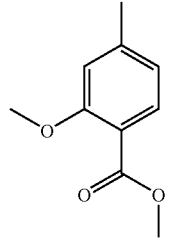

Commercially available 2-hydroxy-4-methylbenzoic acid (1.5 g, 10.0 mmol) and cesium carbonate (13.0 g, 40.0 mmol) were placed in a reaction vessel, and then N,N-dimethylformamide (40 ml) and methyl iodide (2.5 ml) were added thereto. The resulting mixture was stirred at room temperature for 5 hours. The reaction solution was filtered through celite and washed with ethyl acetate (300 ml). The filtrate was sequentially washed with water (100 ml) and a saturated aqueous sodium chloride solution (200 ml). Then, the filtrate was dried over anhydrous sodium sulfate, and concentrated under reduced pressure to yield 2-methoxy-4-methylbenzoic acid methyl ester (1.4 g) as a pale yellow oily material.

Physicochemical properties of 2-methoxy-4-methylbenzoic acid methyl ester

Molecular weight: 180.
ESI (LC/MS positive mode): m/z=181 (M+H$^+$).
Chemical shift value δ in $^1$H-NMR (400 MHz, in dimethylsulfoxide d-6): 2.35 (3H, s), 3.75 (3H, s), 3.80 (3H, s), 6.83 (1H, dd, J=4 Hz, 8 Hz), 6.97 (1H, d, J=4 Hz), 7.56 (1H, d, J=8 Hz).

Step 2: Preparation of 5-iodo-2-methoxy-4-methylbenzoic acid methyl ester

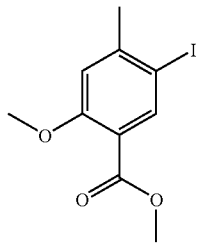

A methanol solution (28 ml) of 2-methoxy-4-methylbenzoic acid methyl ester (1.2 g, 7.0 mmol) obtained in Step 1 above, silver trifluoromethanesulfonate (2.0 g, 7.8 mmol), and iodine (2.0 g, 7.8 mmol) was stirred at room temperature for 1.5 hour. The reaction solution was concentrated under reduced pressure. The resulting pale yellow solid was separated by filtration, and washed with ethyl acetate (300 ml). The washing solution was sequentially washed with 5% aqueous sodium thiosulfate solution (100 ml), and a saturated aqueous sodium chloride solution (100 ml). Then, the solution was dried over anhydrous sodium sulfate and concentrated under reduced pressure. The resulting crude product was purified by silica gel column chromatography (developing solvent: n-hexane:ethyl acetate=2:1) to yield 5-iodo-2-methoxy-4-methylbenzoic acid methyl ester (1.9 g) as a pale yellow solid material.

Physicochemical properties of 5-iodo-2-methoxy-4-methylbenzoic acid methyl ester Molecular weight: 306.
ESI (LC/MS positive mode): m/z=307 (M+H$^+$).
Chemical shift value δ in $^1$H-NMR (400 MHz, in dimethylsulfoxide d-6): 2.40 (3H, s), 3.76 (3H, s), 3.81 (3H, s), 7.19 (1H, s), 8.00 (1H, s).

Step 3: Preparation of 2-methoxy-4-methyl-5-(4,4,5,5-tetramethyl[1,3,2]dioxaborolan-2-yl)benzoic acid methyl ester

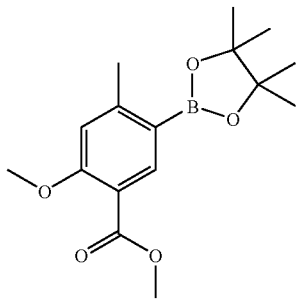

5-Iodo-2-methoxy-4-methylbenzoic acid methyl ester (1.2 g, 4.0 mmol) obtained in Step 2 above was combined with potassium acetate (118 g, 12.0 mmol), bis(pinacolato)diborane (1.2 g, 4.8 mmol), and palladium dichloride-diphenylphosphinoferrocene dichloromethane complex (163 mg, 0.2 mmol), and then anhydrous dimethylsulfoxide (20 ml) was added thereto. The resulting mixture was stirred at 80° C. for 18 hours. The reaction solution was diluted with ethyl acetate (200 ml), and sequentially washed with water (100 ml) twice, and with 1N hydrochloric acid (100 ml), water (100 ml), a saturated aqueous sodium bicarbonate solution (100 ml), water (100 ml), and a saturated aqueous sodium chloride solution (100 ml). The ethyl acetate solution was dried over anhydrous sodium sulfate (30 g). After filtration, the filtrate was concentrated under reduced pressure. The resulting crude product was purified by silica gel column chromatography (developing solvent: n-hexane:ethyl acetate=4:1 to 2:1) to yield 2-methoxy-4-methyl-5-(4,4,5,5-tetramethyl[1,3,2]dioxaborolan-2-yl)benzoic acid methyl ester (1.3 g) as a white solid material.

Physicochemical properties of 2-methoxy-4-methyl-5-(4,4,5,5-tetramethyl[1,3,2]dioxaborolan-2-yl)benzoic acid methyl ester Molecular weight: 306.
ESI (LC/MS positive mode): m/z=307 (M+H$^+$).
Chemical shift value δ in $^1$H-NMR (400 MHz, in dimethylsulfoxide d-6): 1.29 (12H, s), 2.50 (3H, s), 3.76 (3H, s), 3.83 (3H, s), 6.97 (1H, s), 7.98 (1H, s).

Step 4: Preparation of 5-(2-amino-6-chloropyrimidin-4-yl)-2-methoxy-4-methylbenzoic acid methyl ester (Compound 1-2)

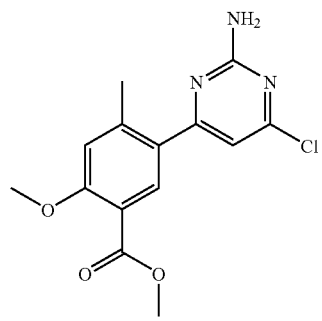 [SMILES: COC(=O)c1cc(-c2cc(Cl)nc(N)n2)c(C)cc1OC]

2-Amino-4,6-dichloropyrimidine (246 mg, 1.5 mmol), palladium acetate (17 mg, 0.07 mmol), triphenylphosphine (59 mg, 0.22 mmol), sodium bicarbonate (168 mg, 2.0 mmol), 1,2-dimethoxyethane (2.5 ml), and water (1.0 ml) were placed in a reaction vessel. The resulting mixture was stirred at 80° C. for 10 minutes. A 1,2-dimethoxyethane (2.5 ml) solution of 2-methoxy-4-methyl-5-(4,4,5,5-tetramethyl[1,3,2]dioxaborolan-2-yl)benzoic acid methyl ester (294 mg, 1.0 mmol) obtained in Step 3 above was added dropwise to the mixture. The resulting mixture was stirred at 80° C. for 14 hours. The reaction solution was diluted with ethyl acetate (100 ml), and washed three times with water (40 ml), and then with a saturated aqueous sodium chloride solution (40 ml). The washed ethyl acetate solution was dried over anhydrous sodium sulfate (10 g). After filtration, the filtrate was concentrated under reduced pressure. The resulting crude product was purified by silica gel column chromatography (developing solvent: n-hexane:ethyl acetate=2:1) to yield 5-(2-amino-6-chloropyrimidin-4-yl)-2-methoxy-4-methylbenzoic acid methyl ester (Compound 1-2) (164 mg) as a yellow solid material.

Physicochemical properties of 5-(2-amino-6-chloro-pyrimidin-4-yl)-2-methoxy-4-methylbenzoic acid methyl ester Molecular weight: 307.
ESI (LC/MS positive mode): m/z=308 (M+H$^+$).
Chemical shift value δ in $^1$H-NMR (400 MHz, in dimethylsulfoxide d-6): 2.47 (3H, s), 3.78 (3H, s), 3.87 (3H, s), 6.82 (1H, s), 7.10 (1H, s), 7.17 (2H, brs), 7.80 (1H, s).

Example 1-3

Production of 5-(2-amino-6-chloropyrimidin-4-yl)-2-ethoxy-4-methylbenzoic acid methyl ester (Compound 1-3)

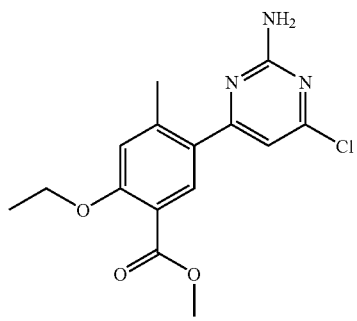 [SMILES: CCOc1cc(C)c(-c2cc(Cl)nc(N)n2)cc1C(=O)OC]

Step 1: Preparation of 2-hydroxy-4-methylbenzoic acid methyl ester

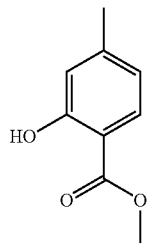

Commercially available 2-hydroxy-4-methylbenzoic acid (1.0 g, 7.0 mmol) and potassium bicarbonate (841 mg, 8.4 mmol) were placed in a reaction vessel, and then N,N-dimethylformamide (10 ml) and methyl iodide (0.65 ml, 10.5 mmol) were added thereto. The resulting mixture was stirred at 40° C. for 4 hours. The reaction solution was diluted with ethyl acetate (200 ml), and sequentially washed with water (70 ml), with a saturated aqueous sodium bicarbonate solution (70 ml), twice with water (70 ml), and with a saturated aqueous sodium chloride solution (70 ml). The ethyl acetate solution was dried over anhydrous sodium sulfate, and then concentrated under reduced pressure to yield 2-hydroxy-4-methylbenzoic acid methyl ester (1.1 g) as a pale yellow oily material.

Physicochemical properties of 2-hydroxy-4-methylbenzoic acid methyl ester

Molecular weight: 166.
ESI (LC/MS positive mode): m/z=167 (M+H$^+$).
Chemical shift value δ in $^1$H-NMR (400 MHz, in dimethylsulfoxide d-6): 2.30 (3H, s), 3.88 (3H, s), 6.77 (1H, dd, J=4 Hz, 8 Hz), 6.81 (1H, d, J=4 Hz), 7.67 (1H, d, J=8 Hz), 10.49 (1H, s).

Step 2: Preparation of 2-ethoxy-4-methylbenzoic acid methyl ester

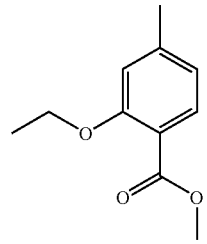

2-Hydroxy-4-methylbenzoic acid methyl ester (1.1 g, 7.0 mmol) obtained in Step 1 above and potassium carbonate (1.5 g, 10.5 mmol) were combined with N,N-dimethylformamide (14 ml) and ethyl iodide (0.6 ml, 8.4 mmol). The resulting mixture was stirred at 80° C. for 16 hours. The reaction solution was diluted with ethyl acetate (200 ml), and washed three times with water (70 ml), and with a saturated aqueous sodium chloride solution (70 ml). Then, the solution was dried over anhydrous sodium sulfate, and concentrated under reduced pressure to yield 2-hydroxy-4-methylbenzoic acid methyl ester (1.1 g) as a pale yellow oily material.

Physicochemical properties of 2-ethoxy-4-methylbenzoic acid methyl ester

Molecular weight: 194.
ESI (LC/MS positive mode): m/z=195 (M+H$^+$).
Chemical shift value δ in $^1$H-NMR (400 MHz, in dimethylsulfoxide d-6): 1.32 (3H, t, J=8 Hz), 2.33 (3H, s), 3.75 (3H, s), 4.06 (2H, q, J=8 Hz), 6.81 (1H, dd, J=4 Hz, 8 Hz), 6.95 (1H, d, J=4 Hz), 7.55 (1H, d, J=8 Hz).

Step 3: Preparation of 5-iodo-2-ethoxy-4-methylbenzoic acid methyl ester

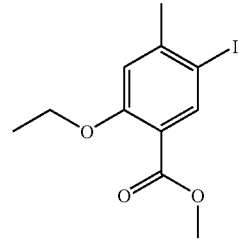

A methanol solution (12 ml) of 2-ethoxy-4-methylbenzoic acid methyl ester (1.1 g, 5.9 mmol) obtained in Step 2 above, silver trifluoromethanesulfonate (1.7 g, 6.6 mmol), and iodine (1.7 g, 6.6 mmol) was stirred at room temperature for 2.5 hours. The reaction solution was concentrated under reduced pressure. Ethyl acetate (100 ml) was added to the resulting residue. Insoluble material was separated by filtration, and washed with ethyl acetate (100 ml). The filtrate and washing solution were combined together, and sequentially washed twice with an 5% aqueous sodium thiosulfate solution (100 ml), and with a saturated aqueous sodium chloride solution (100 ml). Then, the washed solution was dried over anhydrous sodium sulfate. After the anhydrous sodium sulfate was removed by filtration, the solution was concentrated under reduced pressure. The resulting residue was purified by silica gel column chromatography (developing solvent: n-hexane:ethyl acetate=10:1) to yield 5-iodo-2-ethoxy-4-methylbenzoic acid methyl ester (1.8 g) as a pale yellow oily material.

Physicochemical properties of 5-iodo-2-ethoxy-4-methylbenzoic acid methyl ester

Molecular weight: 320.
ESI (LC/MS positive mode): m/z=321 (M+H$^+$).
Chemical shift value δ in $^1$H-NMR (400 MHz, in dimethylsulfoxide d-6): 1.30 (3H, t, J=8 Hz), 2.39 (3H, s), 3.77 (3H, s), 4.08 (2H, q, J=8 Hz), 7.16 (1H, s), 8.00 (1H, s).

Step 4: Preparation of 2-ethoxy-4-methyl-5-(4,4,5,5-tetramethyl[1,3,2]dioxaborolan-2-yl)benzoic acid methyl ester

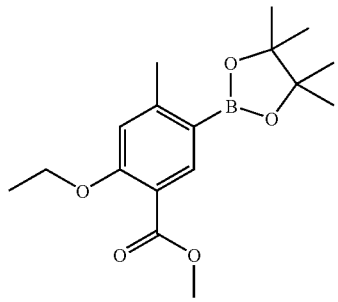 [SMILES: CCOc1cc(C)c(B2OC(C)(C)C(C)(C)O2)cc1C(=O)OC]

5-Iodo-2-ethoxy-4-methylbenzoic acid methyl ester (320 mg, 1.0 mmol) obtained in Step 3 above was combined with potassium acetate (294 mg, 3.0 mmol), bis(pinacolato)diborane (305 mg, 1.2 mmol), and palladium dichloride-diphenylphosphinoferrocene dichloromethane complex (41 mg, 0.05 mmol), and then anhydrous dimethylsulfoxide (5 ml) was added thereto. The resulting mixture was stirred at 80° C. for 16 hours. The reaction solution was diluted with ethyl acetate (100 ml), and sequentially washed twice with water (60 ml), with 1N hydrochloric acid (60 ml), water (60 ml), a saturated aqueous sodium bicarbonate solution (60 ml), water (60 ml), and a saturated aqueous sodium chloride solution (60 ml). The washed ethyl acetate solution was dried over anhydrous sodium sulfate (20 g). After filtration, the filtrate was concentrated under reduced pressure. The resulting residue was purified by silica gel column chromatography (developing solvent: n-hexane:ethyl acetate=2:1) to yield 2-ethoxy-4-methyl-5-(4,4,5,5-tetramethyl[1,3,2]dioxaborolan-2-yl)benzoic acid methyl ester (320 mg) as a white solid material.

Physicochemical properties of 2-methoxy-4-methyl-5-(4,4,5,5-tetramethyl[1,3,2]dioxaborolan-2-yl)benzoic acid methyl ester Molecular weight: 320.
ESI (LC/MS positive mode): m/z=321 (M+H$^+$).
Chemical shift value δ in $^1$H-NMR (400 MHz, in dimethylsulfoxide d-6): 1.29 (12H, s), 1.33 (3H, t, J=8 Hz), 2.51 (3H, s), 3.76 (3H, s), 4.11 (2H, q, J=8 Hz), 6.95 (1H, s), 7.97 (1H, s).

Step 5: Preparation of 5-(2-amino-6-chloropyrimidin-4-yl)-2-ethoxy-4-methylbenzoic acid methyl ester (Compound 1-3)

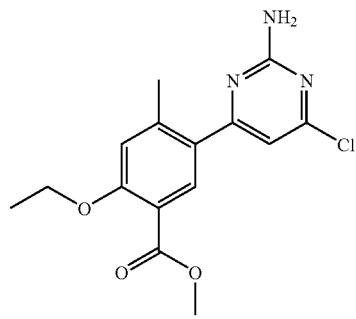 [SMILES: CCOc1cc(C)c(-c2cc(Cl)nc(N)n2)cc1C(=O)OC]

2-Amino-4,6-dichloropyrimidine (246 mg, 1.5 mmol), bis(triphenylphosphine) palladium dichloride (53 mg, 0.07 mmol), sodium bicarbonate (252 mg, 3.0 mmol), 1,4-dioxane (2.5 ml), and water (1.5 ml) were placed in a reaction vessel. The resulting mixture was stirred at 80° C. for 10 minutes. To this mixture, 2-Ethoxy-4-methyl-5-(4,4,5,5-tetramethyl[1,3,2]dioxaborolan-2-yl)benzoic acid methyl ester (320 mg, 1.0 mmol) obtained in Step 4 above was added dropwise after dissolving in 1,4-dioxane (2.5 ml). The resulting mixture was stirred at 80° C. for 20 hours. The reaction solution was diluted with ethyl acetate (100 ml), and washed three times with water (40 ml), and then with a saturated aqueous sodium chloride solution (40 ml). The washed ethyl acetate solution was dried over anhydrous sodium sulfate (10 g). After filtration, the filtrate was concentrated under reduced pressure. The resulting crude product was purified by silica gel column chromatography (developing solvent: n-hexane:ethyl acetate=2:1) to yield 5-(2-amino-6-chloropyrimidin-4-yl)-2-ethoxy-4-methylbenzoic acid methyl ester (Compound 1-3) (210 mg) as a yellow solid material.

Physicochemical properties of 5-(2-amino-6-chloropyrimidin-4-yl)-2-ethoxy-4-methylbenzoic acid methyl ester Molecular weight: 321.
ESI (LC/MS positive mode): m/z=324, 322 (M+H$^+$).
Chemical shift value δ in $^1$H-NMR (400 MHz, in dimethylsulfoxide d-6): 1.35 (3H, t, J=8 Hz), 2.45 (3H, s), 3.78 (3H, s), 4.15 (2H, q, J=8 Hz), 6.81 (1H, s), 7.08 (1H, s), 7.16 (1H, brs), 7.79 (1H, s).

Example 1-4

Production of 5-(2-amino-6-chloropyrimidin-4-yl)-2,4-dimethylbenzoic acid methyl ester (Compound 1-4)

Step 1: Preparation of 5-iodo-2,4-dimethylbenzoic acid methyl ester

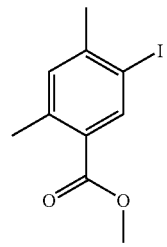

5-Iodo-2,4-dimethylbenzoic acid (2.78 g, 10.1 mmol) obtained in Step 1 of Example 1-1 was placed in a reaction vessel, and then methanol (20 ml) was added thereto. The resulting mixture was cooled to 0° C. Thionyl chloride (2.2 ml, 30.1 mmol) was added dropwise to the mixture over about 10 minutes. The resulting mixture was stirred under reflux for 3 hours. The reaction solution was distilled off under reduced pressure. A saturated aqueous sodium bicarbonate solution was added to the obtained residue. The solution was extracted twice with ethyl acetate. The organic layers were combined together, and washed with a saturated aqueous sodium chloride solution. Then, the organic solution was dried over anhydrous magnesium sulfate. After removal of anhydrous magnesium sulfate by filtration, the liquid was washed with ethyl acetate. The filtrate and washing solution were combined together, and ethyl acetate was distilled off under reduced pressure to yield 2.85 g (97%) of 5-iodo-2,4-dimethylbenzoic acid methyl ester.

Physicochemical properties of
5-iodo-2,4-dimethylbenzoic acid methyl ester

Molecular weight: 290.

Chemical shift value δ in $^1$H-NMR (400 MHz, in chloroform-d): 2.45 (3H, s), 2.51 (3H, s), 3.87 (3H, s), 7.11 (1H, s), 8.33 (1H, s).

Step 2: Preparation of 2,4-dimethyl-5-(4,4,5,5-tetramethyl[1,3,2]dioxaborolan-2-yl)benzoic acid methyl ester

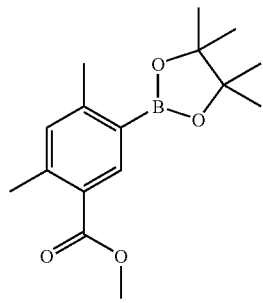

By using the same procedure of the production method as described in Step 3 of Example 1-1, 2,4-dimethyl-5-(4,4,5,5-tetramethyl[1,3,2]dioxaborolan-2-yl)benzoic acid methyl ester was obtained from 5-iodo-2,4-dimethylbenzoic acid methyl ester obtained in Step 1 above and bis(pinacolato)diborane.

Physicochemical properties of 2,4-dimethyl-5-(4,4,5,5-tetramethyl[1,3,2]dioxaborolan-2-yl)benzoic acid methyl ester Molecular weight: 290.
ESI (LC/MS positive mode): m/z=291 (M+H$^+$).

Chemical shift value δ in $^1$H-NMR (400 MHz, in chloroform-d): 1.34 (12H, s), 2.52 (3H, s), 2.57 (3H, s), 3.87 (3H, s), 7.04 (1H, s), 8.29 (1H, s).

Step 3: Preparation of 5-(2-amino-6-chloropyrimidin-4-yl)-2,4-dimethylbenzoic acid methyl ester (Compound 1-4)

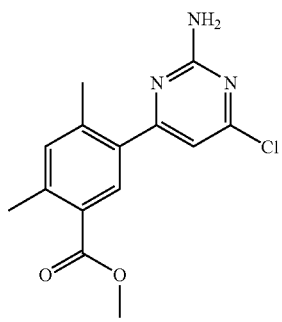 [SMILES: COC(=O)c1cc(-c2cc(Cl)nc(N)n2)c(C)cc1C]

By using the same procedure of the production method as described in Step 4 of Example 1-1, 5-(2-amino-6-chloropyrimidin-4-yl)-2,4-dimethylbenzoic acid methyl ester (Compound 1-4) was obtained from 2,4-dimethyl-5-(4,4,5,5-tetramethyl[1,3,2]dioxaborolan-2-yl)benzoic acid methyl ester obtained in Step 2 above and 2-amino-4,6-dichloropyrimidine.

Physicochemical properties of 5-(2-amino-6-chloropyrimidin-4-yl)-2,4-dimethylbenzoic acid methyl ester Molecular weight: 291.
ESI (LC/MS positive mode): m/z=292, 294 (M+H$^+$).

Chemical shift value δ in $^1$H-NMR (400 MHz, in chloroform-d): 2.43 (3H, s), 2.62 (3H, s), 3.89 (3H, s), 5.26 (2H, brs), 6.79 (1H, s), 7.17 (1H, s), 7.99 (1H, s).

Example 1-5

Production of 4-[5-(tert-butyldimethylsilanyloxy)-2-methylphenyl]-6-chloropyrimidin-2-ylamine (Compound 1-5)

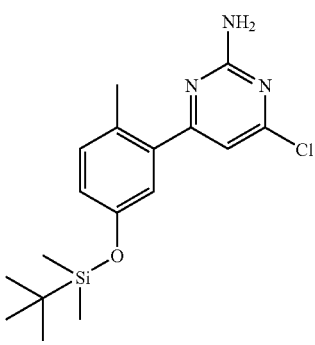 [SMILES: Cc1ccc(O[Si](C)(C)C(C)(C)C)cc1-c1cc(Cl)nc(N)n1]

Step 1: Preparation of 4-benzyloxy-2-iodo-1-methybenzene

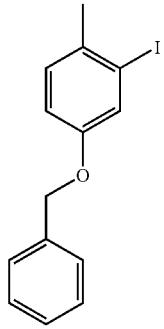 [SMILES: Cc1ccc(OCc2ccccc2)cc1I]

5-Benzyloxy-2-methylphenylamine (20.8 g, 97.5 mmol) was placed in a reaction vessel, and then acetic acid (385 ml) and concentrated hydrochloric acid (97 ml) were added thereto. The resulting mixture was cooled to −5° C. An aqueous sodium nitrite solution (7.73 g, 112.0 mmol) was added dropwise to the mixture over 20 minutes. The resulting mixture was stirred at −5° C. for 30 minutes to prepare the diazonium salt.

To another reaction vessel, potassium iodide (32.4 g, 195.0 mmol) and iodine (6.45 g, 50.8 mmol) were added, and then water (323 ml) was added thereto. After the resulting mixture was stirred at room temperature for 10 minutes, the previously prepared diazonium salt was added dropwise thereto over 40 minutes. The mixture was stirred at room temperature for two hours. Then, the reaction solution was diluted with water (1000 ml), and extracted with dichloromethane (500 ml). The aqueous layer was washed twice with dichloromethane (500 ml), and the organic layers were combined together. The organic solution was then sequentially washed twice with 10% aqueous sodium thiosulfate solution (230 ml), once with 1N aqueous sodium hydroxide solution (665 ml), and once with a saturated aqueous sodium chloride solution (700 ml). The dichloromethane solution was dried over anhydrous sodium sulfate. After filtration, the filtrate was concentrated under reduced pressure to yield 4-benzyloxy-2-iodo-1-methybenzene (24.9 g, 79%) as a crude solid product.

Physicochemical properties of: 4-benzyloxy-2-iodo-1-methybenzene

Molecular weight: 324.

Chemical shift value δ in $^1$H-NMR (400 MHz, in chloroform-d): 2.36 (3H, s), 5.01 (2H, s), 6.87 (1H, dd, J=2.7 Hz, 8.5 Hz), 7.11 (1H, d, J=8.5 Hz), 7.29-7.42 (5H, m), 7.45 (1H, d, J=2.7 Hz).

Step 2: Preparation of 2-(5-benzyloxy-2-methylphenyl)-5,5-dimethyl-[1,3,2]dioxaborinane

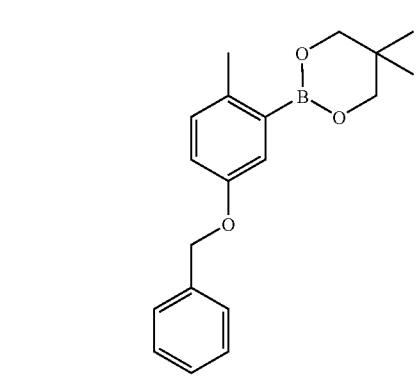 [SMILES: Cc1ccc(OCc2ccccc2)cc1B1OCC(C)(C)CO1]

The crude product containing 4-benzyloxy-2-iodo-1-methybenzene (32.9 g, 101.5 mmol) obtained in Step 1 above and triisopropyl borate (28.1 ml, 121.8 mmol) were placed in a reaction vessel, and then tetrahydrofuran (43 ml) and toluene (170 ml) were added thereto. The resulting mixture was cooled to −78° C., and n-butyllithium (1.6N; n-hexane solution, 76.2 ml, 121.9 mmol) was added dropwise thereto over 30 minutes. The resulting reaction solution was stirred at −78° C. for 30 minutes. After the solution was warmed to 0° C., neopentylglycol (12.7 g, 121.9 mmol) was added thereto and stirred at room temperature for 16 hours. The reaction solution was diluted with dichloromethane (1200 ml), and sequentially washed with a saturated aqueous ammonium chloride solution (1200 ml) and water (1200 ml). The solution was then dried over anhydrous magnesium sulfate. After filtration, the filtrate was concentrated under reduced pressure to yield 2-(5-benzyloxy-2-methylphenyl)-5,5-dimethyl-[1,3,2]dioxaborinane (41.5 g) as a crude product.

Step 3: Preparation of 4-(5-benzyloxy-2-methylphenyl)-6-chloropyrimidin-2-ylamine

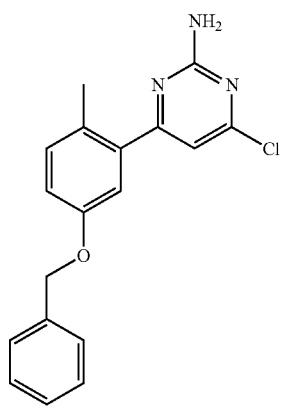 [SMILES: Cc1ccc(OCc2ccccc2)cc1-c1cc(Cl)nc(N)n1]

2-(5-Benzyloxy-2-methylphenyl)-5,5-dimethyl[1,3,2]dioxaborinane (41.5 g) obtained in Step 2 above, 2-amino-4,6-dichloropyrimidine (13.8 g, 84.2 mmol), and dichloroditriphenylphosphine palladium (5.0 g, 7.12 mmol) were placed in a reaction vessel, and then dimethoxyethane (800 ml) and 2N aqueous sodium carbonate solution (63.1 ml, 126.2 mmol) were sequentially added thereto. The resulting mixture was stirred at 85° C. for 4 hours. After cooling to room temperature, the reaction solution was diluted with ethyl acetate (1000 ml), and washed with water (600 ml) and then with a saturated aqueous sodium chloride solution (60 ml). The ethyl acetate solution was dried over anhydrous magnesium sulfate. After filtration, the filtrate was concentrated under reduced pressure. The resulting crude product was purified by silica gel column chromatography (developing solvent: n-hexane:ethyl acetate=6:1 to 3:1) to yield 4-(5-benzyloxy-2-methylphenyl)-6-chloropyrimidin-2-ylamine (10.84 g, 40%) as a pale yellow solid material.

Physicochemical properties of 4-(5-benzyloxy-2-methylphenyl)-6-chloropyrimidin-2-ylamine Molecular weight: 325.
ESI (LC/MS positive mode): m/z=326, 328 (M+H$^+$).

Step 4: Preparation of 3-(2-amino-6-chloropyrimidin-4-yl)-4-methylphenol

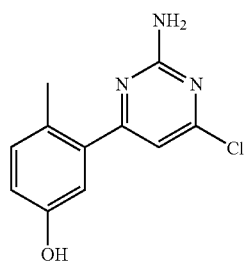 [SMILES: Cc1ccc(O)cc1-c1cc(Cl)nc(N)n1]

4-(5-Benzyloxy-2-methylphenyl)-6-chloropyrimidin-2-ylamine (12.5 g, 38.4 mmol) obtained in Step 3 above was placed in a reaction vessel, and then dichloromethane (500 ml) was added thereto. The resulting solution was cooled to 0° C. Then, a dichloromethane solution of 1.0 M trichloroborane was added dropwise over 30 minutes. The mixture was stirred at 0° C. for 1 hour, and diluted with dichloromethane (1500 ml). A saturated aqueous sodium bicarbonate solution (2000 ml) was added, and the mixture was warmed to room temperature. The organic layer was separated, and then sequentially washed with water (1500 ml) and a saturated aqueous sodium chloride solution (1000 ml). The aqueous layer was extracted with ethyl acetate (3000 ml), and the ethyl acetate solution was sequentially washed with water (1500 ml) and a saturated aqueous sodium chloride solution (1000 ml). The washed organic layers were combined together, and dried over anhydrous magnesium sulfate. After filtration, the filtrate was concentrated under reduced pressure. The resulting crude product was purified by silica gel column chromatography (developing solvent: n-hexane:ethyl acetate=2:1) to yield 3-(2-amino-6-chloropyrimidin-4-yl)-4-methylphenol (6.45 g, 71%) as a white solid material.

Physicochemical properties of 3-(2-amino-6-chloropyrimidin-4-yl)-4-methylphenol

Molecular weight: 235.
ESI (LC/MS positive mode): m/z=236, 238 (M+H$^+$).
Chemical shift value δ in $^1$H-NMR (400 MHz, in dimethylsulfoxide d-6): 2.28 (3H, s), 5.87 (2H, brs), 6.68 (1H, s), 6.81 (1H, dd, J=2.7 Hz, 8.3 Hz), 6.86 (1H, d, J=2.7 Hz), 7.06 (1H, d, J=8.3 Hz), 8.84 (1H, s).

Step 5: Preparation of 4-[5-(tert-butyldimethylsilanyloxy)-2-methylphenyl]-6-chloropyrimidin-2-ylamine (Compound 1-5)

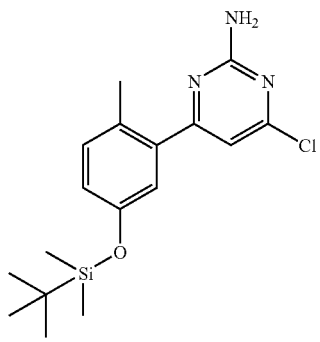 [SMILES: Cc1ccc(O[Si](C)(C)C(C)(C)C)cc1-c1cc(Cl)nc(N)n1]

3-(2-amino-6-chloropyrimidin-4-yl)-4-methylphenol (2.12 g, 9.00 mmol) obtained in Step 4 above was placed in a reaction vessel, and then dichloromethane (60 ml) was added thereto. The mixture was cooled to 0° C. 2,6-Lutidine (1.25 ml, 10.7 mmol) and tert-butyldimethylsilyl trifluoromethanesulfonate (2.27 ml, 9.88 mmol) were sequentially added to the solution. The mixture was stirred at 0° C. for 1 hour and then at room temperature for 30 minutes. The resulting reaction solution was diluted with dichloromethane (150 ml), and sequentially washed with a saturated aqueous sodium bicarbonate solution (150 ml), water (150 ml), and a saturated aqueous sodium chloride solution (150 ml). The dichloromethane solution was dried over anhydrous sodium sulfate. After filtration, the filtrate was concentrated under reduced pressure. The resulting crude product was purified by silica gel column chromatography (developing solvent: n-hexane:ethyl acetate=9:1 to 6:1) to yield 4-[5-(tert-butyldimethylsilanyloxy)-2-methylphenyl]-6-chloropyrimidin-2-ylamine (Compound 1-5) (2.41 g, 77%).

Physicochemical properties of 4-[5-(tert-butyldimethylsilanyloxy)-2-methylphenyl]-6-chloropyrimidin-2-ylamine Molecular weight: 349.
ESI (LC/MS positive mode): m/z=352, 350 (M+H$^+$).

Example 2-1

Production of 4-amino-20,22-dimethyl-7-thia-3,5,11,17-tetraazatricyclo[17.3.1.1$^{2,6}$]tetracosa-1(22),2(24),3,5,19(23),20-hexaene-10,18-dione (Compound 1)

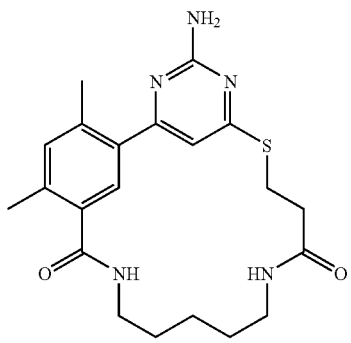

Step 1: Preparation of 5-[2-amino-6-(2-carboxyethylsulfanyl)pyrimidin-4-yl]-2,4-dimethylbenzoic acid tert-butyl ester

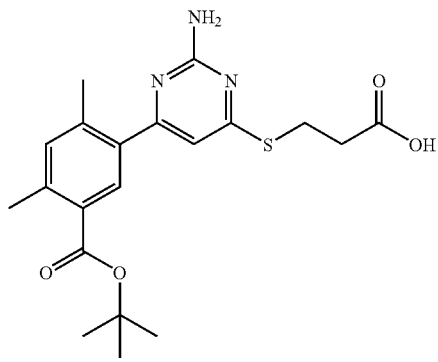 [SMILES: Cc1cc(C)c(-c2cc(SCCC(=O)O)nc(N)n2)cc1C(=O)OC(C)(C)C]

5-(2-Amino-6-chloropyrimidin-4-yl)-2,4-dimethylbenzoic acid tert-butyl ester (197 mg, 0.6 mmol) obtained in Example 1-1 and cesium carbonate (1.9 g, 5.9 mmol) were placed in a reaction vessel, and then N,N-dimethylformamide (3.0 ml) and 3-mercaptopropionic acid (0.5 ml, 5.9 mmol) were added thereto. The resulting mixture was stirred at 80° C. for 2 hours. The reaction solution was acidified using 2N aqueous potassium hydrogen sulfate solution, and the resulting solid material was separated by filtration. The separated solid material was washed with water, and then dried under reduced pressure to yield 5-[2-amino-6-(2-carboxylethylsulfanyl)pyrimidin-4-yl]-2,4-dimethylbenzoic acid tert-butyl ester (178 mg) as a white solid material.

Physicochemical properties of 5-[2-amino-6-(2-carboxylethylsulfanyl)pyrimidin-4-yl]-2,4-dimethylbenzoic acid tert-butyl ester Molecular weight: 403.
ESI (LC/MS positive mode): m/z=404 (M+H$^+$).
Chemical shift value δ in $^1$H-NMR (400 MHz, in dimethylsulfoxide d-6): 1.53 (9H, s), 2.35 (3H, s), 2.49 (3H, s), 2.67 (2H, t, J=6 Hz), 3.28 (2H, t, J=6 Hz), 6.57 (1H, s), 6.77 (2H, brs), 7.21 (1H, s), 7.72 (1H, s).

Step 2: Preparation of 5-{2-amino-6-[2-(5-tert-butoxycarbonylaminopentylcarbamoyl)ethylsulfanyl]pyrimidin-4-yl}-2,4-dimethylbenzoic acid tert-butyl ester 5-[2-Amino-6-(2-carboxylethylsulfanyl)pyrimidin-4-yl]-2,4-dimethylbenzoic acid tert-butyl ester (84 mg, 0.2 mmol) obtained in Step 1 above, 5-aminopentylcarbamic acid tert-butyl ester (64 mg, 0.32 mmol), and N-hydroxybenzotriazole (57 mg, 0.42 mmol) were placed in a reaction vessel, and then N,N-dimethylformamide (3.0 ml) was added thereto. 1-Ethyl-3-(3'-dimethylaminopropyl)carbodiimide hydrochloride (121 mg, 0.63 mmol) and diisopropylethylamine (0.073 ml, 0.42 mmol) were added to the solution. The resulting reaction solution was stirred at room temperature for 12 hours. A saturated aqueous ammonium chloride solution was added to the reaction solution, and the mixture was extracted with ethyl acetate (100 ml). The ethyl acetate was sequentially washed with 1N hydrochloric acid (50 ml), water (50 ml), a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography (developing solvent: ethyl acetate) to yield 5-{2-amino-6-[2-(5-tert-butoxycarbonylaminopentylcarbamoyl)ethylsulfanyl]pyrimidin-4-yl}-2,4-dimethylbenzoic acid tert-butyl ester (113 mg) as a white solid material.

Physicochemical properties of 5-{2-amino-6-[2-(5-tert-butoxycarbonylaminopentylcarbamoyl)ethylsulfanyl]pyrimidin-4-yl}-2,4-dimethylbenzoic acid tert-butyl ester Molecular weight: 587.
ESI (LC/MS positive mode): m/z=588 (M+H$^+$).
Chemical shift value δ in $^1$H-NMR (400 MHz, in dimethylsulfoxide d-6): 1.19-1.26 (2H, m), 1.32-1.42 (4H, m) 1.36 (9H, s), 1.53 (9H, s), 2.35 (3H, s), 2.44-2.52 (2H, m), 2.49 (3H, s), 2.88 (2H, q, J=14 Hz), 3.02 (2H, q, J=12 Hz), 3.25-3.32 (2H, m), 6.57 (1H, s), 6.71 (2H, brs), 6.72-6.76 (1H, m), 7.21 (1H, s), 7.72 (1H, s), 7.78 (1H, t, J=6 Hz).

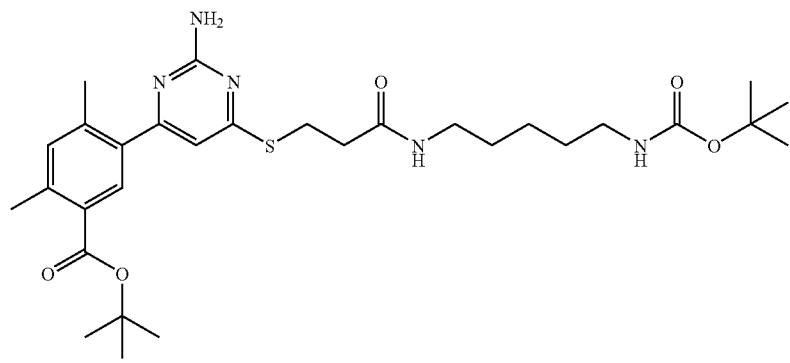 [SMILES: Cc1cc(C)c(-c2cc(SCCC(=O)NCCCCCNC(=O)OC(C)(C)C)nc(N)n2)cc1C(=O)OC(C)(C)C]

Step 3: Preparation of 4-amino-20,22-dimethyl-7-thia-3,5,11,17-tetraazatricyclo[17.3.1.1$^{2,6}$]tetracosa-1(22),2(24),3,5,19 (23),20-hexaene-10,18-dione (Compound 1)

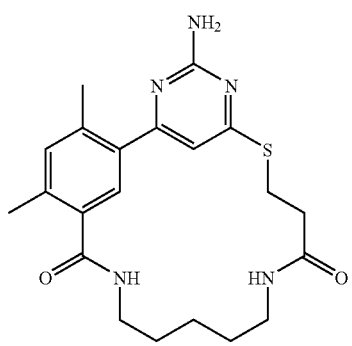

Anisole (0.051 ml, 0.47 mmol) and trifluoroacetic acid (1.0 ml) were added to a dichloromethane (3.2 ml) solution of 5-{2-amino-6-[2-(5-tert-butoxycarbonylaminopentylcarbamoyl)ethylsulfanyl]pyrimidin-4-yl}-2,4-dimethyl benzoic acid tert-butyl ester (111 mg, 0.19 mmol) obtained in Step 2 above. The reaction solution was stirred for 6 hours while gradually warming from 0° C. up to room temperature. The reaction solution was concentrated under reduced pressure, and then benzene (1.5 ml) was added to the residue. The resulting solution was concentrated under reduced pressure. This treatment was repeated three times, and then the obtained pale yellow oily material was dissolved in N,N-dimethylformamide (94.5 ml). N-Hydroxybenzotriazole (128 mg, 0.95 mmol), diisopropylethylamine (0.33 ml, 1.9 mmol), and 1-ethyl-3-(3'-dimethylaminopropyl)carbodiimide hydrochloride (362 mg, 1.9 mmol) were sequentially added to the solution. The resulting reaction solution was reacted at room temperature for 14 hours, and then concentrated under reduced pressure. The resulting residue was diluted with ethyl acetate (100 ml), and sequentially washed twice with water (50 ml), and with a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography with diol-silica gel (developing solvent: ethyl acetate to ethyl acetate:methanol=20:1) and amino-silica gel (ethyl acetate to ethyl acetate:methanol=15:1) to yield 4-amino-20,22-dimethyl-7-thia-3,5,11,17-tetraazatricyclo[17.3.1.1$^{2,6}$]tetracosa-1(22),2(24),3,5,19(23),20-hexaene-10,18-dione (Compound 1) (36 mg) as a white solid material.

Physicochemical properties of 4-amino-20,22-dimethyl-7-thia-3,5,11,17-tetraazatricyclo[17.3.1.1$^{2,6}$]tetracosa-1(22),2(24),3,5,19(23),20-hexaene-10,18-dione Molecular weight: 413.
ESI (LC/MS positive mode): m/z=414 (M+H$^+$).
Chemical shift value δ in $^1$H-NMR (400 MHz, in dimethylsulfoxide d-6): 1.36-1.43 (4H, m), 1.45-1.53 (2H, m), 2.34 (3H, s), 2.48 (3H, s), 2.52-2.57 (2H, m), 3.06-3.11 (2H, m), 3.13-3.19 (2H, m), 3.23-3.28 (2H, m), 6.67 (2H, brs) 6.79 (1H, s), 7.15 (1H, s), 7.48 (1H, s), 7.82 (1H, t, J=5.4 Hz), 8.17 (1H, t, J=5.4 Hz).

Example 2-2

Production of 4-amino-1820-dimethyl-7-thia-3,5,11,15-tetraazatricyclo[15.3.1.1$^{2,6}$]docosa-1(20),2(22),3,5,17(21)18-hexane-10,16-dione (Compound 2)

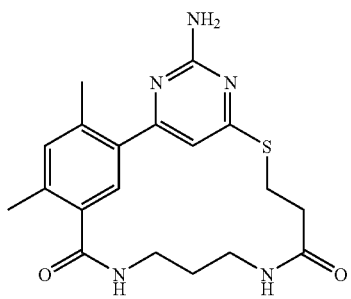 [SMILES: Cc1cc(C)c2cc1C(=O)NCCCNC(=O)CCSc1cc-2nc(N)n1]

Step 1: Preparation of 5-{2-amino-6-[2-(3-tert-butoxycarbonylaminopropylcarbamoyl)ethylsulfanyl]pyrimidin-4-yl}-2,4-dimethyl benzoic acid tert-butyl ester

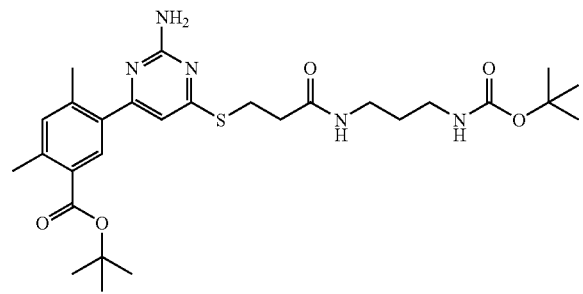

5-[2-Amino-6-(2-carboxylethylsulfanyl)pyrimidin-4-yl]-2,4-dimethyl benzoic acid tert-butyl ester (302 mg, 0.75 mmol) obtained in Step 1 of Example 2-1, 3-aminopropyl-carbamic acid tert-butyl ester (653 mg, 3.75 mmol), and N-hydroxybenzotriazole (507 mg, 3.75 mmol) were placed in a reaction vessel, and then N,N-dimethylformamide (7.5 ml) was added thereto. 1-Ethyl-3-(3'-dimethylaminopropyl)carbodiimide hydrochloride (833 mg, 4.34 mmol) and diisopropylethylamine (0.65 ml, 3.75 mmol) were added to the solution. The resulting reaction solution was stirred at room temperature for 6 hours. A saturated aqueous ammonium chloride solution was added to the reaction solution, and the mixture was extracted with ethyl acetate (100 ml). The ethyl acetate solution was washed with 1N hydrochloric acid (50 ml), water (50 ml), a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography (developing solvent: ethyl acetate) to yield 5-{2-amino-6-[2-(3-tert-butoxycarbonylaminopropylcarbamoyl)ethylsulfanyl]pyrimidin-4-yl}-2,4-dimethyl benzoic acid tert-butyl ester (296 mg) as a white solid material.

Physicochemical properties of 5-{2-amino-6-[2-(3-tert-butoxycarbonylaminopropylcarbamoyl)ethylsulfanyl]-pyrimidin-4-yl}-2,4-dimethyl benzoic acid tert-butyl ester Molecular weight: 559.
ESI (LC/MS positive mode): m/z=560 (M+H$^+$)

Step 2: Preparation of 4-amino-18,20-dimethyl-7-thia-3,5,11,15-tetraazatricyclo[15.3.1.1$^{2,6}$]docosa-1(20),2(22),3,5,17(21),18-hexane-10,16-dione (Compound 2)

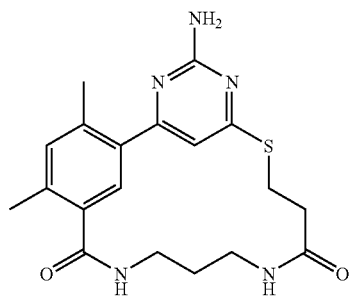 [SMILES: Cc1cc(C)c2cc1C(=O)NCCCNC(=O)CCSc1cc-2nc(N)n1]

Anisole (0.090 ml, 0.83 mmol) and trifluoroacetic acid (2.3 ml) were added to a dichloromethane (5.0 ml) solution of 5-{2-amino-6-[2-(3-tert-butoxycarbonylaminopropylcarbamoyl)ethylsulfanyl]pyrimidin-4-yl}-2,4-dimethyl benzoic acid tert-butyl ester (1185 mg, 0.33 mmol) obtained in Step 1 above. The reaction solution was stirred for 3 hours while gradually warming from 0° C. up to room temperature. The reaction solution was concentrated under reduced pressure, and benzene (1.5 ml) was added to the resulting residue. The mixture was concentrated under reduced pressure. This treatment was repeated three times, and then the obtained pale yellow oily material was dissolved by adding N,N-dimethylformamide (82 ml) and tetrahydrofuran (82 ml). N-Hydroxybenzotriazole (223 mg, 1.65 mmol), diisopropylethylamine (1.15 ml, 6.6 mmol), and 1-ethyl-3-(3'-dimethylaminopropyl)carbodiimide hydrochloride (632 mg, 3.3 mmol) were sequentially added to the mixture. The resulting mixture was reacted at room temperature for 13 hours. The reaction solution was concentrated under reduced pressure. The resulting residue was diluted with ethyl acetate (100 ml). The ethyl acetate solution was washed twice with water (50 ml), and with a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography with diol-silica gel (developing solvent: ethyl acetate to ethyl acetate:methanol=25:1) and amino-silica gel (developing solvent: ethyl acetate to ethyl acetate:methanol=25:1) to yield 4-amino-18,20-dimethyl-7-thia-3,5,11,15-tetraazatricyclo[15.3.1.1$^{2,6}$]docosa-1(20),2(22),3,5,17(21),18-hexane-10,16-dione (Compound 2) (27 mg) as a white solid material.

Physicochemical properties of 4-amino-18,20-dimethyl-7-thia-3,5,11,15-tetraazatricyclo[15.3.1.1$^{2,6}$]docosa-1(20),2(22),3,5,17(21),18-hexane-10,16-dione Molecular weight: 385.
ESI (LC/MS positive mode): m/z=386 (M+H$^+$).
Chemical shift value δ in $^1$H-NMR (400 MHz, in dimethylsulfoxide d-6): 1.67-1.74 (2H, m), 2.40 (3H, s), 2.52-2.59 (2H, m), 2.57 (3H, s), 3.18-3.25 (4H, m), 3.33-3.39 (2H, m), 6.64 (2H, brs), 6.96 (1H, s), 7.14 (1H, s), 7.71 (1H, s), 8.01 (1H, t, J=5.4 Hz), 8.20 (1H, t, J=5.4 Hz).

Example 2-3

Production of 4-amino-15,18,20-trimethyl-7-thia-3,5,11,15-tetraazatricyclo[15.3.1.1$^{2,6}$]docosa-1(20),2(22),3,5,17(21),18-hexane-10,16-dione (Compound 3)

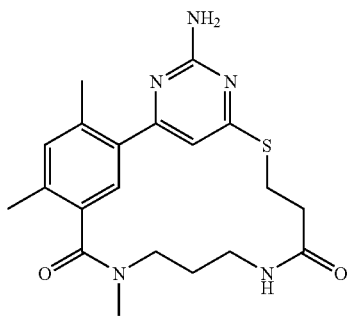 [SMILES: Cc1cc(C)c2cc1C(=O)N(C)CCCNC(=O)CCSc1cc-2nc(N)n1]

Step 1: Preparation of 5-(2-amino-6-{2-[3-(tert-butoxycarbonylmethylamino)propylcarbamoyl]ethylsulfanyl}pyrimidin-4-yl)-2,4-dimethyl benzoic acid tert-butyl ester

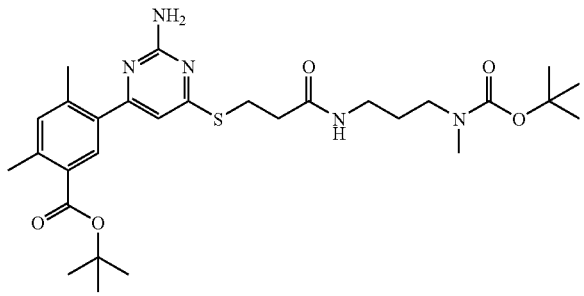 [SMILES: Cc1cc(C)c(-c2cc(SCCC(=O)NCCCN(C)C(=O)OC(C)(C)C)nc(N)n2)cc1C(=O)OC(C)(C)C]

5-[2-Amino-6-(2-carboxylethylsulfanyl)pyrimidin-4-yl]-2,4-dimethyl benzoic acid tert-butyl ester (178 mg, 0.44 mmol) obtained in Step 1 of Example 2-1, 3-aminomethylpropylcarbamic acid tert-butyl ester (125 mg, 0.66 mmol), and N-hydroxybenzotriazole (119 mg, 0.88 mmol) were placed in a reaction vessel, and then N,N-dimethylformamide (6.0 ml) was added thereto. 1-Ethyl-3-(3'-dimethylaminopropyl)carbodiimide hydrochloride (254 mg, 1.32 mmol) and diisopropylethylamine (0.15 ml, 0.88 mmol) were added to the mixture. The resulting mixture was stirred at room temperature for 2.5 hours. After a saturated aqueous ammonium chloride solution was added to the reaction solution, the mixture was extracted with ethyl acetate (100 ml). The ethyl acetate solution was washed with 1N hydrochloric acid (50 ml), water (50 ml), a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography (developing solvent: ethyl acetate) to yield 5-(2-amino-6-{2-[3-(tert-butoxycarbonylmethylamino)propylcarbamoyl]ethylsulfanyl}pyrimidin-4-yl)-2,4-dimethyl benzoic acid tert-butyl ester (227 mg) as a white solid material.

Physicochemical properties of 5-(2-amino-6-{2-[3-(tert-butoxycarbonylmethylamino)-propylcarbamoyl]ethylsulfanyl}-pyrimidin-4-yl)-2,4-dimethyl benzoic acid tert-butyl ester Molecular weight: 573.
ESI (LC/MS positive mode): m/z=574 (M+H$^+$).
Chemical shift value δ in $^1$H-NMR (400 MHz, in dimethylsulfoxide d-6): 1.37 (9H, s), 1.53 (9H, s), 1.54-1.60 (2H, m), 2.35 (3H, s), 2.49 (3H, s), 2.46-2.53 (2H, m), 2.75 (3H, s), 3.03 (2H, q, J=6 Hz), 3.14 (2H, t, J=8 Hz), 3.26-3.32 (2H, m), 6.56 (1H, s) 6.74 (2H, brs), 7.21 (1H, s), 7.72 (1H, s), 7.88 (1H, t, J=6 Hz).

Step 2: Preparation of 4-amino-15,18,20-trimethyl-7-thia-3,5,11,15-tetraazatricyclo[15.3.1.1$^{2,6}$]docosa-1(20),2(22),3,5,17(21),18-hexane-10,16-dione (Compound 3)

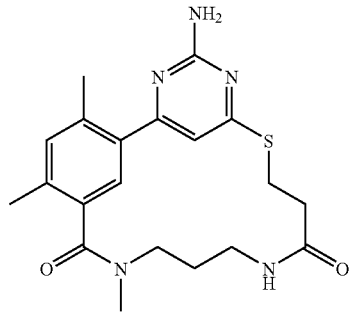 [SMILES: Cc1cc(C)c2cc1C(=O)N(C)CCCNC(=O)CCSc1cc-2nc(N)n1]

Anisole (0.085 ml, 0.75 mmol) and trifluoroacetic acid (2.5 ml) were added to a dichloromethane (5.0 ml) solution of 5-(2-amino-6-{2-[3-(tert-butoxycarbonylmethylamino)propylcarbamoyl]ethylsulfanyl}pyrimidin-4-yl)-2,4-dimethyl benzoic acid tert-butyl ester (172 mg, 0.30 mmol) obtained in Step 1 above. The reaction solution was stirred for 2.5 hours while gradually warming from 0° C. to room temperature. The reaction solution was concentrated under reduced pressure, and benzene (1.5 ml) was added to the resulting residue. The mixture was concentrated under reduced pressure. After this treatment was repeated three times, the obtained pale yellow oily material was dissolved by adding N,N-dimethylformamide (75.0 ml) and tetrahydrofuran (75.0 ml). N-Hydroxybenzotriazole (203 mg, 1.5 mmol), diisopropylethylamine (0.52 ml, 3.0 mmol), and 1-ethyl-3-(3'-dimethylaminopropyl)carbodiimide hydrochloride (575 mg, 3.0 mmol) were sequentially added to the mixture. The resulting mixture was stirred at room temperature for 14 hours. The reaction solution was concentrated under reduced pressure. The resulting residue was diluted with ethyl acetate (100 ml), and sequentially washed twice with water (50 ml), and with a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography with diol-silica gel (developing solvent: ethyl acetate to ethyl acetate:methanol=25:1) and amino-silica gel (developing solvent: ethyl acetate to ethyl acetate:methanol=25:1) to yield 4-amino-15,18,20-trimethyl-7-thia-3,5,11,15-tetraazatricyclo[15.3.1.1$^{2,6}$]docosa-1(20),2(22),3,5,17(21),18-hexane-10,16-dione (Compound 3) (29 mg) as a white solid material.

Physicochemical properties of 4-amino-15,18,20-trimethyl-7-thia-3,5,11,15-tetraazatricyclo[15.3.1.1$^{2,6}$]docosa-1(20),2(22),3,5,17(21),18-hexane-10,16-dione Molecular weight: 399.
ESI (LC/MS positive mode): m/z=400 (M+H$^+$).
Chemical shift value δ in $^1$H-NMR (500 MHz, at 140° C. in dimethylsulfoxide d-6): 1.72-1.78 (2H, m), 2.20 (3H, s), 2.43 (3H, s), 2.56 (2H, t, J=6 Hz), 2.93 (3H, s), 3.04-3.11 (2H, m), 3.16 (2H, t, J=6 Hz), 3.22-3.29 (2H, m), 6.06 (2H, brs) 6.49 (1H, s), 7.13 (1H, s), 7.22 (1H, s), 7.45-7.53 (1H, m).

Example 2-4

Production of 4-amino-18,20-dimethyl-7-thia-3,5,12,15-tetraazatricyclo[15.3.1.1$^{2,6}$]docosa-1(20),2(22),3,5,17(21),18-hexaene-11,16-dione (Compound 4)

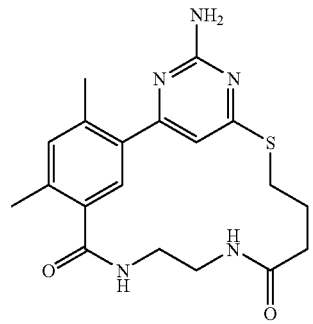 [SMILES: Cc1cc(C)c2cc1C(=O)NCCNC(=O)CCCSc1cc-2nc(N)n1]

Step 1: Preparation of 5-[2-amino-6-(3-carboxylpropylsulfanyl)pyrimidin-4-yl]-2,4-dimethylbenzoic acid tert-butyl ester

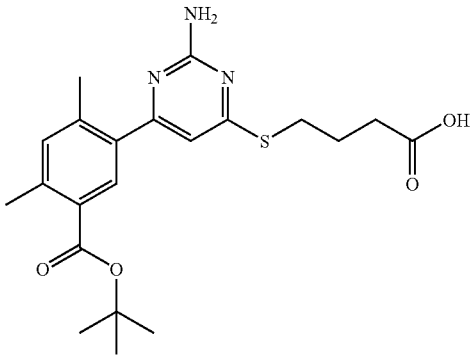 [SMILES: Cc1cc(C)c(-c2cc(SCCCC(=O)O)nc(N)n2)cc1C(=O)OC(C)(C)C]

4,4'-Dithiodibutylic acid (143 mg, 0.6 mmol) was placed in a reaction vessel, and then N,N-dimethylformamide (3.6 ml), water (0.4 ml), and tri(n-butyl)phosphine (0.25 ml, 1.0 mmol) were added thereto. The resulting mixture was stirred at room temperature for 1.5 hour. 5-(2-Amino-6-chloropyrimidin-4-yl)-2,4-dimethylbenzoic acid tert-butyl ester (133 mg, 0.4 mmol) obtained in Example 1-1 and cesium carbonate (1.0 g, 3.2 mmol) were added to the reaction solution, and then N,N-dimethylformamide (2.0 ml) was added thereto. The resulting mixture was stirred at 80° C. for 2 hours. The reaction solution was acidified using 2N aqueous potassium hydrogen sulfate solution, and the resulting solid material was separated by filtration. The separated solid material was washed with water, and then dried under reduced pressure to yield 5-[2-amino-6-(3-carboxylpropylsulfanyl)pyrimidin-4-yl]-2,4-dimethylbenzoic acid tert-butyl ester (222 mg) as a white solid material.

Physicochemical properties of 5-[2-amino-6-(3-carboxylpropylsulfanyl)pyrimidin-4-yl]-2,4-dimethylbenzoic acid tert-butyl ester Molecular weight: 417.
ESI (LC/MS positive mode): m/z=418 (M+H$^+$).
Chemical shift value δ in $^1$H-NMR (400 MHz, in dimethylsulfoxide d-6): 1.53 (9H, s), 1.82-1.91 (2H, m), 2.35 (3H, s), 2.37 (2H, t, J=8 Hz), 2.49 (3H, s), 3.12 (2H, t, J=8 Hz), 6.60 (1H, s), 6.72 (2H, brs), 7.21 (1H, s), 7.72 (1H, s).

Step 2: Preparation of 5-{2-amino-6-[3-(2-tert-butoxycarbonylaminoethylcarbamoyl)propylsulfanyl]pyrimidin-4-yl}-2,4-dimethylbenzoic acid tert-butyl ester

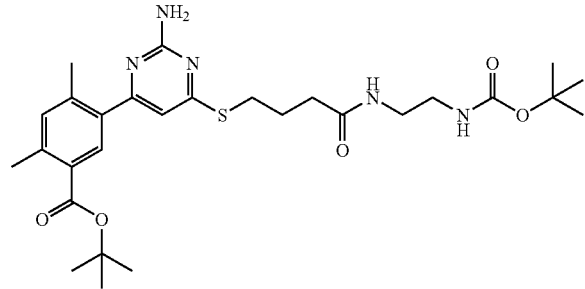 [SMILES: Cc1cc(C)c(-c2cc(SCCCC(=O)NCCNC(=O)OC(C)(C)C)nc(N)n2)cc1C(=O)OC(C)(C)C]

5-[2-Amino-6-(3-carboxylpropylsulfanyl)pyrimidin-4-yl]-2,4-dimethylbenzoic acid tert-butyl ester (114 mg, 0.27 mmol) obtained in Step 1 above, 2-aminoethylcarbamic acid tert-butyl ester (87 mg, 0.54 mmol), and N-hydroxybenzotriazole (74 mg, 0.55 mmol) placed in to a reaction vessel, and then N,N-dimethylformamide (2.0 ml) was added thereto. 1-Ethyl-3-(3'-dimethylaminopropyl)carbodiimide hydrochloride (157 mg, 0.82 mmol) and diisopropylethylamine (0.095 ml, 0.55 mmol) were added to the mixture. The resulting reaction solution was stirred at room temperature for 12 hours. After a saturated aqueous ammonium chloride solution was added to the reaction solution, the mixture was extracted with ethyl acetate (100 ml). The ethyl acetate solution was sequentially washed with 1N hydrochloric acid (50 ml), water (50 ml), a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography (developing solvent: ethyl acetate) to yield 5-{2-amino-6-[3-(2-tert-butoxycarbonylaminoethylcarbamoyl)propylsulfanyl]pyrimidin-4-yl}-2,4-dimethylbenzoic acid tert-butyl ester (127 mg) as a white solid material.

Physicochemical properties of 5-{2-amino-6-[3-(2-tert-butoxycarbonylaminoethylcarbamoyl)propylsulfanyl]pyrimidin-4-yl}-2,4-dimethylbenzoic acid tert-butyl ester Molecular weight: 559.
ESI (LC/MS positive mode): m/z=560 (M+H$^+$).
Chemical shift value δ in $^1$H-NMR (400 MHz, in dimethylsulfoxide d-6): 1.36 (9H, s), 1.53 (9H, s), 1.83-1.90 (2H, m), 2.21 (2H, t, J=8 Hz), 2.35 (3H, s), 2.49 (3H, s), 2.97 (2H, t, J=6 Hz), 3.05 (2H, t, J=6 Hz), 3.09 (2H, t, J=6 Hz), 6.56 (1H, s) 6.68-6.75 (1H, m), 6.73 (2H, brs), 7.21 (1H, s), 7.72 (1H, s), 7.85 (1H, t, J=6 Hz).

Step 3: Preparation of 4-amino-18,20-dimethyl-7-thia-3,5,12,15-tetraazatricyclo[15.3.1.1$^{2,6}$]docosa-1(20),2(22),3,5,17(21),18-hexaene-11,16-dione (Compound 4)

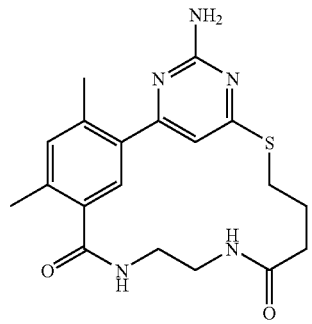 [SMILES: Cc1cc(C)c2cc1C(=O)NCCNC(=O)CCCSc1cc-2nc(N)n1]

Anisole (0.060 ml, 0.55 mmol) and trifluoroacetic acid (1.2 ml) were added to a dichloromethane (3.7 ml) solution of 5-{2-amino-6-[3-(2-tert-butoxycarbonylaminoethylcarbamoyl)propylsulfanyl]pyrimidin-4-yl}-2,4-dimethylbenzoic acid tert-butyl ester (124 mg, 0.22 mmol) obtained in Step 2 above. The mixture was stirred for 8 hours while gradually warming from 0° C. to room temperature. The reaction solution was concentrated under reduced pressure, and then benzene (1.5 ml) was added to the residue. The resulting solution was concentrated under reduced pressure. This treatment was repeated three times, and then the obtained pale yellow oily material was dissolved in N,N-dimethylformamide (111 ml). N-Hydroxybenzotriazole (150 mg, 1.11 mmol), diisopropylethylamine (0.39 ml, 2.2 mmol), and 1-ethyl-3-(3'-dimethylaminopropyl)carbodiimide hydrochloride (426 mg, 2.2 mmol) were sequentially added to the solution. The resulting mixture was reacted at room temperature for 14 hours. The reaction solution was concentrated under reduced pressure. The resulting residue was diluted with ethyl acetate (100 ml), and then sequentially washed twice with water (50 ml), and with a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography with diol-silica gel (developing solvent: ethyl acetate to ethyl acetate:methanol=15:1) and amino-silica gel (developing solvent: ethyl acetate to ethyl acetate:methanol=15:1) to yield 4-amino-18,20-dimethyl-7-thia-3,5,12,15-tetraazatricyclo[15.3.1.1$^{2,6}$]docosa-1(20),2(22),3,5,17(21),18-hexaene-11,16-dione (Compound 4) (17 mg) as a white solid material.

Physicochemical properties of 4-amino-18,20-dimethyl-7-thia-3,5,12,15-tetraazatricyclo[15.3.1.1$^{2,6}$]docosa-1(20),2(22),3,5,17(21),18-hexaene-11,16-dione Molecular weight: 385.
ESI (LC/MS positive mode): m/z=386 (M+H$^+$).
Chemical shift value δ in $^1$H-NMR (400 MHz, in dimethylsulfoxide d-6): 1.87-1.96 (2H, m), 2.31 (2H, t, J=5.6 Hz), 2.40 (3H, s), 2.59 (3H, s), 3.18-3.28 (6H, m), 6.59 (2H, brs) 7.14 (1H, s), 7.14 (1H, s), 7.70 (1H, s), 8.13 (1H, t, J=3.9 Hz), 8.44 (1H, t, J=4.9 Hz).

Example 2-5

Production of 4-amino-20,22-dimethyl-7-thia-3,5,12,17-tetraazatricyclo[17.3.1.1$^{2,6}$]tetracosa-1(22),2(24),3,5,19(23),20-hexane-11,18-dione (Compound 5)

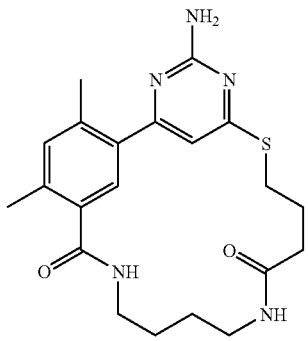 [SMILES: Cc1cc(C)c2cc1C(=O)NCCCCNC(=O)CCCSc1cc-2nc(N)n1]

Step 1: Preparation of 5-{2-amino-6-[3-(4-tert-butoxycarbonylaminobutylcarbamoyl)propylsulfanyl]pyrimidin-4-yl}-2,4-dimethylbenzoic acid tert-butyl ester

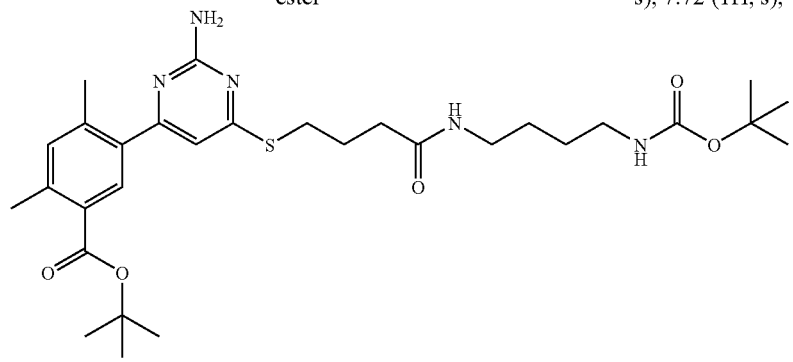

5-[2-Amino-6-(3-carboxylpropylsulfanyl)pyrimidin-4-yl]-2,4-dimethylbenzoic acid tert-butyl ester (104 mg, 0.25 mmol) obtained in Step 1 of Example 2-4, 4-aminobutylcarbamic acid tert-butyl ester (94 mg, 0.50 mmol), and N-hydroxybenzotriazole (67 mg, 0.5 mmol) were placed in a reaction vessel, and then N,N-dimethylformamide (2.0 ml) was added thereto. 1-Ethyl-3-(3'-dimethylaminopropyl)carbodiimide hydrochloride (144 mg, 0.75 mmol) and diisopropylethylamine (0.087 ml, 0.50 mmol) were added to the mixture. The resulting mixture was stirred at room temperature for 2.0 hours. After a saturated aqueous ammonium chloride solution was added to the reaction solution, the mixture was extracted with ethyl acetate (100 ml). The ethyl acetate solution was sequentially washed with 1N hydrochloric acid (50 ml), water (50 ml), a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography (developing solvent: ethyl acetate) to yield 5-{2-amino-6-[3-(4-tert-butoxycarbonylaminobutylcarbamoyl)propylsulfanyl]pyrimidin-4-yl}-2,4-dimethylbenzoic acid tert-butyl ester (119 mg) as a white solid material.

Physicochemical properties of 5-(2-amino-6-{2-[3-(tert-butoxycarbonylmethylamino)propylcarbamoyl]ethylsulfanyl}pyrimidin-4-yl)-2,4-dimethylbenzoic acid tert-butyl ester Molecular weight: 587.
ESI (LC/MS positive mode): m/z=588 (M+H$^+$).
Chemical shift value δ in $^1$H-NMR (400 MHz, in dimethylsulfoxide d-6): 1.31-1.38 (4H, m), 1.36 (9H, s), 1.53 (9H, s), 1.83-1.90 (2H, m), 2.21 (2H, t, J=6 Hz), 2.35 (3H, s), 2.49 (3H, s), 2.85-2.91 (2H, m), 2.97-3.03 (2H, m), 3.09 (2H, t, J=8 Hz), 6.57 (1H, s) 6.71 (2H, brs), 6.72-6.77 (1H, m), 7.21 (1H, s), 7.72 (1H, s), 7.78 (1H, t, J=6 Hz), 8.27 (1H, t, J=4 Hz).

Step 2: Preparation of 4-amino-20,22-dimethyl-7-thia-3,5,12,17-tetraazatricyclo[17.3.1.1$^{2,6}$]tetracosa-1(22),2(24),3,5,19(23),20-hexane-11,18-dione (Compound 5)

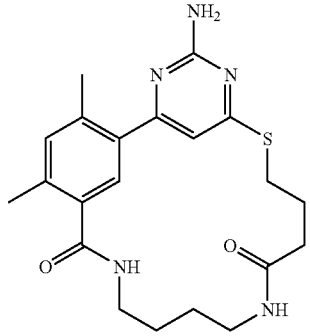 [SMILES: Cc1cc(C)c2cc1C(=O)NCCCCNC(=O)CCCSc1cc-2nc(N)n1]

Anisole (0.053 ml, 0.50 mmol) and trifluoroacetic acid (1.1 ml) were added to a dichloromethane (3.5 ml) solution of 5-(2-amino-6-{2-[3-(tert-butoxycarbonylmethylamino)propylcarbamoyl]ethylsulfanyl}pyrimidin-4-yl)-2,4-dimethylbenzoic acid tert-butyl ester (116 mg, 0.20 mmol) obtained in Step 1 above. The reaction solution was stirred for 8 hours while gradually warming from 0° C. to room temperature. The reaction solution was concentrated under reduced pressure, and then benzene (1.5 ml) was added to the resulting residue. The resulting solution was concentrated under reduced pressure. This treatment was repeated three times. The obtained pale yellow oily material was dissolved in N,N-dimethylformamide (99 ml). N-Hydroxybenzotriazole (134 mg, 1.0 mmol), diisopropylethylamine (0.34 ml, 2.0 mmol), and 1-ethyl-3-(3'-dimethylaminopropyl)carbodiimide hydrochloride (380 mg, 2.0 mmol) were sequentially added to the solution. The resulting mixture was reacted at room temperature for 14 hours. The reaction solution was concentrated under reduced pressure. The resulting residue was diluted with ethyl acetate (100 ml), and sequentially washed twice with water (50 ml), and with a saturated aqueous sodium bicarbonate solution (50 ml), water (50 ml) and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography with diol-silica gel (developing solvent: ethyl acetate to ethyl acetate:methanol=10:1) and amino-silica gel (developing solvent: ethyl acetate to ethyl acetate:methanol=25:1) to yield 4-amino-20,22-dimethyl-7-thia-3,5,12,17-tetraazatricyclo[17.3.1.1$^{2,6}$]tetracosa-1(22),2(24),3,5,19(23),20-hexane-11,18-dione (Compound 5) (40 mg) as a white solid material.

Physicochemical properties of 4-amino-20,22-dimethyl-7-thia-3,5,12,17-tetraazatricyclo[17.3.1.1$^{2,6}$]tetracosa-1(22),2(24),3,5,19(23),20-hexane-11,18-dione Molecular weight: 413.
ESI (LC/MS positive mode): m/z=414 (M+H$^+$).
Chemical shift value δ in $^1$H-NMR (400 MHz, in dimethylsulfoxide d-6): 1.50-1.59 (4H, m), 1.84-1.94 (2H, m), 2.24 (2H, t, J=6 Hz), 2.38 (3H, s), 2.49 (3H, s), 2.86-2.93 (2H, m), 3.04-3.09 (2H, m), 3.24-3.32 (2H, m), 6.61 (2H, brs) 6.99 (1H, s), 7.15 (1H, s), 7.62 (1H, s), 8.05 (1H, t, J=5.9 Hz), 8.27 (1H, t, J=5.4 Hz).

Example 2-6

Production of 4-amino-19,21-dimethyl-7-thia-3,5,11,16-tetraazatricyclo[16.3.1.1$^{2,6}$]tricosa-1(21),2(23),3,5,18(22),19-hexaene-10,17-dione (Compound 6)

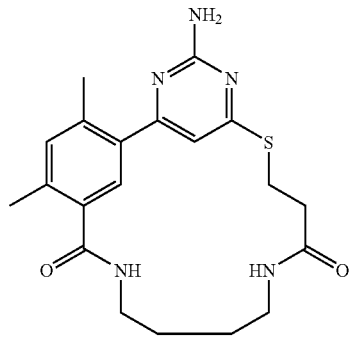 [SMILES: Cc1cc(C)c2cc1C(=O)NCCCCNC(=O)CCSc1cc-2nc(N)n1]

According to Steps 2 and 3 of Example 2-1, 4-amino-19,21-dimethyl-7-thia-3,5,11,16-tetraazatricyclo[16.3.1.1$^{2,6}$]tricosa-1(21),2(23),3,5,18(22),19-hexaene-10,17-dione (Compound 6) was synthesized from 5-[2-amino-6-(2-carboxylethylsulfanyl)pyrimidin-4-yl]-2,4-dimethylbenzoic acid tert-butyl ester obtained in Step 1 of Example 2-1 and commercially available 5-aminobutylcarbamic acid tert-butyl ester.

Physicochemical properties of 4-amino-19,21-dimethyl-7-thia-3,5,11,16-tetraazatricyclo[16.3.1.1$^{2,6}$]tricosa-1(21),2(23),3,5,18 (22),19-hexaene-10,17-dione Molecular weight: 399.
ESI (LC/MS positive mode): m/z=400 (M+H$^+$).
Chemical shift value δ in $^1$H-NMR (270 MHz, in dimethylsulfoxide d-6): 1.39-1.56 (4H, m), 2.36 (3H, s), 2.48-2.66 (5H, m), 2.99-3.09 (2H, m), 3.13-3.29 (4H, m), 6.69 (2H, s), 6.75 (1H, s), 7.16 (1H, s), 7.43 (1H, s), 8.06 (1H, t, J=6 Hz), 8.13 (1H, t, J=6 Hz).

Example 2-7

Production of 4-amino-9,20,22-trimethyl-7-thia-3,5,11,17-tetraazatricyclo[17.3.1.1$^{2,6}$]tetracosa-1(22),2(24), 3,5,19(23),20-hexaene-10,18-dione (Compound 7)

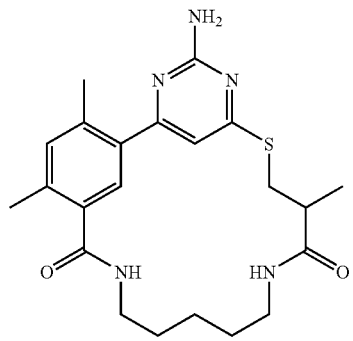

According to Example 2-1, 4-amino-9,20,22-trimethyl-7-thia-3,5,11,17-tetraazatricyclo[17.3.1.1$^{2,6}$]tetracosa-1(22),2 (24),3,5,19(23),20-hexaene-10,18-dione (Compound 7) was synthesized from 5-(2-amino-6-chloropyrimidin-4-yl)-2,4-dimethylbenzoic acid tert-butyl ester obtained in Example 1-1, and commercially available 3-mercapto-2-methylpropionic acid and 5-aminopentylcarbamic acid tert-butyl ester.

Physicochemical properties of 4-amino-9,20,22-trimethyl-7-thia-3,5,11,17-tetraazatricyclo[17.3.1.1$^{2,6}$]tetracosa-1(22),2(24),3,5,19(23),20-hexaene-10, 18-dione Molecular weight: 427.
ESI (LC/MS positive mode): m/z=428 (M+H$^+$).
Chemical shift value δ in $^1$H-NMR (270 MHz, in dimethylsulfoxide d-6): 1.14 (3H, d, J=7 Hz), 1.32-1.59 (6H, m), 2.34 (3H, s), 2.5 (3H, s), 2.71-2.84 (2H, m), 3.01-3.16 (1H, m), 3.29-3.52 (4H, m), 6.70 (2H, s), 6.83 (1H, s), 7.15 (1H, s), 7.52 (1H, s), 7.90-7.98 (1H, m), 8.18 (1H, t, J=5 Hz).

Example 2-8

Production of 4-amino-18,20-dichloro-7-thia-3,5,11,15-tetraazatricyclo[15.3.1.1$^{2,6}$]docosa-1(20),2(22),3,5,17(21),18-hexaene-10,16-dione (Compound 8)

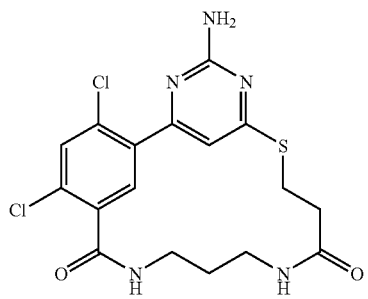 [SMILES: Nc1nc2cc(n1)-c1cc(c(Cl)cc1Cl)C(=O)NCCCNC(=O)CCS2]

Step 1: Preparation of 3-(2-amino-6-chloropyrimidin-4-ylsulfanyl)propionic acid

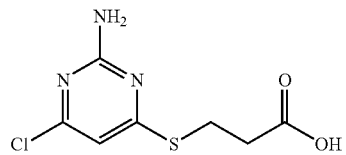 [SMILES: Nc1nc(Cl)cc(SCCC(=O)O)n1]

Commercially available 2-amino-4,6-dichloropyrimidine (0.79 g, 4.84 mmol), 3-mercaptopropionic acid (0.43 g, 4.04 mmol), cesium carbonate (1.3 g, 4.02 mmol), and N,N-dimethylformamide (7.0 ml) were placed in a reaction vessel. The mixture was stirred at 80° C. for 15 minutes. After the reaction solution was cooled to room temperature, ethyl acetate, water, and a saturated aqueous sodium bicarbonate solution were added thereto. The organic layer was separated, and then extracted with a saturated aqueous sodium bicarbonate solution. After the aqueous layers were combined together and washed with ethyl acetate, its pH was adjusted to about 4 using 1N hydrochloric acid. The solution was extracted with ethyl acetate. The extract was sequentially washed with 1N hydrochloric acid and a saturated aqueous sodium chloride solution, and then dried over anhydrous sodium sulfate. After filtration, the filtrate was concentrated under reduced pressure to yield 3-(2-amino-6-chloropyrimidin-4-ylsulfanyl)propionic acid (1.44 g).

Physicochemical properties of 3-(2-amino-6-chloropyrimidin-4-ylsulfanyl)propionic acid Molecular weight: 233.
ESI (LC/MS positive mode): m/z=234, 236 (M+H$^+$).
Chemical shift value δ in $^1$H-NMR (400 MHz, in dimethylsulfoxide d-6): 2.64 (2H, t, J=6.9 Hz), 3.25 (2H, t, J=6.9 Hz), 6.61 (1H, s), 7.17 (2H, brs), 12.4 (1H, brs).

Step 2: Preparation of {3-[3-(2-amino-6-chloropyrimidin-4-ylsulfanyl)propionylamino]propyl}carbamic acid tert-butyl ester

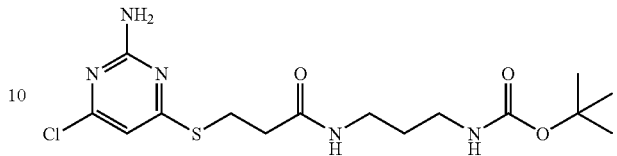

3-(2-Amino-6-chloropyrimidin-4-ylsulfanyl)propionic acid (240 mg) obtained in Step 1 above and N-hydroxybenzotriazole (180 mg, 1.33 mmol) were placed in a reaction vessel, and then N,N-dimethylformamide (4.0 ml) was added thereto. 1-Ethyl-3-(3'-dimethylaminopropyl)carbodiimide hydrochloride (255 mg, 1.33 mmol), 3-aminopropylcarbamic acid tert-butyl ester (155 mg, 0.89 mmol), and diisopropylethylamine (0.79 ml, 4.52 mmol) were added to the solution. The resulting mixture was stirred at room temperature for 4 hours. The reaction was stopped with 1N hydrochloric acid, and the solution was extracted with ethyl acetate. The ethyl acetate solution was sequentially washed with 1N hydrochloric acid, a saturated aqueous sodium bicarbonate solution, and a saturated aqueous sodium chloride solution. The washed ethyl acetate solution was dried over anhydrous sodium sulfate (10 g). After filtration, the filtrate was concentrated under reduced pressure to yield {3-[3-(2-amino-6-chloropyrimidin-4-ylsulfanyl)propionylamino]propyl}carbamic acid tert-butyl ester (175 mg).

Physicochemical properties of {3-[3-(2-amino-6-chloropyrimidin-4-ylsulfanyl)propionylamino]propyl}carbamic acid tert-butyl ester Molecular weight: 389.
ESI (LC/MS positive mode): m/z=390, 392 (M+H$^+$).
Chemical shift value δ in $^1$H-NMR (400 MHz, in chloroform-d): 1.44 (9H, s), 1.59-1.65 (2H, m), 2.62 (2H, t, J=7.3 Hz), 3.15-3.33 (4H, m), 3.37 (2H, t, J=7.3 Hz), 4.85 (1H, brs), 5.44 (2H, brs), 6.53 (1H, s), 6.58 (1H, brs).

Step 3: Preparation of 2,4-dichloro-5-iodobenzoic acid methyl ester

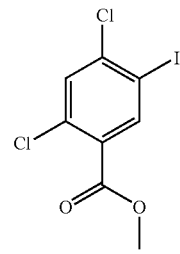

Sodium iodate (4.4 g) and iodine (11.1 g) were added to 90% sulfuric acid (330 ml) and stirred at room temperature for 8 hours. Commercially available 2,4-dichlorobenzoic acid (21 g) was added and stirred at the same temperature for 24 hours. The reaction solution was poured onto ice water (3 l), and the precipitated solid material was separated by filtration. The solid material was then washed with water, and dried under reduced pressure. 2,4-Dichloro-5-iodobenzoic acid (16.8 g) was obtained by recrystallization (acetic acid-water). 2,4-Dichloro-5-iodobenzoic acid (2 g) was dissolved in dichloromethane (20 ml) and methanol (20 ml), and trimethylsilyldiazomethane (2 M; n-hexane solution) was added dropwise thereto until the solution became yellow. After a small amount of acetic acid was added, the mixture was concentrated under reduced pressure. The resulting residue was recrystallized from n-hexane to yield the title compound 2,4-dichloro-5-iodobenzoic acid methyl ester (2 g) as a white solid.

Physicochemical properties of 2,4-dichloro-5-iodobenzoic acid methyl ester

Molecular weight: 331.
ESI (LC/MS positive mode): m/z=331, 333 (M+H$^+$).
Chemical shift value δ in $^1$H-NMR (270 MHz, in DMSO-d$_6$): 3.86 (3H, s), 7.91 (1H, s), 8.31 (1H, s).

Step 4: Preparation of 5-{2-amino-6-[2-(3-tert-butoxycarbonylaminopropylcarbamoyl)ethylsulfanyl]pyrimidin-4-yl}-2,4-dichlorobenzoic acid methyl ester

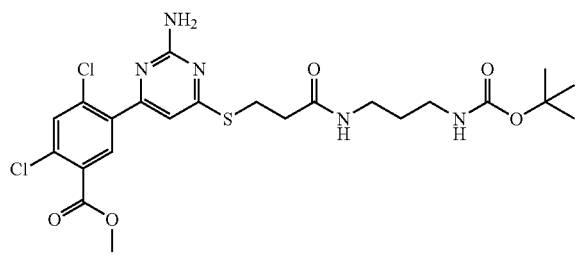 [SMILES: COC(=O)c1cc(-c2cc(SCCC(=O)NCCCNC(=O)OC(C)(C)C)nc(N)n2)c(Cl)cc1Cl]

2,4-Dichloro-5-iodobenzoic acid methyl ester (1.54 g) obtained in Step 3 above, potassium acetate (1.37 g, 14.0 mmol), bis(pinacolato)diborane (1.45 g, 5.6 mmol), and palladium dichloride-diphenylphosphinoferrocene dichloromethane complex (190 mg, 0.23 mmol) were placed in a reaction vessel, and then anhydrous dimethylsulfoxide (15 ml) was added thereto. The resulting mixture was stirred at 80° C. for 2.5 hours. The reaction solution was cooled to room temperature, and then filtered through celite. The residue was sequentially washed with water and ethyl acetate. The organic layer was separated, and sequentially washed with water and a saturated aqueous sodium chloride solution. The washed ethyl acetate solution was dried over anhydrous sodium sulfate. After filtration, the filtrate was concentrated under reduced pressure to yield 2,4-Dichloro-5-(4,4,5,5-tetramethyl[1,3,2]dioxaborolan-2-yl)benzoic acid methyl ester (1.42 g) as a crude product. A mixture of the crude product (150 mg), {3-[3-(2-amino-6-chloropyrimidin-4-ylsulfanyl)propionylamino]propyl}carbamic acid tert-butyl ester (94 mg, 0.24 mmol) obtained in Step 2 above, palladium acetate (3 mg, 0.01 mmol), triphenylphosphine (11 mg, 0.04 mmol), 1N aqueous sodium bicarbonate solution (363 μl), and 1,2-dimethoxyethane (4.0 ml) was stirred at 80° C. for 2 hours. After the reaction solution was cooled to room temperature, palladium dichloride-diphenylphosphinoferrocene dichloromethane complex (10 mg, 0.01 mmol), triphenylphosphine (11 mg, 0.04 mmol), and 1N aqueous sodium bicarbonate solution (363 μl) were added thereto. The resulting mixture was then stirred at 80° C. for 2 hours. After cooling to room temperature, the reaction solution was diluted with ethyl acetate and sequentially washed with water and a saturated aqueous sodium chloride solution. The ethyl acetate solution was dried over anhydrous sodium sulfate. After filtration, the filtrate was concentrated under reduced pressure. The resulting crude product was purified by thin layer chromatography (developing solvent: dichloromethane:methanol=19:1) to yield 5-{2-amino-6-[2-(3-tert-butoxycarbonylaminopropylcarbamoyl)ethylsulfanyl]pyrimidin-4-yl}-2,4-dichlorobenzoic acid methyl ester (51 mg).

Physicochemical properties of 5-{2-amino-6-[2-(3-tert-butoxycarbonylaminopropylcarbamoyl)ethylsulfanyl]pyrimidin-4-yl}-2,4-dichlorobenzoic acid methyl ester Molecular weight: 558.
ESI (LC/MS positive mode): m/z=558, 560 (M+H$^+$).
Chemical shift value δ in $^1$H-NMR (400 MHz, in chloroform-d): 1.44 (9H, s), 1.58-1.64 (2H, m), 2.67 (2H, t, J=7.3 Hz), 3.18-3.24 (2H, m), 3.27-3.30 (2H, m), 3.42 (2H, t, J=7.3 Hz), 3.93 (3H, s), 4.95 (1H, brs), 5.47 (2H, brs), 6.65 (1H, brs), 6.79 (1H, s), 7.58 (1H, s), 8.09 (1H, s).

Step 5: Preparation of 4-amino-18,20-dichloro-7-thia-3,5,11,15-tetraazatricyclo[15.3.1.1$^{2,6}$]docosa-1(20),2(22),3,5,17(21),18-hexaene-10,16-dione (Compound 8)

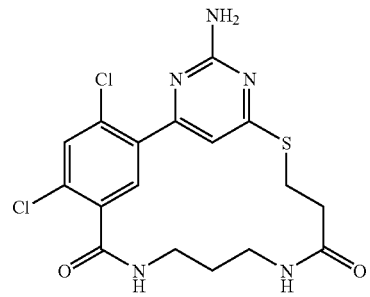 [SMILES: Nc1nc2cc(n1)-c1cc(c(Cl)cc1Cl)C(=O)NCCCNC(=O)CCS2]

According to the method in Step 2 of Example 2-5, 4-amino-18,20-dichloro-7-thia-3,5,11,15-tetraazatricyclo[15.3.1.1$^{2,6}$]docosa-1(20),2(22),3,5,17(21),18-hexaene-10,16-dione (Compound 8) was synthesized from 5-{2-amino-6-[2-(3-tert-butoxycarbonylaminopropylcarbamoyl)ethylsulfanyl]pyrimidin-4-yl}-2,4-dichlorobenzoic acid methyl ester obtained in Step 4 above.

Physicochemical properties of 4-amino-18,20-dichloro-7-thia-3,5,11,15-tetraazatricyclo[15.3.1.1$^{2,6}$]docosa-1(20),2(22),3,5,17(21),18-hexaene-10,16-dione Molecular weight: 426.
ESI (LC/MS positive mode): m/z=426, 428 (M+H$^+$).
Chemical shift value δ in $^1$H-NMR (400 MHz, in dimethylsulfoxide d-6): 1.69-1.75 (2H, m), 2.52-2.56 (2H, m), 3.16-3.24 (4H, m), 3.34-3.41 (2H, m), 6.86 (2H, brs), 6.92 (1H, s), 7.76 (1H, s), 7.92 (1H, s), 7.99 (1H, brt), 8.51 (1H, brt).

Example 2-9

Production of (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid methyl ester (Compound 62)

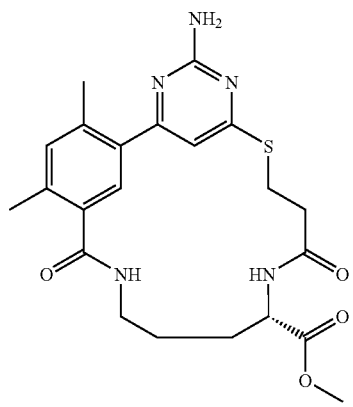

Step 1: Preparation of (S)-2-[3-(2-amino-6-chloropyrimidin-4-ylsulfanyl)propionylamino]-5-tert-butoxycarbonylamino pentanoic acid methyl ester

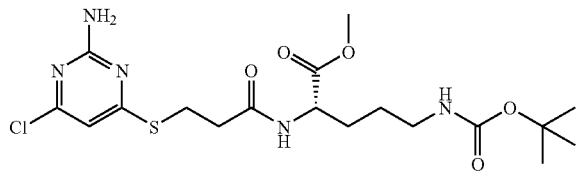 [SMILES: COC(=O)[C@H](CCCNC(=O)OC(C)(C)C)NC(=O)CCSc1cc(Cl)nc(N)n1]

3-(2-Amino-6-chloropyrimidin-4-ylsulfanyl)propionic acid (211 mg, 0.903 mmol) obtained in Step 1 of Example 2-8 was dissolved in a mixture of dichloromethane (5.0 ml) and N,N-dimethylformamide (2.0 ml), and then 1-hydroxybenzotriazole monohydrate (139 mg, 0.887 mmol), (S)-2-amino-5-tert-butoxycarbonylaminopentanoic acid methyl ester (202 mg, 0.822 mmol), 1-ethyl-3-(3'-dimethylaminopropyl)carbodiimide hydrochloride (173 mg, 0.902 mmol), and diisopropylethylamine (0.157 ml, 0.901 mmol) were added thereto. After the resulting mixture was stirred at room temperature for four hours, water (30 ml) was added to the reaction solution. The mixture was extracted three times with ethyl acetate (30 ml). The organic layers were combined together and then sequentially washed with a saturated aqueous sodium chloride solution (20 ml), a saturated aqueous sodium bicarbonate solution (20 ml), and a saturated aqueous sodium chloride solution (20 ml). The washed organic layer was dried over anhydrous sodium sulfate. After filtration, the filtrate was concentrated under reduced pressure. The resulting crude product was purified by silica gel column chromatography (developing solvent: dichloromethane:methanol=30:1) to yield (S)-2-[3-(2-amino-6-chloropyrimidin-4-ylsulfanyl)propionylamino]-5-tert-butoxycarbonylamino pentanoic acid methyl ester (359 mg) as a white amorphous material.

Physicochemical properties of (S)-2-[3-(2-amino-6-chloropyrimidin-4-ylsulfanyl)propionylamino]-5-tert-butoxycarbonylamino pentanoic acid methyl ester Molecular weight: 461.

ESI (LC/MS positive mode): m/z=462, 464 (M+H$^+$)

Chemical shift value δ in $^1$H-NMR (270 MHz, in dimethylsulfoxide d-6): 1.37 (9H, s), 1.37-1.70 (4H, m), 2.50-2.57 (2H, m), 2.85-2.93 (2H, m), 3.20-3.40 (2H, m), 3.62 (3H, s), 4.14-4.30 (1H, m), 6.59 (1H, s), 6.75-6.83 (1H, m), 7.14 (2H, s), 8.32 (1H, d, J=7.3 Hz).

Step 2: Preparation of 5-{2-amino-6-[2-((S)-4-tert-butoxycarbonylamino-1-methoxycarbonylbutylcarbamoyl)ethylsulfanyl]pyrimidin-4-yl}-2,4-dimethylbenzoic acid tert-butyl ester

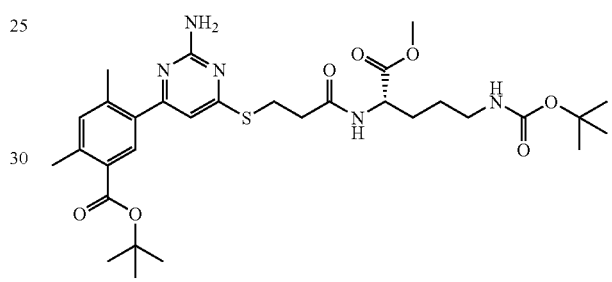

According to the method of Step 4 of Example 1-2 except that acetonitrile was used as a reaction solvent instead of dimethoxyethane, 5-{2-amino-6-[2-((S)-4-tert-butoxycarbonylamino-1-methoxycarbonylbutylcarbamoyl)ethylsulfanyl]pyrimidin-4-yl}-2,4-dimethylbenzoic acid tert-butyl ester (76 mg) was obtained as a white amorphous material from (S)-2-[3-(2-amino-6-chloropyrimidin-4-ylsulfanyl)propionylamino]-5-tert-butoxycarbonylamino pentanoic acid methyl ester (100 mg) obtained in Step 1 above and 2,4-dimethyl-5-(4,4,5,5-tetramethyl[1,3,2]dioxaborolan-2-yl)benzoic acid tert-butyl ester (76 mg) obtained in Step 3 of Example 1-1.

Physicochemical properties of 5-{2-amino-6-[2-((S)-4-tert-butoxycarbonylamino-1-methoxycarbonylbutylcarbamoyl)ethylsulfanyl]pyrimidin-4-yl}-2,4-dimethylbenzoic acid tert-butyl ester Molecular weight: 631.

ESI (LC/MS positive mode): m/z=632 (M+H$^+$)

Chemical shift value δ in $^1$H-NMR (400 MHz, in dimethylsulfoxide d-6): 1.10-1.20 (4H, m), 1.33 (9H, s), 1.53 (9H, s), 2.35 (3H, s), 2.51-2.63 (4H, m), 2.84-2.95 (1H, m), 3.33-3.35 (4H, m), 3.62 (3H, s), 4.18-4.30 (1H, m), 6.56 (1H, s), 6.77 (2H, brs), 7.21 (1H, s), 7.73 (1H, s), 7.94 (1H, brs), 8.33 (1H, d, J=7.6 Hz).

Step 3: Preparation of (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid methyl ester (Compound 62)

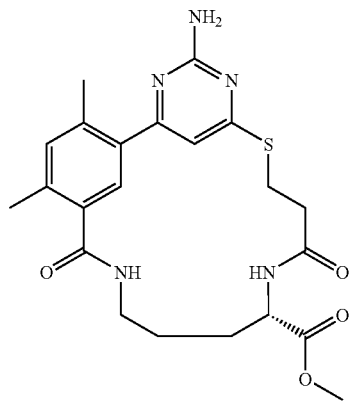

According to the method of Step 3 of Example 2-1, (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid methyl ester (Compound 62) (32 mg) was obtained as a white solid material from 5-{2-amino-6-[2-((S)-4-tert-butoxycarbonylamino-1-methoxycarbonyl-butylcarbamoyl)ethylsulfanyl]pyrimidin-4-yl}-2,4-dimethylbenzoic acid tert-butyl ester (106 mg) obtained in Step 2 above.

Physicochemical properties of (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid methyl ester Molecular weight: 457.
ESI (LC/MS positive mode): m/z=458 (M+H$^+$)
Chemical shift value δ in $^1$H-NMR (400 MHz, in dimethylsulfoxide d-6): 1.35-1.84 (4H, m), 2.37 (3H, s), 2.50 (3H, s), 2.64-2.77 (2H, m), 3.04-3.20 (2H, m), 3.28-3.43 (2H, m), 3.65 (3H, s), 4.38-4.46 (1H, m), 6.82 (1H, s), 7.18 (1H, s), 7.52 (1H, s), 8.10 (1H, t, J=6.0 Hz), 8.45 (1H, d, J=8.2 Hz).

Example 2-10

Production of (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid (2-hydroxyethyl)amide (Compound 46)

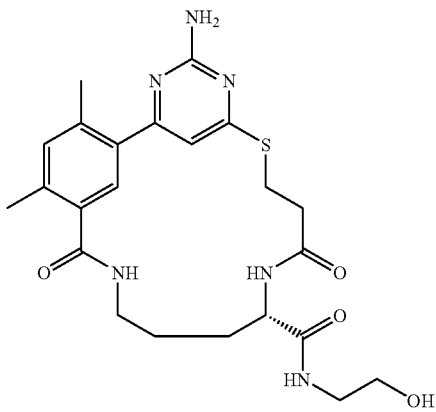 [SMILES: Cc1cc(C)c2cc1C(=O)NCCC[C@@H](C(=O)NCCO)NC(=O)CCSc1cc-2nc(N)n1]

An aqueous solution of 1N lithium hydroxide (0.263 ml) was added at 0° C. to a methanol/tetrahydrofuran solution (1:10 v/v, 2.5 ml) mixed with (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid methyl ester (30 mg) obtained in Step 3 of Example 2-9. After stirring for 10 minutes, the mixture was warmed to room temperature and stirred for 1.5 hours. The pH of the reaction solution was adjusted to about 4 using 1N hydrochloric acid. The solution was extracted four times with ethyl acetate (20 ml). The organic layers were combined together, and dried over anhydrous sodium sulfate. After the inorganic salt was removed by filtration, the filtrate was concentrated under reduced pressure to give crude product (39 mg). An aliquot (20 mg) of the crude product was dissolved in N,N-dimethylformamide (1.0 ml), and then 2-3H-1,2,3-triazolo[4,5-b]pyridin-3-ol (7 mg, 0.053 mmol), O-(7-azabenzotriazol-1-yl)-N,N,N',N'-tetramethyluroniumhexafluorophosphate (20 mg, 0.052 mmol), 2,4,6-trimethylpyridine (14 µl), and 2-aminoethanol (3 µl, 0.053 mol) were added thereto at 0° C. After stirring at 0° C. for 30 minutes, the mixture was warmed to room temperature and stirred for 30 minutes. The reaction solution was concentrated under reduced pressure. The resulting crude product was purified by high performance liquid chromatography (developing solvent: A, acetonitrile containing 0.05% trifluoroacetic acid; B, 0.05% aqueous trifluoroacetic acid solution; gradient condition: B, 1% (0 min) →1% (1 min)→30% (7 min)→95% (8 min)→95% (9 min) →1% (10 min); flow rate, 35 ml/min; column, Waters, SunFire PrepC18, 5 µm, 30×50 mm). A fraction containing the material of interest was neutralized with solid-supported tetraalkyl ammonium carbonate (Polymer Laboratories, PL-HCO$_3$ MP-Resin) to yield (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid (2-hydroxyethyl) amide (Compound 46) (7 mg) was obtained as a white solid material.

Physicochemical properties of (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid (2-hydroxyethyl) amide Molecular weight: 486.
ESI (LC/MS positive mode): m/z=487 (M+H$^+$)
Chemical shift value δ in $^1$H-NMR (400 MHz, in dimethylsulfoxide d-6): 1.34-1.78 (4H, m), 2.36 (3H, s), 2.50 (3H, s), 2.56-2.70 (1H, m), 2.70-2.82 (1H, m), 2.93-3.4 (1H, m), 3.10-3.45 (7H, m), 4.33-4.40 (1H, m), 4.46-4.73 (1H, m) 6.67 (2H, s), 6.81 (1H, s), 7.15 (1H, s), 7.52 (1H, s), 7.99 (1H, t, J=5.5 Hz), 8.06 (1H, t, J=5.7 Hz), 8.14 (1H, d, J=8.2 Hz).

Example 2-11

Production of (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid (2,3-dihydroxypropyl) amide (Compound 48)

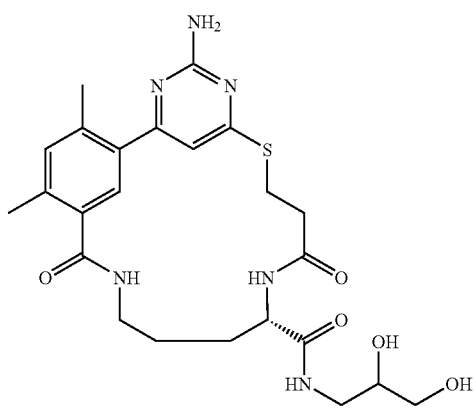 [SMILES: Cc1cc(C)c2cc1C(=O)NCCC[C@@H](C(=O)NCC(O)CO)NC(=O)CCSc1cc-2nc(N)n1]

According to the method of Example 2-10, (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid (2,3-dihydroxypropyl)amide (Compound 48) (6 mg) was obtained as a white solid material from (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid methyl ester (30 mg) obtained in Example 2-9 and 3-amino-1,2-propanediol (6 mg).

Physicochemical properties of (S)-4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid (2,3-dihydroxypropyl) amide Molecular weight: 516.
ESI (LC/MS positive mode): m/z=517 (M+H$^+$)
Chemical shift value δ in $^1$H-NMR (400 MHz, in dimethylsulfoxide d-6): 1.34-1.80 (4H, m), 2.36 (3H, s), 2.50 (3H, s), 2.58-2.70 (1H, m), 2.70-2.82 (1H, s), 2.92-3.08 (2H, m), 3.12-3.54 (7H, m), 4.36-4.42 (1H, m), 4.56 (1H, brs), 4.78 (1H, brs), 6.67 (2H, s), 6.82 (1H, s), 7.15 (1H, s), 7.53 (1H, s), 7.95 (1H, t, J=5.5 Hz), 8.06 (1H, t, J=5.7 Hz), 8.16 (1H, d, J=8.2 Hz).

Example 2-12

Production of (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid methyl ester (Compound 63)

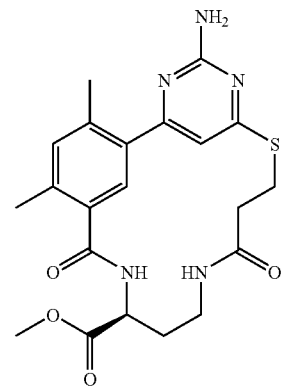 [SMILES: COC(=O)[C@@H]1CCNC(=O)CCSc2cc(nc(N)n2)-c2cc(c(C)cc2C)C(=O)N1]

Step 1: Preparation of 5-{2-amino-6-[2-((S)-3-tert-butoxycarbonylamino-3-methoxycarbonylpropylcarbamoyl)ethylsulfanyl]pyrimidin-4-yl}-2,4-dimethylbenzoic acid tert-butyl ester

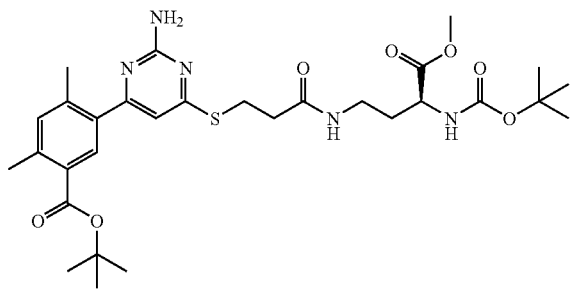 [SMILES: COC(=O)[C@H](CCNC(=O)CCSc1cc(-c2cc(C(=O)OC(C)(C)C)c(C)cc2C)nc(N)n1)NC(=O)OC(C)(C)C]

According to the method of Step 2 of Example 2-1 except that (S)-4-amino-2-tert-butoxycarbonylaminobutyric acid methyl ester hydrochloride (938 mg) was used instead of 5-aminopentylcarbamic acid tert-butyl ester, 5-{2-amino-6-[2-((S)-3-tert-butoxycarbonylamino-3-methoxycarbonylpropylcarbamoyl)ethylsulfanyl]pyrimidin-4-yl}-2,4-dimethylbenzoic acid tert-butyl ester (2.15 g) was obtained as a pale yellow amorphous material from 5-[2-amino-6-(2-carboxylethylsulfanyl)pyrimidin-4-yl]-2,4-dimethylbenzoic acid tert-butyl ester (2.10 g) obtained in Step 1 of Example 2-1.

Physicochemical properties of 5-{2-amino-6-[2-((S)-3-tert-butoxycarbonylamino-3-methoxycarbonylpropylcarbamoyl)ethylsulfanyl]pyrimidin-4-yl}-2,4-dimethylbenzoic acid tert-butyl ester Molecular weight: 617.
ESI (LC/MS positive mode): m/z=618 (M+H$^+$)
Chemical shift value δ in $^1$H-NMR (300 MHz, in dimethylsulfoxide d-6): 1.37 (9H, s), 1.53 (9H, s), 1.62-1.88 (2H, m), 2.34 (3H, s), 2.49 (3H, s), 2.40-2.59 (2H, m), 3.05-3.10 (2H, m), 3.22-3.40 (2H, m), 3.61 (3H, s), 3.97-4.04 (1H, m), 6.55 (1H, s), 6.75 (2H, brs), 7.20 (1H, s), 7.25 (1H, d, J=8.0 Hz), 7.71 (1H, s), 7.94 (1H, brs).

Step 2: Preparation of (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid methyl ester (Compound 63)

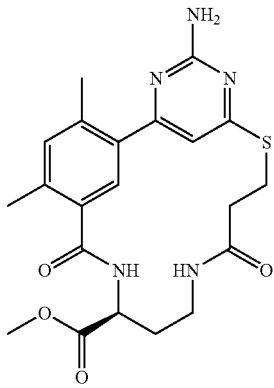 [SMILES: COC(=O)[C@@H]1CCNC(=O)CCSc2cc(nc(N)n2)-c2cc(c(C)cc2C)C(=O)N1]

According to the method of Step 3 of Example 2-1, (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid methyl ester (Compound 63) (1.23 g) was obtained as a white solid material from 5-{2-amino-6-[2-((S)-3-tert-butoxycarbonylamino-3-methoxycarbonylpropylcarbamoyl)ethylsulfanyl]pyrimidin-4-yl}-2,4-dimethylbenzoic acid tert-butyl ester (2.15 g) obtained in Step 1 above.

Physicochemical properties of (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid methyl ester Molecular weight: 617.
ESI (LC/MS positive mode): m/z=618 (M+H$^+$)
Chemical shift value δ in $^1$H-NMR (300 MHz, in dimethylsulfoxide d-6): 1.82-2.01 (2H, m), 2.26-2.43 (2H, m), 2.36 (3H, s), 2.57 (3H, s), 2.63-2.71 (1H, m), 2.80-2.90 (1H, m), 2.98-3.09 (1H, m), 3.30-3.39 (1H, m), 3.66 (3H, s), 4.35 (1H, t, J=7.6 Hz), 6.65 (2H, brs), 7.06 (1H, s), 7.16 (1H, s), 7.83 (1H, s), 8.18 (1H, t, J=5.9 Hz), 8.71 (1H, d, J=7.5 Hz).

Example 2-13

Production of (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid (Compound 64)

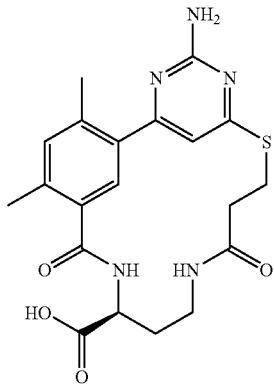 [SMILES: Cc1cc(C)c2cc1C(=O)N[C@H](C(=O)O)CCNC(=O)CCSc1cc-2nc(N)n1]

(S)-4-Amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid methyl ester (1.1 g) obtained in Example 2-12 was dissolved in methanol (24.8 ml), and then a 1N aqueous sodium hydroxide solution (2.7 ml) was added thereto at room temperature. The resulting mixture was stirred at room temperature for six hours, and then water (80 ml) was added thereto. The precipitate was collected by filtration, washed with water, and then dried under reduced pressure to yield (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid (Compound 64) (0.92 g) as a white solid material.

Physicochemical properties of (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid Molecular weight: 429.
ESI (LC/MS positive mode): m/z=430 (M+H$^+$)
Chemical shift value δ in $^1$H-NMR (300 MHz, in dimethylsulfoxide d-6): 1.84-2.02 (2H, m), 2.32-2.43 (2H, m), 2.36 (3H, s), 2.57 (3H, s), 2.62-2.72 (1H, m), 2.79-2.88 (1H, m), 2.99-3.09 (1H, m), 3.60-3.67 (1H, m), 4.28 (1H, t, J=7.2 Hz), 6.64 (2H, brs), 7.07 (1H, s), 7.15 (1H, s), 7.81 (1H, s), 8.16 (1H, t, J=5.5 Hz), 8.58 (1H, d, J=8.0 Hz), 12.57 (1H, brs).

Example 2-14

Preparation of (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid methylamide (Compound 65)

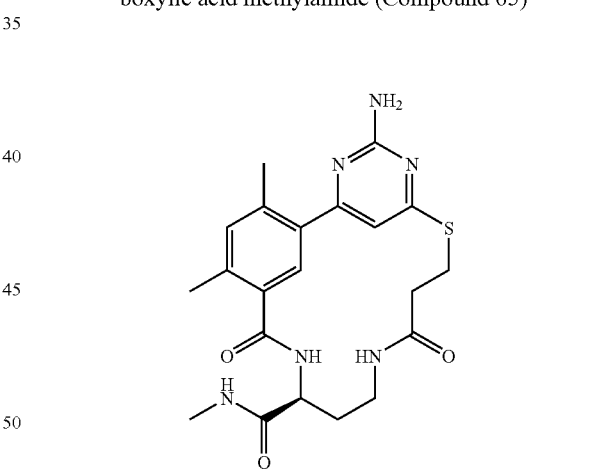

(S)-4-Amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid (25 mg, 0.058 mmol) obtained in Example 2-13 and 1-hydroxybenzotriazole (24 mg, 0.175 mmol) were dissolved in N,N-dimethylformamide (580 μl). Methylamine (2.0 M tetrahydrofuran solution, 88 μl, 0.175 mmol), 1-ethyl-3-(3'-dimethylaminopropyl)carbodiimide hydrochloride (34 mg, 0.175 mmol), and diisopropylethylamine (0.073 ml, 0.42 mmol) were added to the solution. The resulting mixture was stirred overnight at room temperature. The reaction solution was diluted with ethyl acetate, and sequentially washed with a saturated aqueous sodium bicarbonate solution, water (three times), and a saturated aqueous sodium chloride solution. The washed organic layer was dried over anhydrous sodium sulfate. After filtration, the filtrate was concentrated under reduced pressure. The resulting crude product was purified by preparative thin layer silica gel chromatography (developing solvent: dichloromethane:methanol=10:1) to yield (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid methylamide (Compound 65) (7 mg) was obtained as a white solid material.

Physicochemical properties of (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid methylamide Molecular weight: 442.
ESI (LC/MS positive mode): m/z=443 (M+H$^+$)
Chemical shift value δ in $^1$H-NMR (300 MHz, in dimethylsulfoxide d-6): 1.71-2.00 (2H, m), 2.33-3.37 (5H, m), 2.35 (3H, s), 2.57 (3H, s), 2.60 (3H, d, J=4.6 Hz), 3.50-3.58 (1H, m), 4.35 (1H, t, J=8.1 Hz), 6.63 (2H, brs), 7.07 (1H, s), 7.14 (1H, s), 7.81 (1H, s), 7.85 (1H, q, J=4.5 Hz), 8.11 (1H, t, J=5.9 Hz), 8.46 (1H, d, J=7.9 Hz).

Example 2-15

Production of (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid (2-methoxyethyl) amide (Compound 66)

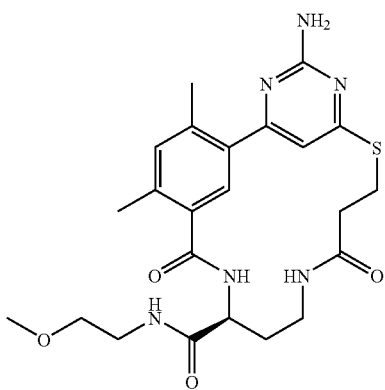 [SMILES: COCCNC(=O)[C@@H]1CCNC(=O)CCSc2cc(nc(N)n2)-c2cc(c(C)cc2C)C(=O)N1]

According to the method of Example 2-14 except that 2-methoxyethylamine (15 μl, 0.175 mmol) was used instead of methylamine, (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid (2-methoxyethyl)amide (Compound 66) (16 mg) was obtained as a white solid material from (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid (25 mg, 0.058 mmol) obtained in Example 2-13.

Physicochemical properties of (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid (2-methoxyethyl) amide Molecular weight: 486.
ESI (LC/MS positive mode): m/z=487 (M+H$^+$)
Chemical shift value δ in $^1$H-NMR (300 MHz, in dimethylsulfoxide d-6): 1.72-1.99 (2H, m), 2.33-2.47 (1H, m), 2.35 (3H, s), 2.57 (3H, s), 2.54-2.69 (1H, m), 2.78-2.88 (1H, m), 3.02-3.36 (6H, m), 3.24 (3H, s), 3.52-3.60 (1H, m), 4.35 (1H, t, J=8.4 Hz), 6.64 (2H, brs), 7.06 (1H, s), 7.14 (1H, s), 7.81 (1H, s), 7.91 (1H, t, J=5.7 Hz), 8.12 (1H, t, J=5.7 Hz), 8.46 (1H, d, J=8.0 Hz).

Example 2-16

Production of (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid dimethylamide (Compound 67)

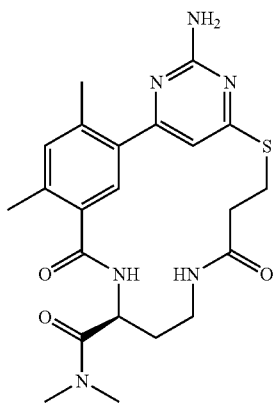 [SMILES: Cc1cc(C)c2cc1C(=O)N[C@H](C(=O)N(C)C)CCNC(=O)CCSc1cc-2nc(N)n1]

According to the method of Example 2-14 except that dimethylamine (2.0 M tetrahydrofuran solution, 88 μl, 0.175 mmol) was used instead of methylamine, (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid dimethylamide (Compound 67) (12 mg) was obtained as a white solid material from (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid (25 mg, 0.058 mmol) obtained in Example 2-13.

Physicochemical properties of (S)-4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid dimethylamide Molecular weight: 456.
ESI (LC/MS positive mode): m/z=457 (M+H$^+$)
Chemical shift value δ in $^1$H-NMR (300 MHz, in dimethylsulfoxide d-6): 1.65-1.94 (2H, m), 2.29-3.41 (5H, m), 2.32 (3H, s), 2.57 (3H, s), 2.84 (3H, s), 3.10 (3H, s), 3.59-3.68 (1H, m), 4.71 (1H, t, J=8.6 Hz), 6.63 (2H, brs), 7.10 (1H, s), 7.13 (1H, s), 7.83 (1H, s), 8.11 (1H, t, J=5.5 Hz), 8.55 (1H, d, J=7.7 Hz).

Example 2-17

Production of (S)-4-amino-14-hydroxymethyl-18,20-dimethyl-7-thia-3,5,11,15-tetraazatricyclo[15.3.1.1$^{2,6}$]docosa-1(20),2(22),3,5,17(21),18-hexaene-10,16-dione (Compound 68)

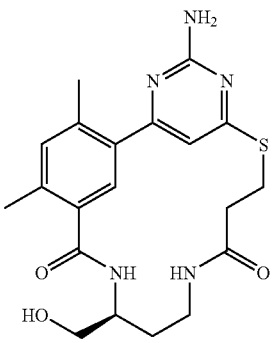 [SMILES: Cc1cc(C)c2cc1C(=O)N[C@H](CO)CCNC(=O)CCSc1cc-2nc(N)n1]

(S)-4-Amino-18,20-dimethyl-10,16-dioxo-7-thia-3,5,11,15-tetraazatricyclo[15.3.1.1$^{2,6}$]docosa-1(20),2(22),3,5,17(21),18-hexaene-14-carboxylic acid (550 mg, 1.28 mmol) obtained in Example 2-13 was dissolved in a mixture of tetrahydrofuran (13 ml) and methanol (1.5 ml). Isobutylchloroformate (250 µl, 1.92 mmol) and N-methylmorpholine (141 µl, 1.28 mmol) were added to the solution at room temperature. After stirring at room temperature for one hour, the mixture was cooled to 0° C. and an aqueous solution (1.5 ml) of sodium borohydride (97 mg, 2.56 mmol) was added thereto. The mixture was warmed to room temperature, and then diluted with ethyl acetate. The solution was sequentially washed with water and a saturated aqueous sodium chloride solution. The washed ethyl acetate solution was dried over anhydrous sodium sulfate. After filtration, the filtrate was concentrated under reduced pressure. The resulting crude product was purified by silica gel column chromatography (developing solvent: dichloromethane:methanol=10:1) to yield (S)-4-amino-14-hydroxymethyl-18,20-dimethyl-7-thia-3,5,11,15-tetraazatricyclo[15.3.1.1$^{2,6}$]docosa-1(20),2(22),3,5,17(21),18-hexaene-10,16-dione (Compound 68) (205 mg) as a white solid material.

Physicochemical properties of (S)-4-amino-14-hydroxymethyl-18,20-dimethyl-7-thia-3,5,11,15-tetraazatricyclo[15.3.1.1$^{2,6}$]docosa-1(20),2(22),3,5,17(21),18-hexaene-10,16-dione Molecular weight: 415.
ESI (LC/MS positive mode): m/z=416 (M+H$^+$)

Chemical shift value δ in $^1$H-NMR (300 MHz, in dimethylsulfoxide d-6): 1.69-1.89 (2H, m), 2.27-2.77 (3H, m), 2.37 (3H, s), 2.57 (3H, s), 3.07-3.60 (3H, m), 3.16 (1H, d, J=4.8 Hz), 3.83-3.93 (1H, m), 4.77 (1H, t, J=5.6 Hz), 6.64 (2H, brs), 6.96 (1H, s), 7.13 (1H, s), 7.71 (1H, s), 8.02 (1H, d, J=8.8 Hz), 8.06 (1H, t, J=5.5 Hz).

Example 2-18

Production of (R)-4-amino-18,20-dimethyl-10,16-dioxo-7-thia-3,5,11,15-tetraazatricyclo[15.3.1.1$^{2,6}$]docosa-1(20),2,4,6(22),17(21),18-hexaene-12-carboxylic acid methyl ester (Compound 69)

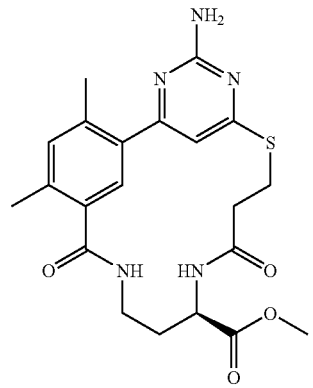

According to the method of Example 2-1 except that (R)-2-amino-4-tert-butoxycarbonyl aminobutyric acid methyl ester hydrochloride was used instead of 5-aminopentylcarbamic acid tert-butyl ester, (R)-4-amino-18,20-dimethyl-10,16-dioxo-7-thia-3,5,11,15-tetraazatricyclo[15.3.1.1$^{2,6}$]docosa-1(20),2,4,6(22),17(21),18-hexaene-12-carboxylic acid methyl ester (Compound 69) (10 mg) was obtained as a white solid material from 5-[2-amino-6-(2-carboxyethylsulfanyl)pyrimidin-4-yl]-2,4-dimethylbenzoic acid tert-butyl ester obtained in Step 1 of Example 2-1.

Physicochemical properties of (R)-4-amino-18,20-dimethyl-10,16-dioxo-7-thia-3,5,11,15-tetraazatricyclo[15.3.1.1$^{2,6}$]docosa-1(20),2,4,6(22),17(21),18-hexaene-12-carboxylic acid methyl ester Molecular weight: 443.
ESI (LC/MS positive mode): m/z=444 (M+H$^+$)

Chemical shift value δ in $^1$H-NMR (300 MHz, in dimethylsulfoxide d-6): 1.83-2.02 (m, 2H), 2.26-2.43 (m, 1H), 2.36 (3H, s), 2.57 (3H, s), 2.63-2.73 (1H, m), 2.80-2.88 (1H, m), 2.99-3.09 (1H, m), 3.33-3.39 (1H, m), 3.62-3.72 (1H, m), 3.66 (3H, s), 4.35 (1H, t, J=7.6 Hz), 6.65 (2H, brs), 7.06 (1H, s), 7.16 (1H, s), 7.83 (1H, s), 8.18 (1H, t, J=5.1 Hz), 8.71 (1H, d, J=7.1 Hz).

Example 2-19

Production of (S)-4-amino-18,20-dimethyl-12-(morpholine-4-carbonyl)-7-thia-3,5,11,15-tetraazatricyclo[15.3.1.1$^{2,6}$]docosa-1(20),2,4,6(22),17(21),18-hexaene-10,16-dione (Compound 70)

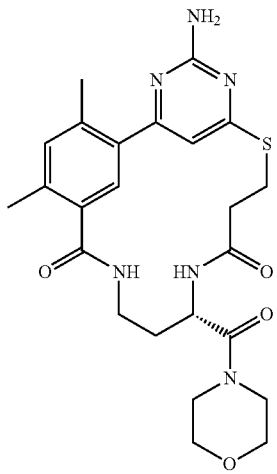 [SMILES: Cc1cc(C)c2cc1C(=O)NCC[C@@H](C(=O)N1CCOCC1)NC(=O)CCSc1cc-2nc(N)n1]

Step 1: Preparation of [(S)-3-(9H-fluoren-9-yl-methoxycarbonylamino)-4-morpholin-4-yl-4-oxobutyl]carbamic acid tert-butyl ester

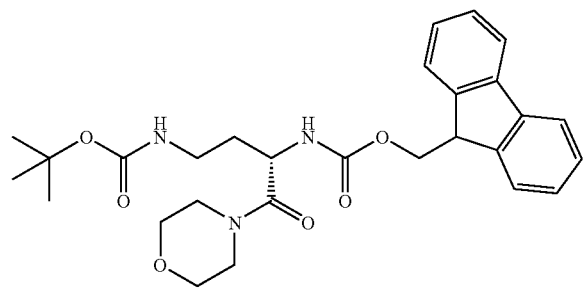 [SMILES: CC(C)(C)OC(=O)NCC[C@H](NC(=O)OCC1c2ccccc2-c2ccccc21)C(=O)N1CCOCC1]

(S)-4-tert-Butoxycarbonylamino-2-(9H-fluoren-9-yl-methoxycarbonylamino)butyric acid (150 mg, 0.341 mmol) was dissolved in N,N-dimethylformamide (1.0 ml), and then 2-3H-1,2,3-triazolo[4,5-b]pyridin-3-ol (51 mg, 0.377 mmol), O-(7-azabenzotriazole-1-yl)-N,N,N',N'-tetramethyluroniumhexafluorophosphate (148 mg, 0.377 mmol),2,4,6-trimethylpyridine (91 µl), and morpholine (45 µl, 0.512 mol) were added thereto at room temperature. After the mixture was stirred at room temperature for 16 hours, a saturated aqueous sodium chloride solution (20 ml) was added to stop the reaction. The mixture was extracted three times with ethyl acetate (20 ml). The ethyl acetate extraction solutions were combined together, and sequentially washed with a saturated aqueous sodium bicarbonate solution (20 ml) and a saturated aqueous sodium chloride solution (20 ml). The washed ethyl acetate solution was dried over anhydrous sodium sulfate. After filtration, the filtrate was concentrated under reduced pressure. The resulting crude product was purified by silica gel column chromatography (developing solvent: n-hexane:ethyl acetate=1:1) to yield [(S)-3-(9H-fluoren-9-ylmethoxycarbonylamino)-4-morpholin-4-yl-4-oxobutyl]carbamic acid tert-butyl ester (172.2 mg) as a white amorphous material.

Physicochemical properties of [(S)-3-(9H-fluoren-9-ylmethoxycarbonylamino)-4-morpholin-4-yl-4-oxobutyl]carbamic acid tert-butyl ester Molecular weight: 509.
ESI (LC/MS positive mode): m/z=510 (M+H$^+$), retention time: 2.67 minutes (developing solvent: A, acetonitrile containing 0.05% trifluoroacetic acid; B, 0.05% aqueous trifluoroacetic acid solution; B, 10% (O min) 95% (3.5 min) 10% (4.5 min); flow rate, 4 ml/min, column: Waters Sunfire C18, 5 µm, 4.6×50 mm)

Step 2: Preparation of ((S)-3-amino-4-morpholin-4-yl-4-oxobutyl)carbamic acid tert-butyl ester

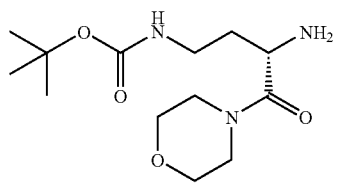 [SMILES: CC(C)(C)OC(=O)NCC[C@H](N)C(=O)N1CCOCC1]

[(S)-3-(9H-fluoren-9-ylmethoxycarbonylamino)-4-morpholin-4-yl-4-oxobutyl]carbamic acid tert-butyl ester (172 mg, 0.338 mol) obtained in Step 1 above was dissolved in N,N-dimethylformamide (1.5 ml), and then piperidine (84 µl) was added thereto. After the solution was stirred at room temperature for 30 minutes, the solvent was concentrated under reduced pressure. The resulting crude product was purified by silica gel column chromatography (developing solvent: dichloromethane:methanol=20:1) to yield ((S)-3-amino-4-morpholin-4-yl-4-oxobutyl)carbamic acid tert-butyl ester (95 mg) as a colorless oily material.

Physicochemical properties of ((S)-3-amino-4-morpholin-4-yl-4-oxobutyl)carbamic acid tert-butyl ester Molecular weight: 287.
ESI (LC/MS positive mode): m/z=288 (M+H$^+$)
Chemical shift value δ in $^1$H-NMR (400 MHz, in dimethylsulfoxide d-6): 1.31-1.42 (10H, m), 1.58-1.70 (1H, m), 3.02 (2H, dd, J=12.8 Hz, 6.4 Hz), 3.40-3.60 (8H, m), 3.69 (1H, dd, J=8.7 Hz, 4.1 Hz), 6.85 (1H, brs).

Step 3: Preparation of 5-(2-amino-6-{2-[(S)-3-tert-butoxycarbonylamino-1-(morpholine-4-carbonyl)propylcarbamoyl]ethylsulfanyl}pyrimidin-4-yl)-2,4-dimethylbenzoic acid tert-butyl ester

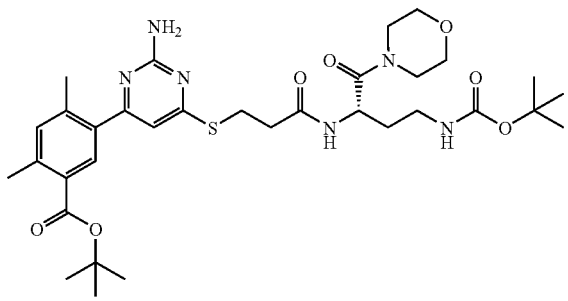 [SMILES: Cc1cc(C)c(-c2cc(SCCC(=O)N[C@@H](CCNC(=O)OC(C)(C)C)C(=O)N3CCOCC3)nc(N)n2)cc1C(=O)OC(C)(C)C]

O-(7-Azabenzotriazol-1-yl)-N,N,N',N'-tetramethyluroniumhexafluorophosphate (58 mg, 0.149 mmol), and diisopropylethylamine (43 µl, 0.247 mmol) were added at room temperature to an N,N-dimethylformamide solution (1.0 ml) of ((S)-3-amino-4-morpholin-4-yl-4-oxobutyl)carbamic acid tert-butyl ester (44 mg) obtained in Step 2 above and 5-[2-amino-6-(2-carboxyethylsulfanyl)pyrimidin-4-yl]-2,4-dimethyl-benzoic acid tert-butyl ester (50.3 mg) obtained in Step 1 of Example 2-1. The reaction solution was stirred for 16 hours, and then concentrated under reduced pressure. The resulting crude product was purified by silica gel column chromatography (developing solvent: dichloromethane: methanol=30:1) to yield 5-(2-amino-6-{2-[(S)-3-tert-butoxycarbonylamino-1-(morpholine-4-carbonyl)propylcarbamoyl]ethylsulfanyl}pyrimidin-4-yl)-2,4-dimethylbenzoic acid tert-butyl ester (84 mg) as a pale yellow oily material.

Physicochemical properties of 5-(2-amino-6-{2-[(S)-3-tert-butoxycarbonylamino-1-(morpholine-4-carbonyl)propylcarbamoyl]ethylsulfanyl}pyrimidin-4-yl)-2,4-dimethylbenzoic acid tert-butyl ester Molecular weight: 672.
ESI (LC/MS positive mode): m/z=673 (M+H$^+$)
Chemical shift value δ in $^1$H-NMR (400 MHz, in dimethylsulfoxide d-6): 1.36 (9H, s), 1.55-1.61 (10H, m), 1.74-1.85 (1H, m), 2.35 (3H, s), 2.50 (3H, s), 2.53-2.60 (1H, m), 2.84-

3.00 (1H, m), 3.24-3.62 (12H, m), 4.64-4.78 (1H, m), 6.56 (1H, s), 6.76 (2H, s), 7.21 (1H, s), 7.72 (1H, s), 8.30 (1H, d, J=8.2 Hz).

Step 4: Preparation of (S)-4-amino-18,20-dimethyl-12-(morpholine-4-carbonyl)-7-thia-3,5,11,15-tetraazatricyclo[15.3.1.1$^{2,6}$]docosa-1(20),2,4,6(22),17(21),18-hexaene-10,16-dione (Compound 70)

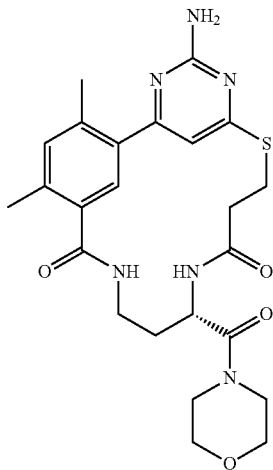

5-(2-Amino-6-{2-[(S)-3-tert-butoxycarbonylamino-1-(morpholine-4-carbonyl) propylcarbamoyl] ethylsulfanyl}pyrimidin-4-yl)-2,4-dimethylbenzoic acid tert-butyl ester (79 mg) obtained in Step 3 above was dissolved in dichloromethane (1.5 ml), and then trifluoroacetic acid (0.5 ml) was added thereto at room temperature. The reaction solution was stirred for two hours, and then concentrated under reduced pressure. Toluene (3 ml) was added to the obtained residue, and then concentrated under reduced pressure. The resulting pale yellow oily material was dissolved in a mixture of N,N-dimethylformamide (29 ml) and tetrahydrofuran (29 ml), and then O-(7-azabenzotriazole-1-yl)-N,N,N',N'-tetramethyluroniumhexafluorophosphate (55.8 mg, 0.142 mmol) and diisopropylethylamine (0.102 ml) were added thereto at room temperature. The reaction solution was stirred for one hour. Water (20 ml) was added to the reaction solution, and concentrated under reduced pressure. A saturated aqueous sodium bicarbonate solution (30 ml) was added to the resulting residue and then extracted twice with ethyl acetate (30 ml). The ethyl acetate solution was washed twice with a saturated aqueous sodium chloride solution (20 ml) and a saturated aqueous sodium bicarbonate solution (20 ml). The washed ethyl acetate solution was dried over anhydrous sodium sulfate. After filtration, the filtrate was concentrated under reduced pressure. The resulting crude product was purified by high performance liquid chromatography (developing solvent: A, acetonitrile containing 0.05% trifluoroacetic acid; B, 0.05% aqueous trifluoroacetic acid solution; gradient condition: B, 1% (0 min)→1% (1 min)→30% (7 min)→95% (8 min)→95% (9 min)→1% (10 min); flow rate, 35 ml/min; column, Waters, SunFire PrepC18, 5 μm, 30×50 mm). A fraction containing the material of interest was neutralized with solid-supported tetraalkyl ammonium carbonate (Polymer Laboratories, PL-HCO$_3$ MP-Resin) to yield (S)-4-amino-18,20-dimethyl-12-(morpholine-4-carbonyl)-7-thia-3,5,11,15-tetraazatricyclo[15.3.1.1$^{2,6}$]docosa-1(20),2,4,6(22),17(21),18-hexaene-10,16-dione (Compound 70)(37 mg) as a white solid material.

Physicochemical properties of (S)-4-amino-18,20-dimethyl-12-(morpholine-4-carbonyl)-7-thia-3,5,11,15-tetraazatricyclo[15.3.1.1$^{2,6}$]docosa-1(20),2,4,6(22),17(21),18-hexaene-10,16-dione Molecular weight: 498.
ESI (LC/MS positive mode): m/z=499 (M+H$^+$)
Chemical shift value δ in $^1$H-NMR (400 MHz, in dimethylsulfoxide d-6): 1.75-1.90 (2H, m), 2.39 (3H, s), 2.57 (3H, s), 2.78-3.07 (2H, m), 3.14-3.70 (12H, m), 4.72-4.80 (1H, m), 6.66 (2H, s), 6.91 (1H, s), 7.13 (1H, s), 7.74 (1H, s), 8.30 (1H, t, J=5.7 Hz), 8.43 (1H, d, J=7.8 Hz).

Example 2-20

Production of (S)-4-amino-18,20-dimethyl-12-morpholin-4-ylmethyl-7-thia-3,5,11,15-tetraazatricyclo[15.3.1.1$^{2,6}$]docosa-1(20),2(22),3,5,17(21),18-hexaene-10,16-dione (Compound 71)

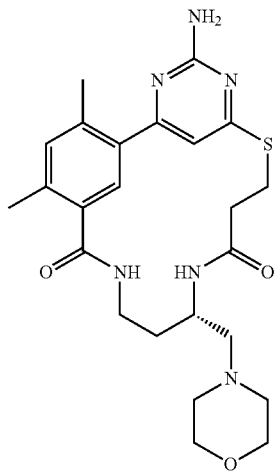 [SMILES: Cc1cc(C)c2cc1C(=O)NCC[C@@H](CN1CCOCC1)NC(=O)CCSc1cc-2nc(N)n1]

Step 1: Preparation of [(S)-3-(9H-fluoren-9-yl-methoxycarbonylamino)-4-hydroxybutyl]carbamic acid tert-butyl ester

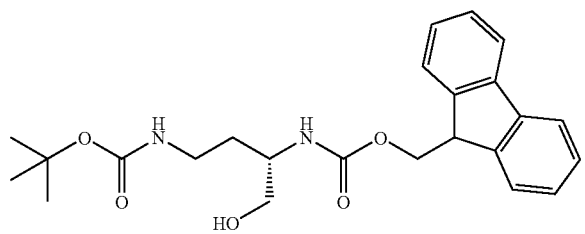 [SMILES: CC(C)(C)OC(=O)NCC[C@@H](CO)NC(=O)OCC1c2ccccc2-c2ccccc21]

(S)-4-tert-Butoxycarbonylamino-2-(9H-fluoren-9-yl-methoxycarbonylamino)butyric acid (493 mg, 1.12 mmol) was dissolved in tetrahydrofuran (1 ml), and then isobutyl chloroformate (0.15 ml, 1.14 mmol) and N-methylmorpholine (0.125 ml, 1.15 mmol) were added thereto at −15° C.

After stirring for one hour, the precipitate was filtrated and washed with tetrahydrofuran (7 ml). The filtrate was cooled to −15° C., and an aqueous solution (4 ml) of sodium borohydride (127 mg, 3.36 mmol) was dropwise added thereto. After stirring for 30 minutes, water (25 ml) was added to the solution and extracted three times with ethyl acetate (20 ml). The ethyl acetate solution was dried over anhydrous sodium sulfate. After filtration, the filtrate was concentrated under reduced pressure. The resulting crude product was purified by silica gel column chromatography (developing solvent: dichloromethane:methanol=50:1) to yield [(S)-3-(9H-fluoren-9-ylmethoxycarbonylamino)-4-hydroxybutyl]carbamic acid tert-butyl ester (411 mg) as a colorless oily material.

Physicochemical properties of [(S)-3-(9H-fluoren-9-ylmethoxycarbonylamino)-4-hydroxybutyl]carbamic acid tert-butyl ester Molecular weight: 426.
ESI (LC/MS positive mode): m/z=427 (M+H$^+$)
Chemical shift value δ in $^1$H-NMR (400 MHz, in dimethylsulfoxide d-6): 1.30-1.46 (10H, m), 1.61-1.73 (1H, m), 2.80-3.06 (2H, m), 3.23-3.46 (3H, m), 4.18-4.36 (3H, m), 4.65 (1H, t, J=5.3 Hz), 6.70 (1H, d, J=10.0 Hz), 7.08 (1H, d, J=8.2 Hz), 7.33 (2H, t, J=7.6 Hz), 7.42 (2H, t, J=7.3 Hz), 7.69-7.74 (2H, m), 7.89 (2H, d, J=7.8 Hz).

Step 2: Preparation of ((S)-3-amino-4-morpholin-4-ylbutyl)carbamic acid tert-butyl ester

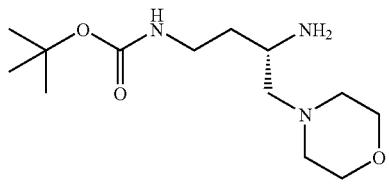 [SMILES: CC(C)(C)OC(=O)NCC[C@H](N)CN1CCOCC1]

[(S)-3-(9H-Fluoren-9-ylmethoxycarbonylamino)-4-hydroxybutyl]carbamic acid tert-butyl ester (128 mg, 0.301 mmol) obtained in Step 1 above was dissolved in dichloromethane (2.0 ml), and then methanesulfonyl chloride (35 μl, 0.452 mmol) and triethylamine (84 μl, 0.603 mmol) were added thereto at 0° C. After stirring for one hour, a saturated aqueous sodium bicarbonate solution (5 ml) and water (15 ml) were added to the mixture. The solution was extracted three times with dichloromethane (20 ml). The dichloromethane solutions were combined together and sequentially washed with a saturated aqueous sodium chloride solution, 0.1N hydrochloric acid, and a saturated aqueous sodium chloride solution. The washed dichloromethane solution was dried over anhydrous sodium sulfate. After filtration, the filtrate was concentrated under reduced pressure. The resulting crude product was dissolved in tetrahydrofuran (2.0 ml), and then morpholine (105 μl, 1.21 mmol) was added thereto. The mixture was heated at 65° C. for 16 hours. Water (5 ml) and 1N hydrochloric acid (1 ml) were added to the reaction solution, and washed with ethyl acetate (5 ml). A saturated aqueous sodium bicarbonate solution (20 ml) was added to the washed aqueous solution. The mixture was extracted three times with ethyl acetate (25 ml) and then three times with dichloromethane (25 ml). The ethyl acetate/dichloromethane solution was dried over anhydrous sodium sulfate. After filtration, the filtrate was concentrated under reduced pressure to yield ((S)-3-amino-4-morpholin-4-ylbutyl)carbamic acid tert-butyl ester (24 mg) as a colorless oily material.

Physicochemical properties of ((S)-3-amino-4-morpholin-4-ylbutyl)carbamic acid tert-butyl ester Molecular weight: 273.
ESI (LC/MS positive mode): m/z=274 (M+H$^+$)
Chemical shift value δ in $^1$H-NMR (400 MHz, in dimethylsulfoxide d-6): 1.10-1.60 (11H, m), 2.09 (2H, d, J=7.0 Hz), 2.23-2.43 (4H, m), 2.74-3.08 (3H, m), 3.52-3.60 (4H, m), 6.80-6.85 (1H, m).

Step 3: Preparation of 5-{2-amino-6-[2-((S)-3-tert-butoxycarbonylamino-1-morpholin-4-ylmethylpropylcarbamoyl)ethylsulfanyl]pyrimidin-4-yl}-2,4-dimethylbenzoic acid tert-butyl ester

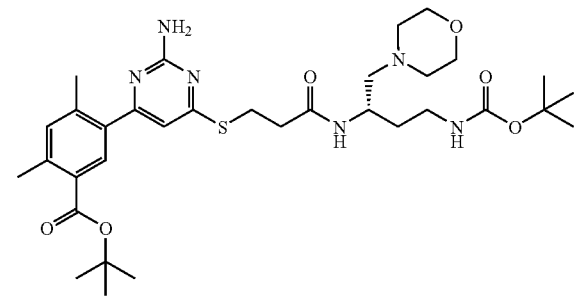 [SMILES: Cc1cc(C)c(-c2cc(SCCC(=O)N[C@@H](CCNC(=O)OC(C)(C)C)CN3CCOCC3)nc(N)n2)cc1C(=O)OC(C)(C)C]

According to the method of Step 3 of Example 2-19, 5-{2-amino-6-[2-((S)-3-tert-butoxycarbonylamino-1-morpholin-4-ylmethylpropylcarbamoyl)ethylsulfanyl]pyrimidin-4-yl}-2,4-dimethylbenzoic acid tert-butyl ester (49 mg) was obtained from ((S)-3-amino-4-morpholin-4-ylbutyl)carbamic acid tert-butyl ester (23 mg) obtained in Step 2 above and 5-[2-amino-6-(2-carboxyethylsulfanyl)pyrimidin-4-yl]-2,4-dimethylbenzoic acid tert-butyl ester (33 mg) obtained in Step 1 of Example 2-1.

Physicochemical properties of 5-{2-amino-6-[2-((S)-3-tert-butoxycarbonylamino-1-morpholin-4-ylmethylpropylcarbamoyl)ethylsulfanyl]pyrimidin-4-yl}-2,4-dimethylbenzoic acid tert-butyl ester Molecular weight: 658.
ESI (LC/MS positive mode): m/z=659 (M+H$^+$)
Chemical shift value δ in $^1$H-NMR (400 MHz, in dimethylsulfoxide d-6): 1.18-1.40 (10H, m), 1.53 (9H, s), 1.60-1.72 (1H, s), 2.16-2.56 (9H, m), 2.49 (3H, s), 2.78-2.90 (1H, m), 2.95-3.08 (1H, m), 3.24-3.40 (4H, m), 3.48-3.56 (4H, m), 3.86-3.96 (1H, m), 6.56 (1H, s), 6.67 (1H, brs), 6.76 (2H, s), 7.21 (1H, s), 7.72 (1H, s) 7.74 (1H, d, J=8.7 Hz).

Step 4: Preparation of (S)-4-amino-18,20-dimethyl-12-morpholin-4-ylmethyl-7-thia-3,5,11,15-tetraazatricyclo[15.3.1.1$^{2,6}$]docosa-1(20),2(22),3,5,17(21),18-hexaene-10,16-dione (Compound 71)

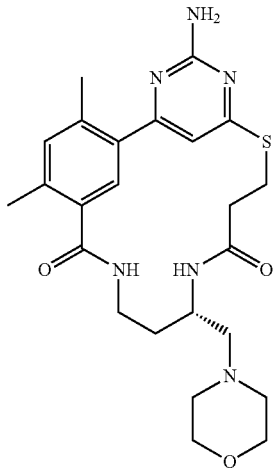 [SMILES: Cc1cc(C)c2cc1C(=O)NCC[C@@H](CN1CCOCC1)NC(=O)CCSc1cc-2nc(N)n1]

According to the method of Step 4 of Example 2-19, (S)-4-amino-18,20-dimethyl-12-morpholin-4-ylmethyl-7-thia-3,5,11,15-tetraazatricyclo[15.3.1.1$^{2,6}$]docosa-1(20),2(22),3,5,17(21),18-hexaene-10,16-dione (Compound 71) (19 mg) was obtained from 5-{2-amino-6-[2-((S)-3-tert-butoxycarbonylamino-1-morpholin-4-ylmethylpropylcarbamoyl)ethylsulfanyl]pyrimidin-4-yl}-2,4-dimethylbenzoic acid tert-butyl ester (47 mg) obtained in Step 3 above.

Physicochemical properties of (S)-4-amino-18,20-dimethyl-12-morpholin-4-ylmethyl-7-thia-3,5,11,15-tetraazatricyclo[15.3.1.1$^{2,6}$]docosa-1(20),2(22),3,5,17(21),18-hexaene-10,16-dione Molecular weight: 484.
ESI (LC/MS positive mode): m/z=485 (M+H$^+$)
Chemical shift value δ in $^1$H-NMR (400 MHz, in dimethylsulfoxide d-6): 1.52-1.65 (1H, m), 1.88-1.98 (1H, m), 2.12-2.25 (2H, m), 2.28-2.62 (11H, m), 2.70 (1H, t, J=12.8 Hz), 2.96-3.03 (2H, m), 3.44 (1H, t, J=12.1 Hz), 3.50-3.62 (4H, m), 3.69 (1H, dd, J=12.8, 6.4 Hz), 3.95 (1H, t, J=7.1 Hz), 6.65 (2H, s), 6.99 (1H, s), 7.13 (1H, s), 7.67 (1H, s), 7.85 (1H, d, J=8.2 Hz), 8.29 (1H, t, J=5.5 Hz).

Example 2-21
Production of 4-amino-18,20-dimethyl-11-(2-morpholin-4-ylethyl)-7-thia-3,5,11,15-tetraazatricyclo[15.3.1.1$^{2,6}$]docosa-1(20),2,4,6(22),17(21),18-hexaene-10,16-dione (Compound 36)

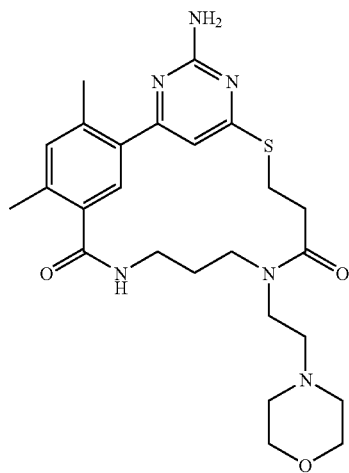 [SMILES: Cc1cc(C)c2cc1C(=O)NCCCN(CCN1CCOCC1)C(=O)CCSc1cc-2nc(N)n1]

Step 1: Preparation of [3-(2-morpholin-4-ylethylamino)propyl]carbamic acid tert-butyl ester

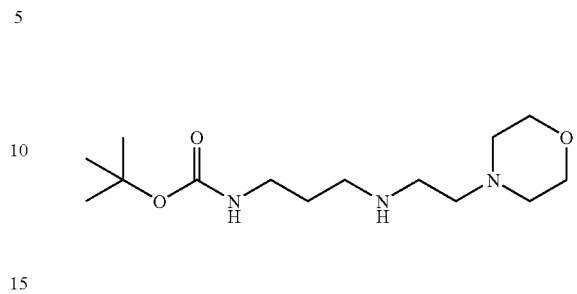

(3-Hydroxypropyl)carbamic acid tert-butyl ester (1.0 g, 5.71 mmol) was dissolved in dichloromethane (13 ml), and then methanesulfonyl chloride (2.2 ml, 28.4 mmol) and triethylamine (4.0 ml, 28.7 mmol) were added thereto at 0° C. The mixture was warmed to room temperature and stirred for one hour. Then, an 15% aqueous sodium hydroxide solution (5.3 ml) was added to the reaction solution at 0° C. The organic layer was separated and washed with a saturated aqueous sodium chloride solution. The solution was dried over anhydrous sodium sulfate. After filtration, the filtrate was concentrated under reduced pressure. The resulting crude product (482 mg, 1.90 mmol) was dissolved in anhydrous acetonitrile (3.0 ml), and then N-(2-aminoethyl)morpholine (0.991 ml, 7.61 mmol) was added thereto. The mixture was heated at 75° C. for 18 hours. The solvent was concentrated under reduced pressure. The resulting residue was dissolved in dichloromethane (30 ml). After water (20 ml) was added to the solution and the organic layer was separated, the aqueous layer was extracted three times with ethyl acetate (80 ml). The dichloromethane extract was washed with a saturated sodium carbonate solution (20 ml), and then combined with the ethyl acetate extract. The resulting solution was dried over anhydrous sodium sulfate. After filtration, the filtrate was concentrated under reduced pressure. The resulting crude product was purified by silica gel column chromatography (developing solvent: dichloromethane:methanol:28% ammonia water=89:10:1) to yield 3-(2-morpholin-4-ylethylamino)propyl)carbamic acid tert-butyl ester (200 mg) was obtained as a colorless oily material.

Physicochemical properties of [3-(2-morpholin-4-ylethylamino)propyl]carbamic acid tert-butyl ester Molecular weight: 287.
ESI (LC/MS positive mode): m/z=288 (M+H$^+$)
Chemical shift value δ in $^1$H-NMR (270 MHz, in dimethylsulfoxide d-6): 1.30-1.55 (11H, m), 2.28-2.61 (8H, m), 2.94 (2H, q, J=6.5 Hz), 3.32 (2H, brs), 3.55 (4H, t, J=4.6 Hz), 6.75-6.83 (1H, m).

Step 2: Method for producing {3-[[3-(2-amino-6-chloropyrimidin-4-ylsulfanyl)propionyl](2-morpholin-4-ylethyl)amino]propyl}carbamic acid tert-butyl ester

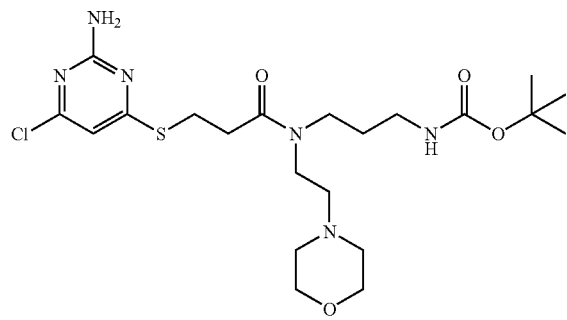 [SMILES: CC(C)(C)OC(=O)NCCCN(CCN1CCOCC1)C(=O)CCSc1cc(Cl)nc(N)n1]

According to the method of Step 1 of Example 2-9, {3-[[3-(2-amino-6-chloropyrimidin-4-ylsulfanyl)propionyl](2-morpholin-4-ylethyl)amino]propyl}carbamic acid tert-butyl ester (299 mg) was obtained from 3-(2-amino-6-chloropyrimidin-4-ylsulfanyl)propionic acid (180 mg) obtained in Step 1 of Example 2-8 and [3-(2-morpholin-4-ylethylamino)propyl]carbamic acid tert-butyl ester (201 mg) obtained in Step 1 above.

Physicochemical properties of {3-[[3-(2-amino-6-chloropyrimidin-4-ylsulfanyl)propionyl](2-morpholin-4-ylethyl)amino]propyl}carbamic acid tert-butyl ester Molecular weight: 503.
ESI (LC/MS positive mode): m/z=503, 505 (M+H$^+$)
Chemical shift value δ in $^1$H-NMR (400 MHz, in dimethylsulfoxide d-6): 1.31 (9H, s), 1.53-1.65 (2H, m), 2.32-2.41 (6H, m), 2.65-2.95 (4H, m), 3.20-3.38 (6H, m), 3.48-3.57 (4H, m), 6.50 (1H, s), 6.81 (1H, brs), 7.15 (2H, s).

Step 3: Preparation of 5-(2-amino-6-{2-[(3-tert-butoxycarbonylaminopropyl)(2-morpholin-4-ylethyl)carbamoyl]ethylsulfanyl}pyrimidin-4-yl)-2,4-dimethylbenzoic acid tert-butyl ester

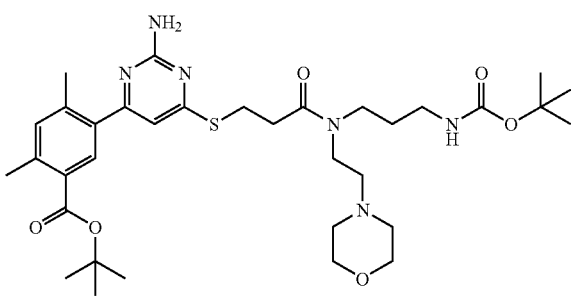 [SMILES: Cc1cc(C)c(-c2cc(SCCC(=O)N(CCCNC(=O)OC(C)(C)C)CCN3CCOCC3)nc(N)n2)cc1C(=O)OC(C)(C)C]

According to the method of Step 2 of Example 2-9, 5-(2-amino-6-{2-[(3-tert-butoxycarbonylaminopropyl)(2-morpholin-4-ylethyl)carbamoyl]ethylsulfanyl}pyrimidin-4-yl)-2,4-dimethylbenzoic acid tert-butyl ester (75 mg) was obtained from {3-[[3-(2-amino-6-chloropyrimidin-4-ylsulfanyl)propionyl](2-morpholin-4-ylethyl)amino]propyl}carbamic acid tert-butyl ester (106 mg) obtained in Step 2 above and 2,4-dimethyl-5-(4,4,5,5-tetramethyl[1,3,2]dioxaborolan-2-yl)benzoic acid tert-butyl ester (53 mg) obtained in Step 3 of Example 1-1.

Physicochemical properties of 5-(2-amino-6-{2-[(3-tert-butoxycarbonylaminopropyl)(2-morpholin-4-ylethyl)carbamoyl]ethylsulfanyl}pyrimidin-4-yl)-2,4-dimethylbenzoic acid tert-butyl ester Molecular weight: 672.
ESI (LC/MS positive mode): m/z=673 (M+H$^+$)
Chemical shift value δ in $^1$H-NMR (400 MHz, in dimethylsulfoxide d-6): 1.36 (9H, s), 1.49-1.67 (11H, m), 2.29-2.40 (9H, m), 2.49 (3H, s), 2.68-2.96 (4H, m), 3.22-3.40 (6H, m), 3.46-3.57 (4H, m), 6.55 (1H, s), 6.70-6.86 (3H, m), 7.21 (1H, s), 7.72 (1H, s).

Step 4: Preparation of 4-amino-18,20-dimethyl-11-(2-morpholin-4-ylethyl)-7-thia-3,5,11,15-tetraazatricyclo[15.3.1.1$^{2,6}$]docosa-1(20),2,4,6(22),17(21),18-hexaene-10,16-dione (Compound 36)

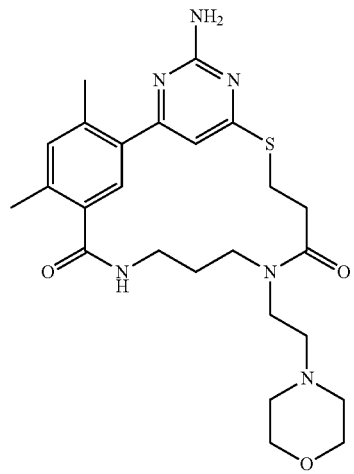 [SMILES: Cc1cc(C)c2cc1C(=O)NCCCN(CCN1CCOCC1)C(=O)CCSc1cc-2nc(N)n1]

According to the method of Step 4 of Example 2-16, 4-amino-18,20-dimethyl-11-(2-morpholin-4-ylethyl)-7-thia-3,5,11,15-tetraazatricyclo[15.3.1.1$^{2,6}$]docosa-1(20),2,4,6(22),17(21),18-hexaene-10,16-dione (Compound 36) (10 mg) was obtained from 5-(2-amino-6-{2-[(3-tert-butoxycarbonylaminopropyl)(2-morpholin-4-ylethyl)carbamoyl]ethylsulfanyl}pyrimidin-4-yl)-2,4-dimethylbenzoic acid tert-butyl ester (28 mg) obtained in Step 3 above.

Physicochemical properties of 4-amino-18,20-dimethyl-11-(2-morpholin-4-ylethyl)-7-thia-3,5,11,15-tetraazatricyclo[15.3.1.1$^{2,6}$]docosa-1(20),2,4,6(22),17(21),18-hexaene-10,16-dione Molecular weight: 498
ESI (LC/MS positive mode): m/z=499 (M+H$^+$)
Chemical shift value δ in $^1$H-NMR (500 MHz, at 150° C. in dimethylsulfoxide d-6): 1.83-1.90 (2H, m), 2.48-2.49 (4H, m), 2.48-2.52 (5H, m), 2.59 (3H, s), 2.98 (2H, t, J=7.0 Hz), 3.31-3.36 (4H, m), 3.45 (2H, t, J=7.0 Hz), 3.51 (2H, t, J=7.5 Hz), 3.54-3.58 (4H, m), 6.00 (2H, s), 7.14 (2H, s), 7.65 (1H, rs), 7.75 (1H, brs).

Example 2-22

Production of 4-amino-11,18,20-trimethyl-7-thia-3,5,11,15-tetraazatricyclo[15.3.1.1$^{2,6}$]docosa-1(20),2,4,6(22),17(21),18-hexaene-10,16-dione (Compound 32)

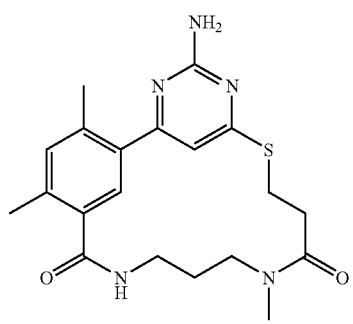 [SMILES: Cc1cc(C)c2cc1C(=O)NCCCN(C)C(=O)CCSc1cc-2nc(N)n1]

Step 1: Preparation of (3-{[3-(2-amino-6-chloropyrimidin-4-ylsulfanyl)propionyl]methylamino}propyl)carbamic acid tert-butyl ester

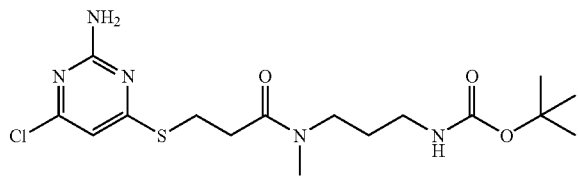 [SMILES: CN(CCCNC(=O)OC(C)(C)C)C(=O)CCSc1cc(Cl)nc(N)n1]

According to the method of Step 1 of Example 2-21 except that methylamine hydrochloride was used instead of N-(2-aminoethyl)morpholine, (3-methylaminopropyl)carbamic acid tert-butyl ester was obtained from (3-hydroxypropyl)carbamic acid tert-butyl ester (473 mg). According to the method of Step 1 of Example 2-9, 3-{[3-(2-amino-6-chloropyrimidin-4-ylsulfanyl)propionyl]methylamino}propyl)carbamic acid tert-butyl ester (139 mg) was obtained from the above (3-methylaminopropyl)carbamic acid tert-butyl ester and 3-(2-amino-6-chloropyrimidin-4-ylsulfanyl)propionic acid (161 mg) obtained in Step 1 of Example 2-8.

Physicochemical properties of (3-{[3-(2-amino-6-chloropyrimidin-4-ylsulfanyl)propionyl]methylamino}propyl)carbamic acid tert-butyl ester Molecular weight: 403.
ESI (LC/MS positive mode): m/z=404, 406 (M+H$^+$)
Chemical shift value δ in $^1$H-NMR (400 MHz, in dimethylsulfoxide d-6): 1.37 (9H, s), 1.50-1.65 (2H, m), 2.66-2.75 (2H, m), 2.78-2.81 (1H, m), 2.85-2.94 (4H, m), 3.20-3.32 (4H, m), 6.58 (1H, s), 6.70-6.90 (1H, m), 7.13 (2H, brs).

Step 2: Preparation of 5-(2-amino-6-{2-[(3-tert-butoxycarbonylaminopropyl)methylcarbamoyl)ethylsulfanyl]pyrimidin-4-yl}-2,4-dimethylbenzoic acid tert-butyl ester

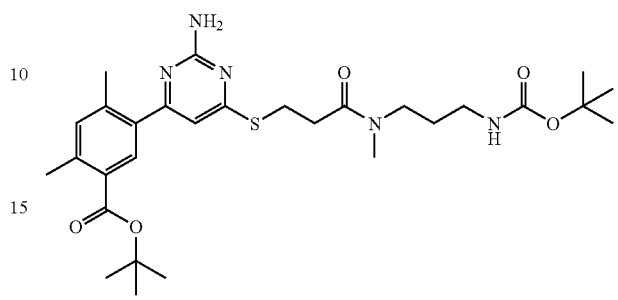

According to the method of Step 2 of Example 2-9, 5-(2-amino-6-{2-[(3-tert-butoxycarbonylaminopropyl)methylcarbamoyl]ethylsulfanyl}pyrimidin-4-yl)-2,4-dimethylbenzoic acid tert-butyl ester (41 mg) was obtained from (3-{[3-(2-amino-6-chloropyrimidin-4-ylsulfanyl)propionyl]methylamino}propyl)carbamic acid tert-butyl ester (70 mg) obtained in Step 1 above and 2,4-dimethyl-5-(4,4,5,5-tetramethyl-[1,3,2]dioxaborolan-2-yl)benzoic acid tert-butyl ester (61 mg) obtained in Step 3 of Example 1-1.

Physicochemical properties of 5-(2-amino-6-{2-[(3-tert-butoxycarbonylaminopropyl)methylcarbamoyl)ethylsulfanyl]pyrimidin-4-yl}-2,4-dimethylbenzoic acid tert-butyl ester Molecular weight: 573.
ESI (LC/MS positive mode): m/z=574 (M+H$^+$)
Chemical shift value δ in $^1$H-NMR (400 MHz, in dimethylsulfoxide d-6): 1.36 (9H, s), 1.50-1.66 (1H, m), 2.35 (3H, s), 2.49 (3H, s), 2.69-2.77 (2H, m), 2.80 (1H, s), 2.85-2.94 (4H, m), 3.20-3.30 (4H, m), 6.55 (1H, s), 6.68-6.90 (3H, m), 7.21 (1H, s), 7.72 (1H, s).

Step 3: Preparation of 4-amino-11,18,20-trimethyl-7-thia-3,5,11,15-tetraazatricyclo[15.3.1.1$^{2,6}$]docosa-1(20),2,4,6(22),17(21),18-hexaene-10,16-dione (Compound 32)

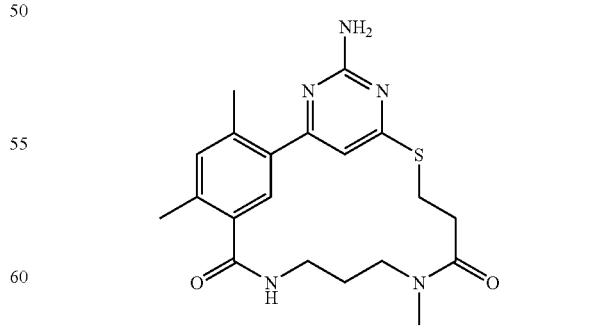

According to the method of Step 4 of Example 2-16, 4-amino-11,18,20-trimethyl-7-thia-3,5,11,15-tetraazatricyclo[15.3.1.1$^{2,6}$]docosa-1(20),2,4,6(22),17(21),18-hexaene-10,16-dione (Compound 32) (11 mg) was obtained from 5-(2- amino-6-{2-[(3-tert-butoxycarbonylaminopropyl) methylcarbamoyl]ethylsulfanyl}pyrimidin-4-yl)-2,4-dimethylbenzoic acid tert-butyl ester (50 mg) obtained in Step 2 above.

Physicochemical properties of 4-amino-11,18,20-trimethyl-7-thia-3,5,11,15-tetraazatricyclo[15.3.1.1$^{2,6}$]docosa-1(20),2,4,6(22),17(21),18-hexaene-10,16-dione Molecular weight: 399.
ESI (LC/MS positive mode): m/z=400 (M+H$^+$)
Chemical shift value δ in $^1$H-NMR (500 MHz, at 150° C. in dimethylsulfoxide d-6): 1.73-1.78 (2H, m), 2.50 (3H, s), 2.59 (3H, s), 2.80-2.88 (5H, m), 3.17-3.28 (4H, m), 3.49 (2H, t, J=7.0 Hz), 6.00 (2H, s), 7.08 (1H, brs), 7.13 (1H, s), 7.60 (1H, s), 7.71 (1H, 1H, brs).

Example 2-23

Production of 4-amino-11-(2-hydroxyethyl)-18,20-dimethyl-7-thia-3,5,11,15-tetraazatricyclo[15.3.1.1$^{2,6}$]docosa-1(20),2,4,6(22),17(21),18-hexaene-10,16-dione (Compound 34)

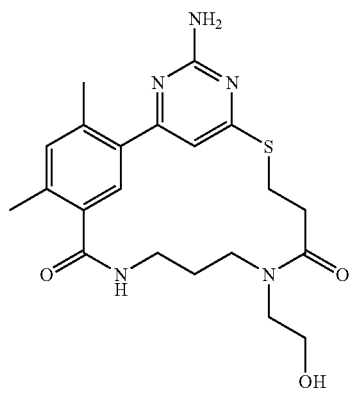 [SMILES: Cc1cc(C)c2cc1C(=O)NCCCN(CCO)C(=O)CCSc1cc-2nc(N)n1]

Step 1: Preparation of [3-(2-hydroxyethylamino)propyl]carbamic acid tert-butyl ester

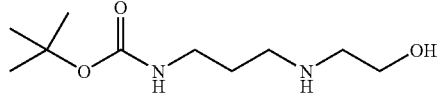

According to the method of Step 1 of Example 2-21 except that 2-aminoethanol (0.49 ml) was used instead of N-(2-aminoethyl)morpholine, [3-(2-hydroxyethylamino)propyl]carbamic acid tert-butyl ester (264 mg) was obtained as a colorless oily material from (3-hydroxypropyl)carbamic acid tert-butyl ester (518 mg).

Physicochemical properties of [3-(2-hydroxyethylamino)propyl]carbamic acid tert-butyl ester Molecular weight: 218.
ESI (LC/MS positive mode): m/z=219 (M+H$^+$)
Chemical shift value δ in $^1$H-NMR (270 MHz, in dimethylsulfoxide d-6): 1.37 (9H, s), 1.42-1.55 (2H, m), 2.44-2.56 (4H, m), 2.94 (2H, q, J=6.4 Hz), 3.42 (2H, t, J=5.8 Hz), 4.44 (1H, brs), 6.78 (1H, t, J=10.0 Hz).

Step 2: Preparation of {3-[[3-(2-amino-6-chloropyrimidin-4-ylsulfanyl)propionyl](2-hydroxyethyl)amino]propyl}carbamic acid tert-butyl ester

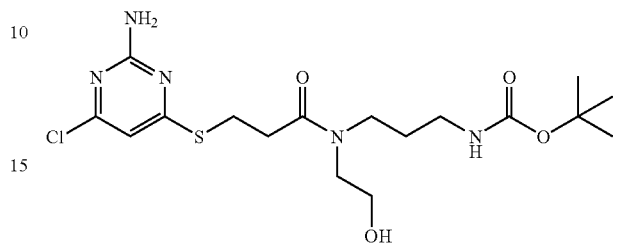

According to the method of Step 1 of Example 2-9, {3-[[3-(2-amino-6-chloropyrimidin-4-ylsulfanyl)propionyl](2-hydroxyethyl)amino]propyl}carbamic acid tert-butyl ester (280 mg) was obtained from 3-(2-amino-6-chloropyrimidin-4-ylsulfanyl)propionic acid (213 mg) obtained in Step 1 of Example 2-8 and [3-(2-hydroxyethylamino)propyl]carbamic acid tert-butyl ester (179 mg) obtained in Step 1 above.

Physicochemical properties of {3-[[3-(2-amino-6-chloropyrimidin-4-ylsulfanyl)propionyl](2-hydroxyethyl)amino]propyl}carbamic acid tert-butyl ester Molecular weight: 433.
ESI (LC/MS positive mode): m/z=434, 436 (M+H$^+$)
Chemical shift value δ in $^1$H-NMR (400 MHz, in dimethylsulfoxide d-6): 1.36 (9H, s), 1.50-1.65 (2H, m), 2.65-2.98 (4H, m), 3.22-3.34 (6H, m), 3.42-3.51 (2H, m), 4.63-4.88 (1H, m), 6.58 (2H, s), 6.71-6.88 (1H, m), 7.13 (1H, s).

Step 3: Preparation of 5-(2-amino-6-{2-[(3-tert-butoxycarbonylaminopropyl)-(2-hydroxyethyl)carbamoyl]ethylsulfanyl}pyrimidin-4-yl)-2,4-dimethylbenzoic acid tert-butyl ester

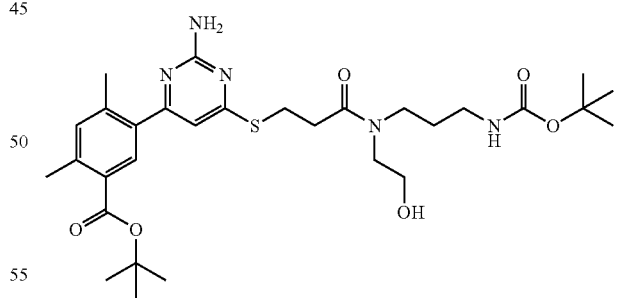

According to the method of Step 2 of Example 2-9, 5-(2-amino-6-{2-[(3-tert-butoxycarbonylaminopropyl)(2-hydroxyethyl)carbamoyl]ethylsulfanyl}pyrimidin-4-yl)-2,4-dimethylbenzoic acid tert-butyl ester (60 mg) was obtained as a white solid material from {3-[[3-(2-amino-6-chloropyrimidin-4-ylsulfanyl)propionyl](2-hydroxyethyl)amino] propyl}carbamic acid tert-butyl ester (78 mg) obtained in Step 2 above and 2,4-dimethyl-5-(4,4,5,5-tetramethyl[1,3,2] dioxaborolan-2-yl)benzoic acid tert-butyl ester (63 mg) obtained in Step 3 of Example 1-1.

Physicochemical properties of 5-(2-amino-6-{2-[(3-tert-butoxycarbonylaminopropyl)(2-hydroxyethyl)carbamoyl]ethylsulfanyl}pyrimidin-4-yl}-2,4-dimethylbenzoic acid tert-butyl ester Molecular weight: 603.

ESI (LC/MS positive mode): m/z=604 (M+H$^+$)

Chemical shift value δ in $^1$H-NMR (400 MHz, in dimethylsulfoxide d-6): 1.32-1.40 (9H, m), 1.51-1.65 (1H, m), 2.34 (3H, s), 2.49 (3H, s), 2.70-2.91 (4H, m), 3.22-3.42 (6H, m), 3.42-3.52 (2H, m), 4.62-4.89 (1H, m), 6.55 (1H, s), 6.71-6.88 (3H, m), 7.21 (1H, s), 7.72 (1H, s).

Step 4: Preparation of 4-amino-11-(2-hydroxyethyl)-18,20-dimethyl-7-thia-3,5,11,15-tetraazatricyclo[15.3.1.1$^{2,6}$]docosa-1(20),2,4,6(22),17(21),18-hexaene-10,16-dione (Compound 34)

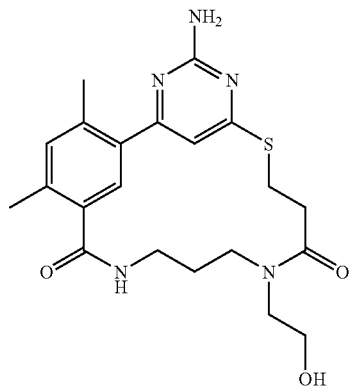 [SMILES: Cc1cc(C)c2cc1C(=O)NCCCN(CCO)C(=O)CCSc1cc-2nc(N)n1]

According to the method of Step 4 of Example 2-19, 4-amino-11-(2-hydroxyethyl)-18,20-dimethyl-7-thia-3,5,11,15-tetraazatricyclo[15.3.1.1$^{2,6}$]docosa-1(20),2,4,6(22),17(21),18-hexaene-10,16-dione (Compound 34) (4.7 mg) was obtained as a white solid material from 5-(2-amino-6-{2-[(3-tert-butoxycarbonylaminopropyl)(2-hydroxyethyl)carbamoyl]ethylsulfanyl}pyrimidin-4-yl)-2,4-dimethylbenzoic acid tert-butyl ester (60 mg) obtained in Step 3 above.

Physicochemical properties of 4-amino-11-(2-hydroxyethyl)-18,20-dimethyl-7-thia-3,5,11,15-tetraazatricyclo[15.3.1.1$^{2,6}$]docosa-1(20),2,4,6(22),17(21),18-hexaene-10,16-dione Molecular weight: 429.

ESI (LC/MS positive mode): m/z=430 (M+H$^+$)

Chemical shift value δ in $^1$H-NMR (500 MHz, at 150° C. in dimethylsulfoxide d-6): 1.81-1.87 (2H, m), 2.42 (3H, s), 2.57 (3H, s), 2.90 (1H, s), 2.94-2.99 (2H, t, J=7.0 Hz), 3.27-3.34 (4H, m), 3.38-3.43 (2H, m), 3.50 (2H, t, J=7.0 Hz), 3.56 (2H, t, J=6.0 Hz), 5.95 (2H, s), 7.11 (1H, s), 7.18 (1H, brs), 7.63 (1H, s). 7.72 (1H, brs).

Example 2-24

Production of (S)-4-amino-19,21-dimethyl-10-oxo-7-thia-16-oxa-3,5,11,24-tetraazatetracyclo[16.3.1.1$^{2,6}$.1$^{7,10}$]tetracosa-1(22),2(23),3,5,17(24),19,21-heptaen-10-one (Compound 83)

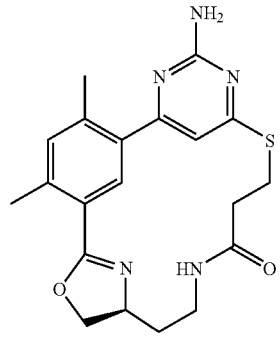 [SMILES: Cc1cc(C)c2cc1C1=N[C@@H](CCNC(=O)CCSc3cc-2nc(N)n3)CO1]

(S)-4-Amino-14-hydroxymethyl-18,20-dimethyl-7-thia-3,5,11,15-tetraazatricyclo[15.3.1.1$^{2,6}$]docosa-1(20),2(22),3,5,17(21),18-hexaene-10,16-dione (200 mg, 0.48 mmol) obtained in Example 2-17 and triethylamine (201 μl, 1.44 mmol) were dissolved in N,N-dimethylformamide (2.4 ml). Methanesulfonyl chloride (56 μl, 0.72 mmol) was added to the solution at room temperature. The resulting mixture was stirred at room temperature for 15 hours. Water (2 ml) was added to the reaction solution and extracted with ethyl acetate (10 ml, three times). The organic layers were combined together, and sequentially washed with water (10 ml, three times) and a saturated aqueous sodium chloride solution (10 ml). The organic solution was dried over anhydrous sodium sulfate. After the inorganic salt was removed by filtration, the filtrate was concentrated under reduced pressure. The resulting residue was purified by silica gel column chromatography (developing solvent: dichloromethane:methanol=20:1) to yield (S)-4-amino-19,21-dimethyl-10-oxo-7-thia-16-oxa-3,5,11,24-tetraazatetracyclo[16.3.1.1$^{2,6}$.1$^{7,10}$]tetracosa-1(22),2(23),3,5,17(24),19,21-heptaen-10-one (Compound 83) (85 mg) as a white solid material.

Physicochemical properties of (S)-4-amino-19,21-dimethyl-10-oxo-7-thia-16-oxa-3,5,11,24-tetraazatetracyclo[16.3.1.1$^{2,6}$.1$^{7,10}$]tetracosa-1(22),2(23),3,5,17(24),19,21-heptaen-10-one Molecular weight: 397.

ESI (LC/MS positive mode): 398 (M+H$^+$).

Chemical shift value δ in $^1$H-NMR (270 MHz, in dimethylsulfoxide d-6): 1.48-1.61 (1H, m), 1.80-1.92 (1H, m), 2.47 (3H, s), 2.55-2.70 (1H, m), 2.61 (3H, s), 2.98-3.14 (2H, m), 3.17 (1H, m), 3.29-3.43 (1H, m), 3.51-3.62 (1H, m), 4.06-4.11 (1H, m), 4.23-4.36 (1H, m), 4.55 (1H, t, J=8.7 Hz), 6.65 (1H, s), 6.71 (2H, brs), 7.20 (1H, s), 7.87 (1H, brs), 8.17 (1H, s).

Example 2-25

Production of 4-amino-20,22-dimethyl-14-oxa-7-thia-3,5,11,17-tetraazatricyclo[17.3.1.1$^{2,6}$]tetracosa-1(22),2(24),3,5,19(23),20-hexaene-10,18-dione (Compound 29)

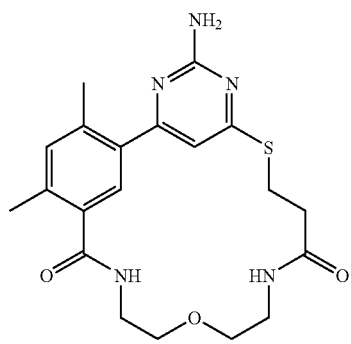

Step 1: Preparation of 5-(2-amino-6-{2-[2-(2-aminoethoxy)ethylcarbamoyl]ethylsulfanyl}pyrimidin-4-yl)-2,4-dimethyl benzoic acid tert-butyl ester

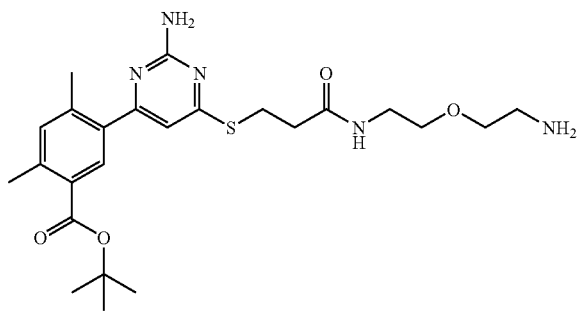 [SMILES: Cc1cc(C)c(-c2cc(SCCC(=O)NCCOCCN)nc(N)n2)cc1C(=O)OC(C)(C)C]

5-[2-Amino-6-(2-carboxylethylsulfanyl)pyrimidin-4-yl]-2,4-dimethylbenzoic acid tert-butyl ester (100 mg, 0.248 mmol) obtained in Step 1 of Example 2-1 and 2,2'-oxybis(ethylamine) (129 mg, 1.239 mmol) were dissolved in N,N-dimethylformamide (4 ml), and then the solution was cooled to 0° C. O-(7-azabenzotriazol-1-yl)-N,N,N',N'-tetramethyluroniumhexafluorophosphate (188 mg, 0.496 mmol) was added to the solution, and stirred at 0° C. for one hour. The reaction solution was diluted with ethyl acetate, and sequentially washed with a saturated aqueous sodium bicarbonate solution (twice) and a saturated aqueous sodium chloride solution. The organic layers were dried over anhydrous sodium sulfate. After the inorganic salt was removed by filtration, the filtrate was purified by aminopropylsilica gel column chromatography (developing solvent: dichloromethane:methanol=50:1 to 20:1) to yield 5-(2-amino-6-{2-[2-(2-aminoethoxy)ethylcarbamoyl]ethylsulfanyl}pyrimidin-4-yl)-2,4-dimethyl benzoic acid tert-butyl ester (78 mg).

Physicochemical properties of 5-(2-amino-6-{2-[2-(2-aminoethoxy)ethylcarbamoyl]ethylsulfanyl}pyrimidin-4-yl)-2,4-dimethyl benzoic acid tert-butyl ester Molecular weight: 489.
ESI (LC/MS positive mode): m/z=490 (M+H$^+$).

Step 2: Preparation of 4-amino-20,22-dimethyl-14-oxa-7-thia-3,5,11,17-tetraazatricyclo[17.3.1.1$^{2,6}$]tetracosa-1(22),2(24),3,5,19(23),20-hexaene-10,18-dione (Compound 29)

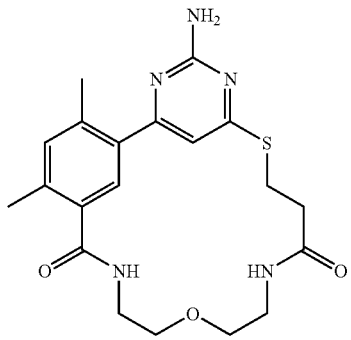

5-(2-Amino-6-{2-[2-(2-aminoethoxy)ethylcarbamoyl]ethylsulfanyl}pyrimidin-4-yl)-2,4-dimethylbenzoic acid tert-butyl ester (78 mg, 0.159 mmol) obtained in Step 1 above was dissolved in dichloromethane (3 ml), and then trifluoroacetic acid (1 ml) was added thereto. After this solution was stirred at room temperature for two hours, the solvent was distilled off under reduced pressure. The resulting crude product was dissolved in a mixed solvent of N,N-dimethylformamide (25 ml) and tetrahydrofuran (75 ml), and then 1-hydroxybenzotriazole (134 mg, 0.795 mmol), diisopropylethylamine (137 μl, 0.795 mmol), and 1-ethyl-3-(3'-dimethylaminopropyl)carbodiimide hydrochloride (152 mg, 2.2 mmol) were sequentially added thereto. After the solution was stirred at room temperature for 16 hours, 1-hydroxybenzotriazole (270 mg, 1.59 mmol), diisopropylethylamine (274 μl, 1.59 mmol), and 1-ethyl-3-(3'-dimethylaminopropyl)carbodiimide hydrochloride (304 mg, 1.59 mmol) were added thereto. After the solution was stirred at 50° C. for seven hours, the solvent was distilled off under reduced pressure. The residue was diluted with ethyl acetate. The ethyl acetate solution was washed with a saturated aqueous sodium bicarbonate solution (twice), and dried over anhydrous sodium sulfate. After the inorganic salt was removed by filtration, the filtrate was concentrated. The resulting residue was purified by preparative thin layer silica gel chromatography (developing solvent: dichloromethane:methanol=15:1). The obtained crude product was washed with dichloromethane to yield 4-amino-20,22-dimethyl-14-oxa-7-thia-3,5,11,17-tetraazatricyclo[17.3.1.1$^{2,6}$]tetracosa-1(22),2(24),3,5,19(23),20-hexaene-10,18-dione (Compound 29) (2 mg) as a white solid material.

Physicochemical properties of 4-amino-20,22-dimethyl-14-oxa-7-thia-3,5,11,17-tetraazatricyclo[17.3.1.1$^{2,6}$]tetracosa-1(22),2(24),3,5,19(23),20-hexaene-10,18-dione Molecular weight: 415.
ESI (LC/MS positive mode): m/z=416 (M+H$^+$).
Chemical shift value δ in $^1$H-NMR (270 MHz, in dimethylsulfoxide d-6): 2.38 (3H, s), 3.11-3.35 (6H, m), 3.36-3.50

(4H, m), 3.52-3.59 (2H, m), 6.68 (2H, brs), 6.84 (1H, s), 7.17 (1H, s), 7.60 (1H, s), 8.05 (1H, t, J=4.7 Hz), 8.24 (1H, t, J=4.5 Hz).

Example 2-26

Production of 4-amino-14,20,22-trimethyl-7-thia-3,5,11,14,17-pentaazatricyclo[17.3.1.1$^{2,6}$]tetracosa-1(22),2(24), 3,5,19(23),20-hexaene-10,18-dione (Compound 30)

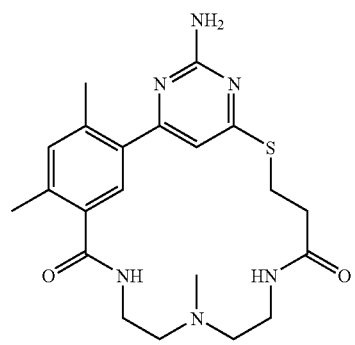 [SMILES: Cc1cc(C)c2cc1C(=O)NCCN(C)CCNC(=O)CCSc1cc-2nc(N)n1]

Step 1: Preparation of 5-[2-amino-6-(2-{2-[(2-aminoethyl)methylamino]ethylcarbamoyl}ethylsulfanyl)pyrimidin-4-yl]-2,4-dimethylbenzoic acid tert-butyl ester

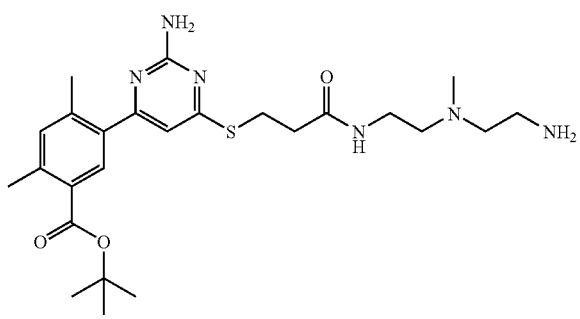

According to the method of Step 2 of Example 2-25 except that N-methyl-2,2'-diaminodiethylamine (305 mg, 2.603 mmol) was used instead of 2,2'-oxybis(ethylamine), 5-[2-amino-6-(2-{2-[(2-aminoethyl)methylamino]ethylcarbamoyl}ethylsulfanyl)pyrimidin-4-yl]-2,4-dimethylbenzoic acid tert-butyl ester (56 mg) was obtained from 5-[2-amino-6-(3-carboxypropylsulfanyl)pyrimidin-4-yl]-2,4-dimethylbenzoic acid tert-butyl ester (150 mg, 0.372 mmol) obtained in Step 1 of Example 2-4.

Physicochemical properties of 5-[2-amino-6-(2-{2-[(2-aminoethyl)methylamino]ethylcarbamoyl}ethylsulfanyl)pyrimidin-4-yl]-2,4-dimethylbenzoic acid tert-butyl ester Molecular weight: 502.
ESI (LC/MS positive mode): m/z=503 (M+H$^+$).

Step 2: Preparation of 4-amino-14,20,22-trimethyl-7-thia-3,5,11,14,17-pentaazatricyclo[17.3.1.1$^{2,6}$]tetracosa-1(22),2(24),3,5,19(23),20-hexaene-10,18-dione (Compound 30)

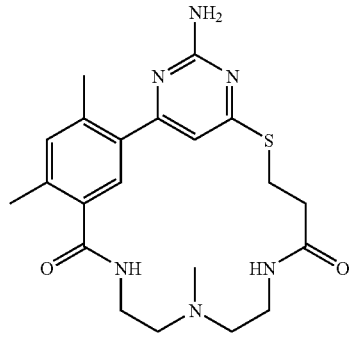 [SMILES: Cc1cc(C)c2cc1C(=O)NCCN(C)CCNC(=O)CCSc1cc-2nc(N)n1]

According to the method of Step 2 of Example 2-25, 4-amino-14,20,22-trimethyl-7-thia-3,5,11,14,17-pentaazatricyclo[17.3.1.1$^{2,6}$]tetracosa-1(22),2(24),3,5,19(23),20-hexaene-10,18-dione (Compound 30) (10 mg) was obtained as a white solid material from 5-[2-amino-6-(2-{2-[(2-aminoethyl)methylamino]ethylcarbamoyl}ethylsulfanyl)pyrimidin-4-yl]-2,4-dimethylbenzoic acid tert-butyl ester (56 mg, 0.111 mmol) obtained in Step 1 above.

Physicochemical properties of 4-amino-14,20,22-trimethyl-7-thia-3,5,11,14,17-pentaazatricyclo[17.3.1.1$^{2,6}$]tetracosa-1(22),2(24),3,5,19(23),20-hexaene-10,18-dione Molecular weight: 428.
ESI (LC/MS positive mode): m/z=429 (M+H$^+$).
Chemical shift value δ in $^1$H-NMR (270 MHz, in dimethylsulfoxide d-6+methanol d-4): 2.14 (3H, s), 2.39 (3H, s), 2.47 (3H, s), 2.34-2.64 (4H, m), 3.09-3.24 (4H, m), 3.24-3.42 (4H, m), 6.84 (1H, s), 7.18 (1H, s), 7.56 (1H, s).

Example 2-27

Production of (S)-4-amino-13-hydroxy-18,20-dimethyl-7-thia-3,5,11,15-tetraazatricyclo[15.3.1.1$^{2,6}$]docosa-1(20),2(22),3,5,17(21),18-hexaene-10,16-dione (Compound 31)

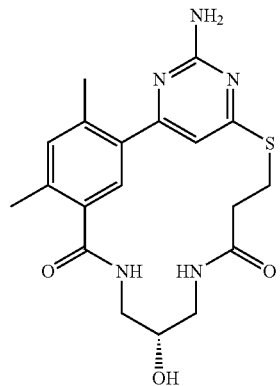 [SMILES: Cc1cc(C)c2cc1C(=O)NC[C@@H](O)CNC(=O)CCSc1cc-2nc(N)n1]

Step 1: Preparation of ((S)-2,3-dihydroxypropyl)carbamic acid tert-butyl ester

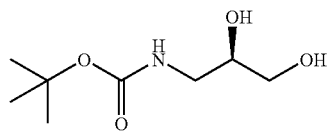

(R)-3-Aminopropane-1,2-diol (3.02 g, 33.09 mmol) was dissolved in a mixed solvent of dichloromethane (5 ml) and methanol (25 ml), and then triethylamine (553 μl, 3.97 mmol) was added thereto. A dichloromethane (11 ml) solution of di-t-butyl bicarbonate (9.12 ml, 39.71 mmol) was dropwise added to the mixture at room temperature. After the mixed solution was stirred at room temperature for five hours, the solvent was distilled off under reduced pressure. The resulting residue was purified by silica gel column chromatography (developing solvent: n-hexane:ethyl acetate=2:3) to yield ((S)-2,3-dihydroxypropyl)carbamic acid tert-butyl ester (5.00 g).

Physicochemical properties of ((S)-2,3-dihydroxypropyl)carbamic acid tert-butyl ester Molecular weight: 191.

Chemical shift value δ in $^1$H-NMR (270 MHz, in chloroform-d): 1.45 (9H, s), 2.78 (1H, d), 2.84 (1H, t), 3.19-3.36 (2H, m), 3.52-3.67 (2H, m), 3.69-3.80 (1H, m), 4.93 (1H, brs).

Step 2: (R)-1-oxiranylmethylcarbamic acid tert-butyl ester

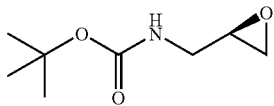

((S)-2,3-Dihydroxypropyl)carbamic acid tert-butyl ester (5.00 g, 26.16 mmol) obtained in Step 1 above was dissolved in pyridine (32 ml), and cooled to 0° C. Methanesulfonyl chloride (2.22 ml, 28.71 mmol) was dropwise added to the solution, and stirred for 10 minutes. This solution was dropwise added to a solution of sodium hydroxide (3.18 g, 79.61 mmol) in water (33 ml) and dimethylsulfoxide (22 ml) at 0° C., and stirred for 10 minutes. This reaction solution was poured into ice water (300 ml), and then extracted with a mixture of n-hexane (80 ml) and ethyl acetate (320 ml). The organic layer was separated and washed with water and a saturated aqueous sodium chloride solution, and then dried over anhydrous sodium sulfate. After the inorganic salt was removed by filtration, the filtrate was concentrated under reduced pressure. The resulting residue was purified by silica gel column chromatography (developing solvent: n-hexane to n-hexane:ethyl acetate=4:1) to yield (R)-1-oxiranylmethylcarbamic acid tert-butyl ester (2.26 g).

Physicochemical properties of (R)-1-oxiranylmethylcarbamic acid tert-butyl ester Molecular weight: 173.

Chemical shift value δ in $^1$H-NMR (270 MHz, in chloroform-d): 2.60 (1H, dd, J=4.7 Hz, 2.6 Hz), 2.78 (1H, dd, J=4.7 Hz, 4.0 Hz), 3.06-3.12 (1H, m), 3.15-3.27 (1H, m), 3.45-6.60 (1H, m), 4.73 (1H, brs).

Step 3: Preparation of (S)-4-amino-13-hydroxy-18,20-dimethyl-7-thia-3,5,11,15-tetraazatricyclo[15.3.1.1$^{2,6}$]docosa-1(20),2(22),3,5,17(21),18-hexaene-10,16-dione (Compound 31)

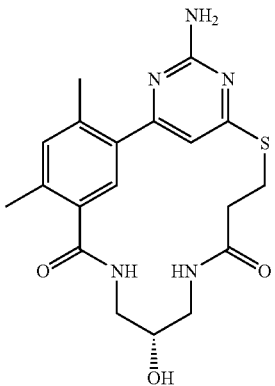 [SMILES: Cc1cc(C)c2cc1C(=O)NC[C@@H](O)CNC(=O)CCSc1cc-2nc(N)n1]

(R)-1-Oxiranylmethylcarbamic acid tert-butyl ester (2.26 g, 13.05 mmol) obtained in Step 2 above was dissolved in ethanol (15 ml), and then 28% ammonia water (6 ml) was added thereto at room temperature. After the solution was stirred at room temperature for 1.5 hour, the solvent was distilled off under reduced pressure. After the resulting residue was dissolved in methanol, the solvent was distilled off under reduced pressure to give a crude product of ((S)-3-amino-2-hydroxypropyl)carbamic acid tert-butyl ester (2.38 g) as a yellow oily material.

The obtained crude product of ((S)-3-amino-2-hydroxypropyl)carbamic acid tert-butyl ester (283 mg, 1.487 mmol) and 5-[2-amino-6-(3-carboxylpropylsulfanyl)pyrimidin-4-yl]-2,4-dimethylbenzoic acid tert-butyl ester (300 mg, 0.744 mmol) obtained in Step 1 of Example 2-1 were dissolved in N,N-dimethylformamide (7 ml), and then 1-hydroxybenzotriazole monohydrate (377 mg, 2.462 mmol) and 1-ethyl-3-(3'-dimethylaminopropyl)carbodiimide hydrochloride (152 mg, 2.2 mmol) were sequentially added thereto. The resulting mixture was stirred at room temperature for three hours. The reaction solution was diluted with ethyl acetate, and then washed with a saturated aqueous ammonium chloride solution (twice) and a saturated aqueous sodium bicarbonate solution (twice). After the organic layer was dried over anhydrous sodium sulfate, the inorganic salt was removed by filtration. The filtrate was concentrated under reduced pressure. The resulting residue was purified by silica gel column chromatography (developing solvent: dichloromethane:methanol=20:1) to yield ((S)-3-amino-2-hydroxypropyl)carbamic acid tert-butyl ester.

The obtained ((S)-3-amino-2-hydroxypropyl)carbamic acid tert-butyl ester was dissolved in dichloromethane (20 ml), and then water (0.1 ml) and trifluoroacetic acid (10 ml) were added thereto. After the solution was stirred at room temperature for one hour, the solvent was distilled off under reduced pressure to yield a crude product of 5-{2-amino-6-[2-((R)-3-amino-2-hydroxypropylcarbamoyl)ethylsulfanyl]pyrimidin-4-yl}-2,4-dimethylbenzoic acid di(trifluoroacetate).

The obtained crude product of 5-{2-amino-6-[2-((R)-3-amino-2-hydroxypropylcarbamoyl)ethylsulfanyl]pyrimidin-4-yl}-2,4-dimethylbenzoic acid di(trifluoroacetate) was dissolved in N,N-dimethylformamide (400 ml), and then 1-hydroxybenzotriazole (1.0 g, 7.44 mmol), diisopropylethylamine (1.28 ml, 7.43 mmol), and 1-ethyl-3-(3'-dimethylaminopropyl)carbodiimide hydrochloride (1.43 g, 7.43 mmol) were sequentially added thereto. After this solution was stirred at room temperature for 10 hours, water (3 ml) was added thereto. After the solvent was distilled off under reduced pressure, the residue was dissolved using ethyl acetate and a small volume of methanol. The solution was sequentially washed with water (twice) and a saturated aqueous sodium bicarbonate solution (twice). The organic layer was dried over anhydrous sodium sulfate. After the inorganic salt was removed by filtration, the filtrate was concentrated under reduced pressure. The resulting residue was purified by silica gel column chromatography (developing solvent: dichloromethane to dichloromethane:methanol=10:1) and preparative aminopropyl silica gel thin layer chromatography (dichloromethane:methanol=9:1) to yield (S)-4-amino-13-hydroxy-18,20-dimethyl-7-thia-3,5,11,15-tetraazatricyclo[15.3.1.1$^{2,6}$]docosa-1(20),2(22),3,5,17(21),18-hexaene-10,16-dione (Compound 31) (17 mg) as a white solid material.

Physicochemical properties of (S)-4-amino-13-hydroxy-18,20-dimethyl-7-thia-3,5,11,15-tetraazatricyclo[15.3.1.1$^{2,6}$]docosa-1(20),2(22),3,5,17(21),18-hexaene-10,16-dione Molecular weight: 401.
ESI (LC/MS positive mode): m/z=402 (M+H$^+$).
Chemical shift value δ in $^1$H-NMR (270 MHz, in chloroform-d): 2.40 (3H, s), 2.57 (3H, s), 2.30-3.48 (7H, m), 3.56-3.71 (2H, m), 5.09 (1H, d), 6.67 (2H, s), 6.94 (1H, s), 7.15 (1H, s), 7.66 (1H, s), 8.04 (1H, t, J=5.7 Hz), 8.18 (1H, t, J=5.4 Hz).

Example 3-1

Production of 4-amino-18-methoxy-20-methyl-7-thia-3,5,10,15-tetraazatricyclo[15.3.1.1$^{2,6}$]docosa-1(20),2(22),3,5,17(21),18-hexaene-11,16-dione (Compound 9)

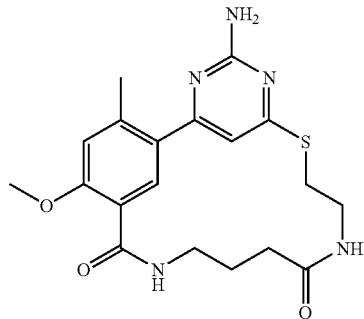 [SMILES: COc1cc(C)c2cc1C(=O)NCCCC(=O)NCCSc1cc-2nc(N)n1]

Step 1: Preparation of 5-[2-amino-6-(2-tert-butoxycarbonylaminoethylsulfanyl)pyrimidin-4-yl]-2-methoxy-4-methylbenzoic acid methyl ester

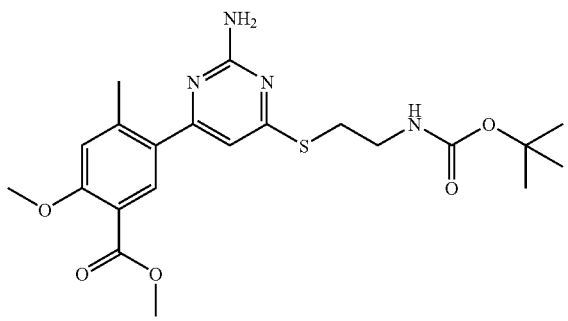 [SMILES: COC(=O)c1cc(-c2cc(SCCNC(=O)OC(C)(C)C)nc(N)n2)c(C)cc1OC]

5-(2-Amino-6-chloropyrimidin-4-yl)-2-methoxy-4-methylbenzoic acid methyl ester (118 mg, 0.38 mmol) obtained in Example 1-2 and potassium carbonate (212 mg, 1.5 mmol) were placed in a reaction vessel, and then N,N-dimethylformamide (1.0 ml) and (2-mercaptoethyl)carbamic acid tert-butyl ester (0.25 ml, 1.5 mmol) were added thereto. The mixture was stirred at room temperature for 15 hours. The reaction solution was diluted with ethyl acetate (100 ml), and sequentially washed twice with a saturated aqueous sodium bicarbonate solution (50 ml), twice with water (50 ml), and with a saturated aqueous sodium chloride solution (50 ml). The ethyl acetate solution was dried over anhydrous sodium sulfate. After filtration, the filtrate was concentrated under reduced pressure. The resulting crude product was purified by silica gel column chromatography (developing solvent: ethyl acetate:n-hexane=1:2) to yield 5-[2-amino-6-(2-tert-butoxycarbonylaminoethylsulfanyl)pyrimidin-4-yl]-2-methoxy-4-methylbenzoic acid methyl ester (143 mg) as a yellow oily material.

Physicochemical properties of 5-[2-amino-6-(2-tert-butoxycarbonylaminoethylsulfanyl)pyrimidin-4-yl]-2-methoxy-4-methylbenzoic acid methyl ester Molecular weight: 448.
ESI (LC/MS positive mode): m/z=449 (M+H$^+$).
Chemical shift value δ in $^1$H-NMR (400 MHz, in dimethylsulfoxide d-6): 1.37 (9H, s), 2.44 (3H, s), 3.14 (2H, t, J=6 Hz), 3.21 (2H, t, J=6 Hz), 3.77 (3H, s), 3.86 (3H, s), 6.64 (1H, s), 6.67 (2H, brs), 6.97-7.03 (1H, brs), 7.07 (1H, s), 7.76 (1H, s).

Step 2: Preparation of 5-{2-amino-6-[2-(4-tert-butoxycarbonylaminobutyrylamino)ethylsulfanyl]pyrimidin-4-yl}-2-methoxy-4-methylbenzoic acid methyl ester

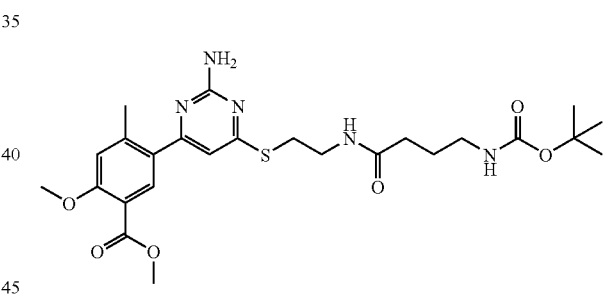

5-[2-Amino-6-(2-tert-butoxycarbonylaminoethylsulfanyl)pyrimidin-4-yl]-2-methoxy-4-methylbenzoic acid methyl ester (52 mg, 0.11 mmol) obtained in Step 1 above was dissolved with dichloromethane (2.5 ml) in a reaction vessel. Trifluoroacetic acid (0.7 ml) was added to the solution and stirred for 4 hours while gradually warming from 0° C. to room temperature. The reaction solution was concentrated under reduced pressure, and then benzene (1.5 ml) was added to the resulting residue. The solution was concentrated under reduced pressure. This treatment was repeated three times. The obtained pale yellow oily material was dissolved in N,N-dimethylformamide (1.5 ml). 4-tert-Butoxycarbonylaminobutanoic acid (35 mg, 0.17 mmol), N-hydroxybenzotriazole (31 mg, 0.23 mmol), and diisopropylethylamine (0.5 ml, 2.8 mmol) were added to the solution, and then 1-ethyl-3-(3'-dimethylaminopropyl)carbodiimide hydrochloride (66 mg, 0.34 mmol) was added thereto. The resulting mixture was stirred at room temperature for 2.5 hours. A saturated ammonium chloride solution was added to the reaction solution, and the mixture was extracted with ethyl acetate (100 ml). The ethyl acetate solution was sequentially washed with 1N hydrochloric acid (50 ml), water (50 ml), a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography (developing solvent: ethyl acetate to ethyl acetate:methanol=25:1) to yield 5-{2-amino-6-[2-(4-tert-butoxycarbonylaminobutyrylamino)ethylsulfanyl]pyrimidin-4-yl}-2-methoxy-4-methylbenzoic acid methyl ester (49 mg) as a colorless syrup-like material.

Physicochemical properties of 5-{2-amino-6-[2-(4-tert-butoxycarbonylaminobutyrylamino)ethylsulfanyl]pyrimidin-4-yl}-2-methoxy-4-methylbenzoic acid methyl ester Molecular weight: 533.
ESI (LC/MS positive mode): m/z=534 (M+H$^+$).
Chemical shift value δ in $^1$H-NMR (400 MHz, in dimethylsulfoxide d-6): 1.37 (9H, s), 1.55-1.63 (2H, m), 2.05 (2H, t, J=8 Hz), 2.44 (3H, s), 2.90 (2H, t, J=8 Hz), 3.17 (2H, t, J=8 Hz), 3.34 (2H, t, J=8 Hz), 3.77 (3H, s), 3.86 (3H, s), 6.64 (1H, s), 6.68 (2H, brs), 6.72-6.77 (1H, m), 7.07 (1H, s), 7.72 (1H, s), 7.76 (1H, s), 8.02 (1H, t, J=6 Hz).

Step 3: Preparation of 4-amino-18-methoxy-20-methyl-7-thia-3,5,10,15-tetraazatricyclo[15.3.1.1$^{2,6}$]docosa-1(20),2(22),3,5,17(21),18-hexaene-11,16-dione (Compound 9)

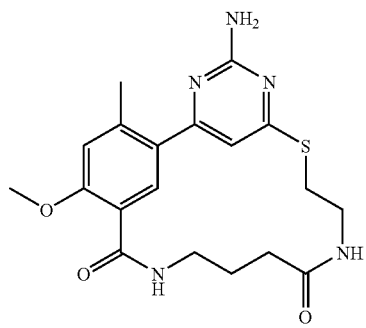 [SMILES: COc1cc(C)c2cc1C(=O)NCCCC(=O)NCCSc1cc-2nc(N)n1]

Trifluoroacetic acid (0.5 ml) was added to a dichloromethane (2.0 ml) solution of 5-{2-amino-6-[2-(4-tert-butoxycarbonylaminobutyrylamino)ethylsulfanyl]pyrimidin-4-yl}-2-methoxy-4-methylbenzoic acid methyl ester (45 mg, 0.08 mmol) obtained in Step 2 above. The reaction solution was stirred for 3.5 hours while gradually warming from 0° C. to room temperature. The reaction solution was concentrated under reduced pressure, and then benzene (1.5 ml) was added to the resulting residue. The solution was concentrated under reduced pressure. This treatment was repeated three times. The resulting colorless syrup-like material was dissolved in tetrahydrofuran (0.7 ml), methanol (0.7 ml), and water (0.5 ml). Lithium hydroxide (18 mg, 0.43 mmol) was added to the mixture, and the resulting mixture was stirred at room temperature for 24 hours. The reaction solution was acidified by adding 4N hydrochloric acid-ethyl acetate solution (0.95 ml). The solvent was distilled off under reduced pressure. The obtained white solid material was dissolved by adding N,N-dimethylformamide (10 ml) and tetrahydrofuran (33 ml). N-Hydroxybenzotriazole (58 mg, 0.43 mmol), diisopropylethylamine (0.15 ml, 0.9 mmol), and 1-ethyl-3-(3'-dimethylaminopropyl)carbodiimide hydrochloride (165 mg, 0.9 mmol) were sequentially added to the solution. The resulting mixture was stirred at room temperature for 2.5 hours. The reaction solution was concentrated under reduced pressure. The resulting residue was diluted with ethyl acetate (100 ml), and sequentially washed twice with water (50 ml), and with a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography with diol-silica gel (developing solvent: ethyl acetate to ethyl acetate:methanol=15:1) and amino-silica gel (developing solvent: ethyl acetate to ethyl acetate:methanol=15:1) to yield 4-amino-18-methoxy-20-methyl-7-thia-3,5,10,15-tetraazatricyclo[15.3.1.1$^{2,6}$]docosa-1(20),2(22),3,5,17(21),18-hexaene-11,16-dione (Compound 9) (4 mg) as a white solid material.

Physicochemical properties of 4-amino-18-methoxy-20-methyl-7-thia-3,5,10,15-tetraazatricyclo[15.3.1.1$^{2,6}$]docosa-1(20),2(22),3,5,17(21),18-hexaene-11,16-dione Molecular weight: 401.
ESI (LC/MS positive mode): m/z=402 (M+H$^+$).
Chemical shift value δ in $^1$H-NMR (400 MHz, in dimethylsulfoxide d-6): 1.72-1.80 (2H, m), 2.36-2.42 (2H, m), 2.64 (3H, s), 3.08-3.15 (2H, m), 3.20-3.27 (2H, m), 3.33-3.40 (2H, m), 3.79 (3H, s), 6.57 (2H, brs), 6.93 (1H, s), 7.27 (1H, s), 7.81 (1H, s), 8.42 (1H, t, J=5.4 Hz), 8.65 (1H, t, J=4.9 Hz)

Example 3-2

Production of 4-amino-18-methoxy-15,20-dimethyl-7-thia-3,5,10,15-tetraazatricyclo[15.3.1.1$^{2,6}$]docosa-1(20),2(22),3,5,17(21),18-hexaene-11,16-dione (Compound 10)

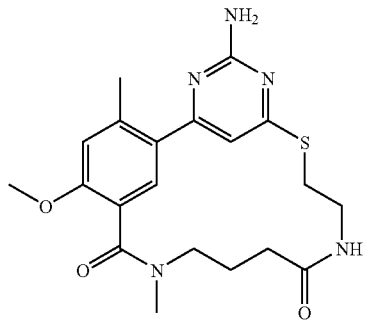 [SMILES: COc1cc(C)c2cc1C(=O)N(C)CCCC(=O)NCCSc1cc-2nc(N)n1]

Step 1: Preparation of 5-(2-amino-6-{2-[4-(tert-butoxycarbonylmethylamino)butyrylamino]ethylsulfanyl}pyrimidin-4-yl)-2-methoxy-4-methylbenzoic acid methyl ester

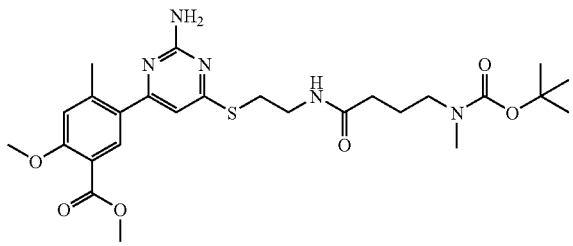 [SMILES: COC(=O)c1cc(-c2cc(SCCNC(=O)CCCN(C)C(=O)OC(C)(C)C)nc(N)n2)c(C)cc1OC]

5-[2-Amino-6-(2-tert-butoxycarbonylaminoethylsulfanyl)pyrimidin-4-yl]-2-methoxy-4-methylbenzoic acid methyl ester (88 mg, 0.20 mmol) obtained in Step 1 of Example 3-1 was dissolved with dichloromethane (2.5 ml) in a reaction vessel, and cooled to 0° C. Trifluoroacetic acid (0.7 ml) was added to the solution, and stirred for 2.5 hours while gradually warming from 0° C. to room temperature. The reaction solution was concentrated under reduced pressure, and then benzene (1.5 ml) was added to the resulting residue. The solution was again concentrated under reduced pressure. This treatment was repeated three times, and the obtained pale yellow oily material was dissolved in N,N-dimethylformamide (3.0 ml). 4-tert-Butoxycarbonylmethylaminobutanoic acid (65 mg, 0.3 mmol) and N-hydroxybenzotriazole (54 mg, 0.4 mmol) were added to the solution. Diisopropylethylamine (0.5 ml, 2.8 mmol) was added to the solution, and then 1-ethyl-3-(3'-dimethylaminopropyl)carbodiimide hydrochloride (115 mg, 0.6 mmol) was added. The resulting mixture was stirred at room temperature for 13 hours. A saturated aqueous ammonium chloride solution was added to the reaction solution, and extracted with ethyl acetate (100 ml). The ethyl acetate solution was sequentially washed with 1N hydrochloric acid (50 ml), water (50 ml), a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography (developing solvent: ethyl acetate to ethyl acetate:methanol=25:1) to yield 5-(2-amino-6-{2-[4-(tert-butoxycarbonylmethylamino)butyrylamino]ethylsulfanyl}pyrimidin-4-yl)-2-methoxy-4-methylbenzoic acid methyl ester (99 mg) as a colorless syrup-like material.

Physicochemical properties of 5-(2-amino-6-{2-[4-(tert-butoxycarbonylmethylamino)butyrylamino]ethylsulfanyl}pyrimidin-4-yl)-2-methoxy-4-methylbenzoic acid methyl ester Molecular weight: 547.
ESI (LC/MS positive mode): m/z=548 (M+H$^+$).
Chemical shift value δ in $^1$H-NMR (400 MHz, in dimethylsulfoxide d-6): 1.37 (9H, s), 1.62-1.70 (2H, m), 2.03 (2H, t, J=8 Hz), 2.44 (3H, s), 2.74 (3H, s), 3.12 (2H, t, J=8 Hz), 3.18 (2H, t, J=6 Hz), 3.34 (2H, t, J=6 Hz), 3.77 (3H, s), 3.86 (3H, s), 6.65 (1H, s), 6.69 (2H, brs), 7.08 (1H, s), 7.76 (1H, s), 8.05 (1H, t, J=4 Hz).

Step 2: Preparation of 4-amino-18-methoxy-15,20-dimethyl-7-thia-3,5,10,15-tetraazatricyclo[15.3.1.1$^{2,6}$]docosa-1(20),2(22),3,5,17(21),18-hexaene-11,16-dione (Compound 10)

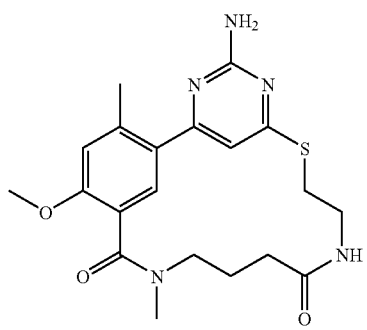 [SMILES: COc1cc(C)c2cc1C(=O)N(C)CCCC(=O)NCCSc1cc-2nc(N)n1]

Trifluoroacetic acid (1.0 ml) was added to a dichloromethane (3.0 ml) solution of 5-(2-amino-6-{2-[4-(tert-butoxycarbonylmethylamino)butyrylamino]ethylsulfanyl}pyrimidin-4-yl)-2-methoxy-4-methylbenzoic acid methyl ester (95 mg, 0.17 mmol) obtained in Step 1 above. The reaction solution was stirred for 3 hours while gradually warming from 0° C. to room temperature. The reaction solution was concentrated under reduced pressure, and then benzene (1.5 ml) was added to the resulting residue. The solution was again concentrated under reduced pressure. After this treatment was repeated three times, the obtained colorless syrup-like material was dissolved in tetrahydrofuran (1.5 ml), methanol (1.5 ml), and water (1.0 ml). Lithium hydroxide (74 mg, 1.75 mmol) was added to the mixture. The reaction solution was stirred at room temperature for 12 hours, and then acidified by adding 4N hydrochloric acid-ethyl acetate solution (1.32 ml). The solvent was distilled off under reduced pressure. N,N-Dimethylformamide (44 ml) and tetrahydrofuran (44 ml) were added to the obtained white solid material. N-Hydroxybenzotriazole (118 mg, 0.87 mmol), diisopropylethylamine (0.38 ml, 1.7 mmol), and 1-ethyl-3-(3'-dimethylaminopropyl)carbodiimide hydrochloride (335 mg, 1.7 mmol) were sequentially added to the mixture. The resulting reaction solution was stirred at room temperature for 2.5 hours. The solution was concentrated under reduced pressure. The resulting residue was diluted with ethyl acetate (100 ml), and then sequentially washed twice with water (50 ml), and with a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography with diol-silica gel (developing solvent: ethyl acetate to ethyl acetate:methanol=15:1) and amino-silica gel (developing solvent: ethyl acetate to ethyl acetate:methanol=15:1) to yield 4-amino-18-methoxy-15,20-dimethyl-7-thia-3,5,10,15-tetraazatricyclo[15.3.1.1$^{2,6}$]docosa-1(20),2(22),3,5,17(21),18-hexaene-11,16-dione (Compound 10) (7 mg) as a white solid material.

Physicochemical properties of 4-amino-18-methoxy-15,20-dimethyl-7-thia-3,5,10,15-tetraazatricyclo[15.3.1.1[2,6]]docosa-1(20),2(22),3,5,17(21),18-hexaene-11,16-dione Molecular weight: 415.
ESI (LC/MS positive mode): m/z=416 (M+H[+]).
Chemical shift value δ in $^1$H-NMR (500 MHz, 140° C., in dimethylsulfoxide d-6): 1.74-1.81 (2H, m), 2.09-2.17 (2H, m), 2.48 (3H, s), 2.89 (3H, s), 3.05 (2H, t, J=6 Hz), 3.24-3.37 (2H, m), 3.41 (2H, t, J=6 Hz), 3.80 (3H, s), 6.00 (2H, brs), 6.78 (1H, s), 6.90 (1H, s), 7.24 (1H, s), 7.59-7.73 (1H, brs).

Example 3-3

Production of 4-amino-18,20-dimethyl-7-thia-3,5,10,15-tetraazatricyclo[15.3.1.1[2,6]]docosa-1(20),2(22),3,5,17(21),18-hexaene-11,16-dione (Compound 11)

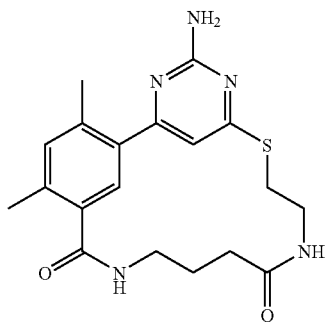

Step 1: Preparation of 5-[2-amino-6-(2-tert-butoxycarbonylaminoethylsulfanyl)pyrimidin-4-yl]-2,4-dimethylbenzoic acid methyl ester

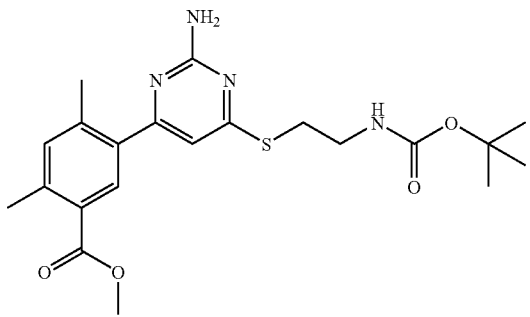 [SMILES: COC(=O)c1cc(-c2cc(SCCNC(=O)OC(C)(C)C)nc(N)n2)c(C)cc1C]

According to the method in Step 1 of Example 3-1, 5-[2-amino-6-(2-tert-butoxycarbonylaminoethylsulfanyl)pyrimidin-4-yl]-2,4-dimethylbenzoic acid methyl ester was synthesized from 5-(2-amino-6-chloropyrimidin-4-yl)-2,4-dimethylbenzoic acid tert-butyl ester obtained in Example 1-1.

Physicochemical properties of 5-[2-amino-6-(2-tert-butoxycarbonylaminoethylsulfanyl)-pyrimidin-4-yl]-2,4-dimethylbenzoic acid methyl ester Molecular weight: 432.
ESI (LC/MS positive mode): m/z=433 (M+H[+]).
Chemical shift value δ in $^1$H-NMR (400 MHz, in chloroform-d): 1.45 (9H, s), 2.40 (3H, s), 2.61 (3H, s), 3.29 (2H, t, J=6.3 Hz), 3.48 (2H, q, J=6.3 Hz), 3.87 (3H, s), 5.07 (2H, brs), 5.41 (1H, brs), 6.64 (1H, s), 7.14 (1H, s), 7.96 (1H, s).

Step 2: Preparation of 5-[2-amino-6-(2-aminoethylsulfanyl)pyrimidin-4-yl]-2,4-dimethylbenzoic acid methyl ester

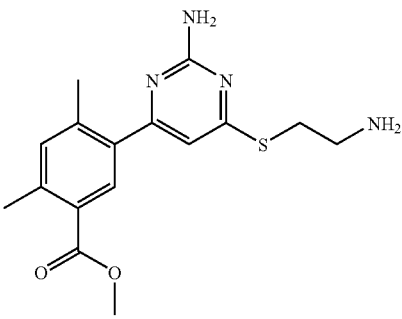 [SMILES: COC(=O)c1cc(-c2cc(SCCN)nc(N)n2)c(C)cc1C]

5-[2-Amino-6-(2-tert-butoxycarbonylaminoethylsulfanyl)pyrimidin-4-yl]-2,4-dimethylbenzoic acid methyl ester (531 mg, 1.23 mmol) obtained in Step 1 above was dissolved in dichloromethane (3.0 ml). Trifluoroacetic acid (1.5 ml) was added to the solution, and stirred at room temperature for 1 hour. The reaction solution was concentrated under reduced pressure. The resulting residue was diluted with ethyl acetate, and then a saturated aqueous sodium bicarbonate solution was added thereto. The organic layer was separated, and the aqueous layer was extracted with ethyl acetate. The organic layers were combined together, and sequentially washed with water and a saturated aqueous sodium chloride solution. The ethyl acetate solution was dried over anhydrous magnesium sulfate. After filtration, the filtrate was concentrated under reduced pressure to yield the crude product of 5-[2-amino-6-(2-aminoethylsulfanyl)pyrimidin-4-yl]-2,4-dimethylbenzoic acid methyl ester (443 mg) as a white solid material.

Physicochemical properties of 5-[2-amino-6-(2-aminoethylsulfanyl)pyrimidin-4-yl]-2,4-dimethylbenzoic acid methyl ester Molecular weight: 332.
ESI (LC/MS positive mode): m/z=333 (M+H[+]).
Chemical shift value δ in $^1$H-NMR (400 MHz, in chloroform-d): 2.39 (3H, s), 2.60 (3H, s), 3.30-3.40 (4H, m), 3.87 (3H, s), 5.92 (2H, brs), 6.64 (1H, s), 7.12 (1H, s), 7.94 (1H, s).

Step 3: Preparation of 5-{2-amino-6-[2-(4-tert-butoxycarbonylaminobutyrylamino)ethylsulfanyl]pyrimidin-4-yl}-2,4-dimethylbenzoic acid methyl ester

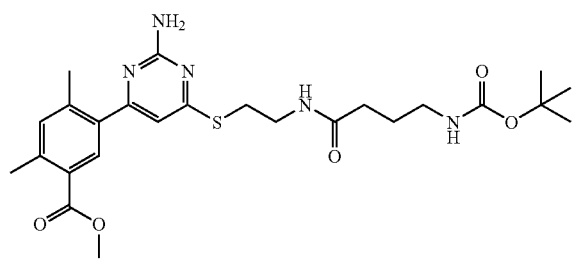

Diisopropylethylamine (0.59 ml, 3.39 mmol) was added to an N,N-dimethylformamide (2.7 ml) solution of 5-[2-amino-6-(2-aminoethylsulfanyl)pyrimidin-4-yl]-2,4-dimethylbenzoic acid methyl ester (225 mg, 0.68 mmol) obtained in Step 2 above, 4-tert-butoxycarbonylaminobutanoic acid (165 mg, 0.81 mmol), N-hydroxybenzotriazole (93 mg, 0.69 mmol), and 1-ethyl-3-(3'-dimethylaminopropyl)carbodiimide hydrochloride (262 mg, 1.37 mmol). The resulting mixture was stirred at room temperature for 2.5 hours. Water was added to the reaction solution, and extracted twice with ethyl acetate. The organic layers were combined together, and then sequentially washed with water and a saturated aqueous sodium chloride solution. The ethyl acetate solution was dried over anhydrous magnesium sulfate. After filtration, the filtrate was concentrated under reduced pressure. The resulting crude product was purified by silica gel column chromatography (developing solvent: dichloromethane:methanol=30:1) to yield 5-{2-amino-6-[2-(3-tert-butoxycarbonylaminobutyrylamino)ethylsulfanyl]pyrimidin-4-yl}-2,4-dimethylbenzoic acid methyl ester (257 mg, 73%) as a white solid.

Physicochemical properties of 5-{2-amino-6-[2-(4-tert-butoxycarbonylaminobutyrylamino)ethylsulfanyl]pyrimidin-4-yl}-2,4-dimethylbenzoic acid methyl ester Molecular weight: 517.
ESI (LC/MS positive mode): m/z=518 (M+H$^+$).
Chemical shift value δ in $^1$H-NMR (400 MHz, in chloroform-d): 1.44 (9H, s), 1.78-1.85 (2H, m), 2.21 (2H, t, J=6.8 Hz), 2.41 (3H, s), 2.61 (3H, s), 3.15-3.23 (2H, m), 3.34 (2H, t, J=5.9 Hz) 3.60 (2H, q, J=5.9 Hz), 3.87 (3H, s), 4.74 (1H, brs), 5.23 (2H, brs), 6.65 (1H, s), 6.93 (1H, brs), 7.14 (1H, s), 7.96 (1H, s).

Step 4: Preparation of 5-{2-amino-6-[2-(4-aminobutyrylamino)ethylsulfanyl]pyrimidin-4-yl}-2,4-dimethylbenzoic acid methyl ester

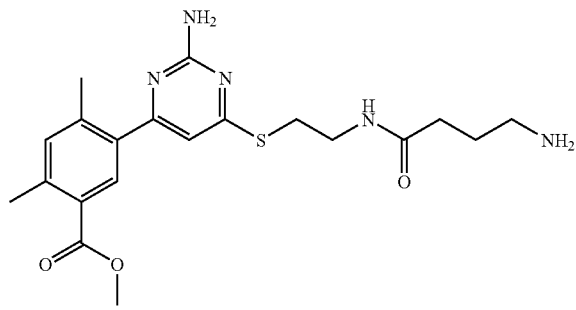 [SMILES: COC(=O)c1cc(-c2cc(SCCNC(=O)CCCN)nc(N)n2)c(C)cc1C]

5-{2-Amino-6-[2-(3-tert-butoxycarbonylaminobutyrylamino)ethylsulfanyl]pyrimidin-4-yl}-2,4-dimethylbenzoic acid methyl ester (255 mg, 0.49 mmol) obtained in Step 3 above was dissolved in dichloromethane (2.0 ml). Trifluoroacetic acid (1.0 ml) was added to the solution, and stirred at room temperature for 1 hour. The reaction solution was concentrated under reduced pressure. After the resulting residue was diluted with ethyl acetate, a saturated aqueous sodium bicarbonate solution was added, and the organic layer was separated. The aqueous layer was extracted with ethyl acetate. The organic layers were combined together. The ethyl acetate solution was dried over anhydrous magnesium sulfate. After filtration, the filtrate was concentrated under reduced pressure to yield the crude product of 5-{2-amino-6-[2-(4-aminobutyrylamino)ethylsulfanyl]pyrimidin-4-yl}-2,4-dimethylbenzoic acid methyl ester (160 mg) as a pale yellow oily material.

Physicochemical properties of 5-{2-amino-6-[2-(4-aminobutyrylamino)ethylsulfanyl]pyrimidin-4-yl}-2,4-dimethylbenzoic acid methyl ester Molecular weight: 417.
ESI (LC/MS positive mode): m/z=418 (M+H$^+$).
Chemical shift value δ in $^1$H-NMR (400 MHz, in chloroform-d): 1.81-1.88 (2H, m), 2.33 (2H, t, J=6.3 Hz), 2.40 (3H, s), 2.60 (3H, s), 2.86 (2H, t, J=6.3 Hz), 3.32 (2H, t, J=5.8 Hz), 3.58 (2H, q, J=5.8 Hz), 3.87 (3H, s), 5.38 (2H, brs), 6.63 (1H, s), 7.10-7.14 (1H, m), 7.14 (1H, s), 7.95 (1H, s).

Step 5: Preparation of 4-amino-18,20-dimethyl-7-thia-3,5,10,15-tetraazatricyclo[15.3.1.1$^{2,6}$]docosa-1(20),2(22),3,5,17(21),18-hexaene-11,16-dione (Compound 11)

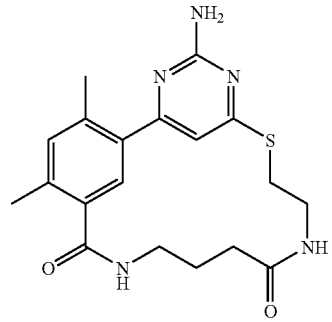

5-{2-Amino-6-[2-(4-aminobutyrylamino)ethylsulfanyl]pyrimidin-4-yl}-2,4-dimethylbenzoic acid methyl ester (153 mg, 0.37 mmol) obtained in Step 4 above was dissolved by adding tetrahydrofuran (2 ml), methanol (2 ml), and water (1 ml), and then lithium hydroxide monohydrate (160 mg, 3.82 mmol) was added thereto. The resulting mixture was stirred at room temperature for 8 hours. The reaction solution was cooled to 0° C., and 4N hydrochloric acid-ethyl acetate solution (2 ml) was added thereto. The solvent was distilled off under reduced pressure. The resulting residue was dissolved in dimethylformamide (255 ml). (3-Dimethylaminopropyl)ethylcarbodiimide hydrochloride (736 mg, 3.84 mmol), N-hydroxybenzotriazole (519 mg, 3.84 mmol), and diisopropylethylamine (2.67 ml, 15.32 mmol) were added to the solution, and stirred at room temperature for 14 hours. The reaction solution was distilled off under reduced pressure. Water was added to the resulting residue, and extracted three times with ethyl acetate. The organic layers were combined together and washed with water and a saturated aqueous sodium chloride solution, and then dried over magnesium sulfate. After filtration, anhydrous magnesium sulfate was washed with ethyl acetate. The filtrate and washing solution was combined together, and ethyl acetate was distilled off under reduced pressure. The resulting residue was purified by silica gel column chromatography (developing solvent: dichloromethane:methanol=20:1) to yield 4-amino-18,20-dimethyl-7-thia-3,5,10,15-tetraazatricyclo[15.3.1.1$^{2,6}$]docosa-1(20),2(22),3,5,17(21),18-hexaene-11,16-dione (Compound 11) (65 mg, 46%).

Physicochemical properties of 4-amino-18,20-dimethyl-7-thia-3,5,10,15-tetraazatricyclo[15.3.1.1$^{2,6}$]docosa-1(20),2(22),3,5,17(21),18-hexaene-11,16-dione Molecular weight: 385.
ESI (LC/MS positive mode): m/z=386 (M+H$^+$).
Chemical shift value δ in $^1$H-NMR (400 MHz, in dimethylsulfoxide d-6): 1.78-1.81 (2H, m), 2.41 (3H, s), 2.41-2.45 (2H, m), 2.59 (3H, s), 3.12-3.18 (2H, m), 3.24-3.28 (2H, m), 3.34-3.42 (2H, m), 6.62 (2H, brs), 7.14 (1H, s), 7.42 (1H, s), 7.89 (1H, s), 8.52 (1H, t, J=5.4), 8.97 (1H, t, J=4.6 Hz).

Example 3-4

Production of 4-amino-17,19-dimethyl-7-thia-3,5,10,14-tetraazatricyclo[14.3.1.1$^{2,6}$]henicosa-1(19),2(21),3,5,16(20),17-hexaene-11,15-dione (Compound 12)

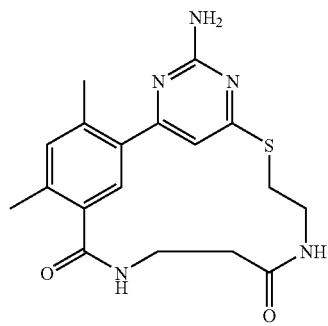 [SMILES: Cc1cc(C)c2cc1C(=O)NCCC(=O)NCCSc1cc-2nc(N)n1]

Step 1: Preparation of 5-{2-amino-6-[2-(3-tert-butoxycarbonylaminopropionylamino)ethylsulfanyl]pyrimidin-4-yl}-2,4-dimethylbenzoic acid methyl ester

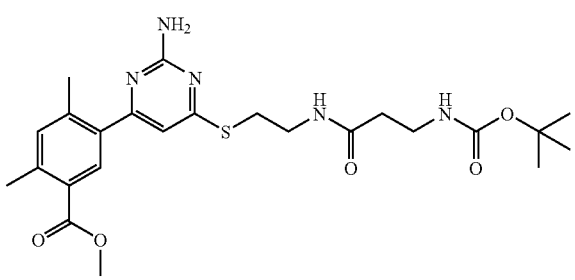 [SMILES: COC(=O)c1cc(-c2cc(SCCNC(=O)CCNC(=O)OC(C)(C)C)nc(N)n2)c(C)cc1C]

According to the method in Step 3 of Example 3-3, 5-{2-amino-6-[2-(3-tert-butoxycarbonylaminopropionylamino)ethylsulfanyl]pyrimidin-4-yl}-2,4-dimethylbenzoic acid methyl ester was synthesized from 5-[2-amino-6-(2-aminoethylsulfanyl)pyrimidin-4-yl]-2,4-dimethylbenzoic acid methyl ester obtained in Step 2 of Example 3-3.

Physicochemical properties of 5-{2-amino-6-[2-(3-tert-butoxycarbonylaminopropionylamino)ethylsulfanyl]pyrimidin-4-yl}-2,4-dimethylbenzoic acid methyl ester Molecular weight: 503.
ESI (LC/MS positive mode): m/z=504 (M+H$^+$).
Chemical shift value δ in $^1$H-NMR (400 MHz, in chloroform-d): 1.44 (9H, s), 2.41 (3H, s), 2.42-2.46 (2H, m), 2.61 (3H, s), 3.31 (2H, t, J=6.3 Hz), 3.41 (2H, q, J=6.3 Hz), 3.61 (2H, q, J=5.7 Hz), 3.87 (3H, s), 5.10 (1H, brs), 5.35 (2H, brs), 6.65 (1H, s), 7.09 (1H, brs), 7.14 (1H, s), 7.96 (1H, s).

Step 2: Preparation of 5-{2-amino-6-[2-(3-amino-propionylamino)ethylsulfanyl]pyrimidin-4-yl}-2,4-dimethylbenzoic acid methyl ester

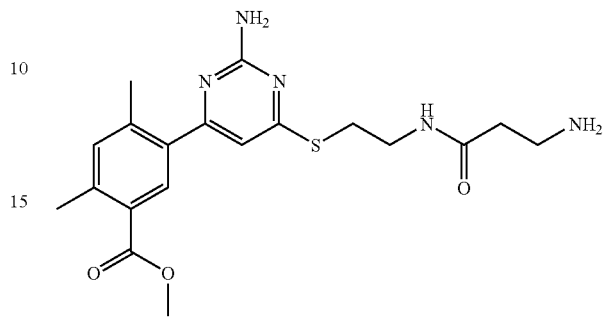

According to the method in Step 4 of Example 3-3, 5-{2-amino-6-[2-(3-amino-propionylamino)ethylsulfanyl]pyrimidin-4-yl}-2,4-dimethylbenzoic acid methyl ester was synthesized from 5-{2-amino-6-[2-(3-tert-butoxycarbonylaminopropionylamino)ethylsulfanyl]pyrimidin-4-yl}-2,4-dimethylbenzoic acid methyl ester obtained in Step 1 above.

Physicochemical properties of 5-{2-amino-6-[2-(3-amino-propionylamino)ethylsulfanyl]pyrimidin-4-yl}-2,4-dimethylbenzoic acid methyl ester Molecular weight: 403.
ESI (LC/MS positive mode): m/z=404 (M+H$^+$).
Chemical shift value δ in $^1$H-NMR (400 MHz, in chloroform-d): 2.33 (3H, s), 2.55 (3H, s), 2.63-2.83 (2H, m), 3.17-3.30 (4H, m), 3.45-3.56 (2H, m), 3.82 (3H, s), 5.80 (2H, brs), 6.53 (1H, s), 7.07 (1H, s), 7.89 (1H, s), 7.96 (1H, rs).

Step 3: Preparation of 4-amino-17,19-dimethyl-7-thia-3,5,10,14-tetraazatricyclo[14.3.1.1$^{2,6}$]henicosa-1(19),2(21),3,5,16(20),17-hexaene-11,15-dione (Compound 12)

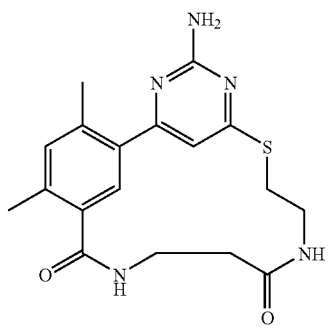 [SMILES: Cc1cc(C)c2cc1C(=O)NCCC(=O)NCCSc1cc-2nc(N)n1]

According to the method in Step 5 of Example 3-3, 4-amino-17,19-dimethyl-7-thia-3,5,10,14-tetraazatricyclo[14.3.1.1$^{2,6}$]henicosa-1(19),2(21),3,5,16(20),17-hexaene-11,15-dione (Compound 12) was synthesized from 5-{2-amino-6-[2-(3-amino-propionylamino)ethylsulfanyl]pyrimidin-4-yl}-2,4-dimethylbenzoic acid methyl ester obtained in Step 2 above.

Physicochemical properties of 4-amino-17,19-dimethyl-7-thia-3,5,10,14-tetraazatricyclo[14.3.1.1[2,6]]henicosa-1(19),2(21),3,5,16(20),17-hexaene-11,15-dione:

ESI (LC/MS positive mode): m/z=372 (M+H[+]).

Chemical shift value δ in $^1$H-NMR (400 MHz, in dimethylsulfoxide d-6): 2.32-2.37 (2H, m), 2.37 (3H, s), 2.60 (3H, s), 3.18-3.23 (2H, m), 3.35-3.46 (4H, m), 6.71 (2H, brs), 6.77 (1H, s), 7.13 (1H, s), 7.46 (1H, s), 8.01-8.06 (2H, m).

Example 3-5

Production of 4-amino-15,18,20-trimethyl-7-thia-3,5,10,15-tetraazatricyclo[15.3.1.1[2,6]]docosa-1(20),2(22),3,5,17(21),18-hexaene-11,16-dione (Compound 13)

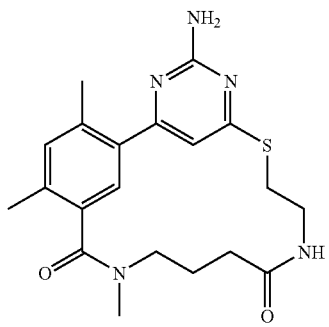

Step 1: Production of 5-(2-amino-6-{2-[4-(tert-butoxycarbonylmethylamino)butyrylamino]ethylsulfanyl}pyrimidin-4-yl)-2,4-dimethylbenzoic acid methyl ester

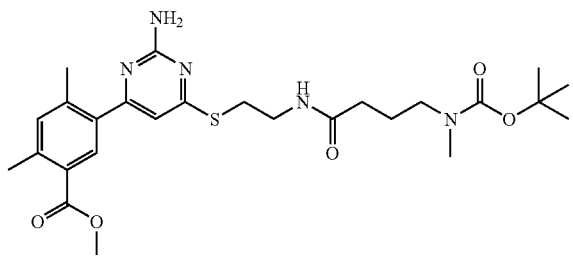 [SMILES: COC(=O)c1cc(-c2cc(SCCNC(=O)CCCN(C)C(=O)OC(C)(C)C)nc(N)n2)c(C)cc1C]

According to the method in Step 3 of Example 3-3, 5-(2-amino-6-{2-[4-(tert-butoxycarbonylmethylamino)-butyrylamino]ethylsulfanyl}pyrimidin-4-yl)-2,4-dimethylbenzoic acid methyl ester was synthesized from 5-[2-amino-6-(2-aminoethylsulfanyl)pyrimidin-4-yl]-2,4-dimethylbenzoic acid methyl ester obtained in Step 2 of Example 3-3.

Physicochemical properties of 5-(2-amino-6-{2-[4-(tert-butoxycarbonylmethylamino)-butyrylamino]ethylsulfanyl}pyrimidin-4-yl)-2,4-dimethylbenzoic acid methyl ester Molecular weight: 531.
ESI (LC/MS positive mode): m/z=532 (M+H[+]).
Chemical shift value δ in $^1$H-NMR (400 MHz, in chloroform-d): 1.46 (9H, s), 1.82-1.89 (2H, m), 2.16 (2H, t, J=6.8 Hz), 2.41 (3H, s), 2.59 (3H, s), 2.81 (3H, s), 3.22-3.36 (2H, m), 3.33 (2H, t, J=6.8 Hz), 3.60 (2H, q, J=6.3 Hz), 3.87 (3H, s), 5.31 (2H, brs), 6.64 (1H, s), 7.14 (1H, s), 7.38 (1H, brs), 7.96 (1H, s).

Step 2: Preparation of 5-{2-amino-6-[2-(4-methylaminobutyrylamino)ethylsulfanyl]pyrimidin-4-yl}-2,4-dimethylbenzoic acid methyl ester

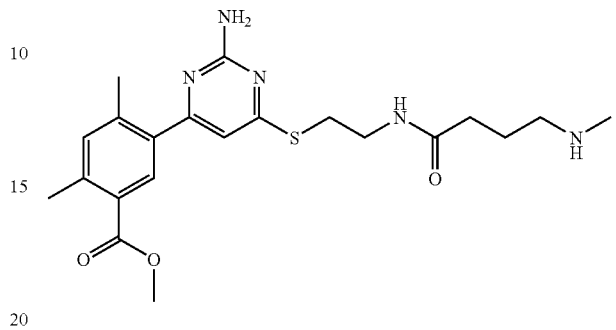

According to the method in Step 4 of Example 3-3, 5-{2-amino-6-[2-(4-methylaminobutyrylamino)ethylsulfanyl]pyrimidin-4-yl}-2,4-dimethylbenzoic acid methyl ester was synthesized from 5-(2-amino-6-{2-[4-(tert-butoxycarbonylmethylamino)-butyrylamino]ethylsulfanyl}pyrimidin-4-yl)-2,4-dimethylbenzoic acid methyl ester obtained as in Step 1 above.

Physicochemical properties of 5-{2-amino-6-[2-(4-methylaminobutyrylamino)ethylsulfanyl]pyrimidin-4-yl}-2,4-dimethylbenzoic acid methyl ester Molecular weight: 431.
ESI (LC/MS positive mode): m/z=432 (M+H[+]).
Chemical shift value δ in $^1$H-NMR (400 MHz, in chloroform-d): 2.01-2.07 (2H, m), 2.40 (3H, s), 2.44 (2H, t, J=6.3 Hz), 2.60 (3H, s), 2.68 (3H, s), 3.05 (2H, t, J=5.9 Hz), 3.31 (2H, t, J=6.3 Hz), 3.57 (2H, t, J=5.9 Hz), 3.87 (3H, s), 5.43 (2H, brs), 6.62 (1H, s), 7.14 (1H, s), 7.51-7.55 (1H, m), 7.94 (1H, s).

Step 3: Preparation of 4-amino-15,18,20-trimethyl-7-thia-3,5,10,15-tetraazatricyclo[15.3.1.1[2,6]]docosa-1(20),2(22),3,5,17(21),18-hexaene-11,16-dione (Compound 13)

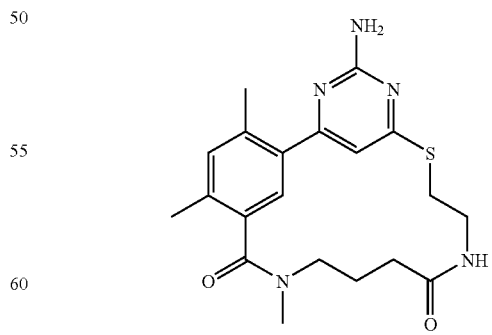

According to the method in Step 5 of Example 3-3, 4-amino-15,18,20-trimethyl-7-thia-3,5,10,15-tetraazatricyclo[15.3.1.1[2,6]]docosa-1(20),2(22),3,5,17(21),18-hexaene-11,16-dione (Compound 13) was synthesized from 5-{2- amino-6-[2-(4-methylaminobutyrylamino)ethylsulfanyl]pyrimidin-4-yl}-2,4-dimethylbenzoic acid methyl ester obtained in Step 2 above.

Physicochemical properties of 4-amino-15,18,20-trimethyl-7-thia-3,5,10,15-tetraazatricyclo[15.3.1.1$^{2,6}$]docosa-1(20),2(22),3,5,17(21),18-hexaene-11,16-dione Molecular weight: 399.
ESI (LC/MS positive mode): m/z=400 (M+H$^+$).
Chemical shift value δ in $^1$H-NMR (500 MHz, in dimethylsulfoxide d-6, at 140° C.): 1.80-1.85 (2H, m), 2.15-2.18 (2H, s), 2.19 (3H, s), 2.43 (3H, s), 2.92 (3H, s), 3.06 (2H, t, J=6.9 Hz), 3.26-3.31 (2H, m), 3.41 (2H, q, J=6.9 Hz), 6.03 (2H, brs), 6.80 (1H, s), 7.10 (1H, s), 7.24 (1H, s).

Example 3-6

Production of 4-amino-20,22-dimethyl-7-thia-3,5,10,17-tetraazatricyclo[17.3.1.1$^{2,6}$]tetracosa-1(22),2(24),3,5,19(23),20-hexaene-11,18-dione (Compound 14)

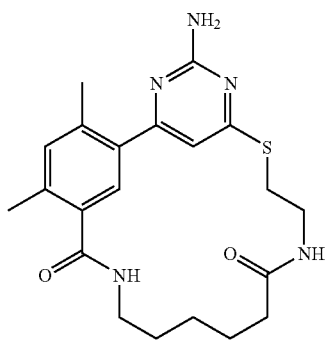 [SMILES: Cc1cc(C)c2cc1C(=O)NCCCCCC(=O)NCCSc1cc-2nc(N)n1]

Step 1: Preparation of 5-{2-amino-6-[2-(6-tert-butoxycarbonylaminohexanoylamino)ethylsulfanyl]pyrimidin-4-yl}-2,4-dimethylbenzoic acid methyl ester

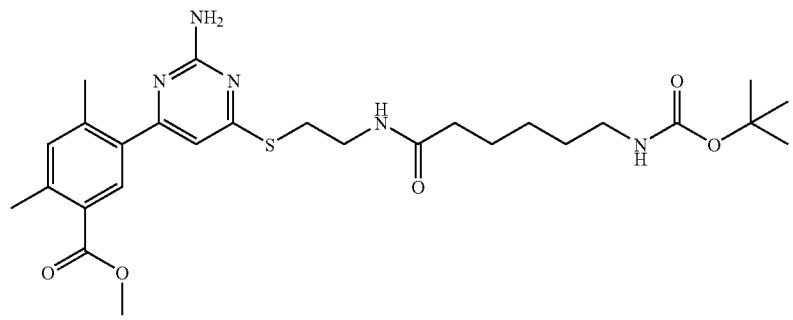 [SMILES: COC(=O)c1cc(-c2cc(SCCNC(=O)CCCCCNC(=O)OC(C)(C)C)nc(N)n2)c(C)cc1C]

According to the method in Step 3 of Example 3-3, 5-{2-amino-6-[2-(6-tert-butoxycarbonylaminohexanoylamino)ethylsulfanyl]pyrimidin-4-yl}-2,4-dimethylbenzoic acid methyl ester was synthesized from 5-[2-amino-6-(2-aminoethylsulfanyl)pyrimidin-4-yl]-2,4-dimethylbenzoic acid methyl ester obtained in Step 2 of Example 3-3.

Physicochemical properties of 5-{2-amino-6-[2-(6-tert-butoxycarbonylaminohexanoylamino)ethylsulfanyl]pyrimidin-4-yl}-2,4-dimethylbenzoic acid methyl ester Molecular weight: 545.
ESI (LC/MS positive mode): m/z=546 (M+H$^+$).
Chemical shift value δ in $^1$H-NMR (400 MHz, in chloroform-d): 1.32-1.36 (2H, m), 1.43 (9H, s), 1.44-1.51 (2H, m), 1.59-1.66 (2H, m), 2.17 (2H, t, J=7.3 Hz), 2.41 (3H, s), 2.61 (3H, s), 3.09 (2H, q, J=6.8 Hz), 3.34 (2H, t, J=6.3 Hz), 3.61 (2H, q, J=6.3 Hz), 3.88 (3H, s), 4.56 (1H, brs), 5.11 (2H, brs), 6.28 (1H, brs), 6.65 (1H, s), 7.14 (1H, s), 7.96 (1H, s).

Step 2: Preparation of 5-{2-amino-6-[2-(6-aminohexanoylamino)ethylsulfanyl]pyrimidin-4-yl}-2,4-dimethylbenzoic acid methyl ester

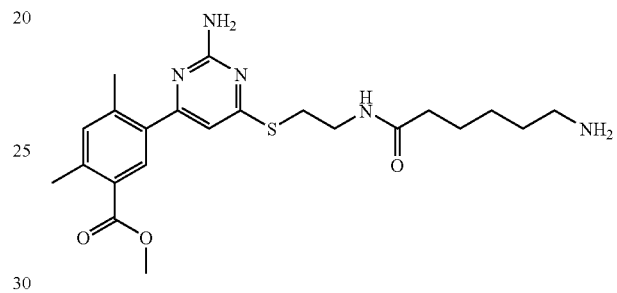

According to the method in Step 4 of Example 3-3, 5-{2-amino-6-[2-(6-aminohexanoylamino)ethylsulfanyl]pyrimidin-4-yl}-2,4-dimethylbenzoic acid methyl ester was synthesized from 5-{2-amino-6-[2-(6-tert-butoxycarbonylaminohexanoylamino)ethylsulfanyl]pyrimidin-4-yl}-2,4-dimethylbenzoic acid methyl ester obtained in Step 1 above.

Physicochemical properties of 5-{2-amino-6-[2-(6-aminohexanoylamino)ethylsulfanyl]pyrimidin-4-yl}-2,4-dimethylbenzoic acid methyl ester Molecular weight: 445.
ESI (LC/MS positive mode): m/z=446 (M+H$^+$).
Chemical shift value δ in $^1$H-NMR (400 MHz, in chloroform-d): 1.31-1.39 (2H, m), 1.57-1.64 (4H, m), 2.16 (2H, t, J=7.3 Hz), 2.38 (3H, s), 2.59 (3H, s), 2.83 (2H, t, J=7.3 Hz), 3.32 (2H, t, J=6.1 Hz), 3.56 (2H, q, J=6.1 Hz), 3.87 (3H, s), 5.56 (2H, brs), 6.60 (1H, s), 6.91 (1H, brt, J=4.9 Hz), 7.14 (1H, s), 7.91 (1H, s).

Step 3: Preparation of 4-amino-20,22-dimethyl-7-thia-3,5,10,17-tetraazatricyclo[17.3.1.1$^{2,6}$]tetracosa-1(22),2(24),3,5,19(23),20-hexaene-11,18-dione (Compound 14)

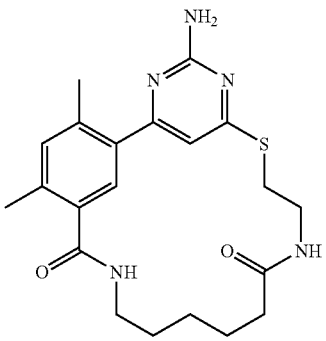 [SMILES: Cc1cc(C)c2cc1C(=O)NCCCCCC(=O)NCCSc1cc-2nc(N)n1]

According to the method in Step 5 of Example 3-3, 4-amino-20,22-dimethyl-7-thia-3,5,10,17-tetraazatricyclo[17.3.1.1$^{2,6}$]tetracosa-1(22),2(24),3,5,19(23),20-hexaene-11,18-dione (Compound 14) was synthesized from 5-{2-amino-6-[2-(6-aminohexanoylamino)ethylsulfanyl]pyrimidin-4-yl}-2,4-dimethylbenzoic acid methyl ester obtained in Step 2 above.

Physicochemical properties of 4-amino-20,22-dimethyl-7-thia-3,5,10,17-tetraazatricyclo[17.3.1.1$^{2,6}$]tetracosa-1(22),2(24),3,5,19(23),20-hexaene-11,18-dione Molecular weight: 413.
ESI (LC/MS positive mode): m/z=414 (M+H$^+$).
Chemical shift value δ in $^1$H-NMR (400 MHz, in dimethylsulfoxide d-6): 1.40-1.47 (2H, m), 1.47-1.55 (4H, m), 2.13-2.14 (2H, m), 2.36 (3H, s), 2.50 (3H, s), 3.01-3.03 (2H, m), 3.26-3.31 (4H, m), 6.62 (2H, brs), 7.14 (1H, s), 7.30 (1H, s), 7.70 (1H, s), 8.07 (1H, t, J=5.1 Hz), 8.27 (1H, t, J=5.4 Hz).

Example 3-7

Production of 4-amino-18,20-dichloro-7-thia-3,5,10,15-tetraazatricyclo[15.3.1.1$^{2,6}$]docosa-1(20),2(22),3,5,17(21),18-hexaene-11,16-dione (Compound 15)

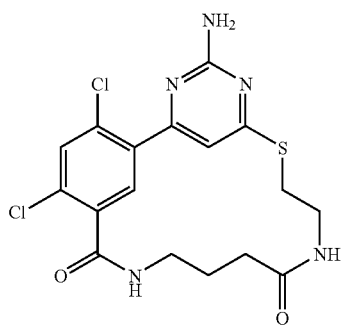 [SMILES: Nc1nc2cc(n1)-c1cc(c(Cl)cc1Cl)C(=O)NCCCC(=O)NCCS2]

Step 1: Preparation of [2-(2-amino-6-chloropyrimidin-4-ylsulfanyl)ethyl]carbamic acid tert-butyl ester

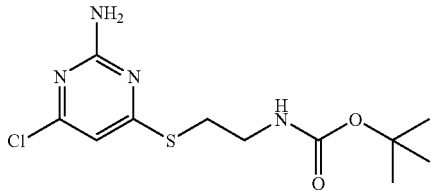 [SMILES: CC(C)(C)OC(=O)NCCSc1cc(Cl)nc(N)n1]

A mixture of commercially available 2-amino-4,6-dichloropyrimidine (428 mg, 2.61 mmol), potassium carbonate (361 mg, 2.61 mmol), N,N-dimethylformamide (5.0 ml), and (2-mercaptoethyl)carbamic acid tert-butyl ester (356 mg, 2.0 mmol) was stirred in a reaction vessel at room temperature for 3 hours. A saturated aqueous ammonium chloride solution was added to the reaction solution, and extracted with ethyl acetate. The organic layer was separated, and then sequentially washed with a saturated aqueous ammonium chloride solution and a saturated aqueous sodium chloride solution. The organic solution was dried over anhydrous sodium sulfate. After filtration, the filtrate was concentrated under reduced pressure. The resulting residue was purified by silica gel column chromatography (developing solvent: n-hexane:ethyl acetate=5:1 to 2:1) to yield [2-(2-amino-6-chloropyrimidin-4-ylsulfanyl)ethyl]carbamic acid tert-butyl ester (548 mg).

Physicochemical properties of 2-(2-amino-6-chloropyrimidin-4-ylsulfanyl)ethyl]carbamic acid tert-butyl ester Molecular weight: 304.
ESI (LC/MS positive mode): m/z=305, 307 (M+H$^+$).
Chemical shift value δ in $^1$H-NMR (400 MHz, in chloroform-d): 1.44 (9H, s), 3.23 (2H, t, J=5.9 Hz), 3.41-3.45 (2H, m), 5.20 (3H, brs), 6.57 (1H, s).

Step 2: Preparation of 5-[2-amino-6-(2-tert-butoxycarbonylaminoethylsulfanyl)pyrimidin-4-yl]-2,4-dichlorobenzoic acid methyl ester

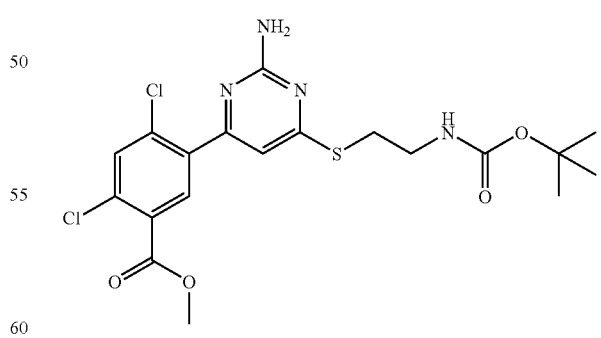

A mixture of the crude product of 2,4-dichloro-5-(4,4,5,5-tetramethyl[1,3,2]dioxaborolan-2-yl)benzoic acid methyl ester (320 mg) obtained in Step 3 of Example 2-8, [2-(2-amino-6-chloropyrimidin-4-ylsulfanyl)ethyl]carbamic acid tert-butyl ester (177 mg, 0.58 mmol) obtained in Step 1 above, palladium acetate (5 mg, 0.02 mmol), triphenylphosphine (19 mg, 0.07 mmol), 1N aqueous sodium bicarbonate solution (725 μl), and dimethoxyethane (4.4 ml) was stirred at 80° C. for 2 hours. After the reaction solution was cooled to room temperature, water was added thereto and extracted with ethyl acetate. The organic layer was sequentially washed with water and a saturated aqueous sodium chloride solution, and then dried over anhydrous sodium sulfate. After filtration, the filtrate was concentrated under reduced pressure. The resulting residue was purified by silica gel column chromatography (developing solvent: n-hexane:ethyl acetate=3:1 to 1:1) to yield 5-[2-amino-6-(2-tert-butoxycarbonylaminoethylsulfanyl)pyrimidin-4-yl]-2,4-dichlorobenzoic acid methyl ester (96 mg).

Physicochemical properties of 5-[2-amino-6-(2-tert-butoxycarbonylaminoethylsulfanyl)pyrimidin-4-yl]-2,4-dichlorobenzoic acid methyl ester Molecular weight: 473.
ESI (LC/MS positive mode): m/z=473, 475 (M+H$^+$).
Chemical shift value δ in $^1$H-NMR (400 MHz, in chloroform-d): 1.36 (9H, s), 3.15-3.23 (2H, m), 3.33-3.42 (2H, m), 3.85 (3H, s), 5.38 (3H, brs), 6.73 (1H, s), 7.51 (1H, s), 8.00 (1H, s).

Step 3: Preparation of 4-amino-18,20-dichloro-7-thia-3,5,10,15-tetraazatricyclo[15.3.1.1$^{2,6}$]docosa-1(20),2(22),3,5,17(21),18-hexaene-11,16-dione (Compound 15)

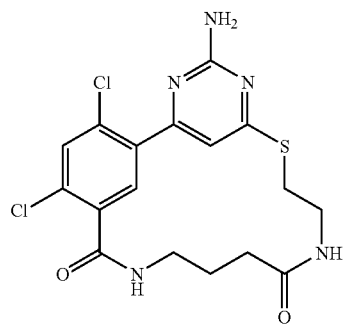 [SMILES: Nc1nc2cc(n1)-c1cc(c(Cl)cc1Cl)C(=O)NCCCC(=O)NCCS2]

According to the method in Steps 2 and 3 of Example 3-1, 4-amino-18,20-dichloro-7-thia-3,5,10,15-tetraazatricyclo[15.3.1.1$^{2,6}$]docosa-1(20),2(22),3,5,17(21),18-hexaene-11,16-dione (Compound 15) was synthesized from 5-[2-amino-6-(2-tert-butoxycarbonylaminoethylsulfanyl)pyrimidin-4-yl]-2,4-dichlorobenzoic acid methyl ester obtained in Step 2 above.

Physicochemical properties of 4-amino-18,20-dichloro-7-thia-3,5,10,15-tetraazatricyclo[15.3.1.1$^{2,6}$]docosa-1(20),2(22),3,5,17(21),18-hexaene-11,16-dione Molecular weight: 426.
ESI (LC/MS positive mode): m/z=426, 428 (M+H$^+$).
Chemical shift value δ in $^1$H-NMR (400 MHz, in dimethylsulfoxide d-6): 1.75-1.83 (2H, m), 2.35-2.41 (2H, m), 3.10-3.16 (2H, m), 3.24-3.32 (2H, m), 3.33-3.41 (2H, m), 6.82 (2H, brs), 7.23 (1H, s), 7.74 (1H, s), 8.12 (1H, s), 8.39 (1H, brt), 8.88 (1H, brt).

Example 3-8

Production of 4,12-diamino-18,20-dimethyl-7-thia-3,5,10,15-tetraazatricyclo[15.3.1.1$^{2,6}$]docosa-1(20),2(22),3,5,17(21),18-hexaene-11,16-dione (Compound 73)

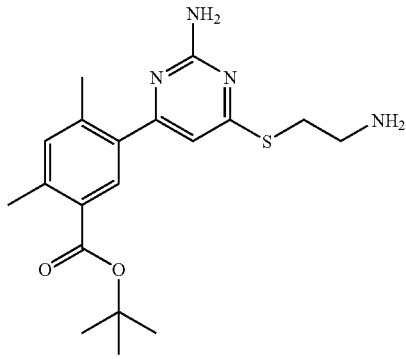

Step 1: Preparation of 5-[2-amino-6-(2-aminoethylsulfanyl)pyrimidin-4-yl]-2,4-dimethylbenzoic acid tert-butyl ester

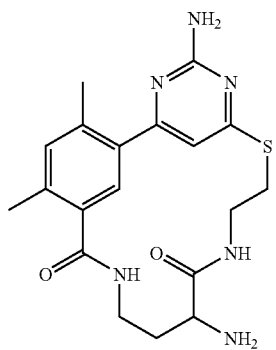 [SMILES: Cc1cc(C)c2cc1C(=O)NCCC(N)C(=O)NCCSc1cc-2nc(N)n1]

5-(2-Amino-6-chloropyrimidin-4-yl)-2,4-dimethylbenzoic acid tert-butyl ester (Compound 1-1) (5.0 g, 15.0 mmol) obtained in Example 1-1 was dissolved in N,N-dimethylformamide (125 ml), and then cesium carbonate (11.5 g, 150.0 mmol) and 2-aminoethanethiol (48.8 g, 150.0 mmol) were added thereto at room temperature. The resulting mixture was stirred at room temperature for three hours, and then diluted with ethyl acetate (500 ml). The solution was sequentially washed with water (500 ml, three times) and a saturated aqueous sodium chloride solution (500 ml). The washed organic layer was dried over anhydrous sodium sulfate. After filtration, the filtrate was concentrated under reduced pressure. The resulting crude product was dissolved in ethyl acetate (20 ml) while heating, and n-hexane (60 ml) was added thereto. The mixture was stirred at room temperature for one hour. The precipitated crystals were collected by filtration. After washing with n-hexane (60 ml), the crystals were dried under reduced pressure to yield 5-[2-amino-6-(2-aminoethylsulfanyl)pyrimidin-4-yl]-2,4-dimethylbenzoic acid tert-butyl ester (4.4 g) as colorless crystals.

Physicochemical properties of 5-[2-amino-6-(2-aminoethylsulfanyl)pyrimidin-4-yl]-2,4-dimethylbenzoic acid tert-butyl ester Molecular weight: 374.

ESI (LC/MS positive mode): 375 (M+H$^+$).

Chemical shift value δ in $^1$H-NMR (300 MHz, in dimethylsulfoxide d-6): 1.53 (9H, s), 2.34 (3H, s), 2.48 (3H, s), 2.78 (2H, t, J=6.7 Hz), 3.11 (2H, t, J=6.7 Hz), 6.56 (1H, s), 6.72 (2H, brs), 7.20 (1H, s), 7.71 (1H, s).

Step 2: Preparation of 5-{2-amino-6-[2-(2,4-bis-tert-butoxycarbonylaminobutyrylamino)ethylsulfanyl]pyrimidin-4-yl}-2,4-dimethylbenzoic acid tert-butyl ester

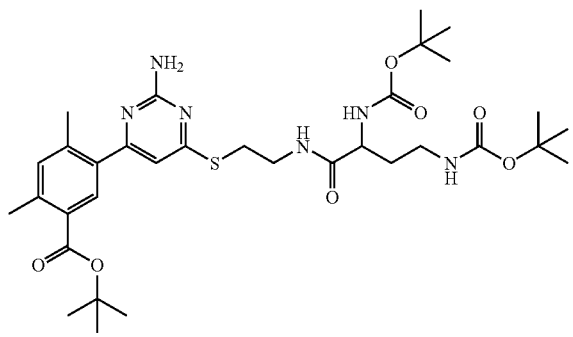 [SMILES: Cc1cc(C)c(-c2cc(SCCNC(=O)C(CCNC(=O)OC(C)(C)C)NC(=O)OC(C)(C)C)nc(N)n2)cc1C(=O)OC(C)(C)C]

5-[2-Amino-6-(2-aminoethylsulfanyl)pyrimidin-4-yl]-2,4-dimethylbenzoic acid tert-butyl ester (1.9 g, 5.10 mmol) obtained in Step 1 above, DL-2,4-bis((tert-butoxycarbonyl)amino)butyric acid (which can be prepared from commercially available DL-2,4-diaminobutyric acid dihydrochloride by the method described in Journal of Inorganic Biochemistry (2004) 98(11): 1933-1946) (4.9 g, 15.3 mmol), and 1-hydroxybenzotriazole (2.1 g, 15.3 mmol) were dissolved in N,N-dimethylformamide (40 ml). 1-Ethyl-3-(3'-dimethylaminopropyl)carbodiimide hydrochloride (2.9 g, 15.3 mmol) and diisopropylethylamine (3.6 ml, 20.4 mmol) were added to the solution, and stirred overnight at room temperature. The reaction solution was diluted with ethyl acetate (400 ml), and then sequentially washed with a saturated aqueous sodium bicarbonate solution (300 ml), water (300 ml, three times), and a saturated aqueous sodium chloride solution (300 ml). After the organic layer was dried over anhydrous sodium sulfate (50 g), the inorganic salt was filtered and washed with ethyl acetate. The filtrate and washing solution were combined together, and concentrated under reduced pressure. The resulting residue was purified by silica gel column chromatography (developing solvent: dichloromethane:methanol=40:1) to yield 5-{2-amino-6-[2-(2,4-bis-tert-butoxycarbonylaminobutyrylamino)ethylsulfanyl]pyrimidin-4-yl}-2,4-dimethylbenzoic acid tert-butyl ester (3.2 g) as a white solid material.

Physicochemical properties of 5-{2-amino-6-[2-(2,4-bis-tert-butoxycarbonylaminobutyrylamino)ethylsulfanyl]pyrimidin-4-yl}-2,4-dimethylbenzoic acid tert-butyl ester Molecular weight: 674.

ESI (LC/MS positive mode): 675(M+H$^+$).

Chemical shift value δ in $^1$H-NMR (300 MHz, in dimethylsulfoxide d-6): 1.36 (18H, s), 1.53 (9H, s), 2.35 (3H, s), 2.49 (3H, s), 1.56-3.42 (8H, m), 3.87 (1H, t, J=5.6 Hz), 6.62 (1H, s), 6.68 (1H, brs), 6.75 (2H, brs), 6.86 (1H, d, J=7.9 Hz), 7.21 (1H, s), 7.72 (1H, s), 8.03 (1H, t, J=6.1 Hz).

Step 3: Preparation of 5-{2-amino-6-[2-(2,4-diaminobutyrylaminoethylsulfanyl)pyrimidin-4-yl}-2,4-dimethylbenzoic acid tri(trifluoroacetate)

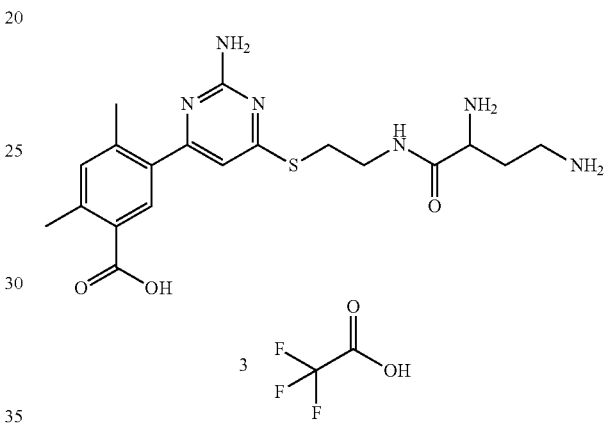

5-{2-Amino-6-[2-(2,4-bis-tert-butoxycarbonylaminobutyrylamino)ethylsulfanyl]pyrimidin-4-yl}-2,4-dimethylbenzoic acid tert-butyl ester obtained in Step 2 above was dissolved in dichloromethane (37 ml). After the solution was cooled to 0° C., trifluoroacetic acid (13 ml) was added thereto. The reaction solution was gradually warmed to room temperature, and then stirred at room temperature for six hours. After the solvent was distilled off under reduced pressure, dichloromethane (10 ml) was added to the residue and again concentrated under reduced pressure. The resulting residue was suspended in ethyl acetate (60 ml). After the suspension was stirred at room temperature for two hours, the insoluble material was collected by filtration. The obtained solid was dried under reduced pressure to yield 5-{2-amino-6-[2-(2,4-diaminobutyrylamino)ethylsulfanyl]pyrimidin-4-yl}-2,4-dimethylbenzoic acid tert-butyl ester tri(trifluoroacetate) (3.6 g) as a white solid material.

Physicochemical properties of 5-{2-amino-6-[2-(2,4-diaminobutyrylamino)ethylsulfanyl]pyrimidin-4-yl}-2,4-dimethylbenzoic acid tri(trifluoroacetate)

Molecular weight: 760 (tri(trifluoroacetate))

ESI (LC/MS positive mode): 419 (M+H$^+$).

Chemical shift value δ in $^1$H-NMR (300 MHz, in dimethylsulfoxide d-6): 2.01 (2H, m), 2.39 (3H, s), 2.54 (3H, s), 2.86 (2H, m), 3.25 (2H, m), 3.50 (2H, m), 3.85 (1H, m), 6.66 (1H, s), 6.83 (2H, brs), 7.25 (1H, s), 7.85 (2H, brs), 7.88 (1H, s), 8.29 (2H, brs), 8.80 (1H, t, J=5.3 Hz).

Step 4: Preparation of 4,12-diamino-18,20-dimethyl-7-thia-3,5,10,15-tetraazatricyclo[15.3.1.1$^{2,6}$]docosa-1(20),2(22),3,5,17(21),18-hexaene-11,16-dione (Compound 73)

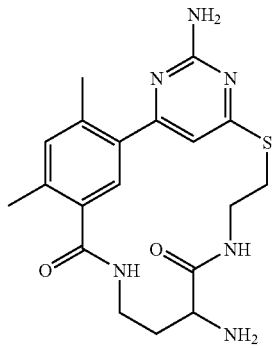 [SMILES: Cc1cc(C)c2cc1C(=O)NCCC(N)C(=O)NCCSc1cc-2nc(N)n1]

1-Hydroxybenzotriazole (888 mg, 6.57 mmol), 1-ethyl-3-(3'-dimethylaminopropyl)carbodiimide hydrochloride (2.5 g, 13.15 mmol), and diisopropylethylamine (11.5 ml, 65.74 mmol) were dissolved in tetrahydrofuran (500 ml). A tetrahydrofuran (160 ml) solution of 5-{2-amino-6-[2-(2,4-diaminobutyrylamino)ethylsulfanyl]pyrimidin-4-yl}-2,4-dimethylbenzoic acid tri(trifluoroacetate) (1.0 g, 1.31 mmol) obtained in Step 3 above was dropwise added to the above solution over 30 minutes. The resulting mixture was stirred for four hours. The reaction solution was diluted with ethyl acetate (2 l), and sequentially washed with a saturated aqueous sodium bicarbonate solution (100 ml) and a saturated aqueous sodium chloride solution (100 ml). After the organic layer was dried over anhydrous sodium sulfate, the inorganic salt was filtered and washed with ethyl acetate. The filtrate and washing solution were combined together, and concentrated under reduced pressure. The resulting residue was purified by silica gel column chromatography (developing solution: dichloromethane:methanol=10:1) to yield 4,12-diamino-18,20-dimethyl-7-thia-3,5,10,15-tetraazatricyclo[15.3.1.1$^{2,6}$]docosa-1(20),2(22),3,5,17(21),18-hexaene-11,16-dione (Compound 73) (119 mg) as a white solid material.

Physicochemical properties of 4,12-diamino-18,20-dimethyl-7-thia-3,5,10,15-tetraazatricyclo[15.3.1.1$^{2,6}$]docosa-1(20),2(22),3,5,17(21),18-hexaene-11,16-dione Molecular weight: 400.

ESI (LC/MS positive mode): 401 (M+H$^+$).

Chemical shift value δ in $^1$H-NMR (300 MHz, in dimethylsulfoxide d-6): 1.81 (2H, m), 2.03 (2H, brs), 2.40 (3H, s), 2.58 (3H, s), 3.10-3.59 (7H, m), 6.63 (2H, brs), 7.13 (1H, s), 7.53 (1H, s), 7.81 (1H, s), 8.57 (1H, brs), 8.86 (1H, t, J=4.8 Hz).

Example 3-9

Production of N-(4-amino-18,20-dimethyl-10,16-dioxo-7-thia-3,5,10,15-tetraazatricyclo[15.3.1.1$^{2,6}$]docosa-1(20),2(22),3,5,17(21),18-hexaen-12-yl)acetamide (Compound 74)

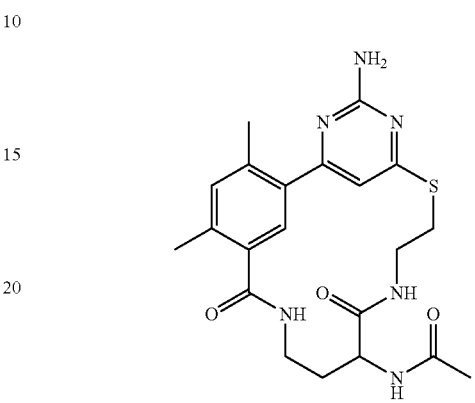

4,12-Diamino-18,20-dimethyl-7-thia-3,5,10,15-tetraazatricyclo[15.3.1.1$^{2,6}$]docosa-1(20),2(22),3,5,17(21),18-hexaene-11,16-dione (10 mg, 0.025 mmol) obtained in Example 3-8 was dissolved in N,N-dimethylformamide (200l). Acetyl chloride (1.9 µl, 0.027 mmol) and triethylamine (10.4 µl, 0.075 mmol) were added to the solution at room temperature, and stirred at room temperature for three hours. The reaction solution was diluted with ethyl acetate, and then sequentially washed with water and a saturated aqueous sodium chloride solution. After the organic layer was dried over anhydrous sodium sulfate, the inorganic salt was filtered and washed with ethyl acetate. The filtrate and washing solution were combined together, and concentrated under reduced pressure. The resulting residue was purified by preparative thin layer silica gel chromatography (developing solution: dichloromethane:methanol=10:1) to yield N-(4-amino-18,20-dimethyl-10,16-dioxo-7-thia-3,5,10,15-tetraazatricyclo[15.3.1.1$^{2,6}$]docosa-1(20),2(22),3,5,17(21),18-hexaen-12-yl)acetamide (Compound 74) (5.6 mg) as a white solid material.

Physicochemical properties of N-(4-amino-18,20-dimethyl-10,16-dioxo-7-thia-3,5,10,15-tetraazatricyclo[15.3.1.1$^{2,6}$]docosa-1(20),2(22),3,5,17(21),18-hexaen-12-yl)acetamide Molecular weight: 442.

ESI (LC/MS positive mode): 443 (M+H$^+$).

Chemical shift value δ in $^1$H-NMR (300 MHz, in dimethylsulfoxide d-6): 1.88 (3H, s), 2.40 (3H, s), 2.58 (3H, s), 1.75-3.40 (8H, m), 4.48 (1H, m), 6.65 (2H, brs), 7.14 (1H, s), 7.42 (1H, s), 7.81 (1H, s), 8.23 (1H, d, J=7.7 Hz), 8.52 (1H, brs), 8.60 (1H, brs).

Example 3-10

Production of N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-2,2,2-trifluoroacetamide (Compound 75)

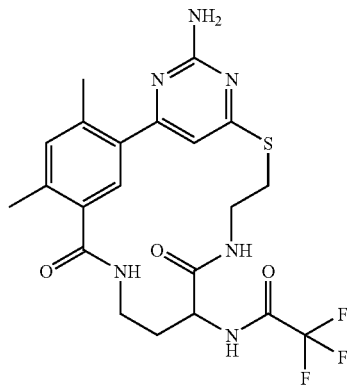 [SMILES: Cc1cc(C)c2cc1C(=O)NCCC(NC(=O)C(F)(F)F)C(=O)NCCSc1cc-2nc(N)n1]

5-{2-Amino-6-[2-(2,4-diaminobutyrylamino)ethylsulfanyl]pyrimidin-4-yl}-2,4-dimethylbenzoic acid tri(trifluoroacetate) (60 mg, 0.079 mmol) obtained in Step 3 of Example 3-8 and 1-hydroxybenzotriazole (43 mg, 0.316 mmol) were dissolved in N,N-dimethylformamide (46 ml). 1-Ethyl-3-(3'-dimethylaminopropyl)carbodiimide hydrochloride (61 mg, 0.316 mmol) and diisopropylethylamine (8.3 µl, 0.473 mmol) were added to the solution, and stirred overnight at room temperature. The reaction solution was diluted with ethyl acetate, and then sequentially washed with a saturated aqueous sodium bicarbonate solution, water (three times), and a saturated aqueous sodium chloride solution. After the organic layer was dried over anhydrous sodium sulfate, the inorganic salt was filtered and washed with ethyl acetate. The filtrate and washing solution were combined together, and concentrated under reduced pressure. The resulting residue was purified by preparative thin layer silica gel chromatography (developing solvent: dichloromethane:methanol=10:1) to yield N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-2,2,2-trifluoroacetamide (Compound 75) (12 mg) as a white solid material.

Physicochemical properties of N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-2,2,2-trifluoroacetamide Molecular weight: 496.
ESI (LC/MS positive mode): 497 (M+H$^+$).
Chemical shift value δ in $^1$H-NMR (300 MHz, in dimethylsulfoxide d-6): 1.88 (1H, m), 2.12 (1H, m), 2.39 (3H, s), 2.59 (3H, s), 3.14-3.49 (7H, m), 4.57 (1H, m), 6.65 (2H, brs), 7.14 (1H, s), 7.27 (1H, s), 7.88 (1H, s), 8.45 (1H, brs), 8.67 (1H, t, J=5.3 Hz), 9.66 (1H, brs).

Example 3-11

Production of (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-methylbutylamide (Compound

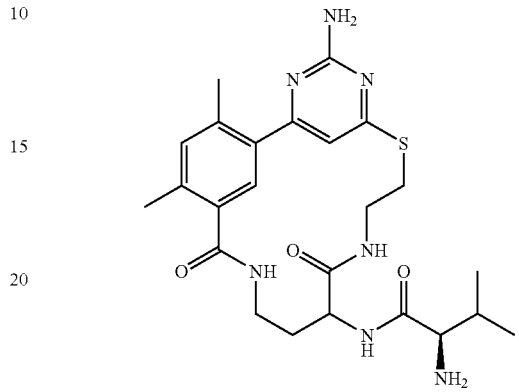

Step 1: Preparation of [(R)-1-(4-amino-18,20-dimethyl-1,16-dioxo-7-thia-3,5,10,15-tetraazatricyclo[15.3.1.1$^{2,6}$]docosa-1(20),2(22),3,5,17(21),18-hexaen-12-ylcarbamoyl)-2-methylpropyl]carbamic acid tert-butyl ester

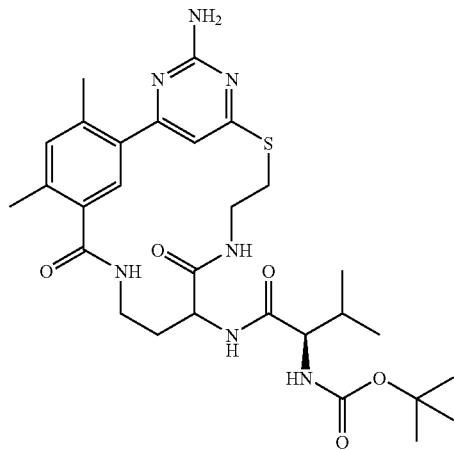 [SMILES: Cc1cc(C)c2cc1C(=O)NCCC(NC(=O)[C@H](NC(=O)OC(C)(C)C)C(C)C)C(=O)NCCSc1cc-2nc(N)n1]

4,12-Diamino-18,20-dimethyl-7-thia-3,5,10,15-tetraazatricyclo[15.3.1.1$^{2,6}$]docosa-1(20),2(22),3,5,17(21),18-hexaene-11,16-dione (10 mg, 0.025 mmol) obtained in Step 4 of Example 3-8, (R)-2-tert-butoxycarbonylamino-3-methylbutyric acid (16 mg, 0.075 mmol), and 1-hydroxybenzotriazole (10 mg, 0.075 mmol) were dissolved in N,N-dimethylformamide (200 µl). 1-Ethyl-3-(3'-dimethylaminopropyl)carbodiimide hydrochloride (14 mg, 0.075 mmol) and diisopropylethylamine (17 µl, 0.100 mmol) were added to the solution, and stirred overnight at room temperature. The reaction solution was diluted with ethyl acetate, and then sequentially washed with a saturated aqueous sodium bicarbonate solution, water, and a saturated aqueous sodium chloride solution. After the organic layer was dried over anhydrous sodium sulfate, the inorganic salt was filtered and washed with ethyl acetate. The filtrate and washing solution were combined together and concentrated under reduced pressure. The resulting residue was purified by preparative thin layer silica gel chromatography (developing solution: dichloromethane:methanol=10:1) to yield two diastereomers (diastereomer A, 6.5 mg; diastereomer B, 6.1 mg) of [(R)-1-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-ylcarbamoyl)-2-methylpropyl]carbamic acid tert-butyl ester.

Physicochemical properties of [(R)-1-(4-amino-18,20-dimethyl-1,16-dioxo-7-thia-3,5,10,15-tetraazatricyclo[15.3.1.1$^{2,6}$]docosa-1(20),2(22),3,5,17(21),18-hexaen-12-ylcarbamoyl)-2-methylpropyl]carbamic acid tert-butyl ester (diastereomer A)

Molecular weight: 599.
ESI (LC/MS positive mode): 600 (M+H$^+$).
Rf value: 0.45 (thin layer silica gel chromatography, developing solvent: dichloromethane methanol=10:1)

Physicochemical properties of [(R)-1-(4-amino-18,20-dimethyl-1,16-dioxo-7-thia-3,5,10,15-tetraazatricyclo[15.3.1.1$^{2,6}$]docosa-1(20),2(22),3,5,17(21),18-hexaen-12-ylcarbamoyl)-2-methylpropyl]carbamic acid tert-butyl ester (diastereomer B)

Molecular weight: 599.
ESI (LC/MS positive mode): 600 (M+H$^+$).
Rf value: 0.52 (thin layer silica gel chromatography, developing solvent: dichloromethane:methanol=10:1)

Step 2-A: Preparation of (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-methylbutylamide (Compound 76) (diastereomer A)

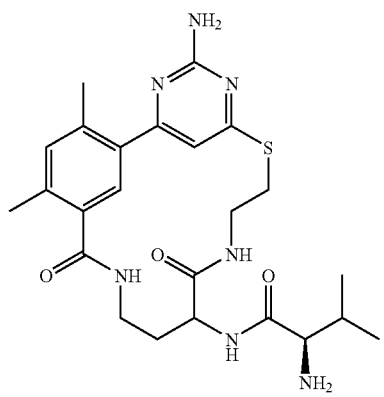 [SMILES: Cc1cc(C)c2cc1C(=O)NCCC(NC(=O)[C@H](N)C(C)C)C(=O)NCCSc1cc-2nc(N)n1]

[(R)-1-(4-Amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-ylcarbamoyl)-2-methylpropyl]carbamic acid tert-butyl ester (diastereomer A, 6.5 mg) obtained in Step 1 above was dissolved in dichloromethane (150 µl). Trifluoroacetic acid (50 µl) was added to the solution, and stirred at room temperature for three hours. After adjusting the pH of the reaction solution to about 8 using a saturated aqueous sodium bicarbonate solution, the reaction solution was extracted three times with a mixture of dichloromethane and methanol (10:1). The organic layers were combined together, washed with a saturated aqueous sodium chloride solution, and dried over anhydrous sodium sulfate. The inorganic salt was filtered and washed with ethyl acetate. The filtrate and washing solution were combined together and concentrated under reduced pressure. The resulting residue was purified by preparative thin layer silica gel chromatography (developing solution: dichloromethane:methanol=10:1) to yield (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-methylbutylamide (Compound 76) (diastereomer A, 5.1 mg) as a white solid material.

Physicochemical properties of (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-methylbutylamide (diastereomer A)

Molecular weight: 499.
ESI (LC/MS positive mode): 500 (M+H$^+$).
Chemical shift value δ in $^1$H-NMR (300 MHz, in dimethylsulfoxide d-6): 0.79 (3H, d, J=6.9 Hz), 0.88 (3H, d, J=6.9 Hz), 2.39 (3H, s), 2.58 (3H, s), 3.06 (1H, d, J=4.6 Hz), 1.88-3.50 (9H, m), 4.53 (1H, m), 6.65 (2H, brs), 7.13 (1H, s), 7.35 (1H, s), 7.82 (1H, s), 8.20 (1H, brs), 8.40 (1H, t, J=5.2 Hz), 8.50 (1H, t, J=5.3 Hz).

Step 2-B: Preparation of (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-methylbutylamide (Compound 76) (diastereomer B)

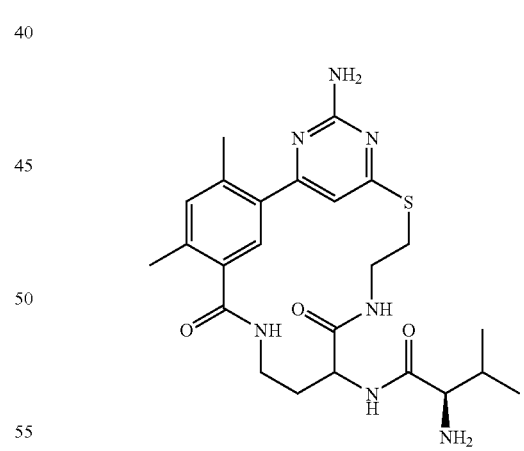

According to the method of Step 2 of Example 3-10, (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-methylbutylamide (Compound 76) (diastereomer B, 5.0 mg) was obtained as a white solid material from [(R)-1-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-ylcarbamoyl)-2-methylpropyl]carbamic acid tert-butyl ester (diastereomer B, 6.1 mg) obtained in Step 1 above.

Physicochemical properties of (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-methylbutylamide (diastereomer B)

Molecular weight: 499.
ESI (LC/MS positive mode): 500 (M+H$^+$).
Chemical shift value δ in $^1$H-NMR (300 MHz, in dimethylsulfoxide d-6): 0.78 (3H, d, J=6.8 Hz), 0.86 (3H, d, J=6.4 Hz), 2.39 (3H, s), 2.58 (3H, s), 3.03 (1H, d, J=5.4 Hz), 1.15-3.50 (9H, m), 4.54 (1H, m), 6.66 (2H, brs), 7.14 (1H, s), 7.40 (1H, s), 7.82 (1H, s), 8.20 (1H, brs), 8.44 (1H, t, J=5.0 Hz), 8.57 (1H, t, J=5.3 Hz).

Example 3-12

Production of (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-(4-hydroxyphenyl)propionamide (Compound 77)

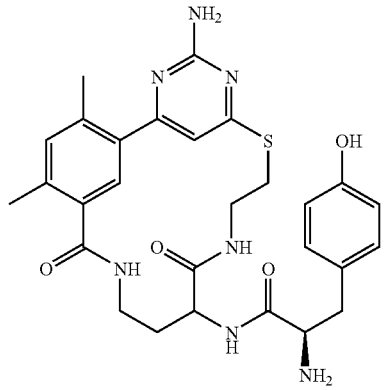 [SMILES: Cc1cc(C)c2cc1C(=O)NCCC(NC(=O)[C@H](N)Cc1ccc(O)cc1)C(=O)NCCSc1cc-2nc(N)n1]

Step 1: Preparation of [(R)-1-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-ylcarbamoyl)-2-(4-hydroxyphenyl)ethyl]carbamic acid tert-butyl ester

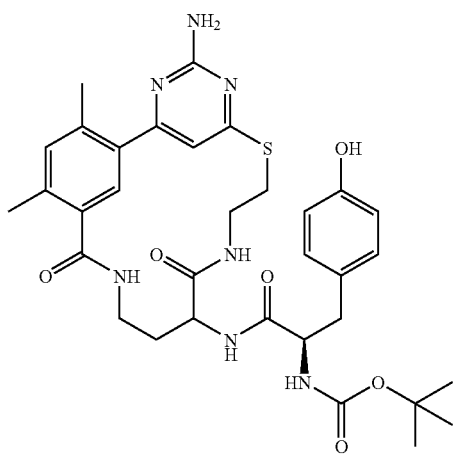 [SMILES: Cc1cc(C)c2cc1C(=O)NCCC(NC(=O)[C@@H](Cc1ccc(O)cc1)NC(=O)OC(C)(C)C)C(=O)NCCSc1cc-2nc(N)n1]

According to the method of Example 3-11, the two diastereomers (diastereomer A: 3.5 mg, diastereomer B: 4.1 mg) of [(R)-1-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-ylcarbamoyl)-2-(4-hydroxyphenyl)ethyl]carbamic acid tert-butyl ester were obtained as a white solid material from 4,12-diamino-18,20-dimethyl-7-thia-3,5,10,15-tetraazatricyclo[15.3.1.1$^{2,6}$]docosa-1(20),2(22),3,5,17(21),18-hexaene-11,16-dione (10 mg, 0.025 mmol) obtained in Step 4 of Example 3-8 and (R)-2-tert-butoxycarbonyl-amino-3-(4-hydroxyphenyl)propionic acid (21 mg, 0.075 mmol).

Physicochemical properties of [(R)-1-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-ylcarbamoyl)-2-(4-hydroxyphenyl)ethyl]carbamic acid tert-butyl ester (diastereomer A)

Molecular weight: 663.
ESI (LC/MS positive mode): 664 (M+H$^+$).
Rf value: 0.50 (thin layer silica gel chromatography, developing solvent: dichloromethane methanol=10:1)

Physicochemical properties of [(R)-1-(4-amino-18,20-dimethyl-1,16-dioxo-7-thia-3,5,10,15-tetraazatricyclo[15.3.1.1$^{2,6}$]docosa-1(20),2(22),3,5,17(21),18-hexaen-12-ylcarbamoyl)-2-(4-hydroxyphenyl)ethyl]carbamic acid tert-butyl ester (diastereomer B)

Molecular weight: 663.
ESI (LC/MS positive mode): 664 (M+H$^+$).
Rf value: 0.56 (thin layer silica gel chromatography, developing solvent: dichloromethane:methanol=10:1)

Step 2-A: Preparation of (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-(4-hydroxyphenyl)propionamide (Compound 77) (diastereomer A)

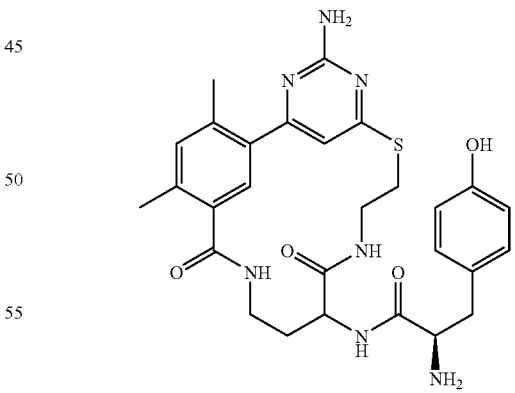

According to the method of Step 2 of Example 3-11, (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-(4-hydroxyphenyl)propionamide (Compound 77) (diastereomer A, 3.3 mg) was obtained as a white solid material from [(R)-1-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12- ylcarbamoyl)-2-(4-hydroxyphenyl)ethyl]carbamic acid tert-butyl ester (diastereomer A, 3.5 mg) obtained in Step 1 above.

Physicochemical properties of (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-(4-hydroxyphenyl)propionamide (diastereomer A):

Molecular weight: 563.

ESI (LC/MS positive mode): 564 (M+H$^+$).

Chemical shift value δ in $^1$H-NMR (300 MHz, in dimethylsulfoxide d-6): 0.82-3.50 (13H, m), 2.39 (3H, s), 2.57 (3H, s), 4.49 (1H, m), 6.65 (2H, brs), 6.67 (2H, d, J=6.5 Hz), 6.98 (2H, d, J=7.5 Hz), 7.13 (1H, s), 7.32 (1H, s), 7.81 (1H, s), 8.16 (1H, brs), 8.25 (1H, brs), 8.38 (1H, brs), 9.18 (1H, brs).

Step 2-B: Preparation of (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-(4-hydroxyphenyl)propionamide (Compound 77)(diastereomer B)

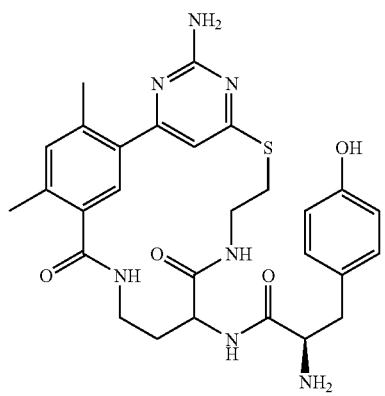 [SMILES: Cc1cc(C)c2cc1C(=O)NCCC(NC(=O)[C@H](N)Cc1ccc(O)cc1)C(=O)NCCSc1cc-2nc(N)n1]

According to the method of Step 2 of Example 3-11, (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-(4-hydroxyphenyl)propionamide (Compound 77) (diastereomer B, 3.9 mg) was obtained as a white solid material from ([(R)-1-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-ylcarbamoyl)-2-(4-hydroxyphenyl)ethyl]carbamic acid tert-butyl ester (diastereomer B, 4.1 mg) obtained in Step 1 above.

Physicochemical properties of (R)-2-amino-N-(4-amino-18,20-dimethyl-11,16-dioxo-7-thia-3,5,10,15-tetraazatricyclo[15.3.1.1$^{2,6}$]docosa-1(20),2(22),3,5,17(21),18-hexaen-12-yl)-3-(4-hydroxyphenyl)propionamide (diastereomer B)

Molecular weight: 563.

ESI (LC/MS positive mode): 564 (M+H$^+$).

Chemical shift value δ in $^1$H-NMR (300 MHz, in dimethylsulfoxide d-6): 0.82-3.50 (13H, m), 2.39 (3H, s), 2.58 (3H, s), 4.48 (1H, m), 6.65 (2H, brs), 6.66 (2H, d, J=6.0 Hz), 6.68 (2H, d, J=8.4 Hz), 7.13 (1H, s), 7.37 (1H, s), 7.80 (1H, s), 8.14 (1H, brs), 8.25 (1H, brs), 8.40 (1H, brs), 9.17 (1H, brs).

Example 3-13

Production of 4-amino-12-dimethylamino-18,20-dimethyl-7-thia-3,5,10,15-tetraazatricyclo[15.3.1.1$^{2,6}$]docosa-1(20),2(22),3,5,17(21,18-hexaene-11,16-dione (Compound 78)

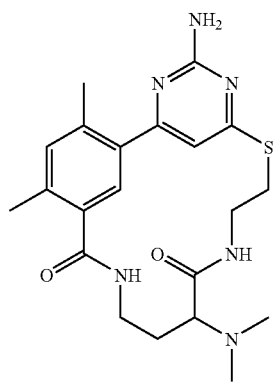

4,12-Diamino-18,20-dimethyl-7-thia-3,5,10,15-tetraazatricyclo[15.3.1.1$^{2,6}$]docosa-1(20),2(22),3,5,17(21),18-hexaene-11,16-dione (30 mg, 0.075 mmol) obtained in Example 3-8 was dissolved in a mixed solvent of methanol (300 μl) and acetic acid (15 μl). An aqueous 20% formaldehyde solution (17 μl, 0.112 mmol) was added to the solution. After this solution was stirred at room temperature for 15 minutes, sodium cyanoborohydride (10 mg, 0.150 mmol) was added thereto. The resulting solution was stirred overnight at room temperature. The reaction solution was diluted with ethyl acetate, and then sequentially washed with a saturated aqueous sodium bicarbonate solution and a saturated sodium chloride solution. The organic layer was dried over anhydrous sodium sulfate, then filtered to remove the inorganic salt, and concentrated under reduced pressure. The resulting residue was purified by preparative thin layer silica gel chromatography (developing solution: dichloromethane:methanol=10:1) to yield 4-amino-12-dimethyl-amino-18,20-dimethyl-7-thia-3,5,10,15-tetraazatricyclo[15.3.1.1$^{2,6}$]docosa-1(20),2(22),3,5,17(21),18-hexaene-11,16-dione (Compound 78) (15 mg) as a white solid material.

Physicochemical properties of 4-amino-12-dimethylamino-18,20-dimethyl-7-thia-3,5,10,15-tetraazatricyclo[15.3.1.1$^{2,6}$]docosa-1(20),2(22),3,5,17(21),18-hexaene-11,16-dione Molecular weight: 428.

ESI (LC/MS positive mode): 429 (M+H$^+$).

Chemical shift value δ in $^1$H-NMR (300 MHz, in dimethylsulfoxide d-6): 1.84 (2H, m), 2.16 (6H, s), 2.40 (3H, s), 2.58 (3H, s), 3.00 (2H, m), 3.19 (3H, m), 3.55 (2H, m), 6.63 (2H, brs), 7.13 (1H, s), 7.42 (1H, s), 7.94 (1H, s), 8.60 (1H, d, J=6.2 Hz), 8.93 (1H, t, J=4.4 Hz).

Example 3-14

Production of 4-amino-10-(2-hydroxyethyl)-18,20-dimethyl-7-thia-3,5,10,15-tetraazatricyclo[15.3.1.1$^{2,6}$]docosa-1(20),2(22),3,5,17(21),18-hexaene-11,16-dione (Compound 79)

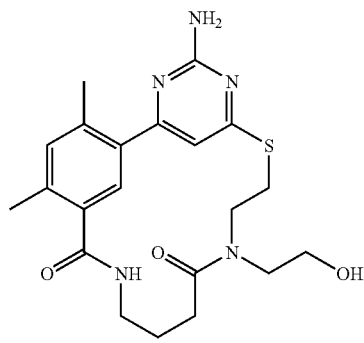 [SMILES: Cc1cc(C)c2cc1C(=O)NCCCC(=O)N(CCO)CCSc1cc-2nc(N)n1]

Step 1: Preparation of 5-(2-amino-6-{2-[(4-tert-butoxycarbonylaminobutyryl)(2-hydroxyethyl)amino]ethylsulfanyl}pyrimidin-4-yl)-2,4-dimethylbenzoic acid tert-butyl ester

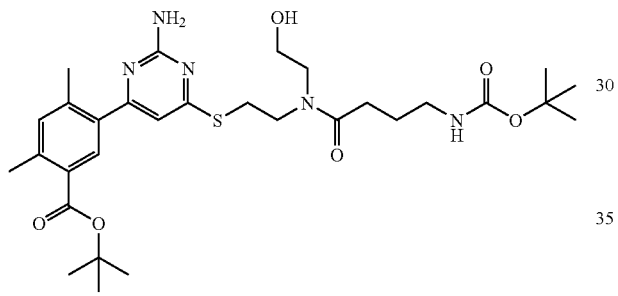

Cystamine (100 mg, 0.444 mmol) was dissolved in N,N-dimethylformamide (1 ml), and then 2-chloroethanol (63 μl, 0.933 mmol) and triethylamine (309 μl, 1.332 mmol) were added thereto. The resulting solution was stirred at 80° C. for three hours. After the reaction solution was cooled to room temperature, N,N-dimethylformamide (1 ml), 4-tert-butoxycarbonylamino butyric acid (270 mg, 1.332 mmol), 1-ethyl-3-(3'-dimethylaminopropyl)carbodiimide hydrochloride (255 mg, 1.332 mmol), and diisopropylethylamine (387 μl, 2.220 mmol) were added thereto. The mixture was stirred overnight at room temperature. The reaction solution was diluted with ethyl acetate and then sequentially washed with a saturated aqueous sodium bicarbonate solution, water (three times), and a saturated aqueous sodium chloride solution. The organic layer was dried over anhydrous sodium sulfate, then filtered to remove the inorganic salt, and concentrated under reduced pressure to yield {3-[(2-{2-[(4-tert-butoxycarbonylaminobutyryl)(2-hydroxyethyl)amino]ethyldisulfanyl}ethyl)(2-hydroxyethyl)carbamoyl]propyl}carbamic acid tert-butyl ester (285 mg, 0.467 mmol) as a yellow oily material.

The obtained {3-[(2-{2-[(4-tert-butoxycarbonylaminobutyryl)(2-hydroxyethyl)amino]ethyldisulfanyl}ethyl)(2-hydroxyethyl)carbamoyl]propyl}carbamic acid tert-butyl ester was dissolved in a mixed solvent of DMF (3 ml) and water (0.3 ml), and then tri-n-butylphosphine (116 μl, 0.467 mmol) was added thereto. The mixture was stirred at room temperature for two hours. The solution was added to an N,N-dimethylformamide (3 ml) solution of 5-(2-amino-6-chloropyrimidin-4-yl)-2,4-dimethylbenzoic acid tert-butyl ester (156 mg, 0.467 mmol) obtained in Example 1-1 and cesium carbonate (456 mg, 1.401 mmol). The resulting mixture was stirred at 80° C. overnight. The reaction solution was diluted with ethyl acetate, and then sequentially washed with an 0.1N aqueous potassium hydrogen sulfate solution, water (twice), and a saturated aqueous sodium chloride solution. The organic layer was dried over anhydrous sodium sulfate, filtered to remove the inorganic salt, and concentrated under reduced pressure. The resulting residue was purified by silica gel column chromatography (developing solvent: dichloromethane:methanol=40:1 to 20:1) to yield 5-(2-amino-6-{2-[(4-tert-butoxycarbonylaminobutyryl)(2-hydroxyethyl)amino]ethylsulfanyl}pyrimidin-4-yl)-2,4-dimethylbenzoic acid tert-butyl ester (57 mg) as a white amorphous material.

Physicochemical properties of 5-(2-amino-6-{2-[(4-tert-butoxycarbonylaminobutyryl)(2-hydroxyethyl)amino]ethylsulfanyl}pyrimidin-4-yl)-2,4-dimethylbenzoic acid tert-butyl ester Molecular weight: 603.
ESI (LC/MS positive mode): 604 (M+H$^+$).

Step 2: Preparation of 4-amino-10-(2-hydroxyethyl)-18,20-dimethyl-7-thia-3,5,10,15-tetraazatricyclo[15.3.1.1$^{2,6}$]docosa-1(20),2(22),3,5,17(21),18-hexaene-11,16-dione (Compound 79)

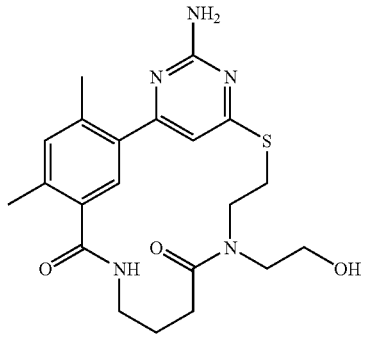 [SMILES: Cc1cc(C)c2cc1C(=O)NCCCC(=O)N(CCO)CCSc1cc-2nc(N)n1]

According to the method of Step 2 of Example 3-8, 4-amino-10-(2-hydroxyethyl)-18,20-dimethyl-7-thia-3,5,10,15-tetraazatricyclo[15.3.1.1$^{2,6}$]docosa-1(20),2(22),3,5,17(21),18-hexaene-11,16-dione (Compound 79) (15 mg) was obtained as a white solid material from 5-(2-amino-6-{2-[(4-tert-butoxycarbonylaminobutyryl)(2-hydroxyethyl)amino]ethylsulfanyl}pyrimidin-4-yl)-2,4-dimethylbenzoic acid tert-butyl ester (57 mg) obtained in Step 1 above.

Physicochemical properties of 4-amino-10-(2-hydroxyethyl)-18,20-dimethyl-7-thia-3,5,10,15-tetraazatricyclo[15.3.1.1$^{2,6}$]docosa-1(20),2(22),3,5,17(21),18-hexaene-11,16-dione Molecular weight: 429.
ESI (LC/MS positive mode): 430 (M+H$^+$).

Chemical shift value δ in $^1$H-NMR (300 MHz, in dimethylsulfoxide d-6): 1.80 (2H, m), 2.43 (3H, s), 2.58 (3H, s), 2.73 (2H, m), 3.22-3.59 (10H, m), 4.88 (1H, t, J=4.7 Hz), 6.62 (2H, brs), 7.14 (1H, s), 7.48 (1H, s), 8.01 (1H, s), 9.06 (1H, t, J=4.2 Hz).

Example 3-15

Production of 4-amino-10-(2-methoxyethyl)-18,20-dimethyl-7-thia-3,5,10,15-tetraazatricyclo[15.3.1.1$^{2,6}$]docosa-1(20),2(22),3,5,17(21),18-hexaene-11,16-dione (Compound 80)

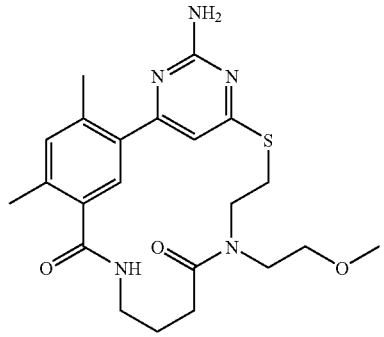

Step 1: Preparation of 5-(2-amino-6-{2-[(4-tert-butoxycarbonylaminobutyryl)(2-methoxyethyl)amino]ethylsulfanyl}pyrimidin-4-yl)-2,4-dimethylbenzoic acid tert-butyl ester

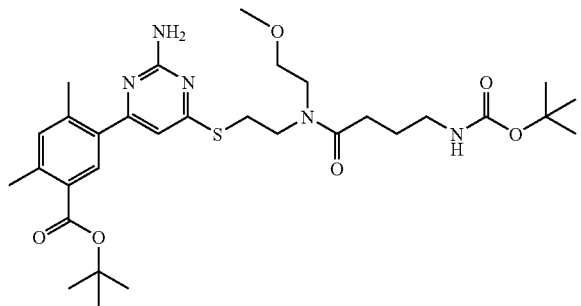 [SMILES: COCCN(CCSc1cc(-c2cc(C(=O)OC(C)(C)C)c(C)cc2C)nc(N)n1)C(=O)CCCNC(=O)OC(C)(C)C]

5-(2-Amino-6-{2-[(4-tert-butoxycarbonylaminobutyryl)(2-methoxyethyl)amino]ethylsulfanyl}pyrimidin-4-yl)-2,4-dimethylbenzoic acid tert-butyl ester (125 mg) was obtained as a pale yellow oily material according to the method of Step 1 of Example 3-14 except that 1-bromo-2-methoxyethane was used instead of 2-chloroethanol.

Physicochemical properties of 5-(2-amino-6-{2-[(4-tert-butoxycarbonylaminobutyryl)(2-methoxyethyl)amino]ethylsulfanyl}pyrimidin-4-yl)-2,4-dimethylbenzoic acid tert-butyl ester Molecular weight: 617.
ESI (LC/MS positive mode): 617 (M+H$^+$).

Step 2: Preparation of 4-amino-10-(2-methoxyethyl)-18,20-dimethyl-7-thia-3,5,10,15-tetraazatricyclo[15.3.1.1$^{2,6}$]docosa-1(20),2(22),3,5,17(21),18-hexaene-11,16-dione (Compound 80)

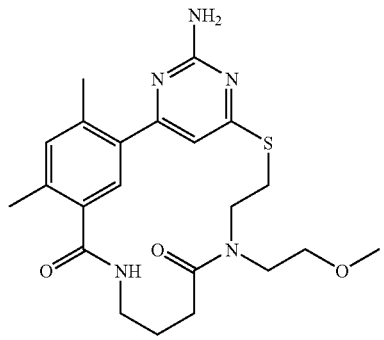

According to the method of Step 2 of Example 3-8, 4-amino-10-(2-methoxyethyl)-18,20-dimethyl-7-thia-3,5,10,15-tetraazatricyclo[15.3.1.1$^{2,6}$]docosa-1(20),2(22),3,5,17(21),18-hexaene-11,16-dione (Compound 80) (30 mg) was obtained as a white solid material from 5-(2-amino-6-{2-[(4-tert-butoxycarbonylaminobutyryl)(2-methoxyethyl)amino]ethylsulfanyl}pyrimidin-4-yl)-2,4-dimethylbenzoic acid tert-butyl ester (125 mg) obtained in Step 1 above.

Physicochemical properties of 4-amino-10-(2-methoxyethyl)-18,20-dimethyl-7-thia-3,5,10,15-tetraazatricyclo[15.3.1.1$^{2,6}$]docosa-1(20),2(22),3,5,17(21),18-hexaene-11,16-dione Molecular weight: 443.
ESI (LC/MS positive mode): 444 (M+H$^+$).
Chemical shift value δ in $^1$H-NMR (300 MHz, in dimethylsulfoxide d-6): 1.81 (2H, s), 2.42 (3H, s), 2.58 (3H, s), 2.70 (2H, m), 3.19-3.62 (13H, m), 6.62 (2H, brs), 7.14 (1H, s), 7.46 (1H, s), 8.00 (1H, s), 9.02 (1H, t, J=4.2 Hz).

Example 3-16

Production of 4-amino-10-(2-morpholin-4-ylethyl)-18,20-dimethyl-7-thia-3,5,10,15-tetraazatricyclo[15.3.1.1$^{2,6}$]docosa-1(20),2(22),3,5,17(21),18-hexaene-11,16-dione (Compound 81)

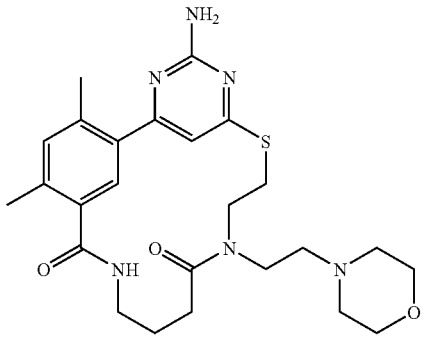 [SMILES: Cc1cc(C)c2cc1C(=O)NCCCC(=O)N(CCN1CCOCC1)CCSc1cc-2nc(N)n1]

Step 1: Preparation of 5-(2-amino-6-{2-[(4-tert-butoxycarbonylaminobutyryl)(2-morpholin-4-ylethyl)amino]ethylsulfanyl}pyrimidin-4-yl)-2,4-dimethylbenzoic acid tert-butyl ester

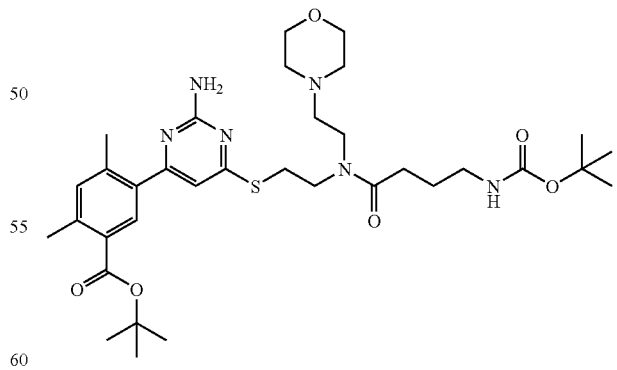

5-(2-Amino-6-{2-[(4-tert-butoxycarbonylaminobutyryl)(2-morpholin-4-ylethyl)amino]ethylsulfanyl}pyrimidin-4-yl)-2,4-dimethylbenzoic acid tert-butyl ester (25 mg) was obtained as a pale yellow oily material according to the method of Step 1 of Example 3-14 except that 4-(2-chloroethyl)morpholine was used instead of 2-chloroethanol.

Physicochemical properties of 5-(2-amino-6-{2-[(4-tert-butoxycarbonylaminobutyryl)(2-morpholin-4-ylethyl)amino]ethylsulfanyl}pyrimidin-4-yl)-2,4-dimethylbenzoic acid tert-butyl ester Molecular weight: 672.
ESI (LC/MS positive mode): 673 (M+H+).

Step 2: Preparation of 4-amino-10-(2-morpholin-4-ylethyl)-18,20-dimethyl-7-thia-3,5,10,15-tetraazatricyclo[15.3.1.1$^{2,6}$]docosa-1(20),2(22),3,5,17(21),18-hexaene-11,16-dione (Compound 81)

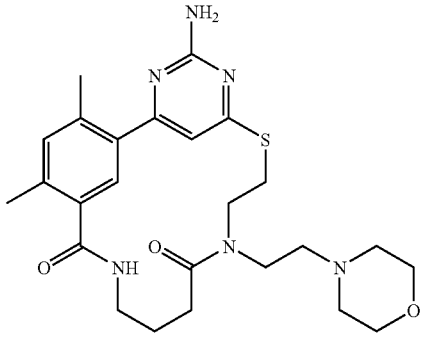 [SMILES: Cc1cc(C)c2cc1C(=O)NCCCC(=O)N(CCN1CCOCC1)CCSc1cc-2nc(N)n1]

According to the method of Step 2 of Example 3-8, 4-amino-10-(2-morpholin-4-ylethyl)-18,20-dimethyl-7-thia-3,5,10,15-tetraazatricyclo[15.3.1.1$^{2,6}$]docosa-1(20),2(22),3,5,17(21),18-hexaene-11,16-dione (Compound 81) (7 mg) was obtained as a white solid material from 5-(2-amino-6-{2-[(4-tert-butoxycarbonylaminobutyryl)(2-morpholin-4-ylethyl)amino]ethylsulfanyl}pyrimidin-4-yl)-2,4-dimethylbenzoic acid tert-butyl ester (25 mg) obtained in Step 1 above.

Physicochemical properties of 4-amino-10-(2-morpholin-4-ylethyl)-18,20-dimethyl-7-thia-3,5,10,15-tetraazatricyclo[15.3.1.1$^{2,6}$]docosa-1(20),2(22),3,5,17(21),18-hexaene-11,16-dione Molecular weight: 498.
ESI (LC/MS positive mode): 499 (M+H+).
Chemical shift value δ in $^1$H-NMR (300 MHz, in dimethylsulfoxide d-6): 1.82 (2H, s), 2.39 (4H, m), 2.42 (3H, s), 2.58 (3H, s), 2.71 (2H, m), 3.22-3.62 (14H, m), 6.62 (2H, brs), 7.14 (1H, s), 7.46 (1H, s), 8.01 (1H, s), 9.05 (1H, t, J=4.2 Hz).

Example 3-17

Production of 4-amino-10,18,20-trimethyl-7-thia-3,5,10,15-tetraazatricyclo[15.3.1.1$^{2,6}$]docosa-1(20),2(22),3,5,17(21),18-hexaene-11,16-dione (Compound 82)

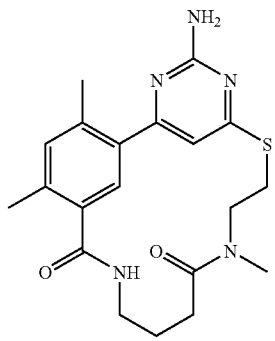 [SMILES: Cc1cc(C)c2cc1C(=O)NCCCC(=O)N(C)CCSc1cc-2nc(N)n1]

Step 1: Preparation of 5-(2-amino-6-{2-[(4-tert-butoxycarbonylaminobutyryl)methylamino]ethylsulfanyl}pyrimidin-4-yl)-2,4-dimethylbenzoic acid tert-butyl ester

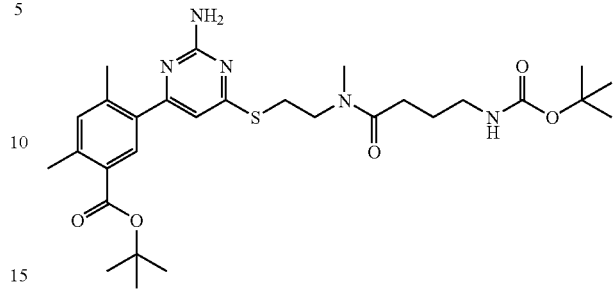

5-(2-Amino-6-{2-[(4-tert-butoxycarbonylaminobutyryl)methylamino]ethylsulfanyl}pyrimidin-4-yl)-2,4-dimethylbenzoic acid tert-butyl ester (490 mg) was obtained as a colorless oily material according to the method of Step 1 of Example 3-14 except that iodomethane was used instead of 2-chloroethanol.

Physicochemical properties of 5-(2-amino-6-{2-[(4-tert-butoxycarbonylaminobutyryl)methylamino]ethylsulfanyl}pyrimidin-4-yl)-2,4-dimethylbenzoic acid tert-butyl ester Molecular weight: 573.
ESI (LC/MS positive mode): 574 (M+H+).

Step 2: Preparation of 4-amino-10,18,20-trimethyl-7-thia-3,5,10,15-tetraazatricyclo[15.3.1.1$^{2,6}$]docosa-1(20),2(22),3,5,17(21),18-hexaene-11,16-dione (Compound 82)

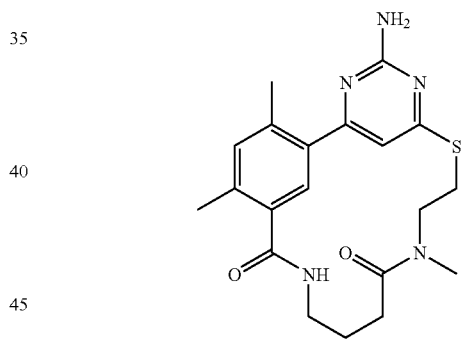

According to the method of Step 2 of Example 3-8, 4-amino-10,18,20-trimethyl-7-thia-3,5,10,15-tetraazatricyclo[15.3.1.1$^{2,6}$]docosa-1(20),2(22),3,5,17(21),18-hexaene-1,16-dione (Compound 82) (9 mg) was obtained as a white solid material from 5-(2-amino-6-{2-[(4-tert-butoxycarbonylaminobutyryl)methylamino]ethylsulfanyl}pyrimidin-4-yl)-2,4-dimethylbenzoic acid tert-butyl ester (63 mg) obtained in Step 1 above.

Physicochemical properties of 4-amino-10,18,20-trimethyl-7-thia-3,5,10,15-tetraazatricyclo[15.3.1.1$^{2,6}$]docosa-1(20),2(22),3,5,17(21),18-hexaene-11,16-dione Molecular weight: 399.
ESI (LC/MS positive mode): 400 (M+H+).
Chemical shift value δ in $^1$H-NMR (300 MHz, in dimethylsulfoxide d-6): 1.81 (2H, m), 2.41 (3H, s), 2.58 (3H, s), 2.61 (2H, m), 3.02 (3H, s), 3.18-3.28 (4H, m), 3.62 (2H, m), 6.63 (2H, brs), 7.13 (1H, s), 7.26 (1H, s), 8.00 (1H, s), 8.84 (1H, t, J=4.6 Hz).

Example 3-18

Production of 4-amino-20,22-dichloro-7-thia-3,5,10, 17-tetraazatricyclo[17.3.1.1$^{2,6}$]tetracosa-1(22),2(24), 3,5,19(23),20-hexaene-11,18-dione (Compound 28)

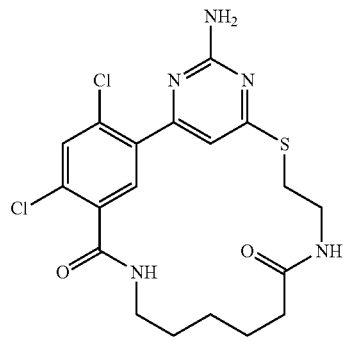 [SMILES: Nc1nc2cc(n1)-c1cc(c(Cl)cc1Cl)C(=O)NCCCCCC(=O)NCCS2]

According to the methods of Steps 2 and 3 of Example 3-1 except that 6-tert-butoxycarbonylaminohexanoic acid (40 mg) was used instead of 4-tert-butoxycarbonylaminobutanoic acid, 4-amino-20,22-dichloro-7-thia-3,5,10,17-tetraazatricyclo[17.3.1.1$^{2,6}$]tetracosa-1(22),2(24),3,5,19(23), 20-hexaene-11,18-dione (Compound 28) (7 mg) was obtained as a white solid material from 5-[2-amino-6-(2-tert-butoxycarbonylaminoethylsulfanyl)pyrimidin-4-yl]-2,4-dichlorobenzoic acid methyl ester obtained in Step 2 of Example 3-7.

Physicochemical properties of 4-amino-20,22-dichloro-7-thia-3,5,10,17-tetraazatricyclo[17.3.1.1$^{2,6}$]tetracosa-1(22),2(24),3,5,19(23),20-hexaene-11, 18-dione Molecular weight: 454.
ESI (LC/MS positive mode): 454, 456.
Chemical shift value δ in $^1$H-NMR (400 MHz, in dimethylsulfoxide d-6): 1.41-1.63 (4H, m), 2.11-2.21 (2H, m), 2.89-3.05 (2H, m), 3.17-3.40 (6H, m), 6.80 (2H, brs), 7.32 (1H, s), 7.76 (1H, s), 7.93 (1H, s), 8.29 (1H, t, J=5.5 Hz), 8.34 (1H, t, J=5.5 Hz).

Example 4-1

Production of 4-amino-20-methoxy-22-methyl-13-oxa-7-thia-3,5,17-triazatricyclo[17.3.1.1$^{2,6}$.1$^{8,12}$] pentacosa-1(22),2(24),3,5,8(25),9,11,19(23),20-nonaen-18-one (Compound 16)

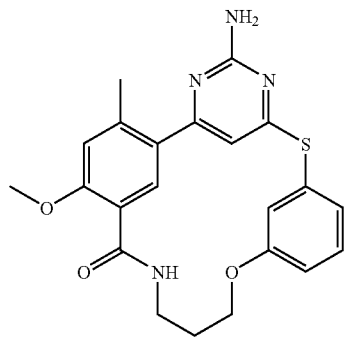 [SMILES: COc1cc(C)c2cc1C(=O)NCCCOc1cccc(c1)Sc1cc-2nc(N)n1]

Step 1: Preparation of 5-[2-amino-6-(3-hydroxyphenylsulfanyl)pyrimidin-4-yl]-2-methoxy-4-methylbenzoic acid methyl ester

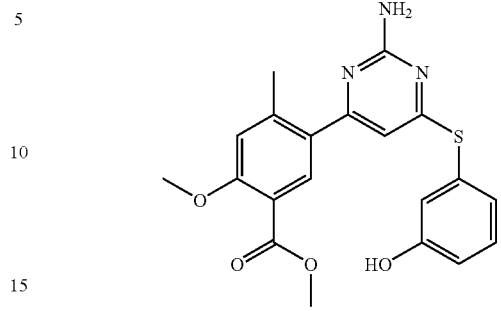

5-(2-Amino-6-chloropyrimidin-4-yl)-2-methoxy-4-methylbenzoic acid methyl ester (154 mg, 0.5 mmol) obtained in Example 1-2 and 3-hydroxybenzenethiol (0.25 ml, 2.5 mmol) were placed in a reaction vessel, and then N,N-dimethylformamide (1.0 ml) and triethylamine (0.35 ml, 2.5 mmol) were added thereto. The solution was stirred at room temperature for 24 hours. The reaction solution was diluted with ethyl acetate (100 ml), and sequentially washed twice with water (50 ml), twice with a saturated aqueous sodium bicarbonate solution (50 ml), and with a saturated aqueous sodium chloride solution (50 ml). The washed ethyl acetate solution was dried over anhydrous sodium sulfate. After filtration, the filtrate was concentrated under reduced pressure. The resulting crude product was purified by silica gel column chromatography (developing solvent: ethyl acetate) to yield 5-[2-amino-6-(3-hydroxyphenylsulfanyl)pyrimidin-4-yl]-2-methoxy-4-methylbenzoic acid methyl ester (170 mg) as a yellow solid material.

Physicochemical properties of 5-[2-amino-6-(3-hydroxyphenylsulfanyl)pyrimidin-4-yl]-2-methoxy-4-methylbenzoic acid methyl ester Molecular weight: 397.
ESI (LC/MS positive mode): m/z=398 (M+H$^+$).
Chemical shift value δ in $^1$H-NMR (400 MHz, in dimethylsulfoxide d-6): 2.23 (3H, s), 3.75, (3H, s), 3.83 (3H, s), 5.95 (1H, s), 6.79 (2H, brs), 6.90 (1H, dd, J=4 Hz, 8 Hz), 6.97-7.08 (3H, m), 7.30 (1H, dd, J=8 Hz, 8 Hz), 7.71 (1H, s), 9.88-9.98 (1H, m).

Step 2: Preparation of 5-{2-amino-6-[3-(3-tert-butoxycarbonylaminopropoxy)-phenylsulfanyl]pyrimidin-4-yl}-2-methoxy-4-methylbenzoic acid methyl ester

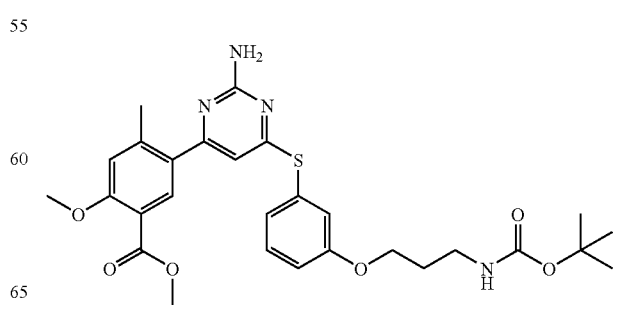

5-[2-Amino-6-(3-hydroxyphenylsulfanyl)pyrimidin-4-yl]-2-methoxy-4-methylbenzoic acid methyl ester (80 mg, 0.2 mmol) obtained in Step 1 above, cesium carbonate (124 mg, 0.38 mmol), and N,N-dimethylformamide (1.0 ml) were added to a reaction vessel. Then 3-bromopropylcarbamic acid tert-butyl ester (100 mg, 0.42 mmol) was added to the mixture. The mixture was stirred at room temperature for 37 hours. The reaction solution was diluted with ethyl acetate (100 ml), and sequentially washed twice with a saturated aqueous ammonium chloride solution (50 ml), twice with water (50 ml), and with a saturated aqueous sodium chloride solution (50 ml). The washed ethyl acetate solution was dried over anhydrous sodium sulfate. After filtration, the filtrate was concentrated under reduced pressure. The resulting crude product was purified by silica gel column chromatography (developing solvent: ethyl acetate) to yield 5-{2-amino-6-[3-(3-tert-butoxycarbonylaminopropoxy)phenylsulfanyl]pyrimidin-4-yl}-2-methoxy-4-methylbenzoic acid methyl ester (103 mg).

Physicochemical properties of 5-{2-amino-6-[3-(3-tert-butoxycarbonylaminopropoxy)phenylsulfanyl]pyrimidin-4-yl}-2-methoxy-4-methylbenzoic acid methyl ester Molecular weight: 554.
ESI (LC/MS positive mode): m/z=555 (M+H$^+$).
Chemical shift value δ in $^1$H-NMR (400 MHz, in dimethylsulfoxide d-6): 1.34 (9H, s), 1.77-1.85 (2H, m), 2.23 (3H, s), 3.07 (2H, dt, J=4 Hz, 6 Hz), 3.75 (3H, s), 3.82 (3H, s), 3.99 (2H, t, J=6 Hz), 5.94 (1H, s), 6.80 (2H, brs), 6.85 (1H, brs), 7.01 (1H, s), 7.07 (1H, dd, J=4 Hz, 8 Hz), 7.15-7.23 (2H, m), 7.42 (1H, dd, J=8 Hz, 8 Hz), 7.71 (1H, s).

Step 3: Preparation of 4-amino-20-methoxy-22-methyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one (Compound 16)

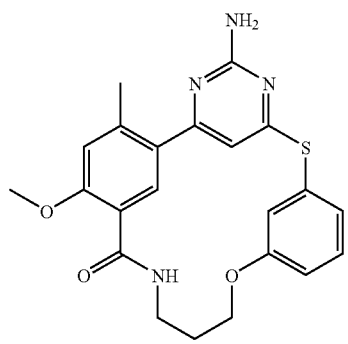 [SMILES: COc1cc(C)c2cc1C(=O)NCCCOc1cccc(c1)Sc1cc-2nc(N)n1]

5-{2-Amino-6-[3-(3-tert-butoxycarbonylaminopropoxy)phenylsulfanyl]pyrimidin-4-yl}-2-methoxy-4-methylbenzoic acid methyl ester (99 mg, 0.18 mmol) obtained in Step 2 above was added to a reaction vessel, and dissolved in dichloromethane (2.5 ml). The solution as cooled to 0° C. Trifluoroacetic acid (1.0 ml) was added to the solution, and stirred at 0° C. for 0.5 hour. The reaction solution was concentrated under reduced pressure, and then benzene (1.5 ml) was added to the resulting residue. The solution was concentrated under reduced pressure. This treatment was repeated three times. The obtained pale yellow oily material was dissolved in tetrahydrofuran (1.5 ml), methanol (1.5 ml), and water (1.0 ml), and then lithium hydroxide (42 mg, 1.0 mmol) was added thereto. The resulting mixture was stirred at room temperature for 14 hours. The reaction solution was acidified by adding 4N hydrochloric acid-ethyl acetate solution (0.75 ml). The solvent was distilled off under reduced pressure. N,N-Dimethylformamide (4.5 ml) and tetrahydrofuran (13.5 ml) were added to the obtained pale yellow solid. N-Hydroxybenzotriazole (122 mg, 0.9 mmol), diisopropyl amine (0.31 ml, 1.8 mmol), and 1-ethyl-3-(3'-dimethylaminopropyl)carbodiimide hydrochloride (345 mg, 1.8 mmol) were sequentially added to the solution. The resulting mixture was reacted at room temperature for 5.5 hours. The reaction solution was concentrated under reduced pressure. The resulting residue was diluted with ethyl acetate (100 ml), and sequentially washed twice with water (50 ml), and with a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography (amino-silica gel; developing solvent: ethyl acetate to ethyl acetate:methanol=25:1) to yield 4-amino-20-methoxy-22-methyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one (Compound 16) (7.2 mg) as a white solid material.

Physicochemical properties of 4-amino-20-methoxy-22-methyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one Molecular weight: 422.
ESI (LC/MS positive mode): m/z=423 (M+H$^+$).
Chemical shift value δ in $^1$H-NMR (400 MHz, in dimethylsulfoxide d-6): 1.93-2.03 (2H, m), 2.58 (3H, s), 3.28-3.35 (2H, m), 3.77 (3H, s), 4.18 (2H, t, J=6 Hz), 6.39 (1H, s), 6.74 (2H, brs), 6.91 (1H, s), 7.05 (1H, dd, J=4 Hz, 8 Hz), 7.18 (1H, dd, J=4 Hz, 8 Hz), 7.28 (1H, s), 7.32-7.35 (1H, m), 7.38 (1H, dd, J=8 Hz, 8 Hz), 8.18 (1H, t, J=6 Hz).

Example 4-2

Production of 4-amino-20-ethoxy-22-methyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one (Compound 17)

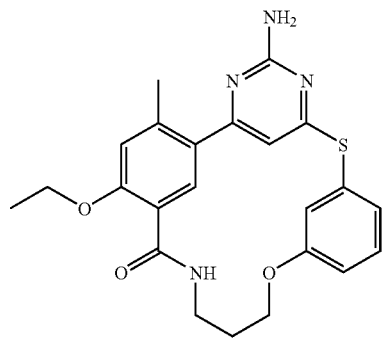 [SMILES: CCOc1cc(C)c2cc1C(=O)NCCCOc1cccc(c1)Sc1cc-2nc(N)n1]

Step 1: Preparation of 5-[2-amino-6-(3-hydroxyphenylsulfanyl)pyrimidin-4-yl]-2-ethoxy-4-methylbenzoic acid methyl ester

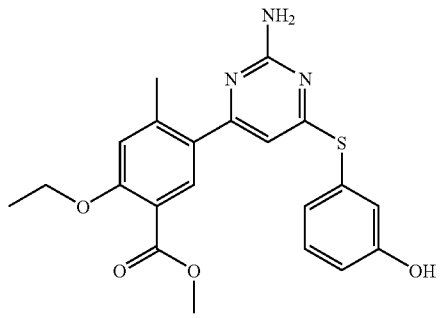 [SMILES: CCOc1cc(C)c(-c2cc(Sc3cccc(O)c3)nc(N)n2)cc1C(=O)OC]

5-(2-Amino-6-chloropyrimidin-4-yl)-2-methoxy-4-methylbenzoic acid methyl ester (96.5 mg, 0.3 mmol) obtained in Example 1-2 and 3-hydroxybenzenethiol (0.15 ml, 1.5 mmol) were placed in a reaction vessel, and then N,N-dimethylformamide (0.6 ml) and triethylamine (0.2 ml, 1.5 mmol) were added thereto. The solution was stirred at room temperature for 20 hours. The reaction solution was diluted with ethyl acetate (100 ml), and sequentially washed twice with water (50 ml), twice with a saturated aqueous sodium bicarbonate solution (50 ml), and with a saturated aqueous sodium chloride solution (50 ml). The washed ethyl acetate solution was dried over anhydrous sodium sulfate, and the solvent was distilled off under reduced pressure. The resulting crude product was purified by silica gel column chromatography (developing solvent: n-hexane:ethyl acetate=1:1 to 1:2) to yield 5-[2-amino-6-(3-hydroxyphenylsulfanyl)pyrimidin-4-yl]-2-ethoxy-4-methylbenzoic acid methyl ester (110 mg) as a white solid material.

Physicochemical properties of 5-[2-amino-6-(3-hydroxyphenylsulfanyl)pyrimidin-4-yl]-2-ethoxy-4-methylbenzoic acid methyl ester Molecular weight: 411.
ESI (LC/MS positive mode): m/z=412 (M+H$^+$).
Chemical shift value δ in $^1$H-NMR (400 MHz, in dimethylsulfoxide d-6): 1.32 (3H, t, J=8 Hz), 2.22 (3H, s), 3.75, (3H, s), 4.10 (2H, q, J=8 Hz), 5.95 (1H, s), 6.79 (2H, brs), 6.90 (1H, dd, J=4 Hz, 8 Hz), 6.96-7.02 (2H, m), 7.05 (1H, dd, J=4 Hz, 8 Hz), 7.31 (1H, dd, J=8 Hz, 8 Hz), 7.69 (1H, s), 9.82 (1H, s).

Step 2: Preparation of 5-{2-amino-6-[3-(3-tert-butoxycarbonylaminopropoxy)phenylsulfanyl]pyrimidin-4-yl}-2-ethoxy-4-methylbenzoic acid methyl ester

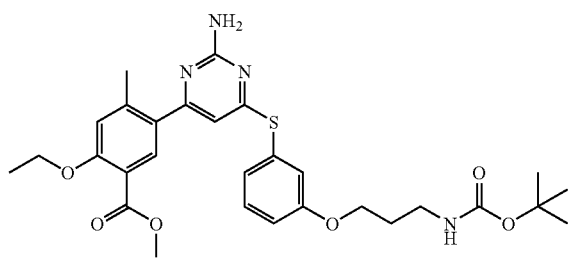 [SMILES: CCOc1cc(C)c(-c2cc(Sc3cccc(OCCCNC(=O)OC(C)(C)C)c3)nc(N)n2)cc1C(=O)OC]

5-[2-Amino-6-(3-hydroxyphenylsulfanyl)pyrimidin-4-yl]-2-ethoxy-4-methylbenzoic acid methyl ester (110 mg, 0.27 mmol) obtained in Step 1 above, cesium carbonate (133 mg, 0.41 mmol), and N,N-dimethylformamide (1.2 ml) were added to a reaction vessel, and then 3-bromopropylcarbamic acid tert-butyl ester (97 mg, 0.41 mmol) was added thereto. The resulting mixture was stirred at room temperature for 4 hours. The reaction solution was diluted with ethyl acetate (100 ml), and sequentially washed twice with a saturated aqueous ammonium chloride solution (50 ml), twice with water (50 ml), and with a saturated aqueous sodium chloride solution (50 ml). The washed ethyl acetate solution was dried over anhydrous sodium sulfate. After filtration, the filtrate was concentrated under reduced pressure. The resulting crude product was purified by silica gel column chromatography (developing solvent: n-hexane:ethyl acetate=2:3) to yield 5-{2-amino-6-[3-(3-tert-butoxycarbonylaminopropoxy)phenylsulfanyl]pyrimidin-4-yl}-2-ethoxy-4-methylbenzoic acid methyl ester (145 mg).

Physicochemical properties of 5-{2-amino-6-[3-(3-tert-butoxycarbonylaminopropoxy)phenylsulfanyl]pyrimidin-4-yl}-2-ethoxy-4-methylbenzoic acid methyl ester Molecular weight: 568.
ESI (LC/MS positive mode): m/z=569 (M+H$^+$).
Chemical shift value δ in $^1$H-NMR (400 MHz, in dimethylsulfoxide d-6): 1.32 (3H, t, J=8 Hz), 1.34 (9H, s), 1.78-1.86 (2H, m), 2.22 (3H, s), 3.07 (2H, td, J=6 Hz, 8 Hz), 4.00 (2H, t, J=6 Hz), 4.08 (2H, q, J=8 Hz), 5.94 (1H, s), 6.80 (2H, brs), 6.84 (1H, brs), 6.99 (1H, s), 7.07 (1H, dd, J=4 Hz, 8 Hz), 7.15-7.22 (2H, m), 7.42 (1H, dd, J=8 Hz, 8 Hz), 7.70 (1H, s).

Step 3: Preparation of 4-amino-20-ethoxy-22-methyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one (Compound 17)

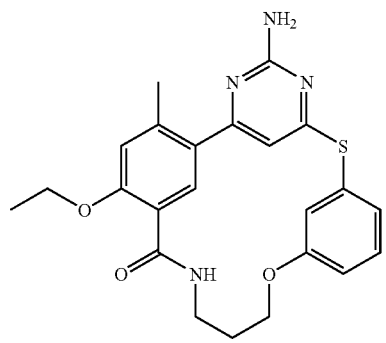 [SMILES: CCOc1cc(C)c2cc1C(=O)NCCCOc1cccc(c1)Sc1cc-2nc(N)n1]

5-{2-Amino-6-[3-(3-tert-butoxycarbonylaminopropoxy)phenylsulfanyl]pyrimidin-4-yl}-2-ethoxy-4-methylbenzoic acid methyl ester (143 mg, 0.25 mmol) obtained in Step 2 above was placed in a reaction vessel, and dissolved in dichloromethane (3.5 ml). The solution was cooled to 0° C. Trifluoroacetic acid (1.2 ml) was added thereto and stirred for 3 hours while gradually warming from 0° C. to room temperature. The reaction solution was concentrated under reduced pressure, and benzene (1.5 ml) was added to the resulting residue. The solution was again concentrated under reduced pressure. This treatment was repeated three times. The resulting pale yellow oily material was dissolved in tetrahydrofuran (2.0 ml), methanol (2.0 ml), and water (1.5 ml), and then lithium hydroxide (73 mg, 1.75 mmol) was added thereto. The resulting mixture was stirred at room temperature for 19 hours. The reaction solution was acidified by adding 4N hydrochloric acid-ethyl acetate solution (1.4 ml). The solvent was distilled off under reduced pressure. The obtained pale yellow solid was dissolved in N,N-dimethylformamide (12.5 ml) and tetrahydrofuran (12.5 ml). N-Hydroxybenzotriazole (170 mg, 1.3 mmol), diisopropylethylamine (0.44 ml, 2.5 mmol), and 1-ethyl-3-(3'-dimethylaminopropyl)carbodiimide hydrochloride (483 mg, 2.5 mmol) were sequentially added to the solution. The resulting mixture was stirred at room temperature for 18 hours. The reaction solution was concentrated under reduced pressure. The resulting residue was diluted with ethyl acetate (100 ml), and sequentially washed twice with water (50 ml), and with a saturated aqueous sodium bicarbonate solution (50 ml), water (50 ml), and a saturated aqueous sodium chloride solution (50 ml). The washed ethyl acetate solution was dried over anhydrous sodium sulfate (10 g). After filtration, the filtrate was concentrated under reduced pressure. The resulting crude product was purified by silica gel column chromatography (aminosilica gel; developing solvent: ethyl acetate) to yield 4-amino-20-ethoxy-22-methyl-13-oxa-7-thia-3,5,17-triazatricyclo [17.3.1.1$^{2,6}$.1$^{8,12}$]pentacosa-1(22),2(24),3,5,8(25),9,11,19 (23),20-nonaen-18-one (Compound 17) (32 mg) as a white solid material.

Physicochemical properties of 4-amino-20-ethoxy-22-methyl-13-oxa-7-thia-3,5,17-triazatricyclo [17.3.1.1$^{2,6}$.1$^{8,12}$]pentacosa-1(22),2(24),3,5,8(25),9, 11,19(23),20-nonaen-18-one Molecular weight: 436.
ESI (LC/MS positive mode): m/z=437 (M+H$^+$).
Chemical shift value δ in $^1$H-NMR (400 MHz, in dimethylsulfoxide d-6): 1.28 (3H, t, J=8 Hz), 1.93-2.02 (2H, m), 2.56 (3H, s), 3.28-3.35 (2H, m), 4.05 (2H, q, J=8 Hz), 4.18 (2H, t, J=6 Hz), 6.39 (1H, s), 6.74 (2H, brs), 6.90 (1H, s), 7.05 (1H, dd, J=4 Hz, 8 Hz), 7.18 (1H, dd, J=4 Hz, 8 Hz), 7.28 (1H, s), 7.32-7.35 (1H, m), 7.38 (1H, dd, J=8 Hz, 8 Hz), 8.15 (1H, t, J=6 Hz).

Example 4-3

Production of 4-amino-20,22-dimethyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one (Compound 18)

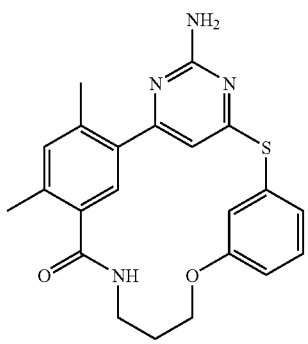 [SMILES: Cc1cc(C)c2cc1C(=O)NCCCOc1cccc(c1)Sc1cc-2nc(N)n1]

Step 1: Preparation of 5-[2-amino-6-(3-hydroxyphenylsulfanyl)pyrimidin-4-yl]-2,4-dimethylbenzoic acid methyl ester

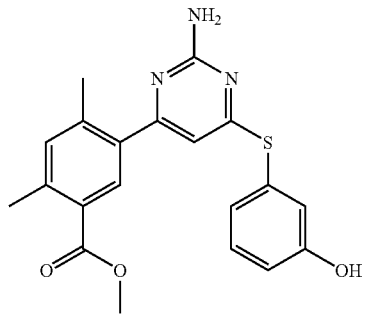 [SMILES: COC(=O)c1cc(-c2cc(Sc3cccc(O)c3)nc(N)n2)c(C)cc1C]

According to the method in Step 1 of Example 4-1, 5-[2-amino-6-(3-hydroxyphenylsulfanyl)pyrimidin-4-yl]-2,4-dimethylbenzoic acid methyl ester (688 mg) was obtained as a white solid material from 5-(2-amino-6-chloropyrimidin-4-yl)-2,4-dimethylbenzoic acid methyl ester (463 mg) obtained in Example 1-4.

Physicochemical properties of 5-[2-amino-6-(3-hydroxyphenylsulfanyl)pyrimidin-4-yl]-2,4-dimethylbenzoic acid methyl ester Molecular weight: 381.
ESI (LC/MS positive mode): m/z=382 (M+H$^+$).
Chemical shift value δ in $^1$H-NMR (270 MHz, in dimethylsulfoxide d-6): 2.20 (3H, s), 2.50 (3H, s), 3.80, (3H, s), 5.95 (1H, s), 6.89-6.93 (3H, m), 6.99-7.07 (2H, m), 7.21 (1H, s), 7.31 (1H, dd, J=7.8 Hz, J=7.8 Hz) 9.88 (1H, s).

Step 2: Preparation of 5-{2-amino-6-[3-(3-tert-butoxycarbonylaminopropoxy)phenylsulfanyl]pyrimidin-4-yl}-2,4-dimethylbenzoic acid methyl ester

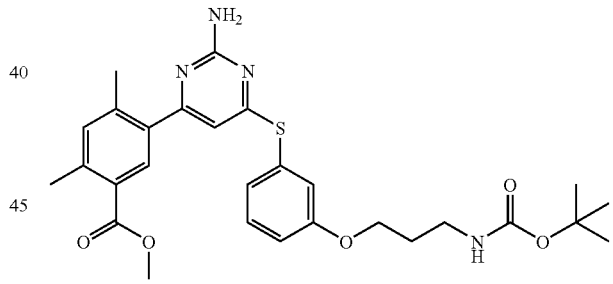

According to the method in Step 2 of Example 4-2, 5-{2-amino-6-[3-(3-tert-butoxycarbonylaminopropoxy)phenylsulfanyl]pyrimidin-4-yl}-2,4-dimethylbenzoic acid methyl ester (65 mg) was obtained from 5-[2-amino-6-(3-hydroxyphenylsulfanyl)pyrimidin-4-yl]-2,4-dimethylbenzoic acid methyl ester (50 mg) obtained in Step 1 above.

Physicochemical properties of 5-{2-amino-6-[3-(3-tert-butoxycarbonylaminopropoxy)phenylsulfanyl] pyrimidin-4-yl}-2,4-dimethylbenzoic acid methyl ester Molecular weight: 538.
ESI (LC/MS positive mode): m/z=539 (M+H$^+$).
Chemical shift value δ in $^1$H-NMR (270 MHz, in chloroform-d): 1.42 (9H, s), 1.92-2.16 (2H, m), 2.25 (3H, s), 2.57 (3H, s), 3.28-3.35 (2H, m), 3.86 (3H, s), 4.02 (2H, t, J=6 Hz), 5.10 (2H, brs), 6.18 (1H, s), 6.87-6.99 (1H, m), 7.08 (1H, s), 7.13-7.37 (3H, m), 7.92 (1H, s).

Step 3: Preparation of 4-amino-20,22-dimethyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one (Compound 18)

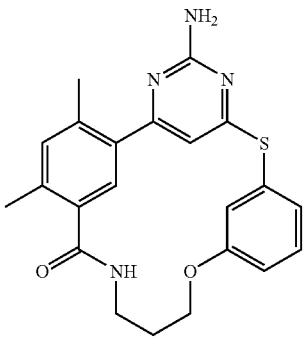 [SMILES: Cc1cc(C)c2cc1C(=O)NCCCOc1cccc(c1)Sc1cc-2nc(N)n1]

According to the method in Step 3 of Example 4-2, 4-amino-20,22-dimethyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one (Compound 18) (14.2 mg) was obtained as a white solid material from 5-{2-amino-6-[3-(3-tert-butoxycarbonylaminopropoxy)phenylsulfanyl]pyrimidin-4-yl}-2,4-dimethylbenzoic acid methyl ester (61 mg) obtained in Step 2 above.

Physicochemical properties of 4-amino-20,22-dimethyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one Molecular weight: 406.
ESI (LC/MS positive mode): m/z=407 (M+H$^+$).
Chemical shift value δ in $^1$H-NMR (270 MHz, in dimethylsulfoxide d-6): 1.86-2.05 (2H, m), 2.33 (3H, s), 2.51 (3H, s), 3.28-3.35 (2H, m), 4.21 (2H, t, J=5.4 Hz), 6.42 (1H, s), 6.84 (2H, brs), 7.05 (1H, dd, J=1.4 Hz, 8.6 Hz) 7.11 (1H, s), 7.18 (1H, d, J=7.8 Hz), 7.33-7.41 (3H, m), 8.29 (1H, t, J=5.7 Hz).

Example 4-4

Production of 4-amino-21,23-dimethyl-13-oxa-7-thia-3,5,18-triazatricyclo[18.3.1.1$^{2,6}$.1$^{8,12}$]hexacosa-1(23),2(25),3,5,8(26),9,11,20(24),21-nonaen-19-one (Compound 19)

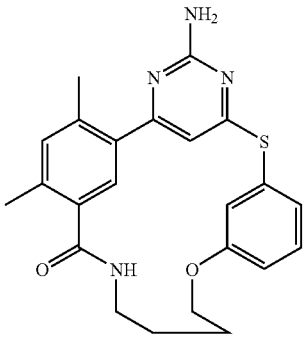 [SMILES: Cc1cc(C)c2cc1C(=O)NCCCCOc1cccc(c1)Sc1cc-2nc(N)n1]

Step 1: Preparation of 5-{2-amino-6-[3-(4-tert-butoxycarbonylaminobutoxy)phenylsulfanyl]pyrimidin-4-yl}-2,4-dimethylbenzoic acid methyl ester

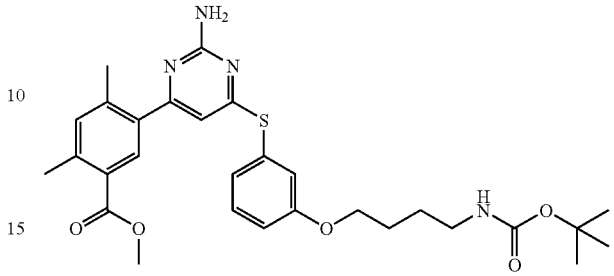

According to the method in Step 2 of Example 4-2, 5-{2-amino-6-[3-(4-tert-butoxycarbonylaminobutoxy)phenylsulfanyl]pyrimidin-4-yl}-2,4-dimethylbenzoic acid methyl ester (60 mg) was obtained from 5-[2-amino-6-(3-hydroxyphenylsulfanyl)pyrimidin-4-yl]-2,4-dimethylbenzoic acid methyl ester (50 mg) obtained in Step 1 of Example 4-3 and 4-bromobutylcarbamic acid tert-butyl ester (47 mg).

Physicochemical properties of 5-{2-amino-6-[3-(4-tert-butoxycarbonylaminobutoxy)phenylsulfanyl]pyrimidin-4-yl}-2,4-dimethylbenzoic acid methyl ester Molecular weight: 552.
ESI (LC/MS positive mode): m/z=539 (M+H$^+$).
Chemical shift value δ in $^1$H-NMR (270 MHz, in chloroform-d): 1.44 (9H, s), 1.54-1.86 (4H, m), 2.24 (3H, s), 2.57 (3H, s), 3.13-3.25 (2H, m), 3.85 (3H, s), 3.97 (2H, t, J=5.9 Hz), 5.05 (2H, brs), 6.18 (1H, s), 6.95-6.98 (1H, m), 7.08 (1H, s), 7.13-7.37 (3H, m), 7.91 (1H, s).

Step 2: Preparation of 4-amino-21,23-dimethyl-13-oxa-7-thia-3,5,18-triazatricyclo[18.3.1.1$^{2,6}$.1$^{8,12}$]hexacosa-1(23),2(25),3,5,8(26),9,11,20(24),21-nonaen-19-one (Compound 19)

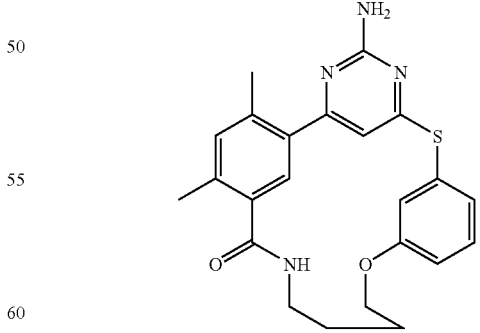

According to the method in Step 3 of Example 4-2, 4-amino-21,23-dimethyl-13-oxa-7-thia-3,5,18-triazatricyclo[18.3.1.1$^{2,6}$.1$^{8,12}$]hexacosa-1(23),2(25),3,5,8(26),9,11,20(24),21-nonaen-19-one (Compound 19) (11.7 mg) was obtained as a white solid material from 5-{2-amino-6-[3-(4- tert-butoxycarbonylaminobutoxy)phenylsulfanyl]pyrimidin-4-yl}-2,4-dimethylbenzoic acid methyl ester (60 mg) obtained in Step 1 above.

Physicochemical properties of 4-amino-21,23-dimethyl-13-oxa-7-thia-3,5,18-triazatricyclo[18.3.1.1$^{2,6}$.1$^{8,12}$]hexacosa-1(23),2(25),3,5,8(26),9,11,20(24),21-nonaen-19-one Molecular weight: 420.
ESI (LC/MS positive mode): m/z=421 (M+H$^+$).
Chemical shift value δ in $^1$H-NMR (270 MHz, in dimethylsulfoxide d-6): 1.57-1.82 (4H, m), 2.30 (3H, s), 2.45 (3H, s), 3.22-3.35 (2H, m), 4.26 (2H, t, J=5 Hz), 6.01 (1H, s), 6.84 (2H, brs), 7.07-7.23 (4H, m) 7.30-7.43 (2H, m), 8.26 (1H, t, J=6 Hz).

Example 4-5

Production of 4-amino-22,24-dimethyl-13-oxa-7-thia-3,5,19-triazatricyclo[19.3.1.1$^{2,6}$.1$^{8,12}$]heptacosa-1(24),2(26),3,5,8(27),9,11,21(25), 22-nonaen-20-one (Compound 20)

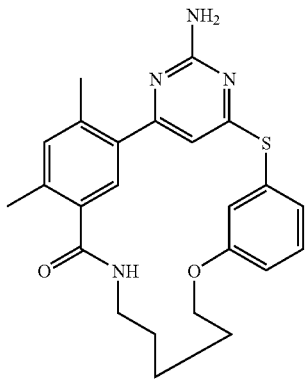 [SMILES: Cc1cc(C)c2cc1C(=O)NCCCCCOc1cccc(c1)Sc1cc-2nc(N)n1]

Step 1: Preparation of 5-{2-amino-6-[3-(5-tert-butoxycarbonylaminopentyloxy)phenylsulfanyl]pyrimidin-4-yl}-2,4-dimethylbenzoic acid methyl ester

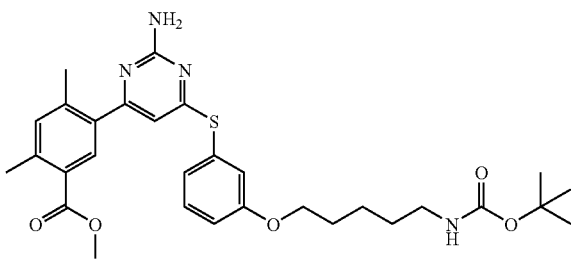 [SMILES: COC(=O)c1cc(-c2cc(Sc3cccc(OCCCCCNC(=O)OC(C)(C)C)c3)nc(N)n2)c(C)cc1C]

According to the method in Step 2 of Example 4-2, 5-{2-amino-6-[3-(5-tert-butoxycarbonylaminopentyloxy)phenylsulfanyl]pyrimidin-4-yl}-2,4-dimethylbenzoic acid methyl ester (62 mg) was obtained from 5-[2-amino-6-(3-hydroxyphenylsulfanyl)pyrimidin-4-yl]-2,4-dimethylbenzoic acid methyl ester (50 mg) obtained in Step 1 of Example 4-3 and 5-bromopentylcarbamic acid tert-butyl ester (47 mg).

Physicochemical properties of 5-{2-amino-6-[3-(5-tert-butoxycarbonylaminopentyloxy)phenylsulfanyl]pyrimidin-4-yl}-2,4-dimethylbenzoic acid methyl ester Molecular weight: 566.
ESI (LC/MS positive mode): m/z=567 (M+H$^+$).
Chemical shift value δ in $^1$H-NMR (270 MHz, in chloroform-d): 1.44 (9H, s), 1.44-1.58 (4H, m), 1.75-1.86 (2H, m), 2.24 (3H, s), 2.57 (3H, s), 3.07-3.21 (2H, m), 3.85 (3H, s), 3.95 (2H, t, J=6 Hz), 5.06 (2H, brs), 6.17 (1H, s), 6.94-6.98 (1H, m), 7.08 (1H, s), 7.13-7.37 (3H, m), 7.91 (1H, s).

Step 2: Production of 4-amino-22,24-dimethyl-13-oxa-7-thia-3,5,19-triazatricyclo[19.3.1.1$^{2,6}$.1$^{8,12}$]heptacosa-1(24),2(26),3,5,8(27),9,11,21(25),22-nonaen-20-one (Compound 20)

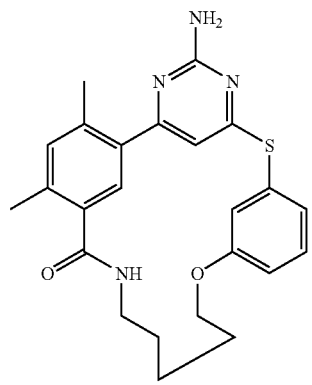 [SMILES: Cc1cc(C)c2cc1C(=O)NCCCCCOc1cccc(c1)Sc1cc-2nc(N)n1]

According to the method in Step 3 of Example 4-2, 4-amino-22,24-dimethyl-13-oxa-7-thia-3,5,19-triazatricyclo[19.3.1.1$^{2,6}$.1$^{8,12}$]heptacosa-1(24),2(26),3,5,8(27),9,11,21(25),22-nonaen-20-one (Compound 20) (16 mg) was obtained as a white solid material from 5-{2-amino-6-[3-(5-tert-butoxycarbonylaminopentyloxy)phenylsulfanyl]pyrimidin-4-yl}-2,4-dimethylbenzoic acid methyl ester (60 mg) obtained in Step 1 above.

Physicochemical properties of 4-amino-22,24-dimethyl-13-oxa-7-thia-3,5,19-triazatricyclo[19.3.1.1$^{2,6}$.1$^{8,12}$]heptacosa-1(24),2(26),3,5,8(27),9,11,21(25),22-nonaen-20-one Molecular weight: 434.
ESI (LC/MS positive mode): m/z=435 (M+H$^+$).
Chemical shift value δ in $^1$H-NMR (270 MHz, in dimethylsulfoxide d-6): 1.43-1.51 (4H, m), 1.66-1.80 (2H, m), 2.27 (3H, s), 2.39 (3H, s), 3.18-3.27 (2H, m), 4.07-4.16 (2H, m), 5.99 (1H, s), 6.85 (2H, brs), 7.00 (1H, s), 7.11-7.19 (4H, m) 7.40 (1H, dd, J=8 Hz, 8 Hz), 8.26 (1H, t, J=6 Hz).

Example 5-1

Production of 4-amino-20,22-dichloro-13,18-dioxa-7-thia-3,5-diazatricyclo[17.3.1.1$^{2,6}$.1$^{8,12}$]pentacosa-1(23),2,4,6(24),8,10,12(25),19,21-nonaene (Compound 21)

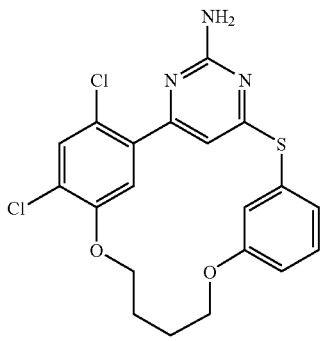 [SMILES: Nc1nc2cc(n1)-c1cc(c(Cl)cc1Cl)OCCCCOc1cccc(c1)S2]

Step 1: Preparation of tert-butyl(2,4-dichloro-5-iodophenoxy)dimethylsilane

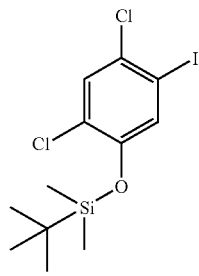 [SMILES: CC(C)(C)[Si](C)(C)Oc1cc(I)c(Cl)cc1Cl]

TBDMSCl (5.22 g) was added to an N,N-dimethylformamide (50 ml) solution of 2,4-dichloro-5-iodophenol (10 g) synthesized according to the production method described in WO 2001/027088 and imidazole (2.83 g), and the resulting mixture was stirred at room temperature for 4 hours. Water (150 ml) was added to the solution, and then extracted with n-hexane (200 ml). Then, the n-hexane solution was sequentially washed twice with water (100 ml) and once with a saturated aqueous sodium chloride solution (100 ml), and dried over anhydrous sodium sulfate. After filtration, the solvent was distilled off. The resulting residue was purified by silica gel column chromatography (developing solvent: n-hexane) to yield pale yellow oily tert-butyl(2,4-dichloro-5-iodophenoxy)dimethylsilane (11.39 g).

Physicochemical properties of tert-butyl(2,4-dichloro-5-iodophenoxy)dimethylsilane Molecular weight: 402.
EI: m/z=402(M$^+$).
Chemical shift value δ in $^1$H-NMR (270 MHz, in chloroform-d): 0.23 (6H, s), 1.01 (9H, s), 7.33 (1H, s), 7.44 (1H, s).

Step 2: Synthesis of 2-[5-(tert-butyldimethylsilanyloxy)-2,4-dichlorophenyl]-5,5-dimethyl[1,3,2]dioxaborinane

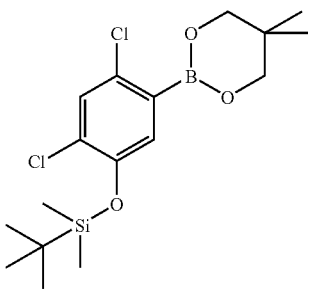 [SMILES: CC1(C)COB(c2cc(O[Si](C)(C)C(C)(C)C)c(Cl)cc2Cl)OC1]

A solution of tert-butyl(2,4-dichloro-5-iodophenoxy)dimethylsilane (857 mg) obtained in Step 1 above in tetrahydrofuran (1 ml) and toluene (4 ml) was prepared under nitrogen atmosphere. The solution was cooled to −78° C. (dry ice/acetone). After triisopropylborate (0.6 ml) was added, n-butyllithium (1.6N; n-hexane solution, 1.62 ml) was added dropwise thereto over 5 minutes. The mixture was stirred at the same temperature for 30 minutes, and then warmed by removing the cold bath. When the inner temperature reached 0° C., 2,2-dimethylpropane-1,3-diol (0.27 g) was added to the solution and then warmed to room temperature. After stirring at room temperature for 8 hours, water (20 ml) was added to the solution and extracted with ethyl acetate (20 ml). The ethyl acetate solution was sequentially washed with a half-saturated aqueous ammonium chloride solution (15 ml), water (15 ml), and a saturated aqueous sodium chloride solution (10 ml). Then, the organic solution was pre-dried over anhydrous sodium sulfate. After filtration, the solvent was distilled off. The resulting residue was purified by silica gel column chromatography (developing solvent: n-hexane:ethyl acetate=20:1 to 9:1) to yield pale yellow oily 2-[5-(tert-butyldimethylsilanyloxy)-2,4-dichlorophenyl]-5,5-dimethyl[1,3,2]dioxaborinane (547 mg).

Physicochemical properties of 2-[5-(tert-butyldimethylsilanyloxy)-2,4-dichlorophenyl]-5,5-dimethyl[1,3,2]dioxaborinane Molecular weight: 388.
EI: m/z=388(M$^+$).
Chemical shift value δ in $^1$H-NMR (270 MHz, in chloroform-d): 0.21 (6H, s), 1.02 (9H, s), 1.05 (6H, s), 3.78 (4H, s), 7.14 (1H, s), 7.33 (1H, s).

Step 3: Preparation of 5-[2-amino-6-(3-hydroxyphenylsulfanyl)pyrimidin-4-yl]-2,4-dichlorophenol

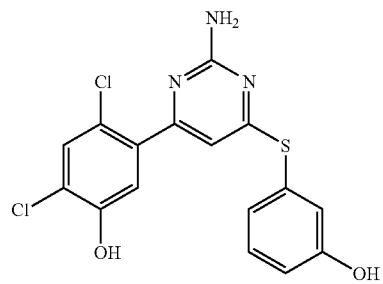

According to the method in Step 1 of Example 4-2, 5-[2-amino-6-(3-hydroxyphenylsulfanyl)pyrimidin-4-yl]-2,4-dichlorophenol (126.7 mg) was obtained from 5-(2-amino-6-chloropyrimidin-4-yl)-2,4-dichlorophenol (107 mg), which was prepared by the method according to Step 2 of Example 2-8 from 2-[5-(tert-butyldimethylsilanyloxy)-2,4-dichlorophenyl]-5,5-dimethyl[1,3,2]dioxaborinane obtained in Step 2 above and commercially available 2-amino-4,6-dichloropyrimidine. The reaction was conducted under heat at 80° C.

Physicochemical properties of 5-[2-amino-6-(3-hydroxyphenylsulfanyl)pyrimidin-4-yl]-2,4-dichlorophenol Molecular weight: 380.
ESI (LC/MS positive mode): m/z=380, 382 (M+H$^+$).
Chemical shift value δ in $^1$H-NMR (270 MHz, in dimethylsulfoxide d-6): 6.13 (1H, s), 6.77-7.04 (5H, m), 7.12 (1H, s), 7.31 (1H, dd, J=8 Hz, J=8 Hz), 7.50 (1H, s), 9.86 (1H, brs), 10.71 (1H, brs).

Step 4: Production of 4-amino-20,22-dichloro-13,18-dioxa-7-thia-3,5-diazatricyclo[17.3.1.1$^{2,6}$.1$^{8,12}$]pentacosa-1(23),2,4,6(24),8,10,12(25),19,21-nonaene (Compound 21)

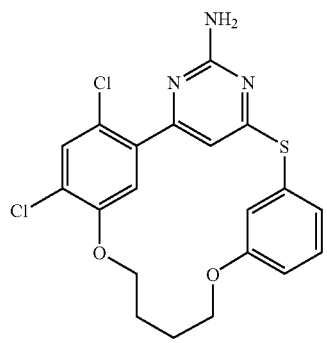

5-[2-Amino-6-(3-hydroxyphenylsulfanyl)pyrimidin-4-yl]-2,4-dichlorophenol (30 mg) obtained in Step 3 above and cesium carbonate (26 mg) were weighed and placed in a reaction vessel, and then N,N-dimethylformamide (1 ml) was added thereto. Then, the mixture was stirred at 100° C. for 30 minutes. N,N-Dimethylformamide (0.5 ml) solution of 1,4-dibromobutane (17 mg) was added to the resulting mixture, and then further stirred at the same temperature overnight. After cooling to room temperature, the mixture was diluted with ethyl acetate. After washing twice with water, the mixture was dried over anhydrous sodium sulfate. After filtration, the filtrate was concentrated under reduced pressure. The resulting crude product was purified by thin layer silica gel chromatography (developing solvent: a mixed solvent of n-hexane and ethyl acetate), and then the obtained eluate was further purified by thin layer silica gel chromatography (developing solvent: a mixed solvent of dichloromethane and methanol) to yield 4-amino-20,22-dichloro-13,18-dioxa-7-thia-3,5-diazatricyclo[17.3.1.1$^{2,6}$.1$^{8,12}$]pentacosa-1(23),2,4,6(24),8,10,12(25),19,21-nonaene (Compound 21) (9.3 mg) as a white solid material.

Physicochemical properties of 4-amino-20,22-dichloro-13,18-dioxa-7-thia-3,5-diazatricyclo[17.3.1.1$^{2,6}$.1$^{8,12}$]pentacosa-1(23),2,4,6(24),8,10,12(25),19,21-nonaene Molecular weight: 434.
ESI (LC/MS positive mode): m/z=434, 436 (M+H$^+$).
Chemical shift value δ in $^1$H-NMR (270 MHz, in chloroform-d): 1.89-2.11 (4H, m), 4.07-4.24 (4H, m), 5.20 (2H, brs), 6.31 (1H, s), 6.83 (1H, s), 6.93 (1H, dd, J=2 Hz, J=8 Hz), 7.17-7.39 (3H, m), 7.42 (1H, s).

Example 5-2

Production of 4-amino-21,23-dichloro-13,19-dioxa-7-thia-3,5-diazatricyclo[18.3.1.1$^{2,6}$.1$^{8,12}$]hexacosa-1(24),2,4,6(24),8,10,12(26),20,22-nonaene (Compound 22)

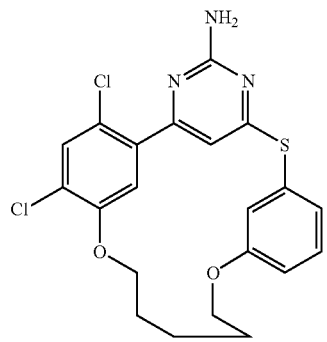 [SMILES: Nc1nc2cc(n1)-c1cc(c(Cl)cc1Cl)OCCCCCOc1cccc(c1)S2]

According to the method in Step 2 of Example 5-1, 4-amino-21,23-dichloro-13,19-dioxa-7-thia-3,5-diazatricyclo[18.3.1.1$^{2,6}$.1$^{8,12}$]hexacosa-1(24),2,4,6(24),8,10,12(26),20,22-nonaene (Compound 22) (13.5 mg) was obtained as a white solid material from 5-[2-amino-6-(3-hydroxyphenylsulfanyl)pyrimidin-4-yl]-2,4-dichlorophenol (30 mg) obtained in Step 1 of Example 5-1 and 1,5-dibromopentane (18.1 mg).

Physicochemical properties of 4-amino-21,23-dichloro-13,19-dioxa-7-thia-3,5-diazatricyclo[18.3.1.1$^{2,6}$.1$^{8,12}$]hexacosa-1(24),2,4,6(24),8,10,12(26),20,22-nonaene Molecular weight: 448.
ESI (LC/MS positive mode): m/z=448, 450 (M+H$^+$).
Chemical shift value δ in $^1$H-NMR (270 MHz, in chloroform-d): 1.54-1.79 (4H, m), 1.82-1.96 (2H, m), 4.10 (2H, t, J=6 Hz), 4.18 (2H, t, J=7 Hz), 5.22 (2H, brs), 5.97 (1H, s), 6.65 (1H, s), 6.99 (1H, ddd, J=1 Hz, 2 Hz, 8 Hz), 7.17-7.26 (2H, m), 7.36 (1H, dd, J=8 Hz, 8 Hz), 7.41 (1H, s).

Example 5-3

Production of 21,23-dichloro-13,16,19-trioxa-7-thia-3,5-diazatricyclo[18.3.1.1$^{2,6}$.1$^{8,12}$]hexacosa-1(23),2(25),3,5,8(26),9,11,20(24),21-nonaen-4-ylamine (Compound 23)

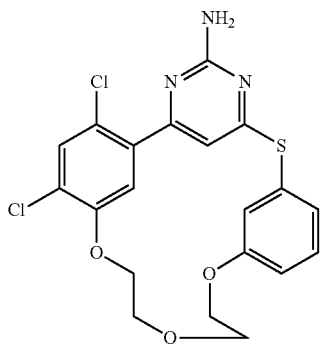 [SMILES: Nc1nc2cc(n1)-c1cc(c(Cl)cc1Cl)OCCOCCOc1cccc(c1)S2]

According to the method in Step 2 of Example 5-1, 21,23-dichloro-13,16,19-trioxa-7-thia-3,5-diazatricyclo[18.3.1.1$^{2,6}$.1$^{8,12}$]hexacosa-1(23),2(25),3,5,8(26),9,11,20(24),21-nonaen-4-ylamine (Compound 23) (9.1 mg) was obtained as a white solid material from 5-[2-amino-6-(3-hydroxyphenylsulfanyl)pyrimidin-4-yl]-2,4-dichlorophenol (30 mg) obtained in Step 1 of Example 5-1 and 2-bromoethyl ether (18.3 mg).

Physicochemical properties of 21,23-dichloro-13,16,19-trioxa-7-thia-3,5-diazatricyclo[18.3.1.1$^{2,6}$.1$^{8,12}$]hexacosa-1(23),2(25),3,5,8(26),9,11,20(24),21-nonaen-4-ylamine Molecular weight: 450.
ESI (LC/MS positive mode): m/z=450, 452 (M+H$^+$).
Chemical shift value δ in $^1$H-NMR (270 MHz, in chloroform-d): 3.71-3.89 (4H, m), 4.21-4.39 (4H, m), 5.23 (2H, brs), 6.06 (1H, s), 6.94 (1H, s), 6.98 (1H, dd, J=2 Hz, 8 Hz), 7.21 (1H, d, J=8 Hz), 7.29 (1H, dd, J=2 Hz, 2 Hz), 7.36 (1H, dd, J=8 Hz, 8 Hz), 7.40 (1H, s).

Example 5-4

Production of 4-amino-22-methyl-13,18-dioxa-7-thia-3,5-diazatricyclo[17.3.1.1$^{2,6}$.1$^{8,12}$]pentacosa-1(23),2(24),3,5,8(25),9,11,19,21-nonaene (Compound 24)

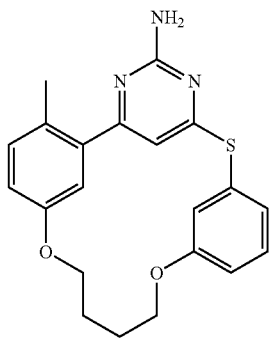 [SMILES: Cc1ccc2cc1-c1cc(nc(N)n1)Sc1cccc(c1)OCCCCO2]

Step 1: Preparation of 3-{2-amino-6-[5-(tert-butyldimethylsilanyloxy)-2-methylphenyl]pyrimidin-4-ylsulfanyl}phenol

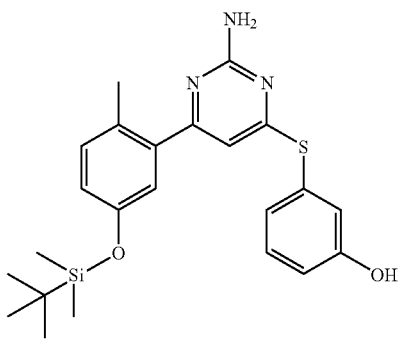 [SMILES: Cc1ccc(O[Si](C)(C)C(C)(C)C)cc1-c1cc(Sc2cccc(O)c2)nc(N)n1]

According to the method in Step 1 of Example 4-1, 3-{2-amino-6-[5-(tert-butyldimethylsilanyloxy)-2-methylphenyl]pyrimidin-4-ylsulfanyl}phenol was synthesized from 4-[5-(tert-butyldimethylsilanyloxy)-2-methylphenyl]-6-chloropyrimidin-2-ylamine obtained in Example 1-5.

Physicochemical properties of 3-{2-amino-6-[5-(tert-butyldimethylsilanyloxy)-2-methylphenyl]pyrimidin-4-ylsulfanyl}phenol Molecular weight: 439.
ESI (LC/MS positive mode): m/z=440 (M+H$^+$).
Chemical shift value δ in $^1$H-NMR (270 MHz, in dimethylsulfoxide d-6): 0.11 (6H, s), 0.91 (9H, s), 2.13 (3H, s), 5.87 (1H, s), 6.67 (1H, d, J=2.3 Hz), 6.77 (1H, dd, J=2.3 Hz, 8.6 Hz), 6.82 (2H, brs), 6.88-6.91 (1H, m), 7.01 (1H, s), 7.05-7.09 (2H, m), 7.30 (1H, t, J=7.9 Hz), 9.85 (1H, s).

Step 2: Preparation of 4-amino-22-methyl-13,18-dioxa-7-thia-3,5-diazatricyclo[17.3.1.1$^{2,6}$.1$^{8,12}$]pentacosa-1(23),2(24),3,5,8(25),9,11,19,21-nonaene (Compound 24)

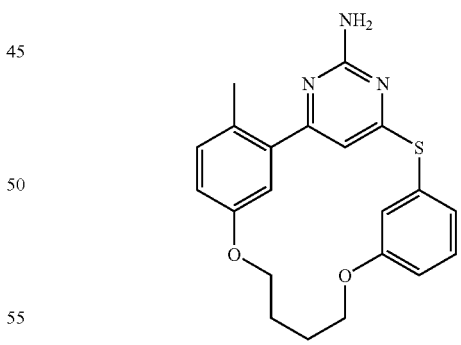

3-{2-Amino-6-[5-(tert-butyl dimethylsilanyloxy)-2-methylphenyl]pyrimidin-4-ylsulfanyl}phenol (Compound 1-I) (2.80 g, 6.37 mmol) obtained in Step 1 above was placed in a reaction vessel, and then N,N-dimethylformamide (100 ml) was added thereto. 1,4-dibromobutane (0.91 ml, 8.46 mmol) and cesium carbonate (2.76 g, 8.47 mmol) were sequentially added to the mixture, and stirred at 110° C. for 5 hours. The reaction solution was cooled to room temperature, and then diluted with ethyl acetate (800 ml). The solution was sequentially washed with water (400 ml) and a saturated aqueous sodium chloride solution (400 ml). The washed ethyl acetate solution was dried over anhydrous magnesium sulfate. After filtration, the filtrate was concentrated under reduced pressure. The resulting crude product was purified by silica gel column chromatography (developing solvent: dichloromethane:ethyl acetate=9:1) to yield 4-amino-22-methyl-13,18-dioxa-7-thia-3,5-diazatricyclo[17.3.1.1$^{2,6}$.1$^{8,12}$]pentacosa-1(23),2(24),3,5,8(25),9,11,19,21-nonaene (Compound 24) (587.2 mg, 22%).

Physicochemical properties of 4-amino-22-methyl-13,18-dioxa-7-thia-3,5-diazatricyclo[17.3.1.1$^{2,6}$.1$^{8,12}$]pentacosa-1(23),2(24),3,5,8(25),9,11,19,21-nonaene Molecular weight: 379.

ESI (LC/MS positive mode): m/z=380 (M+H$^+$).

Chemical shift value δ in $^1$H-NMR (400 MHz, in chloroform-d): 1.95-2.00 (4H, m), 2.43 (3H, s), 4.04 (2H, t, J=8.3 Hz), 4.15 (2H, dd, J=4.4 Hz, 8.3 Hz), 5.08 (2H, brs), 6.41 (1H, s), 6.75 (1H, s), 6.83 (1H, m), 6.92 (1H, m), 7.09 (1H, d, J=8.3 Hz), 7.17-7.20 (1H, d, J=8.3 Hz), 7.32-7.34 (2H, m).

Example 5-5

Preparation of 4-amino-23-methyl-13,19-dioxa-7-thia-3,5-diazatricyclo[18.3.1.1$^{2,6}$.1$^{8,12}$]hexacosa-1(24),2(25),3,5,8(26),9,11,20,22-nonaene (Compound 25)

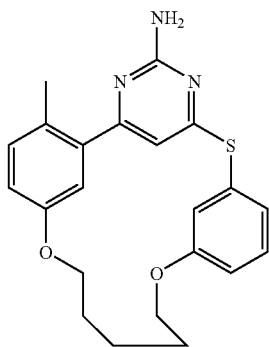 [SMILES: Cc1ccc2cc1-c1cc(nc(N)n1)Sc1cccc(c1)OCCCCCO2]

According to the method in Step 2 of Example 5-4, 4-amino-23-methyl-13,19-dioxa-7-thia-3,5-diazatricyclo[18.3.1.1$^{2,6}$.1$^{8,12}$]hexacosa-1(24),2(25),3,5,8(26),9,11,20,22-nonaene (Compound 25) (32.8 mg, 41%) was obtained from 3-{2-amino-6-[5-(tert-butyldimethylsilanyloxy)-2-methylphenyl]pyrimidin-4-ylsulfanyl}phenol (89.5 mg) obtained in Step 1 of Example 5-4 and 1,5-dibromopentane.

Physicochemical properties of 4-amino-23-methyl-13,19-dioxa-7-thia-3,5-diazatricyclo[18.3.1.1$^{2,6}$.1$^{8,12}$]hexacosa-1(24),2(25),3,5,8(26),9,11,20,22-nonaene Molecular weight: 393.

ESI (LC/MS positive mode): m/z=394 (M+H$^+$).

Example 5-6

Production of 20,22-dichloro-13,18-dioxa-7-thia-3,5,24-triazatricyclo[17.3.1.1$^{2,6}$.1$^{8,12}$]pentacosa-1(22),2(24),3,5,8(25),9,11,19(23),20-nonaen-4-ylamine (Compound 26)

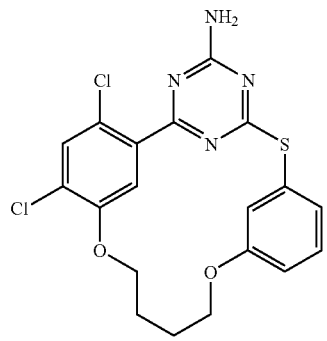 [SMILES: Nc1nc2nc(n1)-c1cc(c(Cl)cc1Cl)OCCCCOc1cccc(c1)S2]

Step 1: Preparation of 4-benzylsulfanyl-6-chloro-4-[1,3,5]triazin-2-ylamine

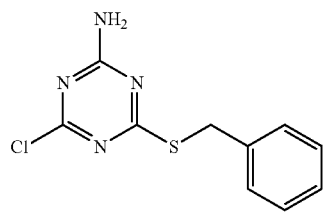 [SMILES: Nc1nc(Cl)nc(SCc2ccccc2)n1]

An N,N-dimethylformamide (120 ml) solution of 4,6-dichloro-[1,3,5]triazin-2-ylamine (10 g) synthesized by the production method described in Japanese Patent Application Kokai Publication No. (JP-A) S60-208968 (unexamined, published Japanese patent application) was cooled to 0° C. in an ice bath. Triethylamine (11 ml) was added thereto, and then benzylmercaptan (6.4 ml) was added dropwise over 5 minutes. The solution was gradually warmed to room temperature, and stirred for 8 hours. Then, water (400 ml) was added to the solution and extracted with ethyl acetate (400 ml). The organic solution was sequentially washed twice with water (400 ml) and once with a saturated aqueous sodium chloride solution (200 ml). The organic solution was pre-dried over anhydrous sodium sulfate. After filtration, the solvent was distilled off. The obtained residue was recrystallized from dichloromethane to yield 4-benzylsulfanyl-6-chloro-4-[1,3,5]triazin-2-ylamine (5.27 g) as a white solid.

Physicochemical properties of 4-benzylsulfanyl-6-chloro-4-[1,3,5]triazin-2-ylamine Molecular weight: 253.

ESI (LC/MS positive mode): m/z=253, 255 (M+H$^+$).

Chemical shift value δ in $^1$H-NMR (270 MHz, in DMSO-d$_6$): 4.34 (2H, s), 7.24-7.34 (3H, m), 7.42-7.44 (2H, m), 8.12 (2H, s).

Step 2: Preparation of 5-(4-amino-6-benzylsulfanyl-[1,3,5]triazin-2-yl)-2,4-dichlorophenol

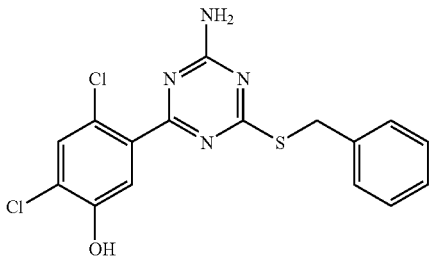 [SMILES: Nc1nc(SCc2ccccc2)nc(-c2cc(O)c(Cl)cc2Cl)n1]

2-[5-(tert-Butyldimethylsilanyloxy)-2,4-dichlorophenyl]-5,5-dimethyl[1,3,2]dioxaborinane (0.5 g) obtained in Step 2 of Example 5-1 and 4-benzylsulfanyl-6-chloro-4-[1,3,5]triazin-2-ylamine (0.32 g) obtained in Step 1 above were dissolved in 1,2-dimethoxyethane (15.5 ml). An aqueous sodium bicarbonate solution (1N, 2.57 ml) and tetrakistriphenylphosphine palladium (0.3 g) were sequentially added to the mixture. After three cycles of nitrogen replacement using a vacuum pump, the mixture was stirred in an oil bath at 80° C. for 4 hours. After allowing the mixture to cool to room temperature, water (50 ml) was added, and then extracted with ethyl acetate (70 ml). The organic solution was washed with a saturated aqueous ammonium chloride solution (50 ml), and dried over anhydrous sodium sulfate. After filtration, the solvent was distilled off. The resulting residue was purified by silica gel column chromatography (developing solvent: n-hexane:ethyl acetate=7:3) to yield 5-(4-amino-6-benzylsulfanyl-[1,3,5]triazin-2-yl)-2,4-dichlorophenol (379 mg) as a pale yellow solid.

Physicochemical properties of 5-(4-amino-6-benzylsulfanyl-[1,3,5]triazin-2-yl)-2,4-dichlorophenol Molecular weight: 379.
ESI (LC/MS positive mode): m/z=379, 381 (M+H$^+$).
Chemical shift value δ in $^1$H-NMR (270 MHz, in CDCl$_3$): 4.43 (2H, s), 5.41 (2H, brs), 7.22-7.49 (7H, m).

Step 3: Preparation of 5-[4-amino-6-(3-hydroxyphenylsulfanyl)-[1,3,5]triazin-2-yl]-2,4-dichlorophenol

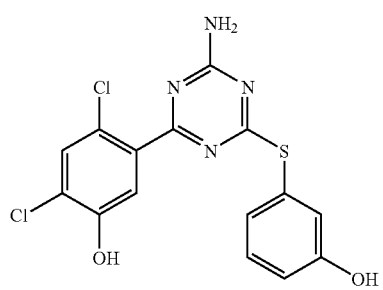 [SMILES: Nc1nc(Sc2cccc(O)c2)nc(-c2cc(O)c(Cl)cc2Cl)n1]

5-(4-Amino-6-benzylsulfanyl-[1,3,5]triazin-2-yl)-2,4-dichlorophenol (150 mg) obtained in Step 2 above was placed in a reaction vessel, and then dichloromethane (10 ml) and methanol (2 ml) were added thereto. The mixture was stirred. m-Chloroperbenzoic acid (210 mg) was added to the resulting suspension at room temperature, and stirred for 30 minutes. The resulting mixture was concentrated under reduced pressure. To this, N,N-dimethylformamide (4.5 ml), triethylamine (0.19 ml), and 3-mercaptophenol (0.12 ml) were added and stirred at room temperature for 4 hours. The reaction solution was diluted with ethyl acetate, and then sequentially washed with a saturated aqueous sodium bicarbonate solution and water. The ethyl acetate solution was dried over anhydrous sodium sulfate. After filtration, the filtrate was concentrated under reduced pressure. The resulting crude product was purified by silica gel column chromatography (developing solvent: a mixed solvent of n-hexane and ethyl acetate) to yield 5-[4-amino-6-(3-hydroxyphenylsulfanyl)-[1,3,5]triazin-2-yl]-2,4-dichlorophenol (54 mg) as a yellow solid.

Physicochemical properties of 5-[4-amino-6-(3-hydroxyphenylsulfanyl)-[1,3,5]triazin-2-yl]-2,4-dichlorophenol Molecular weight: 381.
ESI (LC/MS positive mode): m/z=381, 383 (M+H$^+$).
Chemical shift value δ in $^1$H-NMR (270 MHz, in methanol d-4): 6.86 (1H, ddd, J=1 Hz, 3 Hz, 8 Hz), 7.04-7.19 (2H, m), 7.22 (1H, s), 7.25 (1H, dd, J=8 Hz, 8 Hz), 7.41 (1H, s)

Step 4: Production of 20,22-dichloro-13,18-dioxa-7-thia-3,5,24-triazatricyclo[17.3.1.1$^{2,6}$.1$^{8,12}$]pentacosa-1(22),2(24),3,5,8(25),9,11,19(23),20-nonaen-4-ylamine (Compound 26)

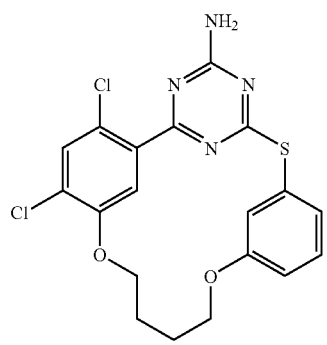 [SMILES: Nc1nc2nc(n1)-c1cc(c(Cl)cc1Cl)OCCCCOc1cccc(c1)S2]

According to the method in Step 2 of Example 5-1, 20,22-dichloro-13,18-dioxa-7-thia-3,5,24-triazatricyclo[17.3.1.1$^{2,6}$.1$^{8,12}$]pentacosa-1(22),2(24),3,5,8(25),9,11,19(23),20-nonaen-4-ylamine (Compound 26) (7.7 mg) was obtained as a white solid material from 5-[4-amino-6-(3-hydroxyphenylsulfanyl)-[1,3,5]triazin-2-yl]-2,4-dichlorophenol (27 mg) obtained in Step 1 and 1,4-dibromobutane (15.3 mg).

Physicochemical properties of 20,22-dichloro-13,18-dioxa-7-thia-3,5,24-triazatricyclo[17.3.1.1$^{2,6}$.1$^{8,12}$]pentacosa-1(22),2(24),3,5,8(25),9,11,19(23),20-nonaen-4-ylamine Molecular weight: 435.
ESI (LC/MS positive mode): m/z=435, 437 (M+H$^+$).
Chemical shift value δ in $^1$H-NMR (270 MHz, in dimethylsulfoxide d-6): 1.82-2.02 (4H, m), 4.04-4.23 (4H, m), 7.01-7.08 (2H, m), 7.34 (1H, dd, J=8 Hz, 8 Hz), 7.50 (1H, dd, J=2 Hz, 2 Hz), 7.63 (1H, s), 7.71 (1H, s), 7.80 (1H, brs), 7.85 (1H, brs).

Example 5-7

Production of 21,23-dichloro-13,16,19-trioxa-7-thia-3,5,25-triazatricyclo[18.3.1.1$^{2,6}$.1$^{8,12}$]hexacosa-1(23),2(25),3,5,8(25),9,11,20(24),21-nonaen-4-ylamine (Compound 27)

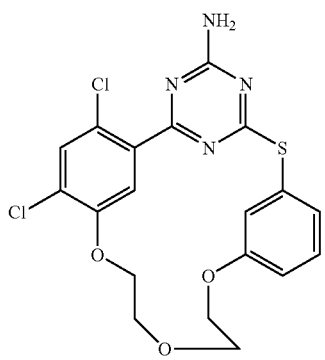 [SMILES: Nc1nc2nc(n1)-c1cc(c(Cl)cc1Cl)OCCOCCOc1cccc(c1)S2]

According to the method in Step 2 of Example 5-1, 21,23-dichloro-13,16,19-trioxa-7-thia-3,5,25-triazatricyclo[18.3.1.1$^{2,6}$.1$^{8,12}$]hexacosa-1(23),2(25),3,5,8(25),9,11,20(24),21-nonaen-4-ylamine (Compound 27) (7.1 mg) was obtained as a white solid material from 5-[4-amino-6-(3-hydroxyphenylsulfanyl)-[1,3,5]triazin-2-yl]-2,4-dichlorophenol (27 mg) obtained in Step 1 of Example 5-6 and 2-bromoethyl ether (16.4 mg).

Physicochemical properties of 21,23-dichloro-13,16,19-trioxa-7-thia-3,5,25-triazatricyclo[18.3.1.1$^{2,6}$.1$^{8,12}$]hexacosa-1(23),2(25),3,5,8(25),9,11,20(24),21-nonaen-4-ylamine Molecular weight: 451.
ESI (LC/MS positive mode): m/z=451, 453 (M+H$^+$).
Chemical shift value δ in $^1$H-NMR (270 MHz, in dimethylsulfoxide d-6): 3.82-3.91 (4H, m), 4.14-4.29 (4H, m), 7.05-7.11 (2H, m), 7.33 (1H, dd, J=8 Hz, 8 Hz), 7.47-7.49 (2H, m), 7.64 (1H, s), 7.83 (1H, brs), 7.86 (1H, brs).

Example 6

Production of 4-amino-18,20-dimethyl-13-oxetan-3-yl-7-thia-3,5,11,15-tetraazatricyclo[15.3.1.1$^{2,6}$]docosa-1(20),2(22),3,5,17(21),18-hexaene-10,16-dione (Compound 72)

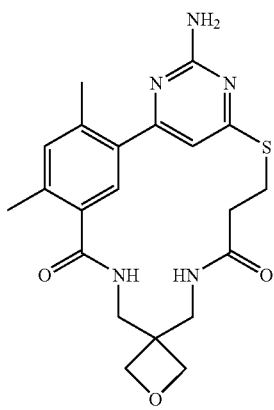 [SMILES: Cc1cc(C)c2cc1C(=O)NCC1(CNC(=O)CCSc3cc-2nc(N)n3)COC1]

Step 1: Preparation of (3-aminomethyloxetan-3-ylmethyl)tritylamine

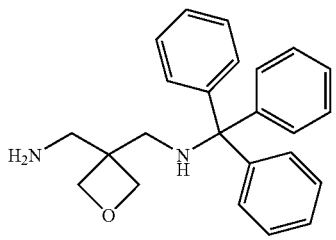 [SMILES: NCC1(CNC(c2ccccc2)(c2ccccc2)c2ccccc2)COC1]

A dichloromethane suspension (3.0 ml) of C-(3-aminomethyloxetan-3-yl)methylamine (411 mg, 3.54 mmol) prepared according to the method described in J. Org. Chem., (1985),50(17), 3211; and Japanese Patent Application Kokai Publication No. (JP-A) S61-69784 (unexamined, published Japanese patent application) was cooled to 0° C., and a dichloromethane solution (3.0 ml) of triphenylmethyl chloride (246 mg, 0.88 mmol) was added thereto. The mixture was stirred at 0° C. for 30 minutes, and then at room temperature for one hour. A saturated aqueous sodium bicarbonate solution (1.0 ml) and water (15 ml) were added to the solution. The mixture was extracted three times with dichloromethane (20 ml). The organic layers were combined together, and dried over anhydrous sodium sulfate. After the inorganic salt was removed by filtration, the filtrate was concentrated under reduced pressure. The resulting crude product was purified by silica gel column chromatography (developing solvent: dichloromethane:methanol=20:1) to yield (3-aminomethyloxetan-3-ylmethyl)tritylamine (162 mg) as a white amorphous material.

Physicochemical properties of (3-aminomethyloxetan-3-ylmethyl)tritylamine

Molecular weight: 358.
ESI (LC/MS positive mode): m/z=359 (M+H$^+$).
Chemical shift value δ in $^1$H-NMR (400 MHz, in dimethylsulfoxide d-6): 1.33 (2H, brs), 2.31 (2H, s), 2.77 (1H, brs), 2.89 (2H, s), 4.17 (2H, d, J=6.0 Hz), 4.25 (2H, d, J=6.0 Hz), 7.19 (3H, t, J=7.3 Hz), 7.30 (6H, t, J=7.8 Hz), 7.43 (6H, d, J=7.3 Hz)

Step 2: Preparation of 5-(2-amino-6-chloropyrimidin-4-yl)-2,4-dimethyl-N-{3-[(tritylamino)methyl]oxetan-3-ylmethyl}benzamide

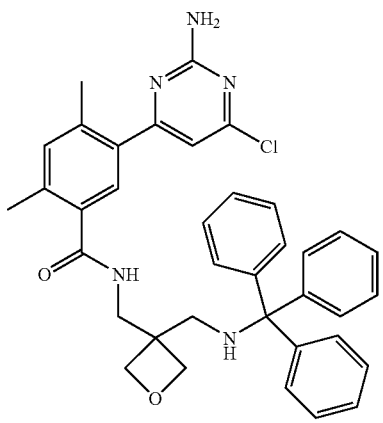 [SMILES: Cc1cc(C)c(-c2cc(Cl)nc(N)n2)cc1C(=O)NCC1(CNC(c2ccccc2)(c2ccccc2)c2ccccc2)COC1]

Trifluoroacetic acid (0.67 ml) was added to a dichloromethane (2.0 ml) solution of 5-(2-amino-6-chloropyrimidin-4-yl)-2,4-dimethylbenzoic acid tert-butyl ester (100 mg, 0.33 mmol) obtained in Step 4 of Example 1-1. The mixture was stirred at room temperature for four hours, and then concentrated under reduced pressure. The resulting white solid material was dissolved in N,N-dimethylformamide (1.0 ml), and then diisopropylethylamine (0.105 ml, 0.603 mmol), N-hydroxysuccinimide (38 mg, 0.333 mmol), and 1-ethyl-3-(3'-dimethylaminopropyl)carbodiimide hydrochloride (64 mg, 0.335 mmol) were added thereto. The mixture was stirred at room temperature for 5.5 hours, and then an N,N-dimethylformamide (2.0 ml) solution of (3-aminomethyloxetan-3-ylmethyl)tritylamine (160 mg, 0.446 mmol) obtained in Step 1 above was added thereto. The prepared reaction solution was stirred at room temperature for 17 hours. A saturated aqueous sodium chloride solution (20 mL) was added to the reaction solution, and extracted three times with ethyl acetate (20 ml). The extract was sequentially washed three times with a saturated aqueous sodium bicarbonate solution (30 ml) and then three times with a saturated aqueous sodium chloride solution (30 ml). The washed ethyl acetate solution was dried over anhydrous sodium sulfate. After filtration, the filtrate was concentrated under reduced pressure. The resulting crude product was purified by silica gel column chromatography (developing solvent: dichloromethane:methanol=30:1) to yield 5-(2-amino-6-chloropyrimidin-4-yl)-2,4-dimethyl-N-{3-[(tritylamino)methyl]oxetan-3-ylmethyl}benzamide (169 mg) as a white solid material.

Physicochemical properties of 5-(2-amino-6-chloropyrimidin-4-yl)-2,4-dimethyl-N-{3-[(tritylamino)methyl]oxetan-3-ylmethyl}benzamide Molecular weight: 617.
ESI (LC/MS positive mode): m/z=618, 620 (M+H$^+$)
Chemical shift value δ in $^1$H-NMR (400 MHz, in dimethylsulfoxide d-6): 2.18 (3H, s), 2.28 (2H, d, J=8.2 Hz), 2.36 (3H, s), 3.02 (1H, t, J=8.2 Hz), 3.70 (2H, d, J=6.0 Hz), 4.25 (2H, d, J=6.0 Hz), 4.37 (2H, d, J=6.0 Hz), 6.75 (1H, s), 7.10-7.16 (5H, m), 7.23 (6H, d, J=7.8 Hz), 7.26 (2H, s), 7.37-7.46 (5H, m), 7.95 (1H, s), 8.36 (1H, t, J=6.0 Hz).

Step 3: Preparation of 3-{2-amino-6-[2,4-dimethyl-5-({3-[(tritylamino)methyl]oxetan-3-ylmethyl}carbamoyl)phenyl]pyrimidin-4-ylsulfanyl}propanoic acid

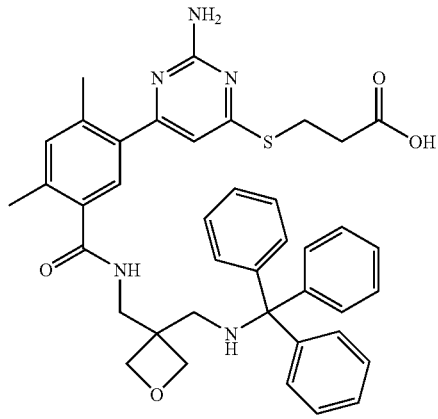 [SMILES: Cc1cc(C)c(-c2cc(SCCC(=O)O)nc(N)n2)cc1C(=O)NCC1(CNC(c2ccccc2)(c2ccccc2)c2ccccc2)COC1]

3-Mercaptopropionic acid (84 μl, 0.937 mmol) and cesium carbonate (316 mg, 0.970 mmol) were added to an N,N-dimethylformamide (1.0 ml) solution of 5-(2-amino-6-chloropyrimidin-4-yl)-2,4-dimethyl-N-{3-[(tritylamino)methyl]oxetan-3-ylmethyl}benzamide (119 mg, 0.192 mmol) obtained in Step 2 above. The resulting mixture was stirred at 80° C. for 1.5 hour. The reaction solution was slightly acidified with 1N hydrochloric acid, and the precipitated solid was collected by filtration. The separated solid was washed with water, and then dried under reduced pressure. The resulting crude product was purified by silica gel column chromatography (developing solvent: dichloromethane:methanol=15:1) to yield 3-{2-amino-6-[2,4-dimethyl-5-({3-[(tritylamino)methyl]oxetan-3-ylmethyl}carbamoyl)phenyl]pyrimidin-4-ylsulfanyl}propanoic acid (77 mg) as a white solid material.

Physicochemical properties of 3-{2-amino-6-[2,4-dimethyl-5-({3-[(tritylamino)methyl]oxetan-3-ylmethyl}carbamoyl)phenyl]pyrimidin-4-ylsulfanyl}propanoic acid Molecular weight: 687.
ESI (LC/MS positive mode): m/z=688 (M+H$^+$)
Chemical shift value δ in $^1$H-NMR (400 MHz, in dimethylsulfoxide d-6): 2.17 (3H, s), 2.28 (2H, d, J=8.2 Hz), 2.33 (3H, s), 2.63-2.69 (2H, m), 3.01 (1H, t, J=8.2 Hz), 3.25-3.32 (2H, m), 3.69 (2H, d, J=5.5 Hz), 4.23 (2H, d, J=6.0 Hz), 4.37 (2H, d, J=6.0 Hz), 6.52 (1H, s), 6.74 (2H, s), 7.07 (1H, s), 7.08-7.13 (3H, m), 7.14 (1H, m), 7.18-7.27 (6H, m), 7.35-7.45 (6H, m), 8.33 (1H, d, J=6.4 Hz).

Step 4: Preparation of 4-amino-18,20-dimethyl-13-oxetan-3-yl-7-thia-3,5,11,15-tetraazatricyclo[15.3.1.1$^{2,6}$]docosa-1(20),2(22),3,5,17(21),18-hexaene-10,16-dione (Compound 72)

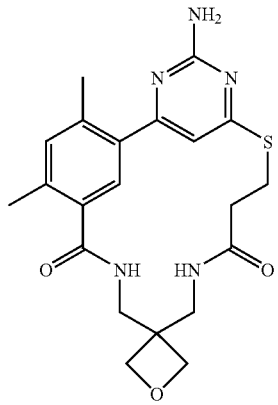 [SMILES: Cc1cc(C)c2cc1C(=O)NCC1(CNC(=O)CCSc3cc-2nc(N)n3)COC1]

Water (40 μl) and a dichloromethane (0.5 ml) solution of 10% trifluoroacetic acid were dropwise added to 3-{2-amino-6-[2,4-dimethyl-5-({3-[(tritylamino)methyl]oxetan-3-ylmethyl}carbamoyl)phenyl]pyrimidin-4-ylsulfanyl}propanoic acid (36 mg, 0.059 mmol) obtained in Step 3 above. After confirming that the clear colorless solution changed to yellow, diisopropylethylamine (0.30 ml) was added thereto. The reaction solution was diluted with N,N-dimethylformamide (24.0 ml), and dropwise added to an N,N-dimethylformamide solution (5.0 ml) of O-(7-azabenzotriazol-1-yl)-N,N,N',N'-tetramethyluroniumhexafluorophosphate (28 mg, 0.070 mmol). This reaction solution was stirred at room temperature for 18 hours. Water (5 ml) was added to stop the reaction. The solvent was distilled off under reduced pressure. A saturated aqueous sodium bicarbonate solution (20 ml) was added to the residue, and extracted three times with ethyl acetate (20 ml). The organic layers were combined together and washed with a saturated aqueous sodium chloride solution (20 ml). The washed organic layer was dried over anhydrous sodium sulfate. After filtration, the filtrate was concentrated under reduced pressure. The resulting crude product was purified by thin layer silica gel chromatography (developing solvent: ethyl acetate:methanol=15:1) to yield 4-amino-18,20-dimethyl-13-oxetan-3-yl-7-thia-3,5,11,15-tetraazatricyclo[15.3.1.1$^{2,6}$]docosa-1(20),2(22),3,5,17(21),18-hexaene-10,16-dione (Compound 72)(3 mg) as a white solid material.

Physicochemical properties of 4-amino-18,20-dimethyl-13-oxetan-3-yl-7-thia-3,5,11,15-tetraazatricyclo[15.3.1.1$^{2,6}$]docosa-1(20),2(22),3,5,17(21),18-hexaene-10,16-dione Molecular weight: 427.

ESI (LC/MS positive mode): m/z=428 (M+H$^+$)

Chemical shift value δ in $^1$H-NMR (400 MHz, in dimethylsulfoxide d-6): 2.43 (3H, s), 2.55-2.65 (5H, m), 3.15-3.25 (2H, m), 3.58 (2H, d, J=5.5 Hz), 3.70 (2H, d, J=5.5. Hz), 4.30-4.40 (4H, m), 6.67 (2H, s), 6.97 (1H, s), 7.16 (1H, s), 7.70 (1H, s), 8.04 (1H, t, J=5.5 Hz), 8.17 (1H, t, J=5.5 Hz).

Compounds 33, 35, 37 to 45, 47, 49 to 61 listed in Table 1 below can also be synthesized by the general synthesis methods described above and methods described in Examples.

TABLE 1

| Compound No. | Formula | Compound name |
|---|---|---|
| 33 | | 4-amino-11,19,21-trimethyl-7-thia-3,5,11,16-tetraazatricyclo[16.3.1.1$^{2,6}$]tricosa-1(21),2(23),3,5,18(22),19-hexaene-10,17-dione |
| 35 | | 4-amino-11-(2-hydroxyethyl)-19,21-dimethyl-7-thia-3,5,11,16-tetraazatricyclo[16.3.1.1$^{2,6}$]tricosa-1(21),2(23),3,5,18(22),19-hexaene-10,17-dione |
| 37 | | 4-amino-19,21-dimethyl-11-(2-morpholin-4-ylethyl)-7-thia-3,5,11,16-tetraazatricyclo[16.3.1.1$^{2,6}$]tricosa-1(21),2(23),3,5,18(22),19-hexaene-10,17-dione |

TABLE 1-continued

| Compound No. | Formula | Compound name |
|---|---|---|
| 38 | | 4-amino-18,20-dimethyl-11-[2-(4-methylpiperazin-1-yl)ethyl]-7-thia-3,5,11,15-tetraazatricyclo[15.3.1.1$^{2,6}$]-docosa-1(20),2(22),3,5,17(21),18-hexaene-10,16-dione |
| 39 | | 4-amino-19,21-dimethyl-11-[2-(4-methylpiperazin-1-yl)ethyl]-7-thia-3,5,11,16-tetraazatricyclo[16.3.1.1$^{2,6}$]-tricosa-1(21),2(23),3,5,18(22),19-hexaene-10,17-dione |
| 40 | | 4,9-diamino-18,20-dimethyl-7-thia-3,5,11,15-tetra-azatricyclo[15.3.1.1$^{2,6}$]docosa-1(20),2(22),3,5,17(21),18-hexaene-10,16-dione |

TABLE 1-continued

| Compound No. | Formula | Compound name |
| --- | --- | --- |
| 41 | | 4,9-diamino-19,21-dimethyl-7-thia-3,5,11,16-tetraazatricyclo[16.3.1.1$^{2,6}$]tricosa-1(21),2(23),3,5,18(22),19-hexaene-10,17-dione |
| 42 | | N-(4-amino-18,20-dimethyl-10,16-dioxo-7-thia-3,5,11,15-tetraazatricyclo[15.3.1.1$^{2,6}$]docosa-1(20),2(22),3,5,17(21),18-hexaen-9-yl)acetamide |
| 43 | | N-(4-amino-19,21-dimethyl-10,17-dioxo-7-thia-3,5,11,16-tetraazatricyclo[16.3.1.1$^{2,6}$]tricosa-1(21),2(23),3,5,18(22),19-hexaen-9-yl)acetamide |
| 44 | | 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid amide |

TABLE 1-continued
| Compound No. | Formula | Compound name |
|---|---|---|
| 45 | 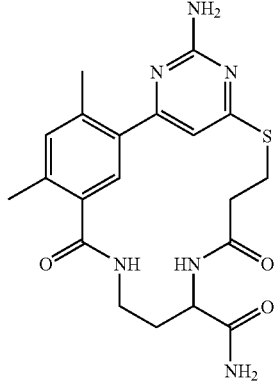 [SMILES: Cc1cc(C)c2cc1C(=O)NCCC(C(N)=O)NC(=O)CCSc1cc-2nc(N)n1] | 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid amide |
| 47 | 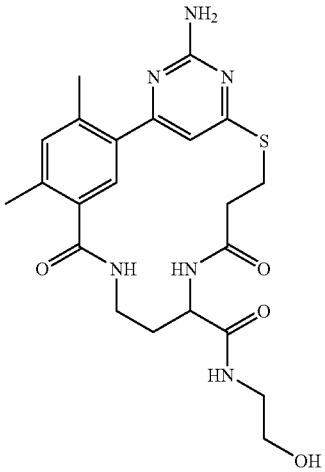 [SMILES: Cc1cc(C)c2cc1C(=O)NCCC(C(=O)NCCO)NC(=O)CCSc1cc-2nc(N)n1] | 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid (2-hydroxyethyl) amide |
| 49 | 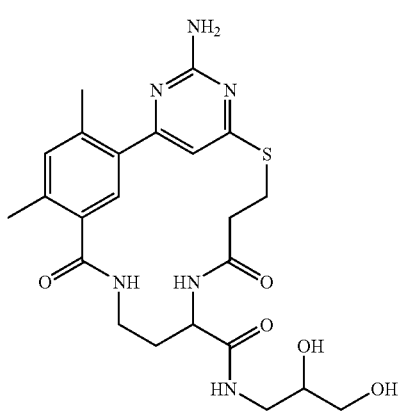 [SMILES: Cc1cc(C)c2cc1C(=O)NCCC(C(=O)NCC(O)CO)NC(=O)CCSc1cc-2nc(N)n1] | 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid (2,3-dihydroxypropyl) amide |

TABLE 1-continued

| Compound No. | Formula | Compound name |
|---|---|---|
| 50 | 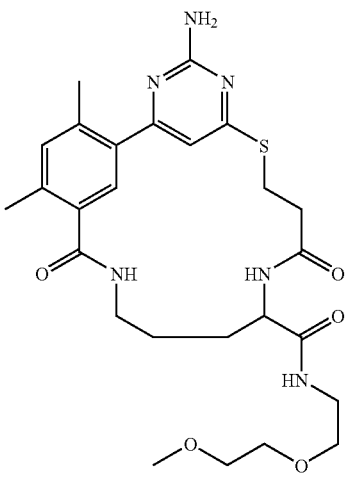 [SMILES: COCCOCCNC(=O)C1CCCNC(=O)c2cc(c(C)cc2C)-c2cc(nc(N)n2)SCCC(=O)N1] | 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid [2-(2-methoxyethoxy)ethyl] amide |
| 51 | 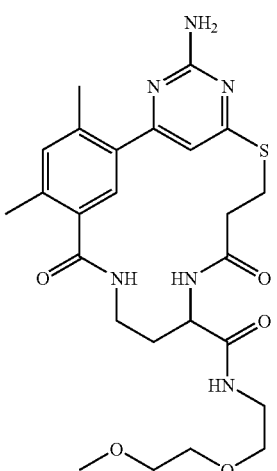 | 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid [2-(2-methoxyethoxy)ethyl] amide |
| 52 | 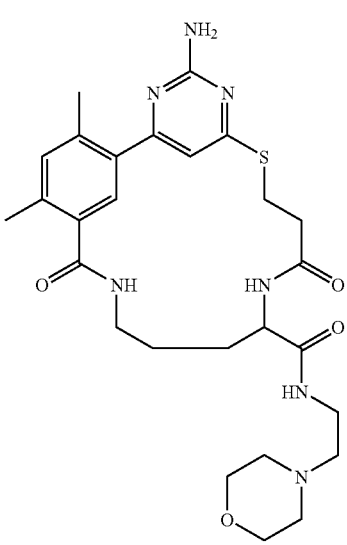 [SMILES: Cc1cc(C)c2cc1C(=O)NCCCC(C(=O)NCCN1CCOCC1)NC(=O)CCSc1cc-2nc(N)n1] | 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid (2-morpholin-4-ylethyl) amide |

TABLE 1-continued

| Compound No. | Formula | Compound name |
|---|---|---|
| 53 | | 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid (2-morpholin-4-ylethyl) amide |
| 54 | | 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid [2-(4-methylpiperazin-1-yl)ethyl] amide |
| 55 | | 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid [2-(4-methylpiperazin-1-yl)ethyl] amide |

TABLE 1-continued

| Compound No. | Formula | Compound name |
|---|---|---|
| 56 | | 4-amino-18,20-dimethyl-7-thia-3,5,10,12,15-penta-azatricyclo[15.3.1.1$^{2,6}$]docosa-1(20),2(22),3,5,17(21),18-hexaene-11,16-dione |
| 57 | | 4-amino-19,21-dimethyl-7-thia-3,5,10,12,16-penta-azatricyclo[16.3.1.1$^{2,6}$]tricosa-1(21),2(23),3,5,18(22),19-hexaene-11,17-dione |
| 58 | | 4-amino-18,20-dimethyl-10-oxa-7-thia-3,5,12,15-tetraazatricyclo[15.3.1.1$^{2,6}$]docosa-1(20),2(22),3,5,17(21),18-hexaene-11,16-dione |
| 59 | | 4-amino-19,21-dimethyl-11-oxa-7-thia-3,5,13,16-tetraazatricyclo[16.3.1.1$^{2,6}$]tricosa-1(21),2(23),3,5,18(22),19-hexaene-12,17-dione |

TABLE 1-continued

| Compound No. | Formula | Compound name |
|---|---|---|
| 60 | | 4-amino-12-hydroxymethyl-18,20-dimethyl-7-thia-3,5,11,15-tetraazatricyclo[15.3.1.1$^{2,6}$]docosa-1(20),2(22),3,5,17(21),18-hexaene-10,16-dione |
| 61 | | 4-amino-12-dimethylaminomethyl-18,20-dimethyl-7-thia-3,5,11,15-tetraazatricyclo[15.3.1.1$^{2,6}$]docosa-1(20),2(22),3,5,17(21),18-hexaene-10,16-dione |

Test Example 1

Assay for the Activity of Inhibiting HSP90 Enzyme

The compounds of the present invention represented by formula (1) were assayed for the activity of inhibiting HSP90 enzyme.

1) Methods for Preparing a Purified Enzyme Solution

Human HSP90 alpha gene (GenBank Accession No. X115183; Nucleic Acids Res. 1989 Sep. 12; 17 (17): 7108) was inserted into the pET vector (Novagen) to construct the expression plasmid pETHuHSP90a. Introduction of pETHuHSP90a into E. coli (BL21 codon plus; Stratagene) was followed by O/N incubation in the presence of 0.1 mM IPTG, and the collected E. coli cells were disrupted by ultrasonication in a Lysis buffer (50 mM Tris-HCl (pH8.0), 10 mM MgCl$_2$, 0.1% Triton X-100, Protease inhibitor cocktail tablets (Roche Diagnostics)). The cell lysate solution was centrifuged (10,000 rpm×30 minutes), and the supernatant obtained after centrifugation was used as a crude extract. The crude extract was fractionated using HisPrep FF column and HiTrap Q column (Amersham) to prepare a purified enzyme solution.

2) Enzyme Assay Method

An enzyme solution for assays was prepared by dilution of the purified enzyme solution using an assay buffer (50 mM Tris HCl pH7.6, 20 mM KCl, 5 mM MgCl$_2$).

80 µL aliquots of the enzyme solution for assays were placed into a 96-well plate (Falcon), and negative control wells were prepared by adding into each well, 80 µL of the assay buffer alone that does not contain the purified enzyme solution.

10 µL each of various concentrations of the test substances (10% DMSO solution) was added to each well, and for the positive control wells, 10 µL of 10% DMSO was added. 10 µL of 10% DMSO was also added to the negative control well.

10 µL of 1 mM ATP was added to all of the wells, and the reaction was carried out at 37° C. for two hours.

100 µL of malachite green solution (0.03% Malachite green, 0.2% Ammonium molybdate, 5% Triton X-100, 0.7 N HCl) was added, and OD655 was measured (BioRAD Microplate reader, model 3550-UV) after carrying out the reaction at room temperature for ten minutes.

The values of the negative control wells was subtracted as background from the values measured for all wells, and 50% inhibition concentration (IC$_{50}$) of the agent was calculated using the value of the positive control well as 0% inhibition.

3) Results

The results of measuring inhibitory activity against human HSP90 alpha are shown in Table 2. As indicated in Table 2, all of the compounds of the present invention showed good HSP90 enzyme inhibitory activity.

Test Example 2

Measurement of Cell Growth Inhibition

Cell growth inhibitory activities of the compounds of the present invention represented by formula (1) were measured by the following method.

1) Methods

HCT116 cell line (CCL-247, colon cancer cell line), NCI-H460 cell line (HTB-177, lung cancer cell line), DU145 cell line (HTB-81, prostate cancer cell line), and NCI-N87 cell line (CRL-5822, gastric cancer cell line) purchased from ATCC were used for the evaluation. Cells were maintained under conditions recommended by the provider of each cell line. Cells suspended in a medium were added to solutions containing various concentrations of the test substance, and the cells were cultured at 37° C. in a 5% $CO_2$ incubator. Four days later, Cell Counting Kit-8 was added, and absorbance measurements were taken following the protocol included in the kit. The value measured for samples which do not contain the test substances was defined as 0% inhibition and the value measured for samples which do not contain test substances and cells were defined as 100% inhibition, and the 50% inhibition concentration ($IC_{50}$) was calculated.

2) Results

Table 2 shows an example of the results of cell growth inhibitory activity on HCT116 cells. All of the compounds of the present invention showed good cell growth inhibitory activity.

TABLE 2

| Compound No. (Example) | Formula | Enzyme-inhibiting activity (IC50, μM) Human HSP90α | Cell growth-inhibiting activity (IC50, μM) Colon cancer HCT116 |
|---|---|---|---|
| 1 (2-1) | | 0.8 | 0.21 |
| 2 (2-2) | | 1.7 | 0.18 |
| 3 (2-3) | | 1.6 | 0.92 |

TABLE 2-continued

| Compound No. (Example) | Formula | Enzyme-inhibiting activity (IC50, μM) Human HSP90α | Cell growth-inhibiting activity (IC50, μM) Colon cancer HCT116 |
|---|---|---|---|
| 4 (2-4) | | 1.0 | 0.29 |
| 5 (2-5) | | 1.0 | 0.50 |
| 6 (2-6) | | 3.4 | 0.13 |
| 7 (2-7) | | 1.6 | 0.40 |

TABLE 2-continued
| Compound No. (Example) | Formula | Enzyme-inhibiting activity (IC50, μM) Human HSP90α | Cell growth-inhibiting activity (IC50, μM) Colon cancer HCT116 |
|---|---|---|---|
| 8 (2-8) | 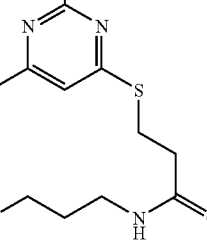 | 2.0 | 0.21 |
| 46 (2-10) | 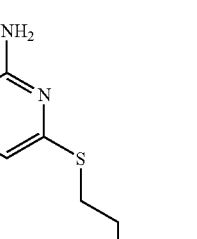 | 1.1 | >10 |
| 48 (2-11) | 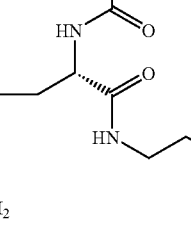 | 0.8 | >10 |
| 63 (2-12) | 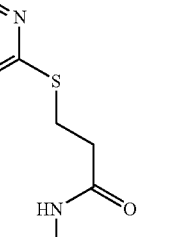 | 2.8 | 0.2 |

TABLE 2-continued

| Compound No. (Example) | Formula | Enzyme-inhibiting activity (IC50, μM) Human HSP90α | Cell growth-inhibiting activity (IC50, μM) Colon cancer HCT116 |
|---|---|---|---|
| 65 (2-14) | | 2.8 | 9.0 |
| 66 (2-15) | | 2.5 | >10 |
| 67 (2-16) | | 5.5 | >5 |
| 68 (2-17) | | 1.7 | 7.1 |

TABLE 2-continued

| Compound No. (Example) | Formula | Enzyme-inhibiting activity (IC50, μM) Human HSP90α | Cell growth-inhibiting activity (IC50, μM) Colon cancer HCT116 |
|---|---|---|---|
| 69 (2-18) | | 2.9 | 3.2 |
| 70 (2-19) | | 2.7 | >10 |
| 71 (2-20) | | 2.9 | 9.1 |

TABLE 2-continued
| Compound No. (Example) | Formula | Enzyme-inhibiting activity (IC50, μM) Human HSP90α | Cell growth-inhibiting activity (IC50, μM) Colon cancer HCT116 |
| --- | --- | --- | --- |
| 36 (2-21) | 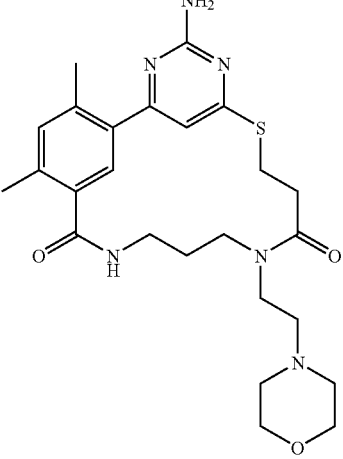 | 0.7 | 1.8 |
| 32 (2-22) | 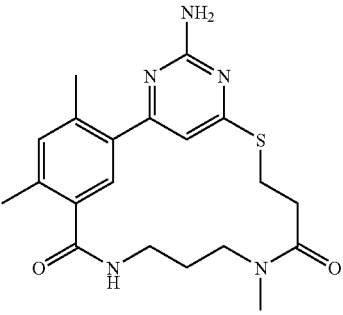 [SMILES: Cc1cc(C)c2cc1C(=O)NCCCN(C)C(=O)CCSc1cc-2nc(N)n1] | 0.5 | 0.4 |
| 34 (2-23) | 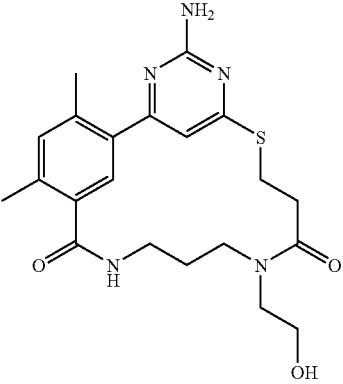 [SMILES: Cc1cc(C)c2cc1C(=O)NCCCN(CCO)C(=O)CCSc1cc-2nc(N)n1] | 2.8 | 1.1 |
| 83 (2-24) | 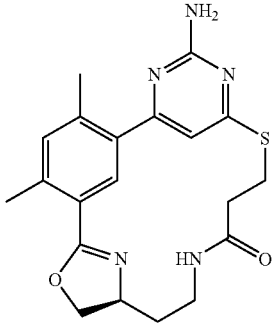 [SMILES: Cc1cc(C)c2cc1C1=N[C@@H](CCNC(=O)CCSc3cc-2nc(N)n3)CO1] | 2.8 | 0.4 |

TABLE 2-continued

| Compound No. (Example) | Formula | Enzyme-inhibiting activity (IC50, μM) Human HSP90α | Cell growth-inhibiting activity (IC50, μM) Colon cancer HCT116 |
| --- | --- | --- | --- |
| 29 (2-25) | | 1.7 | 0.3 |
| 30 (2-26) | | 1.8 | 0.5 |
| 31 (2-27) | | 0.8 | 1.3 |
| 9 (3-1) | | 1.9 | >10 |

TABLE 2-continued

| Compound No. (Example) | Formula | Enzyme-inhibiting activity (IC50, μM) Human HSP90α | Cell growth-inhibiting activity (IC50, μM) Colon cancer HCT116 |
|---|---|---|---|
| 10 (3-2) | | 1.1 | >10 |
| 11 (3-3) | | 1.2 | 0.25 |
| 12 (3-4) | | 1.3 | 0.72 |
| 13 (3-5) | | 1.2 | 4.4 |

TABLE 2-continued

| Compound No. (Example) | Formula | Enzyme-inhibiting activity (IC50, μM) Human HSP90α | Cell growth-inhibiting activity (IC50, μM) Colon cancer HCT116 |
|---|---|---|---|
| 14 (3-6) | | 0.8 | 0.15 |
| 15 (3-7) | | 1.6 | 0.14 |
| 73 (3-8) | | 2.3 | 0.5 |
| 74 (3-9) | | 2.3 | 5.7 |

TABLE 2-continued

| Compound No. (Example) | Formula | Enzyme-inhibiting activity (IC50, μM) Human HSP90α | Cell growth-inhibiting activity (IC50, μM) Colon cancer HCT116 |
|---|---|---|---|
| 75 (3-10) | | 1.9 | 0.5 |
| 76 (3-11) | | 4.3, 6.2 | 5.0, 7.1 |
| 77 (3-12) | | 5.0, 3.4 | 6.5, >10 |
| 78 (3-13) | | 2.8 | 0.5 |

TABLE 2-continued

| Compound No. (Example) | Formula | Enzyme-inhibiting activity (IC50, μM) Human HSP90α | Cell growth-inhibiting activity (IC50, μM) Colon cancer HCT116 |
| --- | --- | --- | --- |
| 79 (3-14) | | 3.0 | 0.4 |
| 80 (3-15) | | 2.5 | 0.2 |
| 81 (3-16) | | 3.0 | 1.1 |
| 82 (3-17) | | 2.5 | 0.2 |

TABLE 2-continued

| Compound No. (Example) | Formula | Enzyme-inhibiting activity (IC50, μM) Human HSP90α | Cell growth-inhibiting activity (IC50, μM) Colon cancer HCT116 |
|---|---|---|---|
| 28 (3-18) | | 1.4 | 0.2 |
| 16 (4-1) | | 1.6 | 4.0 |
| 17 (4-2) | | 1.3 | 4.1 |
| 18 (4-3) | | 2.9 | 0.78 |

TABLE 2-continued

| Compound No. (Example) | Formula | Enzyme-inhibiting activity (IC50, μM) Human HSP90α | Cell growth-inhibiting activity (IC50, μM) Colon cancer HCT116 |
|---|---|---|---|
| 19 (4-4) | | 2.7 | 2.5 |
| 20 (4-5) | | 1.5 | 3.1 |
| 21 (5-1) | | 1.8 | 1.5 |
| 22 (5-2) | | 1.7 | 2.4 |

TABLE 2-continued
| Compound No. (Example) | Formula | Enzyme-inhibiting activity (IC50, μM) Human HSP90α | Cell growth-inhibiting activity (IC50, μM) Colon cancer HCT116 |
|---|---|---|---|
| 23 (5-3) | 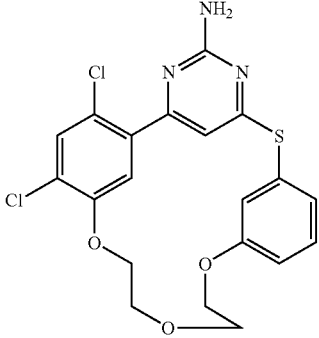 | 1.1 | 1.4 |
| 24 (5-4) | 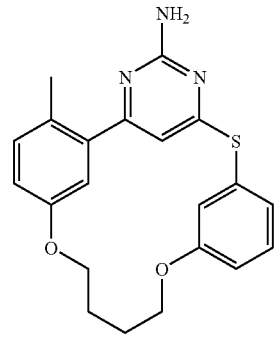 [SMILES: Cc1ccc2cc1-c1cc(nc(N)n1)Sc1cccc(c1)OCCCCO2] | 1.8 | 5.5 |
| 25 (5-5) | 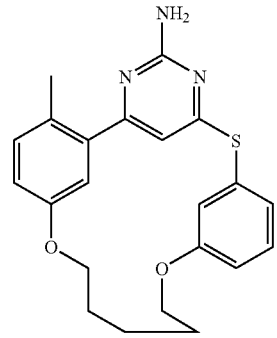 [SMILES: Cc1ccc2cc1-c1cc(nc(N)n1)Sc1cccc(c1)OCCCCCO2] | 1.9 | 3.7 |
| 26 (5-6) | 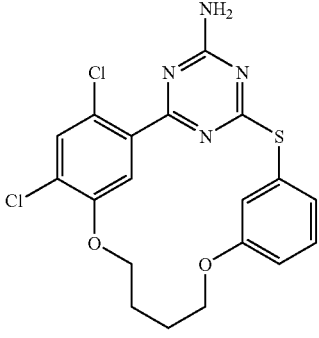 [SMILES: Nc1nc2nc(n1)-c1cc(c(Cl)cc1Cl)OCCCCOc1cccc(c1)S2] | 3.3 | 7.4 |

TABLE 2-continued

| Compound No. (Example) | Formula | Enzyme-inhibiting activity (IC50, μM) Human HSP90α | Cell growth-inhibiting activity (IC50, μM) Colon cancer HCT116 |
|---|---|---|---|
| 27 (5-7) | | 2.1 | 1.4 |
| 72 (6) | | 2.2 | 1.0 |

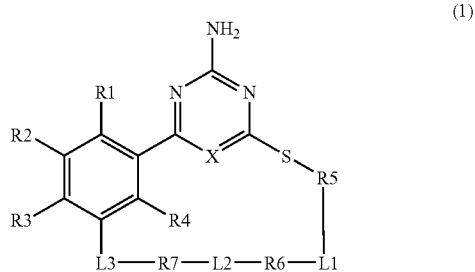

INDUSTRIAL APPLICABILITY

As shown in the Examples above, the compounds of the present invention represented by formula (1) have the activity of inhibiting both HSP90 enzyme and cell growth, and thus are expected to be used as unique, single/concomitant anticancer agents that act simultaneously on multiple potential targets.

The invention claimed is:

1. A compound represented by formula (1) or a pharmaceutically acceptable salt thereof:

(1)

wherein X represents CH or N;

$R^1$ represents a hydrogen atom, a halogen atom, a cyano group, a $C_{1-6}$ alkyl group, a $C_{1-4}$ haloalkyl group, a $C_{2-6}$ alkenyl group, a $C_{2-6}$ alkynyl group, a $C_{1-6}$ alkoxy group, or a $C_{1-6}$ alkylthio group;

$R^2$ represents a hydrogen atom, a halogen atom, a $C_{1-6}$ alkyl group, a $C_{2-6}$ alkenyl group, or a $C_{2-6}$ alkynyl group, or $R_2$ and $R_3$ together form a ring;

$R^3$ represents a hydrogen atom, a halogen atom, a cyano group, a $C_{1-6}$ alkyl group, a $C_{2-6}$ alkenyl group, a $C_{2-6}$ alkynyl group, or a $C_{1-6}$ alkoxy group, or $R^2$ and $R^3$ together form a ring;

$R^4$ represents a hydrogen atom, a halogen atom, a $C_{1-6}$ alkyl group, a $C_{2-6}$ alkenyl group, or a $C_{2-6}$ alkynyl group;

$R^5$, $R^6$, and $R^7$ each independently represent a $C_{1-6}$ alkylene group, a $C_{2-6}$ alkenylene group, a $C_{2-6}$ alkynylene group, a $C_{3-10}$ cycloalkylene group, a $C_{3-10}$ cycloalkenylene group, a $C_{6-12}$ arylene group, or -3 to 12-membered monocyclic heterocyclic ring-, each of which may have a substituent;

$L^1$, $L^2$, and $L^3$ each independently represent a single bond, —CONR$^8$—, —NR$^8$CO—, —NR$^8$—, —O—, —SO$_2$NR$^8$—, —NR$^8$SO$_2$—, —COO—, —NR$^8$CONR$^{8'}$—, —NR$^8$COO—, or —OCONR$^8$—;

$R^8$ and $R^{8'}$ each independently represent a hydrogen atom or a $C_{1-6}$ alkyl group which may have a substituent.

2. The compound of claim 1, or a pharmaceutically acceptable salt thereof, wherein $R^1$ represents a halogen atom, a cyano group, a $C_{1-6}$ alkyl group, a $C_{1-4}$ haloalkyl group, or a $C_{2-6}$ alkynyl group.

3. The compound of claim 1, or a pharmaceutically acceptable salt thereof, wherein $R^1$ represents a chlorine atom, a cyano group, a methyl group, or an ethynyl group.

4. The compound of claim 1, or a pharmaceutically acceptable salt thereof, wherein $R^1$ represents a chlorine atom or a methyl group.

5. The compound of claim 1, or a pharmaceutically acceptable salt thereof, wherein $R^2$ represents a hydrogen atom.

6. The compound of claim 1, or a pharmaceutically acceptable salt thereof, wherein $R^3$ represents a hydrogen atom, a halogen atom, a $C_{1-4}$ alkyl group, or a $C_{1-4}$ alkoxy group.

7. The compound of claim 1, or a pharmaceutically acceptable salt thereof, wherein $R^3$ represents a methyl group.

8. The compound of claim 1, or a pharmaceutically acceptable salt thereof, wherein $R^3$ represents a chlorine atom.

9. The compound of claim 1, or a pharmaceutically acceptable salt thereof, wherein $R^3$ represents a methoxy group or an ethoxy group.

10. The compound of claim 1, or a pharmaceutically acceptable salt thereof, wherein $R^4$ represents a hydrogen atom.

11. The compound of claim 1, or a pharmaceutically acceptable salt thereof, wherein $R^5$, $R^6$, and $R^7$ each independently represents a $C_{1-6}$ alkylene group, phenylene group, or -3- to 12-membered monocyclic heterocyclic ring-, which is optionally substituted with a substituent selected from Group A:

Group A: a $C_{1-6}$ alkyl group (optionally substituted with a hydroxyl group or a dimethylamino group), a halogen atom, a hydroxyl group, a cyano group, a group represented by —$NR^9R^{10}$ (wherein $R^9$ and $R^{10}$ each independently represents a hydrogen atom, a $C_{1-3}$ alkyl group, or a group represented by —C(=O)$CH_3$, —C(=O)$CF_3$, —C(=O)CH($NH_2$)CH($CH_3$)$_2$, or —C(=O)CH($NH_2$)(4-OH)Ph), and a group represented by —C(=O)$NR^{11}R^{12}$ (wherein $R^{11}$ and $R^{12}$ each independently represents a hydrogen atom or a $C_{1-6}$ alkyl group which may have a substituent (wherein the substituent is at least one selected from the group consisting of a hydroxyl group, $C_{1-6}$ alkoxy group, a $C_{1-3}$ alkoxy $C_{1-3}$ alkoxy group, a morpholinyl group, a piperidinyl group, and a 4-methylpiperidinyl group), or $R^{11}$ and $R^{12}$ together form a 3- to 12-membered monocyclic heterocyclic ring), or a group represented by —C(=O)$OR^{13}$ ($R^{13}$ represents a hydrogen atom or a $C_{1-3}$ alkyl group).

12. The compound of claim 1, or a pharmaceutically acceptable salt thereof, wherein any one of $R^5$, $R^6$, and $R^7$ is a $C_{1-6}$ alkylene group substituted with a 3- to 12-membered monocyclic alicyclic monospiro ring that is optionally substituted with a substituent, or a $C_{1-6}$ alkylene group substituted with a 3- to 12-membered monocyclic heterocyclic monospiro ring that is optionally substituted with a substituent.

13. The compound of claim 1, or a pharmaceutically acceptable salt thereof, wherein $L^1$ and $L^2$ each independently represents a single bond, —$CONR^8$—, —$NR^8CO$—, —$NR^8CONR^{8'}$—, —$NR^8COO$—, —$NR^8$—, or —O—.

14. The compound of claim 1, or a pharmaceutically acceptable salt thereof, wherein $L^1$ represents —$CONR^8$—, —$NR^8CO$—, —$NR^8CONR^{8'}$—, —$NR^8COO$—, or —O—.

15. The compound of claim 1, or a pharmaceutically acceptable salt thereof, wherein $L^2$ represent a single bond, —O—, or —$NR^8$—.

16. The compound of claim 1, or a pharmaceutically acceptable salt thereof, wherein $L^3$ represents —$CONR^8$— or —O—.

17. The compound of claim 1, or a pharmaceutically acceptable salt thereof, wherein X represents CH.

18. The compound of claim 1, or a pharmaceutically acceptable salt thereof, wherein the compound is selected from the group consisting of:

(1) 4-amino-20,22-dimethyl-7-thia-3,5,11,17-tetraazatricyclo[17.3.1.1$^{2,6}$]tetracosa-1(22),2(24),3,5,19(23),20-hexaene-10,18-dione;

(2) 4-amino-18,20-dimethyl-7-thia-3,5,11,15-tetraazatricyclo[15.3.1.1$^{2,6}$]docosa-1(20),2(22),3,5,17(21),18-hexaene-10,16-dione;

(3) 4-amino-15,18,20-trimethyl-7-thia-3,5,11,15-tetraazatricyclo[15.3.1.1$^{2,6}$]docosa-1(20),2(22),3,5,17(21),18-hexaene-10,16-dione;

(4) 4-amino-18,20-dimethyl-7-thia-3,5,12,15-tetraazatricyclo[15.3.1.1$^{2,6}$]docosa-1(20),2(22),3,5,17(21),18-hexaene-11,16-dione;

(5) 4-amino-20,22-dimethyl-7-thia-3,5,12,17-tetraazatricyclo[17.3.1.1$^{2,6}$]tetracosa-1(22),2(24),3,5,19(23),20-hexaene-11,18-dione;

(6) 4-amino-19,21-dimethyl-7-thia-3,5,11,16-tetraazatricyclo[16.3.1.1$^{2,6}$]tricosa-1(21),2(23),3,5,18(22),19-hexaene-10,17-dione;

(7) 4-amino-9,20,22-trimethyl-7-thia-3,5,11,17-tetraazatricyclo[17.3.1.1$^{2,6}$]tetracosa-1(22),2(24),3,5,19(23),20-hexaene-10,18-dione;

(8) 4-amino-18,20-dichloro-7-thia-3,5,11,15-tetraazatricyclo[15.3.1.1$^{2,6}$]docosa-1(20),2(22),3,5,17(21),18-hexaene-10,16-dione;

(9) 4-amino-18-methoxy-20-methyl-7-thia-3,5,10,15-tetraazatricyclo[15.3.1.1$^{2,6}$]docosa-1(20),2(22),3,5,17(21),18-hexaene-11,16-dione;

(10) 4-amino-18-methoxy-15,20-dimethyl-7-thia-3,5,10,15-tetraazatricyclo[15.3.1.1$^{2,6}$]docosa-1(20),2(22),3,5,17(21),18-hexaene-11,16-dione;

(11) 4-amino-18,20-dimethyl-7-thia-3,5,10,15-tetraazatricyclo[15.3.1.1$^{2,6}$]docosa-1(20),2(22),3,5,17(21),18-hexaene-11,16-dione;

(12) 4-amino-17,19-dimethyl-7-thia-3,5,10,14-tetraazatricyclo[14.3.1.1$^{2,6}$]henicosa-1(19),2(21),3,5,16(20),17-hexaene-11,15-dione;

(13) 4-amino-15,18,20-trimethyl-7-thia-3,5,10,15-tetraazatricyclo[15.3.1.1$^{2,6}$]docosa-1(20),2(22),3,5,17(21),18-hexaene-11,16-dione;

(14) 4-amino-20,22-dimethyl-7-thia-3,5,10,17-tetraazatricyclo[17.3.1.1$^{2,6}$]tetracosa-1(22),2(24),3,5,19(23),20-hexaene-11,18-dione;

(15) 4-amino-18,20-dichloro-7-thia-3,5,10,15-tetraazatricyclo[15.3.1.1$^{2,6}$]docosa-1(20),2(22),3,5,17(21),18-hexaene-11,16-dione;

(16) 4-amino-20-methoxy-22-methyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one;

(17) 4-amino-20-ethoxy-22-methyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one;

(18) 4-amino-20,22-dimethyl-13-oxa-7-thia-3,5,17-triazatricyclo[17.3.1.1$^{2,6}$.1$^{8,12}$]pentacosa-1(22),2(24),3,5,8(25),9,11,19(23),20-nonaen-18-one;

(19) 4-amino-21,23-dimethyl-13-oxa-7-thia-3,5,18-triazatricyclo[18.3.1.1$^{2,6}$.1$^{8,12}$]hexacosa-1(23),2(25),3,5,8(26),9,11,20(24),21-nonaen-19-one;

(20) 4-amino-22,24-dimethyl-13-oxa-7-thia-3,5,19-triazatricyclo[19.3.1.1$^{2,6}$.1$^{8,12}$]heptacosa-1(24),2(26),3,5,8(27),9,11,21(25),22-nonaen-20-one;

(21) 4-amino-20,22-dichloro-13,18-dioxa-7-thia-3,5-diazatricyclo[17.3.1.1$^{2,6}$.1$^{8,12}$]pentacosa-1(23),2,4,6(24),8,10,12(25),19,21-nonaene;

(22) 4-amino-21,23-dichloro-13,19-dioxa-7-thia-3,5-diazatricyclo[18.3.1.1$^{2,6}$.1$^{8,12}$]hexacosa-1(24),2,4,6(24),8,10,12(26),20,22-nonaene;

(23) 21,23-dichloro-13,16,19-trioxa-7-thia-3,5-diazatricyclo[18.3.1.1$^{2,6}$.1$^{8,12}$]hexacosa-1(23),2(25),3,5,8(26),9,11,20(24),21-nonaen-4-ylamine;

(24) 4-amino-22-methyl-13,18-dioxa-7-thia-3,5-diazatricyclo[17.3.1.1$^{2,6}$.1$^{8,12}$]pentacosa-1(23),2(24),3,5,8(25),9,11,19,21-nonaene;

(25) 4-amino-23-methyl-13,19-dioxa-7-thia-3,5-diazatricyclo[18.3.1.1$^{2,6}$.1$^{8,12}$]hexacosa-1(24),2(25),3,5,8(26),9,11,20,22-nonaene;

(26) 20,22-dichloro-13,18-dioxa-7-thia-3,5,24-triazatricyclo[17.3.1.1$^{2,6}$.1$^{8,12}$]pentacosa-1(22),2(24),3,5,8(25),9,11,19(23),20-nonaen-4-ylamine;

(27) 21,23-dichloro-13,16,19-trioxa-7-thia-3,5,25-triazatricyclo[18.3.1.1$^{2,6}$.1$^{8,12}$]hexacosa-1(23),2(25),3,5,8(25),9,11,20(24),21-nonaen-4-ylamine;

(28) 4-amino-20,22-dichloro-7-thia-3,5,10,17-tetraazatricyclo[17.3.1.1$^{2,6}$]tetracosa-1(22),2(24),3,5,19(23),20-hexaene-11,18-dione;

(29) 4-amino-20,22-dimethyl-14-oxa-7-thia-3,5,11,17-tetraazatricyclo[17.3.1.1$^{2,6}$]tetracosa-1(22),2(24),3,5,19(23),20-hexaene-10,18-dione;

(30) 4-amino-14,20,22-trimethyl-7-thia-3,5,11,14,17-pentaazatricyclo[17.3.1.1$^{2,6}$]tetracosa-1(22),2(24),3,5,19(23),20-hexaene-10,18-dione;

(31) 4-amino-13-hydroxy-18,20-dimethyl-7-thia-3,5,11,15-tetraazatricyclo[15.3.1.1$^{2,6}$]docosa-1(20),2(22),3,5,17(21),18-hexaene-10,16-dione;

(32) 4-amino-11,18,20-trimethyl-7-thia-3,5,11,15-tetraazatricyclo[15.3.1.1$^{2,6}$]docosa-1(20),2,4,6(22),17(21),18-hexaene-10,16-dione;

(33) 4-amino-11,19,21-trimethyl-7-thia-3,5,11,16-tetraazatricyclo[16.3.1.1$^{2,6}$]tricosa-1(21),2(23),3,5,18(22),19-hexaene-10,17-dione;

(34) 4-amino-11-(2-hydroxyethyl)-18,20-dimethyl-7-thia-3,5,11,15-tetraazatricyclo[15.3.1.1$^{2,6}$]docosa-1(20),2,4,6(22),17(21),18-hexaene-10,16-dione;

(35) 4-amino-11-(2-hydroxyethyl)-19,21-dimethyl-7-thia-3,5,11,16-tetraazatricyclo[16.3.1.1$^{2,6}$]tricosa-1(21),2(23),3,5,18(22),19-hexaene-10,17-dione;

(36) 4-amino-18,20-dimethyl-11-(2-morpholin-4-ylethyl)-7-thia-3,5,11,15-tetraazatricyclo[15.3.1.1$^{2,6}$]docosa-1(20),2,4,6(22),17(21),18-hexaene-10,16-dione;

(37) 4-amino-19,21-dimethyl-11-(2-morpholin-4-ylethyl)-7-thia-3,5,11,16-tetraazatricyclo[16.3.1.1$^{2,6}$]tricosa-1(21),2(23),3,5,18(22),19-hexaene-10,17-dione;

(38) 4-amino-18,20-dimethyl-11-[2-(4-methylpiperazin-1-yl)ethyl]-7-thia-3,5,11,15-tetraazatricyclo[15.3.1.1$^{2,6}$]docosa-1(20),2(22),3,5,17(21),18-hexaene-10,16-dione;

(39) 4-amino-19,21-dimethyl-11-[2-(4-methylpiperazin-1-yl)ethyl]-7-thia-3,5,11,16-tetraazatricyclo[16.3.1.1$^{2,6}$]tricosa-1(21),2(23),3,5,18(22),19-hexaene-10,17-dione;

(40) 4,9-diamino-18,20-dimethyl-7-thia-3,5,11,15-tetraazatricyclo[15.3.1.1$^{2,6}$]docosa-1(20),2(22),3,5,17(21),18-hexaene-10,16-dione;

(41) 4,9-diamino-19,21-dimethyl-7-thia-3,5,11,16-tetraazatricyclo[16.3.1.1$^{2,6}$]tricosa-1(21),2(23),3,5,18(22),19-hexaene-10,17-dione;

(42) N-(4-amino-18,20-dimethyl-10,16-dioxo-7-thia-3,5,11,15-tetraazatricyclo[15.3.1.1$^{2,6}$]docosa-1(20),2(22),3,5,17(21),18-hexaen-9-yl)acetamide;

(43) N-(4-amino-19,21-dimethyl-10,17-dioxo-7-thia-3,5,11,16-tetraazatricyclo[16.3.1.1$^{2,6}$]tricosa-1(21),2(23),3,5,18(22),19-hexaen-9-yl)acetamide;

(44) 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid amide;

(45) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid amide;

(46) 4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid (2-hydroxyethyl)amide;

(47) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid (2-hydroxyethyl)amide;

(48) 4-amino-19,21-dimethyl-10,17-dioxo-7-thia-3,5,11,16-tetraazatricyclo[16.3.1.1$^{2,6}$]tricosa-1(21),2,4,6(23),18(22),19-hexaene-12-carboxylic acid (2,3-dihydroxypropyl)amide;

(49) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid (2,3-dihydroxypropyl)amide;

(50) 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid [2-(2-methoxyethoxy)ethyl]amide;

(51) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid [2-(2-methoxyethoxy)ethyl]amide;

(52) 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid (2-morpholin-4-ylethyl)amide;

(53) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid (2-morpholin-4-ylethyl)amide;

(54) 4-amino-19,21-dimethyl-10,17-dioxo-7-thia-3,5,11,16-tetraazatricyclo[16.3.1.1$^{2,6}$]tricosa-1(21),2(23),3,5,18(22),19-hexaene-12-carboxylic acid [2-(4-methylpiperazin-1-yl)ethyl]amide;

(55) 4-amino-18,20-dimethyl-10,16-dioxo-7-thia-3,5,11,15-tetraazatricyclo[15.3.1.1$^{2,6}$]docosa-1(20),2(22),3,5,17(21),18-hexaene-12-carboxylic acid [2-(4-methylpiperazin-1-yl)ethyl]amide;

(56) 4-amino-18,20-dimethyl-7-thia-3,5,10,12,15-pentaazatricyclo[15.3.1.1$^{2,6}$]docosa-1(20),2(22),3,5,17(21),18-hexaene-11,16-dione;

(57) 4-amino-19,21-dimethyl-7-thia-3,5,10,12,16-pentaazatricyclo[16.3.1.1$^{2,6}$]tricosa-1(21),2(23),3,5,18(22),19-hexaene-11,17-dione;

(58) 4-amino-18,20-dimethyl-10-oxa-7-thia-3,5,12,15-tetraazatricyclo[15.3.1.1$^{2,6}$]docosa-1(20),2(22),3,5,17(21),18-hexaene-11,16-dione;

(59) 4-amino-19,21-dimethyl-11-oxa-7-thia-3,5,13,16-tetraazatricyclo[16.3.1.1$^{2,6}$]tricosa-1(21),2(23),3,5,18(22),19-hexaene-12,17-dione;

(60) 4-amino-12-hydroxymethyl-18,20-dimethyl-7-thia-3,5,11,15-tetraazatricyclo[15.3.1.1$^{2,6}$]docosa-1(20),2(22),3,5,17(21),18-hexaene-10,16-dione;

(61) 4-amino-12-dimethylaminomethyl-18,20-dimethyl-7-thia-3,5,11,15-tetraazatricyclo[15.3.1.1$^{2,6}$]docosa-1(20),2(22),3,5,17(21),18-hexaene-10,16-dione;

(62) (S)-4-amino-19,21-dimethyl-10,17-dioxo-7-thia-3,5, 11,16-tetraazatricyclo [16.3.1.1$^{2,6}$]tricosa-1(21),2,4,6 (23),18(22),19-hexaene-12-carboxylic acid methyl ester;
(63) (S)-4-amino-18,20-dimethyl-10,16-dioxo-7-thia-3,5, 11,15-tetraazatricyclo[15.3.1.1$^{2,6}$]docosa-1(20),2(22), 3,5,17(21),18-hexaene-14-carboxylic acid methyl ester;
(64) (S)-4-amino-18,20-dimethyl-10,16-dioxo-7-thia-3,5, 11,15-tetraazatricyclo[15.3.1.1$^{2,6}$]docosa-1(20),2(22), 3,5,17(21),18-hexaene-14-carboxylic acid;
(65) (S)-4-amino-18,20-dimethyl-10,16-dioxo-7-thia-3,5, 11,15-tetraazatricyclo[15.3.1.1$^{2,6}$]docosa-1(20),2(22), 3,5,17(21),18-hexaene-14-carboxylic acid methylamide;
(66) (S)-4-amino-18,20-dimethyl-10,16-dioxo-7-thia-3,5, 11,15-tetraazatricyclo[15.3.1.1$^{2,6}$]docosa-1(20),2(22), 3,5,17(21),18-hexaene-14-carboxylic acid (2-methoxyethyl)amide;
(67) (S)-4-amino-18,20-dimethyl-10,16-dioxo-7-thia-3,5, 11,15-tetraazatricyclo[15.3.1.1$^{2,6}$]docosa-1(20),2(22), 3,5,17(21),18-hexaene-14-carboxylic acid dimethylamide;
(68) (S)-4-amino-14-hydroxymethyl-18,20-dimethyl-7-thia-3,5,11,15-tetraazatricyclo[15.3.1.1$^{2,6}$]docosa-1 (20),2(22),3,5,17(21),18-hexaene-10,16-dione;
(69) (R)-4-amino-18,20-dimethyl-10,16-dioxo-7-thia-3,5, 11,15-tetraazatricyclo[15.3.1.1$^{2,6}$]docosa-1(20),2,4,6 (22),17(21),18-hexaene-12-carboxylic acid methyl ester;
(70) (S)-4-amino-18,20-dimethyl-12-(morpholine-4-carbonyl)-7-thia-3,5,11,15-tetraazatricyclo[15.3.1.1$^{2,6}$] docosa-1(20),2,4,6(22),17(21),18-hexaene-10,16-dione;
(71) (S)-4-amino-18,20-dimethyl-12-morpholin-4-ylmethyl-7-thia-3,5,11,15-tetraazatricyclo[15.3.1.1$^{2,6}$] docosa-1(20),2(22),3,5,17(21),18-hexaene-10,16-dione;
(72) 4-amino-18,20-dimethyl-13-oxetan-3-yl-7-thia-3,5, 11,15-tetraazatricyclo[15.3.1.1$^{2,6}$]docosa-1(20),2(22), 3,5,17(21),18-hexaene-10,16-dione;
(73) 4,12-diamino-18,20-dimethyl-7-thia-3,5,10,15-tetraazatricyclo[15.3.1.1$^{2,6}$]docosa-1(20),2(22),3,5,17 (21),18-hexaene-11,16-dione;
(74) N-(4-amino-18,20-dimethyl-10,16-dioxo-7-thia-3,5, 10,15-tetraazatricyclo[15.3.1.1$^{2,6}$]docosa-1(20),2(22), 3,5,17(21),18-hexaen-12-yl)acetamide;
(75) N-(4-amino-18,20-dimethyl-11,16-dioxo-7-thia-3,5, 10,15-tetraazatricyclo[15.3.1.1$^{2,6}$]docosa-1(20),2(22), 3,5,17(21),18-hexaen-12-yl)-2,2,2-trifluoroacetamide;
(76) (R)-2-amino-N-(4-amino-18,20-dimethyl-11,16-dioxo-7-thia-3,5,10,15-tetraazatricyclo[15.3.1.1$^{2,6}$] docosa-1(20),2(22),3,5,17(21),18-hexaen-12-yl)-3-methylbutylamide;
(77) (R)-2-amino-N-(4-amino-18,20-dimethyl-11,16-dioxo-7-thia-3,5,10,15-tetraazatricyclo[15.3.1.1$^{2,6}$] docosa-1(20),2(22),3,5,17(21),18-hexaen-12-yl)-3-(4-hydroxyphenyl)propionamide;
(78) 4-amino-12-dimethylamino-18,20-dimethyl-7-thia-3,5,10,15-tetraazatricyclo[15.3.1.1$^{2,6}$]docosa-1(20),2 (22),3,5,17(21),18-hexaene-11,16-dione;
(79) 4-amino-10-(2-hydroxyethyl)-18,20-dimethyl-7-thia-3,5,10,15-tetraazatricyclo[15.3.1.1$^{2,6}$]docosa-1 (20),2(22),3,5,17(21),18-hexaene-11,16-dione;
(80) 4-amino-10-(2-methoxyethyl)-18,20-dimethyl-7-thia-3,5,10,15-tetraazatricyclo[15.3.1.1$^{2,6}$]docosa-1 (20),2(22),3,5,17(21),18-hexaene-11,16-dione;
(81) 4-amino-10-(2-morpholin-4-ylethyl)-18,20-dimethyl-7-thia-3,5,10,15-tetraazatricyclo[15.3.1.1$^{2,6}$] docosa-1(20),2(22),3,5,17(21),18-hexaene-11,16-dione;
(82) 4-amino-10,18,20-trimethyl-7-thia-3,5,10,15-tetraazatricyclo[15.3.1.1$^{2,6}$]docosa-1(20),2(22),3,5,17 (21),18-hexaene-11,16-dione; and
(83) (S)-4-amino-19,21-dimethyl-10-oxo-7-thia-16-oxa-3,5,11,24-tetraazatetracyclo[16.3.1.1$^{2,6}$.1$^{7,10}$]tetracosa-1(22),2(23),3,5,17(24),19,21-heptaen-10-one.

19. A pharmaceutical composition comprising as an active ingredient the compound of claim 1, or a pharmaceutically acceptable salt thereof.

20. A method of treating cancer, comprising administering an effective amount of the compound of claim 1, or a pharmaceutically acceptable salt thereof, to a patient in need of treatment of cancer, wherein the cancer is colon cancer.

* * * * *